United States Patent [19]

Summers, Jr. et al.

[11] Patent Number: 5,486,525

[45] Date of Patent: Jan. 23, 1996

[54] PLATELET ACTIVATING FACTOR ANTAGONISTS: IMIDAZOPYRIDINE INDOLES

[75] Inventors: James B. Summers, Jr.; Steven K. Davidsen, both of Libertyville; Michael L. Curtin, Lindenhurst; H. Robin Heyman, Chicago; George S. Sheppard, Wilmette; Lianhong Xu, Libertyville; George M. Carrera, Jr., Des Plaines; Robert B. Garland, Northbrook, all of Ill.

[73] Assignee: Abbott Laboratories, Abbott Park, Ill.

[21] Appl. No.: 347,528

[22] Filed: Dec. 5, 1994

Related U.S. Application Data

[63] Continuation-in-part of Ser. No. 324,631, Oct. 18, 1994, which is a continuation-in-part of Ser. No. 168,564, Dec. 16, 1993, abandoned.

[51] Int. Cl.$^6$ ............... A61K 31/435; C07D 471/04
[52] U.S. Cl. ............... 514/303; 514/394; 546/118; 548/302.1; 548/305.1
[58] Field of Search ............ 546/118; 548/305.1, 548/302.1; 514/303, 394

[56] References Cited

FOREIGN PATENT DOCUMENTS

| | | |
|---|---|---|
| 0171037 | 2/1986 | European Pat. Off. ...... C07D 209/12 |
| 444451 | 9/1991 | European Pat. Off. ...... C07D 413/06 |
| 2427207 | 1/1975 | Germany . |
| 3200705 | 7/1983 | Germany . |
| WO93/01813 | 2/1993 | WIPO ............... A61K 31/44 |

OTHER PUBLICATIONS

Chem. Abstr., 96:11505t (1992).
Chem. Abstr., 102: 93257b (1985).
Chem. Abstr., 108: 48713k (1988).
Chem. Abstr., 111: 150783g (1989).
Chem. Abstr., 113: 6344p (1990).

Primary Examiner—Bernard Dentz
Attorney, Agent, or Firm—Jerry F. Janssen

[57] ABSTRACT

The present invention relates to compounds of formula

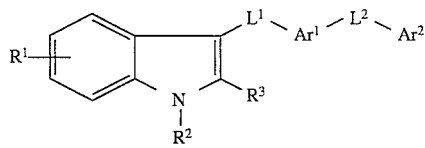

and the pharmaceutically acceptable salts thereof which are potent antagonists of PAF and are useful in the treatment of PAF-related disorders including asthma, shock, respiratory distress syndrome, acute inflammation, transplanted organ rejection, gastrointestinal ulceration, allergic skin diseases, delayed cellular immunity, parturition, fetal lung maturation, and cellular differentiation.

10 Claims, No Drawings

PLATELET ACTIVATING FACTOR ANTAGONISTS: IMIDAZOPYRIDINE INDOLES

This application is a continuation-in-part of Ser. No. 08/324,631 filed Oct. 18, 1994 which is a continuation-in-part of Ser. No. 08/168,564 filed Dec. 16, 1993 now abandoned.

TECHNICAL FIELD

This invention relates to compounds having pharmacological activity, to compositions containing these compounds, and to a medical method of treatment employing the compounds and compositions. More particularly, this invention concerns certain indolecarbonyl pyridylpyrrolothiazole compounds and their salts which have platelet activating factor (PAF) antagonist activity, to pharmaceutical compositions containing these compounds, and to a method of treating PAF-mediated disorders.

BACKGROUND OF THE INVENTION

Platelet activating factor (PAF) is a phospholipid released from human and other animal cells and is an acetylglyceryl ether of phosphorylcholine as represented by the following formula:

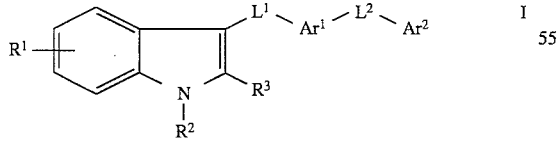

where n is 15 or 17.

PAF is physiologically active and causes contraction of the airway smooth muscle, increased vascular permeability, platelet aggregation, hypotension, and the like. It is now recognized as a powerful mediator of inflammation and may play a physiological or pathobiological role in a variety of clinical conditions, such as asthma and pulmonary dysfunction, acute inflammation, transplanted organ rejection, shock, thrombosis, anaphylaxis, gastrointestinal ulceration, allergic skin diseases, retinal and corneal diseases, chemically induced liver cirrhosis, and ovimplantation in pregnancy. Accordingly, compounds possessing PAF antagonistic effects should be of value in the treatment of any of the above conditions.

SUMMARY OF THE INVENTION

The present invention provides, in its principal aspect, compounds having PAF antagonist activity of formula I:

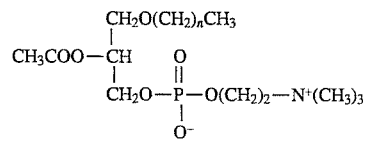

or the pharmaceutically acceptable salt thereof where $R^1$ is one or more groups independently selected from the group consisting of (a) hydrogen, (b) halogen, (c) hydroxy, (d) cyano, (e) alkyl of one to six carbon atoms, (f) alkynyl of two to four carbon atoms, (g) alkoxy of one to six carbon atoms, (h) alkanoyl of one to seven carbon atoms, (i) —$COOR^6$, where $R^6$ is hydrogen, alkyl of one to ten carbon atoms, or phenylalkyl where the alkyl portion is of one to four carbon atom, (j) phenyl, optionally substituted with (j-1) alkyl of one to six carbon atoms, (j-2) alkoxy of one to six carbon atoms, (j-3) halogen, (j-4) —$NR^4R^5$, where $R^4$ and $R^5$ are independently selected from hydrogen and alkyl of one to six carbon atoms, or $R^4$ and $R^5$ together with the nitrogen atom to which they are attached form a pyrrolidinyl, piperidinyl, piperazinyl, or morpholinyl ring, (j-5) —$COOR^6$, (j-6) —$CONR^4R^5$, or (j-7) —$SO_2NR^4R^5$, (k) —$C(O)NR^4R^5$, (l) —$OC(O)NR^4R^5$, (m) —$NHC(O)NR^4R^5$, (n) 2- or 3-furyl, (o) 2- or 3-thienyl, (p) 2-, 4-, or 5-thiazolyl, (q) 2-, 3-, or 4-pyridyl, (r) 2-, or 4-pyrimidyl, (s) phenlyalkyl, in which the alkyl portion contains one to six carbon atoms and the phenyl moiety is optionally substituted with halogen, alkyl of one to six carbon atoms, or alkoxy of one to six carbon atoms, (t) benzoyl, optionally substituted with halogen, alkyl of one to six carbon atoms, or alkoxy of one to six carbon atoms, (u) phenoxy, optionally substituted with halogen, alkyl of one to six carbon atoms, or alkoxy of one to six carbon atoms, (v) phenylalkyloxy, in which the alkyl portion contains from one to six carbon atoms and the phenyl moiety is optionally substituted with halogen, alkyl of one to six carbon atoms, or alkoxy of one to six carbon atoms, and (w) phenylalkanoyl, in which the alkanoyl portion contains one to seven carbon atoms and the phenyl moiety is optionally substituted with halogen, alkyl of one to six carbon atoms, or alkoxy of from one to six carbon atoms.

$R^2$ is selected from the group consisting of (a) hydrogen, (b) alkyl of one to six carbon atoms, (c) —$(CH_2)_pCOOR^6$, where p is 0, 1, 2, 3, or 4, (d) —$(CH_2)_qNR^4R^5$, where q is 2, 3, or 4, (e) —$(CH_2)_pCOR^6$, (f) —$(CH_2)_qOR^6$, (g) —$(CH_2)_pSO_2R^6$, (h) —$(CH_2)_pSO_2NR^4R^5$, (i) —$(CH_2)_pCONR^7R^8$, where $R^7$ and $R^8$ are independently selected from (i-1) hydrogen, (i-2) alkyl of one to six carbon atoms, (i-3) —$(CH_2)_rCOOR^6$, where r is 1, 2, 3, or 4, (i-4) —$(CH_2)_rNR^4R^5$, (i-5) —$(CH_2)_rOH$, (i-6) —$(CH_2)_rSO_2R^6$, and (i-7) —$(CH_2)_rSO_2NR_4R^5$, (j) —$(CH_2)_pCN$, (k) —$(CH_2)_p$-1H-tetrazol- 5-yl, (l) —$CONHNH_2$, and (m) phenylalkyl wherein the alkyl portion is of one to four carbon atoms, and the phenyl moiety is optionally substituted with halogen, alkyl of one to six carbon atoms, or alkoxy of from one to six carbon atoms, or $R^7$ and R, taken together with the nitrogen atom to which they are attached, for a pyrrolidinyl or morpholinyl ring.

$R^3$ is selected from the group consisting of hydrogen and alkyl of from one to six carbon atoms, and $L^1$ is selected from the group consisting of (a)>C=O,(b)

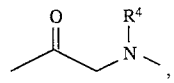

(c)>C=$NNR^9R^{10}$, where $R^9$, and $R^{10}$ are independently selected from hydrogen, alkyl of one to six carbon atoms, alkoxycarbonyl of two to six carbon atoms, aminocarbonyl, alkylaminocarbonyl of two to six carbon atoms, dialkylaminocarbonyl in which the alkyl groups are independently of one to six carbon atoms, alkanoyl of one to six carbon atoms, and phenyl, optionally substituted with halogen, alkyl of one to six carbon atoms, or alkoxy of from one to six carbon atoms, (c)>C=$NOR^9$, (d)>S(O)$_n$, where n is 1 or 2, and (e) —$NHSO_2$—.

Ar¹ is a valence bond or a radical of formula

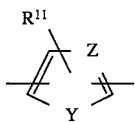

where Y is O, S, or —CH=CH—, Z is N or CH, and R¹¹ is selected from the group consisting of hydrogen, alkyl of one to six carbon atoms, alkenyl of two to six carbon atoms, alkoxy of one to six carbon atoms, and halogen.

L² is a valence bond or straight-chain alkylene of one to six carbon atoms, optionally substituted with one or more groups selected from (a) alkyl of one to six carbon atoms, (b) alkenyl of two to six carbon atoms, (c) alkoxycarbonyl of one to six carbon atoms, (d) alkoxy of one to six carbon atoms, (e) alkylthio of one to six carbon atoms, (f) alkoxyalkyl in which the alkoxy and alkyl portions are independently one to six carbon atoms, (g) alkylthioalkyl in which the alkyl portions are independently one to six carbon atoms, (h) phenylalkyl wherein the alkyl portion is one to six carbon atoms and where the phenyl ring is optionally substituted with alkyl of one to six carbon atoms, haloalkyl of one to six carbon atoms, alkoxy of one to six carbon atoms, hydroxy, or halogen, and (i) thiophenyl where the phenyl ring is optionally substituted with alkyl of one to six carbon atoms, haloalkyl of one to six carbon atoms, alkoxy of one to six carbon atoms, hydroxy, or halogen, provided that L² is optionally substituted alkyl when Ar¹ is a valence bond.

Ar² is selected from the group consisting of

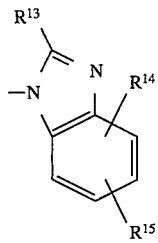

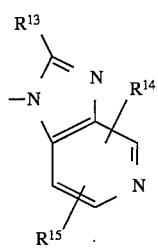

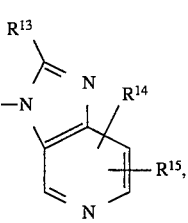

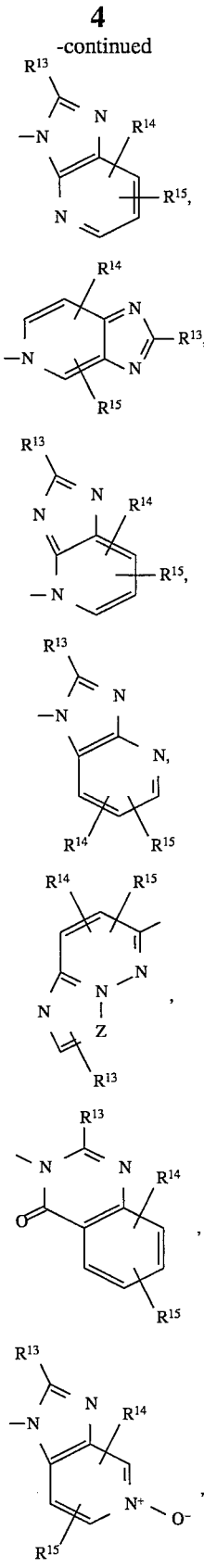

-continued

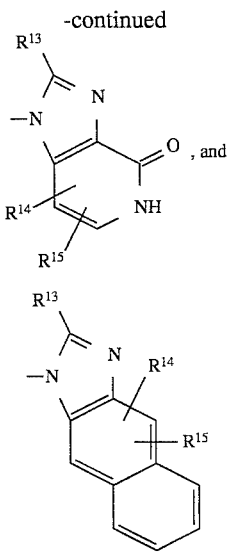

where Z is defined above, and $R^{13}$ is selected from the group consisting of (a) alkyl of one to six carbon atoms, (b) alkenyl of two to six carbon atoms, (c) alkoxy of one to six carbon atoms, (d) alkylthio of one to six carbon atoms, (e) alkoxyalkyl in which the alkoxy and alkyl portions are independently one to six carbon atoms, (f) alkylthioalkyl in which the alkyl portions are independently one to six carbon atoms, (g) haloalkyl, (h) phenylalkyl wherein the alkyl portion is of one to six carbon atoms and the phenyl ring is optionally substituted with alkyl of one to six carbon atoms, haloalkyl of one to six carbon atoms, alkoxy of one to six carbon atoms, hydroxy, or halogen, (i) cycloalkyl of three to eight carbon atoms, and (j) thiophenyl where the phenyl ring is optionally substituted with alkyl of one to six carbon atoms, haloalkyl of one to six carbon atoms, alkoxy of one to six carbon atoms, hydroxy, or halogen. $R^{14}$ and $R^{15}$ are independently selected from the group consisting of (a) hydrogen, (b) alkyl of one to six carbon atoms, (c) alkenyl of two to six carbon atoms, (d) halogen, (e) cyano, (f) carboxyl, (g) alkoxycarbonyl of from two to six carbon atoms, (h) aminocarbonyl, (i) alkylaminocarbonyl of one to six carbon atoms, (j) dialkylaminocarbonyl in which the alkyl groups are independently one to six carbon atoms, (k) alkanoyl, (l) hydroxyalkyl, (m) haloalkyl, (n) alkoxy of one to six carbon atoms, (o) alkylthio of one to six carbon atoms, (p) alkylsulfinyl of one to six carbon atoms, (q) alkylsulfonyl of one to six carbon atoms, (r) amino, (s) alkonylamino, and (t) nitro, or $R^{14}$ and $R^{15}$, together with the carbon atoms to which they are attached define a phenyl ring or 5- to 7-membered cycloalkylene ring.

Compounds of the present invention may exhibit stereoisomerism by virtue of the presence of one or more asymmetric or chiral centers in the compounds. The present invention contemplates the various stereoisomers and mixtures thereof. Desired enantiomers are obtained by chiral synthesis from commercially available chiral starting materials by methods well known in the art, or may be obtained from mixtures of the enantiomers by resolution using known techniques.

In another aspect, the present invention provides pharmaceutical compositions useful for the treatment of PAF-mediated disorders comprising a therapeutically effective amount of a compound of formula I above in combination with a pharmaceutically acceptable carrier.

In another aspect, the present invention provides a method of inhibiting PAF activity by administering to a host mammal in need of such treatment an effective amount of a PAF-inhibiting compound having structure I above.

In yet another aspect of the present invention, there is provided a method of treating PAF-mediated disorders including asthma, shock, respiratory distress syndrome, acute inflammation, delayed cellular immunity, parturition, fetal lung maturation, and cellular differentiation by administering to a host mammal in need of such treatment a therapeutically effective amount of a compound of structure I above.

DETAILED DESCRIPTION OF THE INVENTION

Definitions of Terms

As used throughout this specification and the appended claims, the following terms have the meanings specified.

The term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "alkylamino" refers to a group having the structure —NHR' wherein R' is alkyl, as previously defined, Examples of alkylamino include methylamino, ethylamino, iso-propylamino and the like.

The term "alkylaminocarbonyl" refers to an alkylamino group, as previously defined, attached to the parent molecular moiety through a carbonyl group. Examples of alkylaminocarbonyl include methylamino-carbonyl, ethylaminocarbonyl, isopropylaminocarbonyl and the like.

The term "alkylthio" refers to an alkyl group, as defined above, attached to the parent molecular moiety through a sulfur atom and includes such examples as methylthio, ethylthio, propylthio, n-, sec- and tert-butylthio and the like.

The term "alkanoyl" represents an alkyl group, as defined above, attached to the parent molecular moiety through a carbonyl group. Alkanoyl groups are exemplified by formyl, acetyl, propionyl, butanoyl and the like.

The term "alkanoylamino" refers to an alkanoyl group, as previously defined, attached to the parent molecular moiety through a nitrogen atom. Examples of alkanoylamino include formamido, acetamido, and the like.

The term "N-alkanoyl-N-alkylamino" refers to an alkanoyl group, as previously defined, attached to the parent molecular moiety through an aminoalkyl group. Examples of N-alkanoyl-N-alkylamino include N-methylformamido, N-methyl-acetamido, and the like.

The terms "alkoxy" or "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxyalkoxyl" refers to an alkyl group, as defined above, attached through an oxygen to an alkyl group, as defined above, attached in turn through an oxygen to the parent molecular moiety. Examples of alkoxyalkoxyl include methoxymethoxyl, methoxyethyoxyl, ethoxyethoxyl and the like.

The term "alkoxyalkyl" refers to an alkoxy group, as defined above, attached through an alkylene group to the parent molecular moiety.

The term "alkoxycarbonyl" represents an ester group; i.e. an alkoxy group, attached to the parent molecular moiety through a carbonyl group such as methoxycarbonyl, ethoxycarbonyl, and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenylene" denotes a divalent group derived from a straight or branched chain hydrocarbon containing at least one carbon-carbon double bond. Examples of alkenylene include —CH=CH—, —CH$_2$CH=CH—, —C(CH$_3$)=CH—, —CH$_2$CH=CHCH$_2$—, and the like.

The term "alkynylene" refers to a divalent group derived by the removal of two hydrogen atoms from a straight or branched chain acyclic hydrocarbon group containing a carbon-carbon triple bond. Examples of alkynylene include —CH≡CH—, —CH≡CH—CH$_2$, —CH≡CH—CH(CH$_3$)—, and the like.

The term "aryl" is used herein to mean substituted and unsubstituted aromatic carbocyclic radicals and substituted and unsubstituted heterocyclic aromatic radicals including, but not limited to, phenyl, 1-naphthyl or 2-naphthyl, fluorenyl, pyridyl, quinolyl, thienyl, thiazolyl, pyrimidyl, indolyl, and the like.

The term "heterocyclic aromatic" is used herein to refer to 5- and 6-membered aromatic rings having in the ring one, two, or three heteroatoms selected from N, O, ans S, and also including benzo fused analogs of these 5- and 6-membered heterocyclic aromatic rings including, but not limited to pyridyl, quinolyl, furyl, benzofuryl, thienyl, thiazolyl, pyrimidyl, indolyl, and the like.

The term "cycloalkyl" denotes a monovalent group derived from a monocyclic or bicyclic saturated carbocyclic ring compound by the removal of a single hydrogen atom. Examples include cyclopropyl, cyclobutyl, cyclopentyl, cyclohexyl, bicyclo[2.2.1]heptanyl, and bicyclo[2.2.2]octanyl.

The term "cycloalkylene" refers to a divalent group derived from a saturated is carbocyclic hydrocarbon by the removal of two hydrogen atoms, for example cyclopentylene, cyclohexylene, and the like.

The term "carbocyclic aryl" denotes a monovalent carbocyclic ring group derived by the removal of a single hydrogen atom from a monocyclic or bicyclic fused or non-fused ting system obeying the "4n+2p electron" or Huckel aromaticity rule. Examples of carbocyclic aryl groups include phenyl, 1- and 2-naphthyl, biphenylyl, fluorenyl, and the like.

The term "(carbocyclic aryl)alkyl" refers to a carbocyclic aryl ring group as defined above, attached to the parent molecular moiety through an alkylene group. Representative (carbocyclic aryl)alkyl groups include phenylmethyl, phenylethyl, phenylpropyl, 1-naphthylmethyl, and the like.

The term "carbocyclic aryloxyalkyl" refers to a carbocyclic aryl group, as defined above, attached to the parent molecular moiety through an oxygen atom and thence through an alkylene group. Such groups are exemplified by phenoxymethyl, 1- and 2-naphthyloxymethyl, phenoxyethyl and the like.

The term "(carbocyclic aryl)alkoxyalkyl" denotes a carbocyclic aryl group as defined above, attached to the parent molecular moiety through an alkoxyalkyl group. Representative (carbocyclic aryl)alkoxyalkyl groups include phenylmethoxymethyl, phenylethoxymethyl, 1- and 2-naphthylmethoxyethyl, and the like.

"Carbocyclic arylthioalkyl" represents a carbocyclic aryl group as defined above, attached to the parent molecular moeity through a sulfur atom and thence through an alklyene group and are typified by phenylthiomethyl, 1- and 2-naphthylthioethyl and the like.

The term "dialkylamino" refers to a group having the structure —NR'R" wherein R' and R" are independently selected from alkyl, as previously defined. Additionally, R' and R" taken together may optionally be —(CH$_2$)$_{kk}$— where kk is an integer of from 2 to 6. Examples of dialkylamino include, dimethylamino, diethylaminocarbonyl, methylethylamino, piperidino, and the like.

The term "haloalkyl" denotes an alkyl group, as defined above, having one, two, or three halogen atoms attached thereto and is exemplified by such groups as chloromethyl, bromoethyl, trifluoromethyl, and the like.

The term "hydroxyalkyl" represents an alkyl group, as defined above, substituted by one to three hydroxyl groups with the proviso that no more than one hydroxy group may be attached to a single carbon atom of the alkyl group.

The term "phenoxy" refers to a phenyl group attached to the parent molecular moiety through an oxygen atom.

The term "phenylthio" refers to a phenyl group attached to the parent molecular moiety through a sulfur atom.

The term "pyridyloxy" refers to a pyridyl group attached to the parent molecular moiety through an oxygen atom.

The term "metabolically cleavable group" denotes a group which is cleaved in vivo to yield the parent molecule of the structural formulae indicated above wherin M is hydrogen. Examples of metabolically clearable groups include —COR, —COOR, —CONRR and —CH$_2$OR radicals where R is selected independently at each occurrence from alkyl, trialkylsilyl, carbocyclic aryl or carbocyclic aryl substituted with one or more of C$_1$–C$_4$alkyl, halogen, hydroxy or C$_1$–C$_4$alkoxy. Specific examples of representative metabolically clearable groups include acetyl, methoxycarbonyl, benzoyl, methoxymethyl and trimethylsilyl groups.

By "pharmaceutically acceptable salt" it is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M Berge, et al. describe pharmaceutically acceptable salts in detail in *J. Pharmaceutical Sciences*, 1977, 66: 1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The terms "PAF-related disorders" and "PAF-mediated disorders" are used herein to mean disorders related to PAF or mediated by PAF, including asthma, shock, respiratory distress syndromes, acute inflammation, gastric ulceration, transplant organ rejection, psoriasis, allergic skin disease, ischemia and reperfusion injury, delayed cellular immunity, parturition, fetal lung maturation, and cellular differentiation.

Preferred Embodiments

In one preferred embodiment, the compounds of this invention are represented by formula I wherein $R^3$ is hydrogen; $L^1$ is >C=O or —SO$_2$—; $R^1$ is one or more groups indpendently selected from the group consisting of (a) hydrogen, (b) halogen, (c) alkyl of one to six carbon atoms, (d) alkynyl of two to four carbon atoms, (e) alkoxy of one to six carbon atoms, (f) —COOR$^6$ where $R^6$ is hydrogen or alkyl of one to six carbon atoms, (g) phenyl, optionally substituted with alkyl of one to six carbon atoms, alkoxy of one to six carbon atoms, or halogen, (h) phenylalkyl where the alkyl portion contains one to six carbon atoms and the phenyl moiety is optionally substituted with alkyl of one to six carbon atoms, alkoxy of one to six carbon atoms, or halogen, (i) phenoxy optionally substituted with halogen, alkyl of one to six carbon atoms, or alkoxy of one to six carbon atoms, and (j) —OC(O)NR$^4$R$^5$; $L^2$ is a valence bond or methylene;

Ar$^1$ is

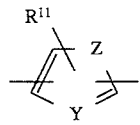

wherein Y is O, S, or —CH=CH—, Z is N or CH, and $R^{11}$; and Ar$^2$ is selected from the group consisting of

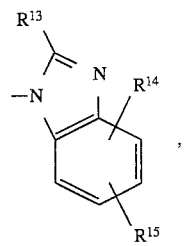

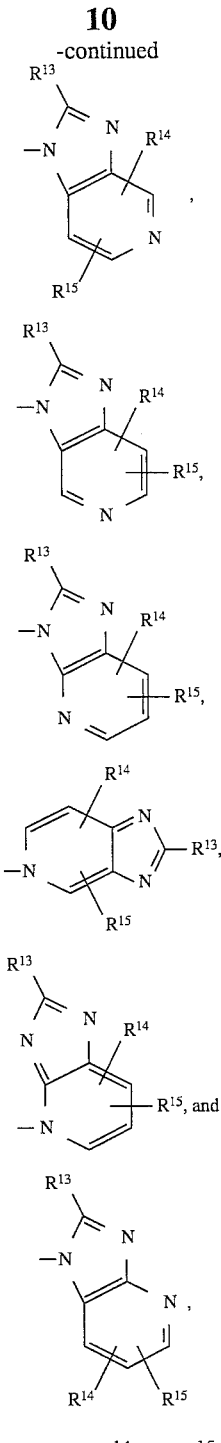

wherein $R^{13}$ is methyl and $R^{14}$ and $R^{15}$ are hydrogen.

In another preferred embodiment, the compounds of this invention are represented by formula I wherein Ar$^1$ is a valence bond and $L^2$ is straight-chain alkylene of one to six carbon atoms.

In another preferred embodiment, the compounds of this invention are represented by formula I wherein $R^1$ is hydrogen, —COOR$^6$ where $R^6$ is hydrogen or alkyl of one to six carbon atoms, 4-fluorophenyl, phenylmethyl, or 4-fluorophenoxy; $R^2$ is N,N-dimethylcarbamoyl or 2-ethoxyethyl; $L^1$ is >C=O or —SO$_2$—; Ar$^1$ is a valence bond, and $L^2$ is straight-chain alkylene of one to six carbon atoms.

In the most preferred embodiment the compounds of this invention are represented by formula I wherein $R^1$ is selected from the group consisting of hydrogen, —COOR$^6$ where $R^6$ is hydrogen or alkyl of one to six carbon atoms, alkynyl of two to four carbon atoms, 4-fluorophenyl, phenylmethyl, or 4-fluorophenoxy; $R^2$ is N,N-dimethylcarbamoyl or 2-ethoxyethyl; $L^1$ is >C=O or —$SO_2$—; $Ar^1$ is phenyl or phenyl substituted with alkyl of one to six carbon atoms, alkoxy of one to six carbon atoms, or halogen, $L^2$ is methylene; and $R^3$ and $Ar^2$ are defined immediately above.

Compounds contemplated as falling within the scope of this invention include, but are not limited to:

6-(4-fluorophenyl)-3-{4-[(1H-2-methylbenzimidazolyl)methyl] benzoyl)}indole,
1-N,N-dimethylcarbamoyl-6-(4-fluorophenyl)-3-{4-[(1H-2-methylbenzimidazolyl)methyl]benzoyl}indole,
6-(4-fluorophenyl)-3-{4-[(1H-2-methylimidazo[4.5-c]pyrid-1-yl)methyl]benzoyl}indole,
1-N,N-dimethylcarbamoyl-6-(4-fluorophenyl)-3-{4-[ (1H-2-methylimidazo[4.5-c] pyrid-1-yl)methyl] benzoyl}indole,
1-N,N-dimethylcarbamoyl-6-(4-fluorophenyl)-3-{4-[(1H-2-methylimidazo[4.5 -c]pyrid-1-yl)methyl]benzoyl}indole hydrochloride,
6-(4-fluorophenyl)-3-{4-[(3H-2-methylimidazo[ 4.5-c]pyrid-3-yl)methyl] benzoyl}indole,
1-N,N-dimethylcarbamoyl-6-(4-fluorophenyl)-3-{4-[(3H-2-methylimidazo[4.5 -c]pyrid-3-yl)methyl]benzoyl}indole,
1-N,N-dimethylcarbamoyl-6-(4-fluorophenyl)-3-[4-(5H-2-methylimidazo[4.5-c]pyrid-5-ylmethyl)benzoyl]indole,
6-(4-fluorophenyl)-3-[4-(1H-2-methylimidazo[4.5-c]pyridyl)benzoyl]indole,
1-N,N-dimethylcarbamoyl-6-(4-fluorophenyl)-3-[4-(1H-2-methylimidazo[4.5-c]pyrid-1-yl)benzoyl]indole,
6-(4-fluorophenyl)-3-{3-[(1H-2-methylimidazo[4.5-c]pyridyl)methyl]benzoyl}indole,
1-N,N-dimethylcarbamoyl-6-(4-fluorophenyl)-3-{3-[(1H-2-methylimidazo[4.5-c]pyridyl)methyl]benzoyl}indole,
3-4-[(1H-2-methylimidazo[4.5-c]pyrid-1-yl)methyl] benzoyl}indole,
1-N,N-dimethylcarbamoyl-3-{4-[(1H-2-methylimidazo [4.5-c] pyridyl)methyl]benzoyl}indole,
3-[4-(5H-2-methylimidazo[4.5-c]pyrid-5-ylmethyl)benzoyl]indole,
1-N,N-dimethylcarbamoyl-3-[4-(5H-2-methylimidazo[4.5-c]pyrid-5 -ylmethyl)benzoyl]indole,
3-{3-[(1H-2-methylimidazo[4.5-c]pyridyl)methyl] benzoyl}indole,
1-N,N-dimethylcarbamoyl-3-{3-[(1H-2-methylimidazo [4.5-c]pyrid-1 -yl)methyl]benzoyl}indole,
3-{3-[(3H-2-methylimidazo[4.5-c]pyridyl)methyl] benzoyl}indole,
1-N,N-dimethylcarbamoyl-3-{3-[(3H-2-methylimidazo [4.5-c]pyridyl)methyl]benzoyl}indole,
3-{4-[(1H-2-methylimidazo[4.5-c]pyrid-1-yl)] benzoyl}indole,
1-N,N-dimethylcarbamoyl-3-{4-[(1H-2-methylimidazo [4.5-c]pyrid-1 -yl)benzoyl}indole,
1-N,N-dimethylcarbamoyl-6-(4-fluorophenyl)-3-[(3H-2-methylimidazo[4.5-c]pyrid-3-yl)methylcarbonyl]indole,
1-N,N-dimethylcarbamoyl-6-(4-fluorophenyl)-3-[(1H-2-methylimidazo[4.5-c]pyrid-1-yl)methylcarbonyl]indole,
1-N,N-dimethylcarbamoyl-3-[(3H-2-methylimidazo[4.5-c] pyrid-3 -yl)methylcarbonyl]indole,
1-N,N-dimethylcarbamoyl-3-[(1H-2-methylimidazo[4.5-c] pyrid-1 -yl)methylcarbonyl]indole,
1-N,N-dimethylcarbamoyl-3-{4-[(3H-2-methylimidazo [4.5-b]pyrid-3-yl)methyl]benzoyl}indole,
1-N,N-dimethylcarbamoyl-3-{4-[(1H-2-methylimidazo [4.5-b]pyrid-1-yl)methyl]benzoyl}indole,
1-N,N-dimethylcarbamoyl-3-{4-[1H-2-trifluoromethylimidazo[4.5-c]pyrid-1-yl)methyl]benzoyl}indole,
1-N,N-dimethylcarbamoyl-3-{4-[1H-imidazo[4.5-c]pyrid-1-yl)methyl]benzoyl}indole,
1-N,N-dimethylcarbamoyl-3-{4-[1H-2-(2-propyl)imidazo [4.5-c]pyrid-1-yl)methyl]benzoyl}indole,
1-N,N-dimethylcarbamoyl-3-{4-[1H-2-phenylimidazo[4.5-c]pyrid-1-yl)methyl]benzoyl}indole,
1-N,N-dimethylcarbamoyl-3-{4-[1H-2-ethylimidazo[4.5-c] pyrid-1 -yl)methyl]benzoyl}indole,
3-{3-[(5H-2-methylimidazo[4.5-c]pyrid-5-yl)methyl] benzoyl}indole,
1-N,N-dimethylcarbamoyl-3-{3-[(5H-2-methylimidazo [4.5-c] pyrid-5-yl)methyl]benzoyl}indole,
1-p-toluenesulfonyl-6-(4-fluorophenyl)-3-{4-[ (1H-2-methylimidazo[4.5-c]pyridyl)methyl]benzoyl}indole,
1-N,N-dimethylcarbamoyl-6-(4-fluorophenyl)-3-[(3H-2-methylimidazo[4.5-c]pyrid-3-yl)pent-5-ylcarbonyl]indole,
1-N,N-dimethylcarbamoyl-6-(4-fluorophenyl)-3-[(1H-2-methylimidazo[4.5-c]pyrid-1-yl)pent-5-ylcarbonyl]indole,
1-N,N-dimethylcarbamoyl-6-(4-fluorophenyl)-3-[(5H-2-methylimidazo[4.5-c]pyrid-5-yl)pent-5-ylcarbonyl]indole,
1-N,N-dimethylcarbamoyl-6-(4-fluorophenoxy)-3-{4-[(3H-2-methylimidazo[4.5-c]pyrid-3-yl)methyl] benzoyl}indole,
1-N,N-dimethylcarbamoyl-6-(4-fluorophenoxy)-3-{4-(1H-2-methylimidazo[4.5-c]pyrid-1-yl)methyl] benzoyl}indole,
1-N,N-dimethylcarbamoyl-5-phenylmethoxy-3-{4-[(1H-2-methylimidazo[4.5-c]pyrid-1-yl)methyl]benzoyl}indole,
1-N,N-dimethylcarbamoyl-6-(4-methoxyphenyl)-3-{4-[(1H-2-methylimidazo[4.5-c]pyrid-1-yl)methyl] benzoyl}indole,
1-N,N-dimethylcarbamoyl-6-(pyrid-3-yl)-3-{4-[(1H-2 -methylimidazo[4.5-c]pyrid-1-yl)methyl]benzoyl}indole,
1-N,N-dimethylcarbamoyl-6-bromo-3-{4-[(1H-2-methylimidazo[4.5-c]pyrid-1 -yl)methyl]benzoyl}indole,
1-N,N-dimethylcarbamoyl-6-chloro-3-{4-[(1H-2-methylimidazo[ 4.5-c]pyrid-1-yl)methyl]benzoyl}indole,
1-N,N-dimethylcarbamoyl-5-methoxy-3-{4-[(1H-2-methylimidazo[4.5-c]pyrid-1 -yl)methyl]benzoyl}indole,
1-N,N-dimethylcarbamoyl-6-(4-fluorophenyl)-3-{4-[(1H-2-methylimidazo[4.5-c]pyrid-1-yl)methyl] benzoyloxime}indole,
1-N,N-dimethylcarbamoyl-6-(4-fluorophenyl)-3-{4-[(1H-2-methylimidazo[4.5 -c]pyrid-1-yl)methyl] benzoylhydrazone}indole,
1-methyl-6-(4-fluorophenyl)-3-{4-[(1H-2-methylimidazo [4.5-c]pyrid-1 -yl)methyl]benzoyl}indole,
1-tert-butyloxycarbonyl-6-(4-fluorophenyl)-3-{4-[(1H-2-methylimidazo[4.5-c]pyrid-1-yl)methyl]benzoyl}indole,
1-methoxycarbonyl-6-(4-fluorophenyl)-3-{4-[(1H-2-methylimidazo[ 4.5-c]pyrid-1-yl)methyl]benzoyl}indole,
1-phenoxycarbonyl-6-(4-fluorophenyl)-3-(4-[( 1 H-2-methylimidazo[4.5-c] pyrid-1-yl)methyl]benzoyl}indole,
1-carbamoyl-6-(4-fluorophenyl)-3-{4-[(1-H-2 -methylimidazo[4.5-c]pyrid-1-yl)methyl]benzoyl{indole,
1-N-methylcarbamoyl-6-(4-fluorophenyl)-3-{4-[(1H-2-methylimidazo[ 4.5-c]pyrid-1-yl)methyl]benzoyl}indole,
1-N-phenyl-N-methylcarbamoyl-6-(4-fluorophenyl)-3-{4-[(1H-2-methylimidazo[4.5-c]pyrid-1-yl)methyl] benzoyl}indole,
1-(N-methyl-N-(dimethylaminoethyl))carbamoyl-6-(4-fluorophenyl)-3-{4-[(1H-2-methylimidazo[4.5-c]pyrid-1-yl)methyl]benzoyl}indole,
1-N-(2-hydroxyethyl)carbamoyl-6-(4-fluorophenyl)-3-{4-[ (1H-2-methylimidazo[4.5-c]pyrid-1-yl)methyl] benzoyl}indole, 1-hydrazinocarbonyl-6-(4-fluorophenyl)-3-{4-[(1H-2-methylimidazo[4.5-c]pyrid-1-yl)methyl]benzoyl}indole,
1-N-carboxymethylcarbamoyl-6-(4-fluorophenyl)-3-{4-[(1H-2-methylimidazo[4.5-c]pyrid-1-yl)methyl]benzoyl}indole,
1-N-(2-(imidazol-4-yl)ethyl)carbamoyl-6-(4-fluorophenyl)-3-{4-[(1H-2-methylimidazo[4.5-c]pyrid-1-yl)methyl]benzoyl}indole,
1-(2-hydroxyethyl)-6-(4-fluorophenyl)-3-{4-[(1H-2-methylimidazo[4.5-c]pyrid-1-yl)methyl]benzoyl}indole,
1-(2-aminoethyl)-6-(4-fluorophenyl)-3-{4-[(1H-2-methylimidazo[4.5-c]pyrid-1-yl)methyl]benzoyl}indole,
1-(2-methanesulfonylaminoethyl)-6-(4-fluorophenyl)-3-{4-[(1H-2-methylimidazo[4.5-c]pyrid-1-yl)methyl]benzoyl}indole,
1-(2-sulfamylethyl)-6-(4-fluorophenyl)-3-{4-[(1H-2-methylimidazo[4.5-c]pyrid-1-yl)methyl]benzoyl}indole,
1-(2-carbomethoxyethyl)-6-(4-fluorophenyl)-3-{4-[(1H-2-methylimidazo[4.5-c]pyrid-1-yl)methyl]benzoyl}indole,
1-(2-carboethoxyethyl)-6-(4-fluorophenyl)-3-{4-[(1H-2-methylimidazo[4.5-c]pyrid-1-yl)methyl]benzoyl}indole,
1-(2-carboxyethyl)-6-(4-fluorophenyl)-3-{4-[(1H-2-methylimidazo[4.5-c]pyrid-1-yl)methyl]benzoyl}indole,
1-(2-tert-butoxycarbonylaminoethyl)-6-(4-fluorophenyl)-3-{4-[(1H-2-methylimidazo[4.5-c]pyrid-1-yl)methyl]benzoyl}indole,
1-cyanomethyl-6-(4-fluorophenyl)-3-{4-[(1H-2-methylimidazo[4.5-c]pyrid-1-yl)methyl]benzoyl}indole,
1-carboxymethyl-6-(4-fluorophenyl)-3-{4-[(1H-2-methylimidazo[4.5-c]pyrid-1-yl)methyl]benzoyl}indole,
1-N-methylcarbamoylmethyl-6-(4-fluorophenyl)-3-{4-[(1H-2-methylimidazo[4.5-c]pyrid-1-yl)methyl]benzoyl}indole,
1-(1H-tetrazol-5-ylmethyl)-6-(4-fluorophenyl)-3-{4-[(1H-2-methylimidazo[4.5-c]pyrid-1-yl)methyl]benzoyl}indole,
1-methanesulfonyl-6-(4-fluorophenyl)-3-{4-[(1H-2-methylimidazo[4.5-c]pyrid-1-yl)methyl]benzoyl}indole,
1-ethanesulfonyl-6-(4-fluorophenyl)-3-{4-[(1H-2-methylimidazo[4.5-c]pyrid-1-yl)methyl]benzoyl}indole,
1-phenylsulfonyl-6-(4-fluorophenyl)-3-{4-[(1H-2-methylimidazo[4.5-c]pyrid-1-yl)methyl]benzoyl}indole,
1-N,N-dimethylsulfamyl-6-(4-fluorophenyl)-3-{4-[(1H-2-methylimidazo[4.5-c]pyrid-1-yl)methyl]benzoyl}indole,
1-N,N-dimethylcarbamoyl-6-phenylmethyl-3-{4-[(3H-2-methylimidazo[4.5-c]pyrid-3-yl)methyl]benzoyl}indole,
1-N,N-dimethylcarbamoyl-6-phenylmethyl-3-{4-[(1H-2-methylimidazo[4.5-c]pyrid-1-yl)methyl]benzoyl}indole,
1-N,N-dimethylcarbamoyl-4-methoxycarbonyl-3-{4-[(3H-2-methylimidazo[4.5-c]pyrid-3-yl)methyl]benzoyl}indole,
1-N,N-dimethylcarbamoyl-4-methoxycarbonyl-3-{4-[(1H-2-methylimidazo[4.5-c]pyrid-1-yl)methyl]benzoyl}indole,
1-N,N-dimethylcarbamoyl-3-{4-[(1H-2-methylimidazo[4.5-c]pyrid-1-yl)methyl]phenylsulfonyl}indole,
1-(morpholin-4-ylcarbonyl)-6-(4-fluorophenyl)-3-{4-[(1H-2-methylimidazo[4.5-c]pyrid-1-yl)methyl]benzoyl}indole,
1-(N,N-dimethylcarbamoylmethyl)-6-(4-fluorophenyl)-3-{4-[(1H-2-methylimidazo[4.5-c]pyridyl)methyl]benzoyl}indole,
1-N,N-dimethylcarbamoyl-6-(4-fluorophenyl)-3-{5-[(1H-2-methylimidazo[4.5-c]pyrid-1-yl)methyl]thien-2-oyl}indole,
1-N,N-dimethylcarbamoyl-6-(4-fluorophenyl)-3-{5-[(1H-2-methylimidazo[4.5-c]pyrid-1-yl)methyl]fur-2-oyl}indole,
1-N,N-dimethylcarbamoyl-6-(4-fluorophenyl)-3-{4-[(3H-2-methylimidazo[4.5-c]pyrid-3-yl)methyl]thiazo-2-oyl}indole,
1-N,N-dimethylcarbamoyl-6-(4-fluorophenyl)-3-{4-[(1H-2-methylimidazo[4.5-c]pyrid-1-yl)methyl]thiazo-2-oyl}indole,
1-methyl-3-{4-[(1H-2-methylimidazol4.5-c]pyrid-1-yl)methyl]phenylsulfonylamino}indole,
4,7-dimethoxycarbonyl-3-{4-[(1H-2-methylimidazo[4,5-c]pyrid-1-yl)methyl]benzoyl}indole,
4,7-dimethyl-3-{4-[(1H-2-methylimidazo[4,5-c]pyrid-1-yl)methyl]benzoyl}indole,
4,7-dimethyl-3-{4-[(3H-2-methylimidazo[4,5-c]pyrid-3-yl)methyl]benzoyl}indole,
7-benzyloxy-3-{4-[(1H-2-methylimidazo[4,5-c]pyrid-1-yl)methyl]benzoyl}indole,
7-(4-fluorophenyl)-3-{4-[(1H-2-methylimidazo[4,5-c]pyrid-1-yl)methyl]benzoyl}indole,
6-(4-fluorophenyl)-3-{N-[3-(1H-2-methylimidazo[4.5-c]pyrid-1-yl)propyl]sarcosyl}indole-1-carboxylic acid dimethyl amide,
1-N,N-dimethylcarbamoyl-4-methoxycarbonyl-3-{3-fluoro-4-[(1H-2-methylimidazo[4,5-c]pyrid-1-yl)methyl]benzoyl}indole,
1-N,N-dimethylcarbamoyl-6-benzyloxy-3-{3-fluoro-4-[(1H-2-methylimidazo-[4,5-c]pyrid-1-yl)methyl]benzoyl}indole,
1-N,N-dimethylcarbamoyl-4-methoxycarbonyl-3-{5-[(1H-2-methylimidazo[4,5-c]pyrid-1-yl)methyl]thien-2-oyl}indole,
1-N,N-dimethylcarbamoyl-6-(4-fluorophenyl)-3-{4-[(1H-2-methylimidazo[4.5-c]pyrid-1-yl)methyl]phenylaminocarbonyl}indole hydrochloride,
1-N,N-dimethylcarbamoyl-5-(4-fluorophenyl)-3-{4-[(1H-2-methylimidazo[4.5-c]pyrid-1-yl)methyl]benzoyl}indole,
1-N,N-dimethylcarbamoyl-6-(4-fluorophenyl)3-{4-[(1H-2-methylimidazo[4.5-c]pyrid-1-yl)methyl]phenylsulfonyl}indole,
1-N,N-dimethylcarbamoyl-4-bromo-3-{4-[(1H-2-methylimidazo[4.5-c]pyrid-1-yl)methyl]benzoyl}indole,
1-N,N-dimethylcarbamoyl-4-acetyl-3-{4-[(1H-2-methylimidazo[4.5-c]pyrid-1-yl)methyl]benzoyl}indole,
1-N,N-dimethylcarbamoyl-4-(fur-2-yl)-3-{4-[(1H-2-methylimidazo[4.5-c]pyrid-1-yl)methyl]benzoyl}indole,
1-N,N-dimethylcarbamoyl-4-(benzo[b]fur-2-yl)-3-{4-[(1H-2-methylimidazo[4.5-c]pyrid-1-yl)methyl]benzoyl}indole,
1-N,N-dimethylcarbamoyl-4-(trimethylsilylethynyl)-3-{4-[(1H-2-methylimidazo[4.5-c]pyrid-1-yl)methyl]benzoyl}indole,
1-N,N-dimethylcarbamoyl-4-ethynyl-3-{4-[(1H-2-methylimidazo[4.5-c]pyrid-1-yl)methyl]benzoyl}indole,
4-(4-fluorophenyl)-3-{4-[(1H-2-methylimidazo[4.5-c]pyrid-1-yl)methyl]benzoyl}indole,
1-N,N-dimethylcarbamoyl-4-chloro-3-{4-[(1H-2-methylimidazo[4.5-c]pyrid-1-yl)methyl]benzoyl}indole,
1-N,N-dimethylcarbamoyl-4-fluoro-3-{4-[(1H-2-methylimidazo[4.5-c]pyrid-1-yl)methyl]benzoyl}indole,
1-N,N-dimethylcarbamoyl-2-methyl-3-{4-[(1H-2-methylimidazo[4.5-c]pyrid-1-yl)methyl]benzoyl}indole,
1,4-di-N,N-dimethylcarbamoyl-3-{4-[(1H-2-methylimidazo[4.5-c]pyrid-1-yl)methyl]benzoyl}indole,
1-N,N-dimethylcarbamoyl-5-methoxycarbonyl-3-{4-[(1H-2-methylimidazo[4.5-c]pyrid-1-yl)methyl]benzoyl}indole,
1-N,N-dimethylcarbamoyl-4-methoxycarbonyl-6-(4-fluorophenyl)-3-{4-[(1H-2-methylimidazo[4.5-c]pyrid-1-yl)methyl]benzoyl}indole, 4-methoxycarbonyl-3-{4-[(1H-2-methylimidazo[4.5-c]pyrid-1-yl)methyl]benzoyl}indole 4-methoxycarbonyl-1-(pyrrolidin-1-ylcarbonyl)-3-{4-[(1H-2-methylimidazo[4.5-c]pyrid-1-yl)methyl]benzoyl}indole, 1-N,N-dimethylcarbamoyl-4-benzyloxycarbonyl-3-{4-[(1H-2-methylimidazo[4.5-c]pyrid-1-yl)methyl]benzoyl}indole, 1-N,N-dimethylcarbamoyl-3-{4-[(1H-2-methylimidazo[4.5-c]pyrid-1-yl)methyl]benzoyl}indole-4-carboxylic acid, 1-N,N-dimethylcarbamoyl-4-(N-nonylcarbamoyl)-3-{4-[(1H-2-methylimidazo[4.5-c]pyrid-1-yl)methyl]benzoyl}indole, 1-N,N-dimethylcarbamoyl-4-(dec-1-yloxycarbonyl)-3-{4-[(1H-2-methylimidazo[4.5-c]pyrid-1-yl)methyl]benzoyl}indole, 1-N,N-dimethylcarbamoyl-4-methoxy-3-{4-[(1H-2-methylimidazo[4.5-c]pyrid-1-yl)methyl]benzoyl}indole, 1-N,N-dimethylcarbamoyl-4-methyl-3-{4-[(1H-2-methylimidazo[4.5-c]pyrid-1-yl)methyl]benzoyl}indole, 1-N,N-dimethylcarbamoyl-4-methoxycarbonyl-3-[(1H-2-methylimidazo[4.5-c]pyrid-1-yl)hex-6-ylcarbonyl]indole, 1-N,N-dimethylcarbamoyl-4-methoxycarbonyl-3-{4-[(1H-2-methylbenzimidazolyl)methyl]benzoyl}indole, 4-methoxycarbonyl-1-(pyrrolidin-1-ylcarbonyl)3-{4-[(1H-2-methylbenzimidazolyl)methyl]benzoyl}indole, 1-N,N-dimethylcarbamoyl-4-methoxycarbonyl-3-[(1H-2-methylimidazo[4.5-c]pyrid-1-yl)pent-5-ylcarbonyl]indole, 1-N,N-dimethylcarbamoylmethyl-4-methoxycarbonyl-3-[(1H-2-methylimidazo[4.5-c]pyrid-1-yl)pent-5-ylcarbonyl]indole, 1-N,N-dimethylcarbamoyl-4-methoxycarbonyl-3-[(1H-2-methylimidazo[4.5-c]pyrid-1-yl)pent-5-ylcarbonyl]indole, 1-N,N-dimethylcarbamoyl-4-methoxycarbonyl-3-{4-[(2-methyl-4-(3H)quinazolinone-3-yl)methyl]benzoyl}indole, 1-(2-ethoxyethyl)-4-methoxycarbonyl-3-{4-[(1H-2-methylimidazo[4.5-c]pyrid-1-yl)methyl]benzoyl}indole, 1-N,N-dimethylsulfamoyl-4-methoxycarbonyl-3-{4-[(1H-2-methylimidazo[4.5-c]pyrid-1-yl)methyl]benzoyl}indole, 1-N,N-dimethylsulfamoyl-4-methoxycarbonyl-3-{4-[(1H-2-methylimidazo[4.5-c]pyrid-1-yl)methyl]benzoyl}indole, 1-acetoxymethyl-4-methoxycarbonyl-3-{4-[(1H-2-methylimidazo[4.5-c]pyrid-1-yl)methyl]benzoyl}indole, 1-(2-propanesulfonyl)-4-methoxycarbonyl-3-{4-[(1H-2-methylimidazo[4.5-c]pyrid-1-yl)methyl]benzoyl}indole, 1-(1-pinacolyl)-4-methoxycarbonyl-3-{4-[(1H-2-methylimidazo[4.5-c]pyrid-1-yl)methyl]benzoyl}indole, 1-carbamoyl-4-methoxycarbonyl-3-{4-[(1H-2-methylimidazo[4.5-c]pyrid-1yl)methyl]benzoyl}indole, 1-N-methylcarbamoyl-4-methoxycarbonyl-3-{4-[(1H-2-methylimidazo[4.5-c]pyrid-1-yl)methyl]benzoyl}indole, 1-(2-ethoxyethyl)-4-chloro-3-{4-[(1H-2-methylimidazo[4.5-c]pyrid-1-yl)methyl]benzoyl}indole, 1-N,N-dimethylcarbamoyl-4-methoxycarbonyl-3-{3-methoxy-4-[(1H-2-methylimidazo[4.5-c]pyrid-1-yl)methyl]benzoyl}indole, 1-N,N-dimethylcarbamoyl-4-methoxycarbonyl-3-{3-methoxy-4-[(3H-2-methylimidazo[4.5-c]pyrid-3-yl)methyl]benzoyl}indole, 1-N,N-dimethylcarbamoyl-4-methoxycarbonyl-3-{4-[(1H-2-methylimidazo[4.5-c]pyrid-1-yl)methyl]phenylsulfonyl}indole, 1-N,N-dimethylcarbamoyl-4-methoxycarbonyl-3-{4-[(1H-2-methylimidazo[4.5-c]pyrid-1-yl)methyl]phenylsulfonyl}indole, 1-N,N-dimethylcarbamoyl-4-ethynyl-3-{4-[(1H-2-methylimidazo[4.5-c]pyrid-1-yl)methyl]benzoyl}indole, 1-N,N-dimethylcarbamoyl-4-hydroxy-3-{4-[(1H-2-methylimidazo[4.5-c]pyrid-1-yl)methyl]benzoyl}indole, 1-N,N-dimethylcarbamoyl-6-bromo-4-methoxycarbonyl-3-{4-[(1H-2-methylimidazo[4.5-c]pyrid-1-yl)methyl]benzoyl}indole, 1-N,N-dimethylcarbamoyl-6-(benzo[b]fur-2-yl)-4-methoxycarbonyl-3-{4-[(1H-2-methylimidazo[4.5-c]pyrid-1-yl)methyl]benzoyl}indole, 1-N,N-dimethylcarbamoyl-6-(fur-2-yl)-4-methoxycarbonyl-3-{4-[(1H-2-methylimidazo[4.5-c]pyrid-1-yl)methyl]benzoyl}indole, 1-N,N-dimethylcarbamoyl-4-(N,N-dimethylaminocarbonyloxy)-3-{4-[(1H-2-methylimidazo[4.5-c]pyrid-1-yl)methyl]benzoyl}indole, 1-N,N-dimethylcarbamoyl-4-(N,N-dimethylaminocarbonylamino)-3-{4-[(1H-2-methylimidazo[4.5-c]pyrid-1-yl)methyl]benzoyl}indole, 1-N,N-dimethylcarbamoyl-4-cyano-3-{4-[(1H-2-methylimidazo[4.5-c]pyrid-1yl)methyl]benzoyl}indole hydrochloride, -N,N-dimethylcarbamoyl-4-methoxycarbonyl-3-{4-[(1H-2-methylimidazo[4.5-c]pyrid-1-yl)methyl]benzyl}indole, 1-N,N-dimethylcarbamoyl-4-chloro-3-{4-[(1H-2-methylimidazo[4.5-b]pyrid-1-yl)methyl]benzoyl}indole, 1-N,N-dimethylcarbamoyl-4-methoxycarbonyl-3-{4-[(3H-2-methylimidazo[4.5-b]pyrid-3-yl)methyl]benzoyl}indole, 1-N,N-dimethylcarbamoyl-4-methoxycarbonyl-3-{4-[(1H-2-methylimidazo[4.5-b]pyrid-1-yl)methyl]benzoyl}indole, 1-N,N-dimethylcarbamoyl-4-methoxycarbonyl-3-{4-[(5H-2-methylimidazo[4.5-c]pyrid-5-yl)methyl]benzoyl}indole, 1-N,N-dimethylcarbamoyl-4-methoxycarbonyl-3-{4-[1-(1H-2-methylimidazo[4.5-c]pyrid-1-yl)eth-1-yl]benzoyl}indole, 1-N,N-dimethylcarbamoyl-4-methoxycarbonyl-3-{4-[1-(1H-imidazo[4.5-c]pyrid-1-yl)eth-1-yl]benzoyl}indole, 1-N,N-dimethylcarbamoyl-4-methoxycarbonyl-3-{4-[(1H-2-methyl-5-, and 6-chlorobenzimidazolyl)methyl]benzoyl}indole, 1-N,N-dimethylcarbamoyl-4-chloro-3-{4-[(1H-2-methyl-5-, and 6-chlorobenzimidazolyl)methyl]benzoyl}indole, 1-(2-ethoxyethyl)-4-methoxycarbonyl-3-{4-[(1H-2-methyl-5-, and 6-chlorobenzimidazolyl)methyl]benzoyl}indole, 1-(pyrrolidin-1-ylcarbonyl)-4-methoxycarbonyl-3-{4-[(1H-2-methyl-5-, and 6-chlorobenzimidazolyl)methyl]benzoyl}indole, 1-N,N-dimethylcarbamoyl-4-methoxycarbonyl-3-{4-[(1H-2-(trifluoromethyl)benzimidazolyl)methyl]benzoyl}indole, 1-N,N-dimethylcarbamoyl-4-methoxycarbonyl-3-{4-[(1H-2-methyl-5- and 6-methylbenzimidazolyl)methyl]benzoyl}indole, 1-N,N-dimethylcarbamoyl-4-methoxycarbonyl-3-{4-[(1H-2-methyl-4- and 7-methylbenzimidazolyl)methyl]benzoyl}indole, 1-N,N-dimethylcarbamoyl-4-methoxycarbonyl-3-{4-[(1H-2-methyl-5- and 6-methylbenzimidazolyl)methyl]benzoyl}indole, 1-N,N-dimethylcarbamoyl-4-methoxycarbonyl-3-{4-[(1H-2-methyl-5- and 6-methylbenzimidazolyl)methyl]benzoyl}indole, 1-N,N-dimethylcarbamoyl-4-methoxycarbonyl-3-{4-[(1H-2-methyl-5,6-dichlorobenzimidazolyl)methyl]benzoyl}indole, 1-N,N-dimethylcarbamoyl-4-methoxycarbonyl-3-{4-[(1H-2-methyl-5- and 6-methoxycarbonylbenzimidazolyl)methyl]benzoyl}indole, 1-(pyrrolidin-1-ylcarbonyl)-4-methoxycarbonyl-3-{4-[(1H-2-methyl-5- and 6-methoxycarbonylbenzimidazolyl)methyl]benzoyl}indole, 1-(pyrrolidin-1-ylcarbonyl)-4-methoxycarbonyl-3-{4-[(1H-2-methyl-5- and 6-methylbenzimidazolyl)methyl]benzoyl}indole, 1-N,N-dimethylcarbamoyl-4-methoxycarbonyl-3-{ 4-[(3H-2, 4, 6-trimethylimidazo[4.5-c ]pyrid-3-yl)methyl]benzoyl}indole, 1-(pyrrolidin-1-ylcarbonyl)-4-methoxycarbonyl-3-{4-[(1H-5-trifluoromethyl- 2-methylmethylbenzimidazolyl)methyl]benzoyl}indole, 1-N,N-dimethylcarbamoyl-4-methoxycarbonyl-3-{4-[(5-oxide-1H-2-methylimidazo[4.5-c]pyrid-1-yl)methyl]benzoyl}indole, 1-N,N-dimethylcarbamoyl-4-methoxycarbonyl-3-{4-[(4-chloro-1H-2-methylimidazo[4.5-c]pyrid-1-yl)methyl]benzoyl}indole, 1-N,N-dimethylcarbamoyl-4-methoxycarbonyl-3-{4-[ (1,5-H-2-methylimidazo[4.5-c]pyrid-4-one-1-yl)methyl]benzoyl}indole, 1-N,N-dimethylcarbamoyl-4-ethoxycarbonyl-3-{4-[ (1H-2-methylimidazo[4.5-c]pyrid-1-yl)methyl]benzoyl}indole, 1-N,N-dimethylcarbamoyl-4-(2-propyloxycarbonyl)-3-{4-[(1H-2-methylimidazo[4.5-c]pyrid-1-yl)methyl]benzoyl}indole, 1-N,N-dimethylcarbamoyl-4-methoxycarbonyl-3-{4-[(1H-2-methylnaphtho[2,3-d]imidazol-1-yl)methyl]benzoyl}indole, 1-N,N-Dimethylcarbamoyl-4-(N,N-dimethylaminocarbonyloxy)-3-{ 3-fluoro-4[(1H-2-methylimidazo[4,5-c]pyrid-1-yl)methyl]benzoyl}indole, and 1-N,N-Dimethylcarbamoyl-4-ethynyl-3-{3-fluoro-4-[ (1H-2-methylimidazo-[4,5-c]pyrid-1-yl)methyl]benzoyl}indole.

PArticularly preferred compounds of the present invention are

1-N,N-dimethylcarbamoyl-4-(N,N-dimethylaminocarbonyloxy)-3-{ 3-fluoro-4-[(1H-2-methylimidazo[4,5-c]pyrid-1-yl)methyl]benzoyl}indole, 1-N,N-dimethylcarbamoyl-4-ethynyl-3-{3-fluoro-4-[(1H-2-methylimidazo-[4,5-c]pyrid-1-yl)methyl]benzoyl}indole, 1-N,N-dimethylcarbamoyl-4-ethynyl-3-{4-[(1H-2-methylimidazo-[4.5-c]pyrid-1-yl)methyl]benzoyl}indole, 1-N,N-dimethylcarbamoyl-4-(N,N-dimethylaminocarbonyloxy)-3-{4-[(1H-2-methylimidazo[4.5-c]pyrid-1-yl)methyl]benzoyl}indole, and 1-N,N-Dimethylcarbamoyl-4-methoxycarbonyl-3-{4-[(1H-2-methylimidazo[4.5-c]pyrid-1-yl)methyl]benzoyl}indole, or a pharmaceutically acceptable salt thereof.

PAF Inhibitory Activity of the Compounds of the Present Invention

The ability of representative compounds of the present invention to inhibit PAF activity was determined in an in vitro test using the following method.

Citrated whole rabbit blood was obtained from Pel-Freez (Rogers, AR). Rabbit platelets were prepared by centrifugation and washing. The platelets were lysed by freeze-thawing and sonication; platelet membranes were prepared by centrifugation and washing. Final membrane preparations were stored frozen in 10 mM Tris/5 mM MgCl$_2$/2 mM EDTA (TME buffer, pH 7.0) with 0.25M sucrose added for membrane stabilization.

The standard PAF receptor binding assay contained 10 µg platelet membrane protein, 0.6 nM [$^3$H]C$_{18}$-PAF (from Amersham or New England Nuclear; specific activity 120–180 Ci/mmol), with and without test compound, in "binding buffer" consisting of TME with 0.25% bovine serum albumin added (Sigma, RIA grade). The final volume of the assay was 100 µl. The assay was conducted in Milliliter-Gv™ (Millipore Corp.) filtration plates; incubation time was for 60 minutes at room temperature (22°–23° C.). "Specific binding" was operationally defined as the arithmetic difference between "total binding" of 0.6 nM [$^3$H]C$_{18}$-PAF (in the absence of added PAF) and "nonspecific binding" (in the presence of 1 µM PAF). After the prescribed incubation, platelet membranes were filtered under vacuum and washed as with 1 milliliter of "binding buffer". The filters were dried and removed. The bound radioactivity was quantitated with a Berthold TLC-Linear Analyzer model LB2842.

Dose-response curves of inhibition of specific [$^3$H]C$_{18}$-PAF binding by test compounds were conducted in triplicate, with at least four doses covering the active range. Experiments were repeated at least once. IC$_{50}$ values (concentration producing 50% inhibition) were determined by point-to-point evaluation. K$_i$ values of inhibitory binding constants were calculated according to the method of Cheng and Prusoff [*Biochem. Pharmacol.* 22 (1973) 3099–3108] whereby $$K_i = \frac{IC_{50}}{1 + ([[^3H]PAF]/K_d[^3H]PAF)}$$

$$= \frac{IC50}{1 + (0.6 \text{ nM}/0.6 \text{ nM})}$$

$$= \frac{IC50}{2}$$

The values of K$_i$ for representative compounds of the present invention appear in Table 1.

TABLE 1

| Example | K$_i$ (nM) or % Inhibition | Example | K$_i$ (nM) or % Inhibition |
|---|---|---|---|
| 2 | 56 | 30 | 342 |
| 3 | 75 | 31 | 44 |
| 4 | 2.3 | 32 | 10% @ 1.0 µM |
| 6 | 140 | 33 | 29 |
| 7 | 700 | 90 | 2.9 |
| 9 | 60 | 95 | 130 |
| 10 | 258 | 96 | 7.7 |
| 11 | 86 | 102 | 10 |
| 12 | 140 | 107 | 0.6 |
| 13 | 150 | 112 | 150 |
| 14 | 5 | 122 | 0.8 |
| 16 | 18% @ 100 µM | 126 | 62 |
| 17 | 422 | 131 | 4.7 |
| 18 | 323 | 135 | 1.3 |
| 19 | 280 | 138 | 2.2 |
| 20 | 26% @ 100 µM | 141 | 20 |
| 22 | 146 | 143 | 0.9 |
| 23 | 7% @ 1.0 µM | 150 | 40 |
| 24 | 6% @ 1.0 µM | 156 | 19 |
| 25 | 14% @ 1.0 µM | 159 | 9 |
| 26 | 7% @ 1.0 µM | 162 | 14 |
| 27 | 160 | 167 | 450 |

TABLE 1-continued

| Example | $K_i$ (nM) or % Inhibition | Example | $K_i$ (nM) or % Inhibition |
|---|---|---|---|
| 28 | 87 | 174 | 4 |
| 29 | 494 | | |

Pharmaceutical Compositions

The present invention also provides pharmaceutical compositions which comprise one or more of the compounds of formula I above formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions, or emulsions as well as sterile powders for reconstitution into sterile injectable solutions or dispersions just prior to use. Examples of suitable aqueous and nonaqueous carders, diluents, solvents, or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain pan of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Compositions for rectal or vaginal administration are preferably suppositories which can be prepared by mixing the compounds of this invention with suitable non-irritating excipients or careers such as cocoa butter, polyethylene glycol, or a suppository wax which are solid at room temperature but liquid at body temperature and therefore melt in the rectum or vaginal cavity and release the active compound.

Compounds of the present invention can also be administered in the form of as liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments, and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved.

Generally dosage levels of about 0.001 to about 100 mg, more preferably of about 0.01 to about 20 mg, and most preferably about 0.1 to about 10 mg of active compound per kilogram of body weight per day are administered orally to a mammalian patient. If desired, the effective daily dose may be divided into multiple doses for purposes of administration, e.g. two to four separate doses per day.

Preparation of Compounds of the Invention

The compounds of this invention can be prepared by a variety of synthetic routes. Representative procedures are outlined as follows. It should be understood that $R^1$, $R^2$, $R^3$, and $Ar^2$ as used herein correspond to the groups identified above.

A general route to the compounds of this invention is shown in Scheme 1. Indolyl zinc reagent 1 is prepared by treatment of the corresponding indole with ethylmagnesium bromide and zinc chloride. Conversion of benzoic acid 2 to the acid chloride by reaction with oxalyl chloride, followed by addition of indolyl zinc reagent 1 forms 3, which is convened to the desired final product as described in PCT/US92/05890 (international publication no. WO 93/18 13).

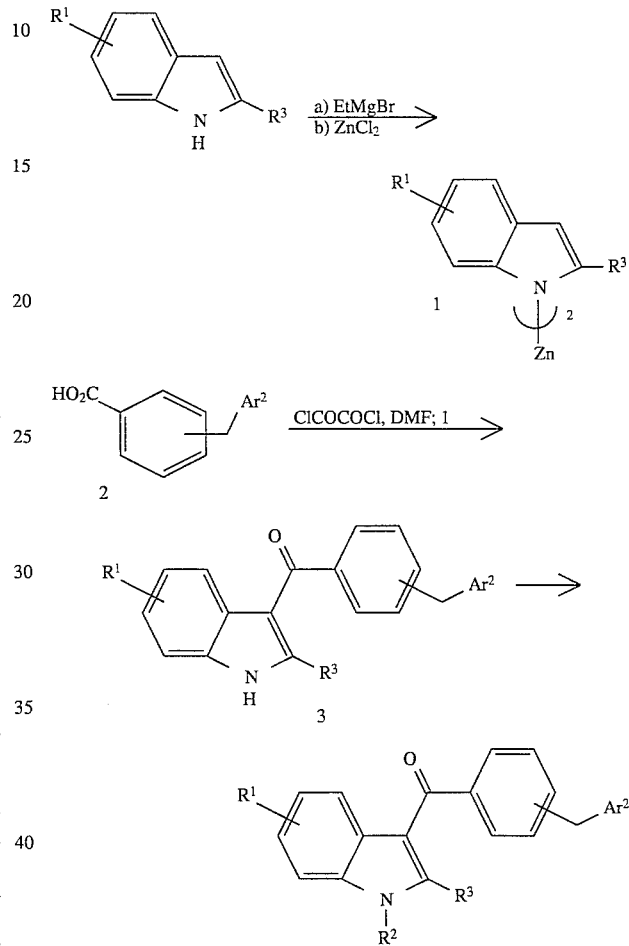

Scheme 1

Preparation of the intermediate benzoic acid 2 is shown in Scheme 2. 1,2-phenylenediamine is condensed with acetic anhydride to form 2-methylbenzimidazole which is then reacted with benzyl halide 5 (where X is Br, Cl, I, methansulfonyl, or p-toluenesulfonyl), in the presence of base to form 6. Hydrolysis of ester 6 gives benzoic acid 2. Condensation of 3,4-diaminopyridine with acetic anhydride followed by reaction with benzyl halide 5 as described above gives a mixture of 1-, 3-, and 5-substituted imidazo[4,5-c] pyridines (compounds 8, 9, and 10) which are separated by chromatography on silica gel and convened to 2 as described above. Similarly, imidazo[4,5-b]pyridines 12, 13, and 14 are prepared from 2,3-diaminopyridine.

Scheme 2

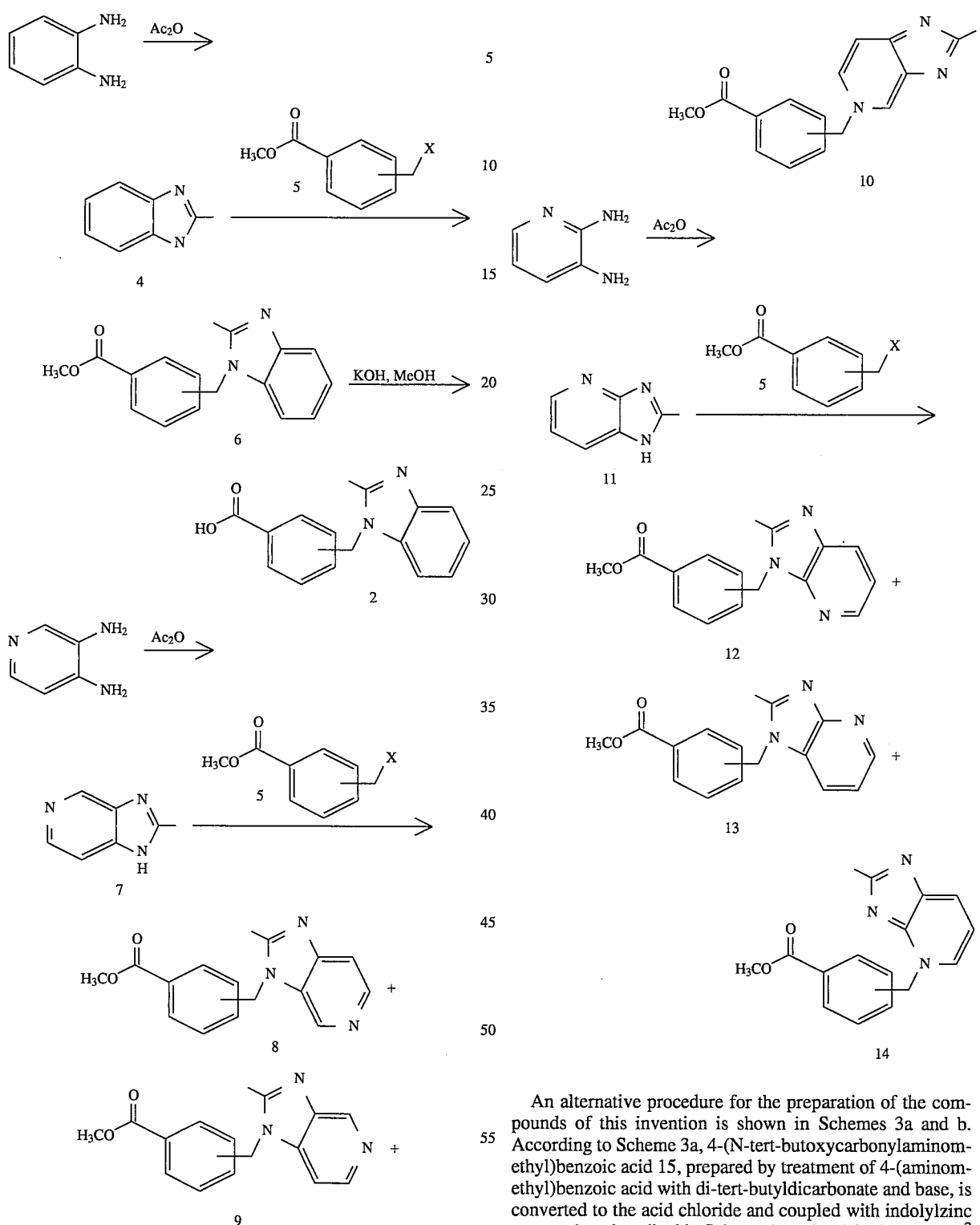

An alternative procedure for the preparation of the compounds of this invention is shown in Schemes 3a and b. According to Scheme 3a, 4-(N-tert-butoxycarbonylaminomethyl)benzoic acid 15, prepared by treatment of 4-(aminomethyl)benzoic acid with di-tert-butyldicarbonate and base, is converted to the acid chloride and coupled with indolylzinc reagent 1 as described in Scheme 1 to give 16. The group $R^2$ is then introduced as described in Scheme 1, and the tert-butoxycarbonyl group is hydrolyzed with HCl to form amine 18. Reaction of 18 with substituted nitropyridine 19, wherein any one of A, B, C, and D is N, and X is halogen or alkoxy, followed by reduction of the nitro group, preferably by hydrgenolysis catalyzed by palladium on carbon, gives key intermediate 20.

Scheme 3a

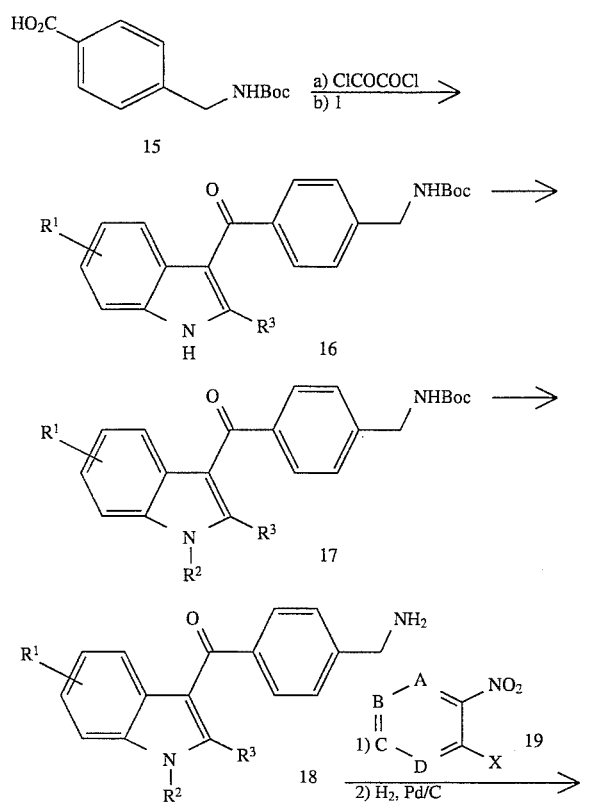

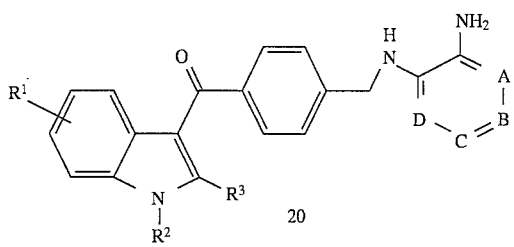

The conversion of diaminopyridine 20 to the compounds of this invention is shown in Scheme 3b. Reaction of 20 with ethyl(ethoxymethylene)cyanoacetate provides the compounds 21 in which $R^{13}$ is H. Introduction of alkyl groups is accomplished by reaction of 20 with the appropriate anhydride as shown in the preparation of compounds 22 and 24. Compounds of formula 23 are prepared by reaction of 20 with benzoyl chloride.

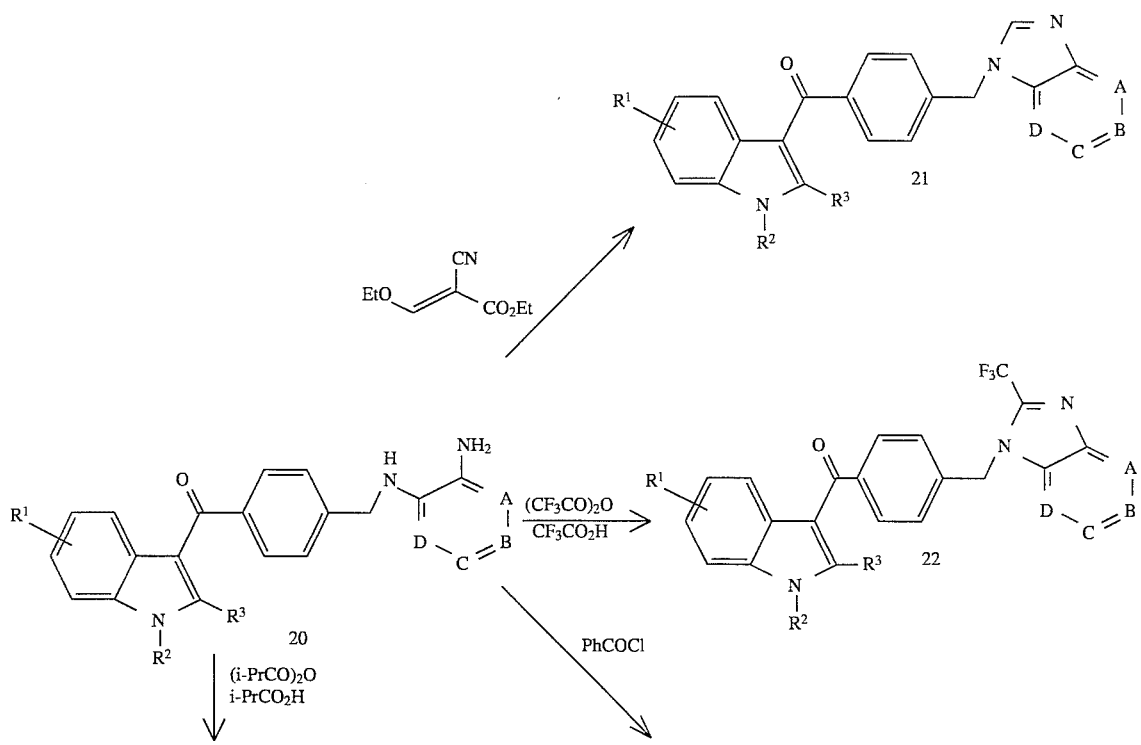

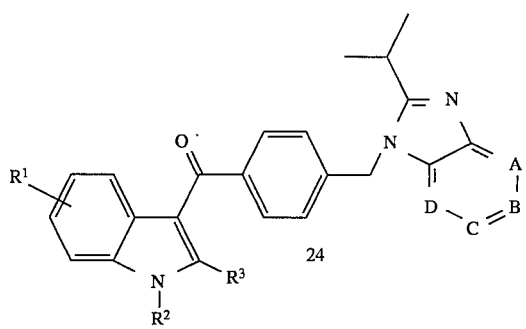

24

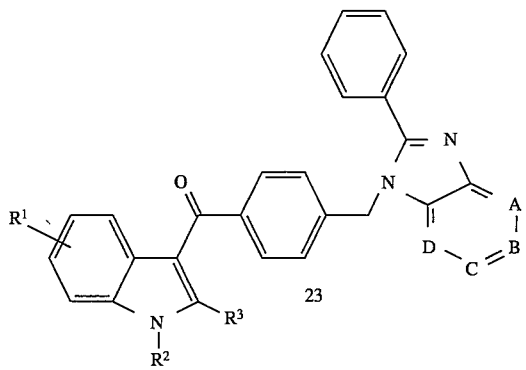

23

The preparation of the compounds of this invention where $Ar^1$ is thienyl is shown in Scheme 4. 2-carbomethoxy-5-bromomethylthiophene 25 is prepared from 5-methyl-2-thiophenecarboxylic acid by reaction with diazomethane and N-bromosuccinimide. Reaction of imidazopyridine 26, wherein any one of A, B, C, or D is N, with bromomethylthiophene 25 in the presence of potassium tert-butoxide and DMSO gives 27, which is hydrolzed to thiophenecarboxylic acid 28 with lithium hydroxide. The desired compound 29 is then prepared from 28 as described in Scheme 1 above.

Scheme 4

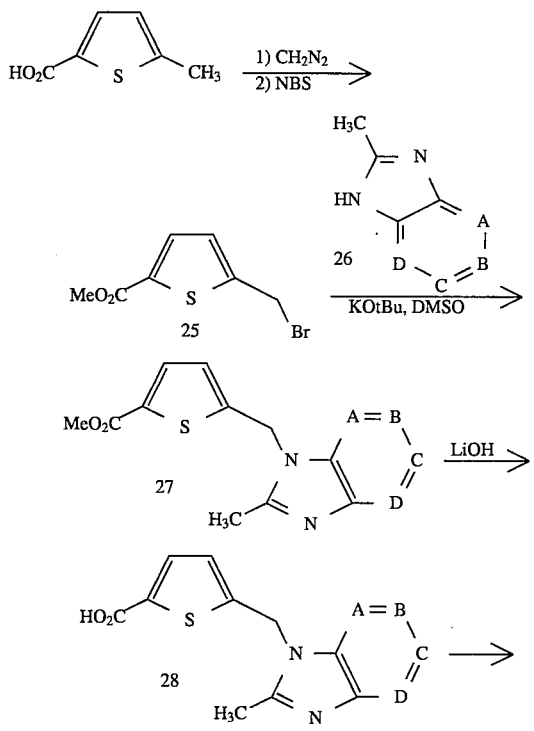

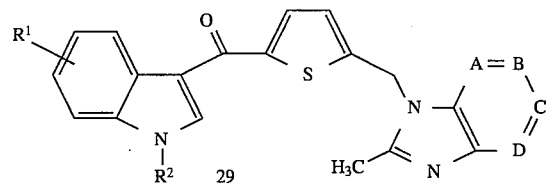

29

The preparation of the compounds of this invention in which $Ar^1$ is furyl is shown in Scheme 5. 5-acetoxy-2-carboxyethylfuran 30 is hydrolyzed with potassium carbonate in ethanol to give furyl alcohol 31, which is converted to furyl azide 32 by treatment with methanesulfonyl chloride and lutidine to give the mesylate, followed by displacement with sodium azide. Raney nicked hydrogenolysis of the azide gives amine 33. Reaction of 33 with ethoxynitropyridine 34, in which any one of A, B, C, or D is nitrogen, followed by reduction with tin(II) chloride gives diamine 36 which is converted to the desired compound 37 as described in Scheme 3b.

Scheme 5

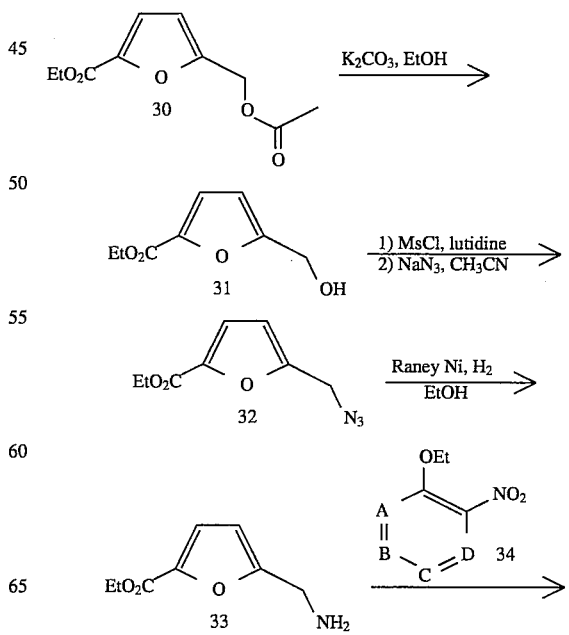

Scheme 5 -continued

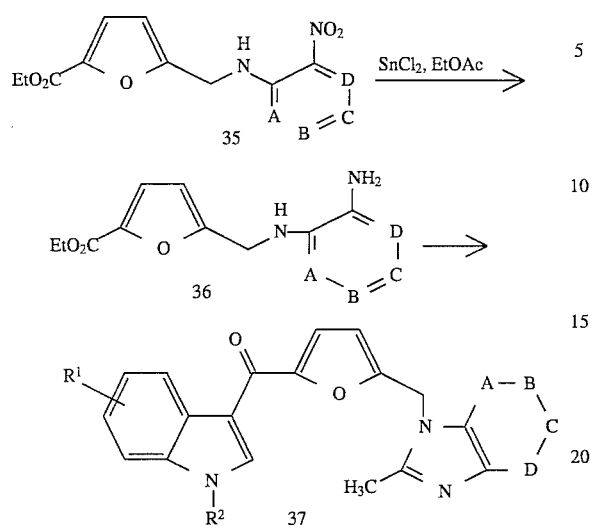

The preparation of compounds in which L¹ is sulfonylamino is outlined in Scheme 6. Heating 1-methylindole and 4-azidomethylphenylsulfonyl azide 38, prepared by reaction of p-toluenesulfonyl chloride with N-bromosuccinimide followed by sodium azide, gives azide 39. Reduction of 39 with triphenylphosphine gives the primary amine 40. Reaction with ethoxynitropyridine 34, in which any one of A, B, C, or D is nitrogen, followed by reduction with tin(II) chloride gives diamine 41 which is converted to the desired compound 42 as described in Scheme 3b.

Scheme 6

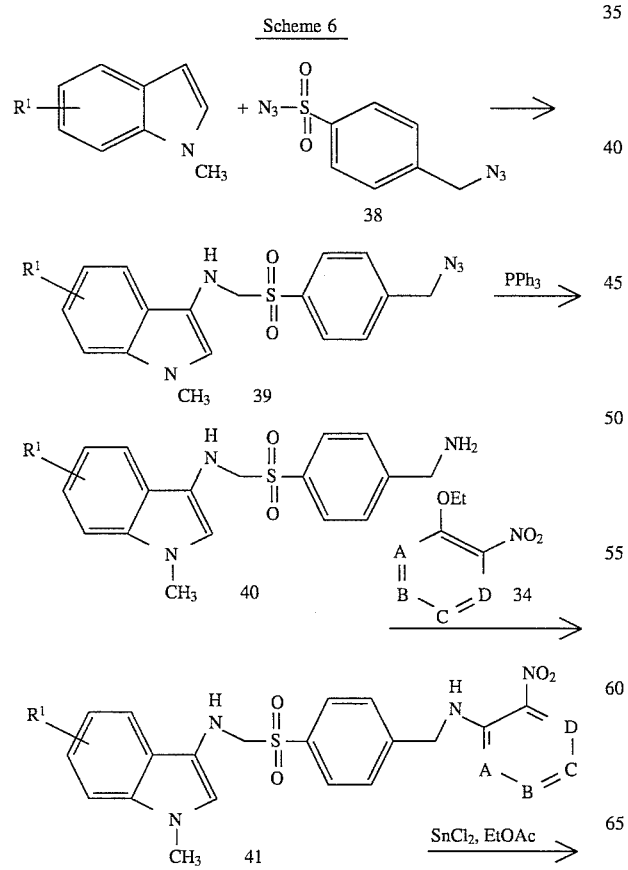

Scheme 6 -continued

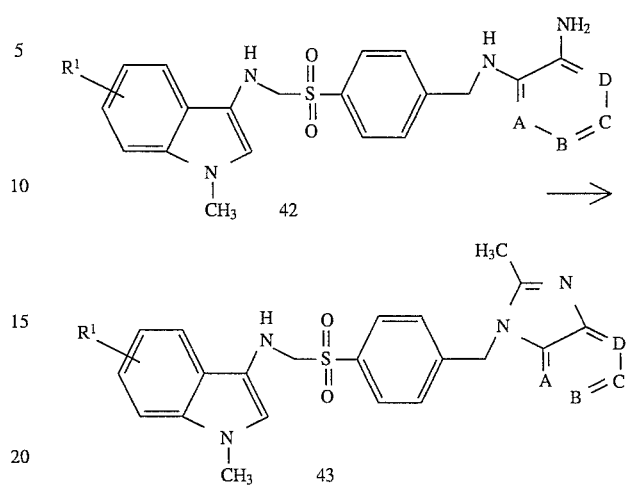

The preparation of compounds in which L¹ is —SO₂— is shown in Scheme 7. According to Scheme 7, the desired substituted indole is reacted with p-tolyldisulfide and sulfonyl chloride in the presence of triethylamine to form 3-(p-tolylthio)indole 44. Reaction of 44 with phenylsulfonyl chloride and KOH gives 1-phenylsulfonylindole derivative 45 which is oxidized to 46 with H₂O₂ in acetic acid. Bromination of 46 with N-bromosuccinimide and benzoyl peroxide gives bromomethyl compound 47. Displacement of bromide with potassium bis(t-butyloxycarbonyl)amide and deprotection with trifluoroacetic acid followed by sodium carbonate gives benzyl amine 49. Reaction of 49 with ethoxynitropyridine 34, in which any one of A, B, C, or D is nitrogen, followed by reduction with iron and NH₄Cl gives diamine 51 which is converted to imidazopyridine 52 as described in Scheme 3b. The desired final product 53 is then prepared as described in PCT/US92/05890 (international publication no. WO 93/1813).

Scheme 7

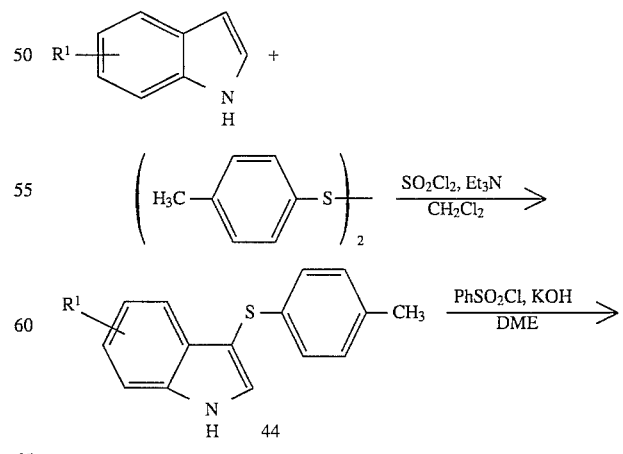

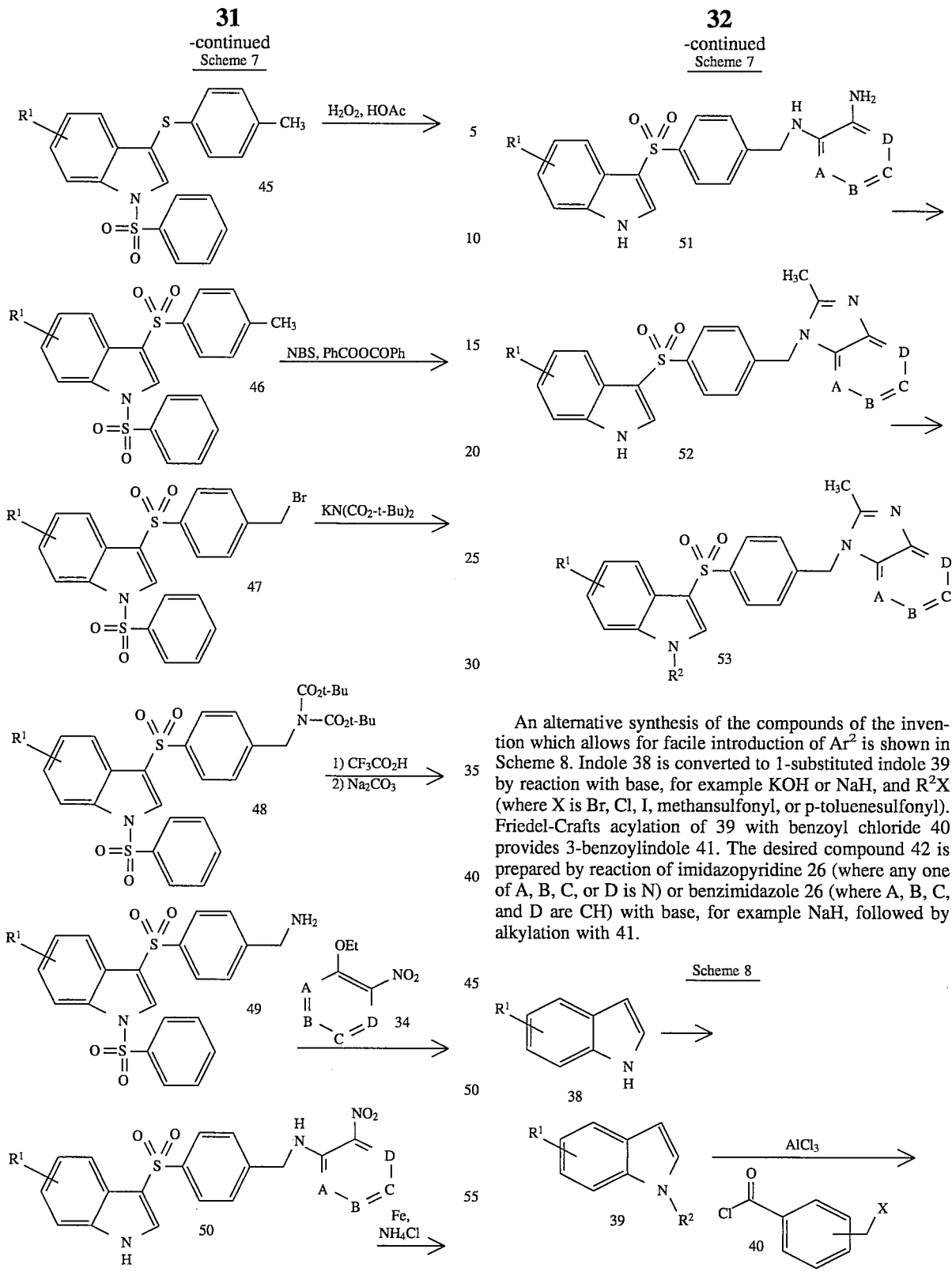

An alternative synthesis of the compounds of the invention which allows for facile introduction of Ar² is shown in Scheme 8. Indole 38 is converted to 1-substituted indole 39 by reaction with base, for example KOH or NaH, and R²X (where X is Br, Cl, I, methansulfonyl, or p-toluenesulfonyl). Friedel-Crafts acylation of 39 with benzoyl chloride 40 provides 3-benzoylindole 41. The desired compound 42 is prepared by reaction of imidazopyridine 26 (where any one of A, B, C, or D is N) or benzimidazole 26 (where A, B, C, and D are CH) with base, for example NaH, followed by alkylation with 41.

-continued
Scheme 8

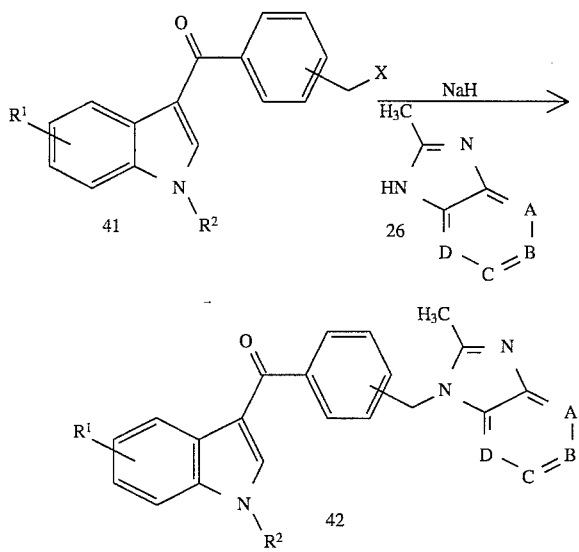

The foregoing may be better understood by the following examples, which are presented for the purpose of illustration and are not intended to limit the scope of the invention.

EXAMPLE 1

Preparation of
6-(4-fluorophenyl)-3-{4-[(1H-2-methylbenzimidazolyl)-methyl]benzoyl}indole Step 1: 2-Methylbenzimidazole.

A solution of 1,2-diaminobenzene (5.00 g, 46.3 mmol) in acetic anhydride (36.5 mL) was heated for 17 hours at 90° C. and then stirred for 17 hours at ambient temperature. The reaction mixture was taken to pH 9 by dropwise addition of $NH_4OH$, with ice added as necessary to keep the mixture cool, followed by cooling in an ice bath. The resulting precipitate was filtered, rinsed with $H_2O$, and dried in a vacuum oven to give 5.28 g of 2-methylbenzimidazole as a brown solid.

Step 2: Methyl 4-(1H-2-methylbenzimidazol-1-ylmethyl)benzoate.

To a solution under $N_2$ of 2-methylbenzimidazole (2.00 g, 15.2 mmol), prepared as in step 1, in THF (75.8 mL) was added NaH (437 mg, 18.2 mmol) in one portion. The resulting brown suspension was stirred for one hour at ambient temperature, then cooled to 0° C. and a solution of methyl(4-bromomethyl)benzoate (2.89 g, 12.6 mmol) in THF (14.0 mL) was added dropwise via syringe, after which the ice bath was removed and the reaction mixture was stirred for 17 hours at ambient temperature. The reaction mixture was poured into a mixture of $H_2O$ and ethyl acetate and the layers were separated. The organic phase was washed twice with $H_2O$, and the aqueous phase was washed three times with ethyl acetate. The combined organic layers were dried over $MgSO_4$, filtered, and concentrated in vacuo. Chromatography on silica gel (5% methanol/$CH_2Cl_2$) gave methyl 4-(2-methylbenzimidazol-1-ylmethyl)benzoate (2.82 g) as a yellow solid.

Step 3: 4-(2-Methyl-1H-benzimidazolylmethyl)benzoic acid.

To a solution under $N_2$ of methyl 4-(1H-2-methylbenzimidazol-1-ylmethyl)benzoate (2.72 g, 9.71 mmol) in methanol (21.6 mL) was added 1M aqueous KOH (11.7 mL, 11.7 mmol). The reaction mixture was stirred for 1.33 hours at ambient temperature. Aqueous 1M HCl was added until a pH of about 4 was obtained, and the reaction mixture was concentrated in vacuo. The residue was cooled in an ice bath for 30 min and filtered. The resulting tan precipitate was dried in the vacuum oven and the filtrate was extracted twice with ethyl acetate and twice with $CH_2Cl_2$. The combined extracts were dried over $MgSO_4$, filtered, and concentrated in vacuo to give a tan solid which was combined with the original precipitate to give 2.51 g of 4-(1H-2-methylbenzimidazol-1-ylmethyl)benzoic acid.

Step 4: 6-(4-Fluorophenyl)-3-{4-[(1H-2-methylbenzimidazol-1-yl)methyl]benzoyl}indole.

To a suspension of 4-(1H-2-methylbenzimidazol-1-ylmethyl)benzoic acid (1.50 g, 5.63 mmol), prepared as in step 3, in THF (28 mL) was added NaH (195 mg, 8.46 mmol) in a single portion. The reaction mixture was stirred for 10 min, then DMF (85 μL, 1.13 mmol) and oxalyl chloride (953 μL, 11.3 mmol) were added. After stirring for 4 hours at ambient temperature, the reaction mixture was concentrated in vacuo to give a gray powder which was placed under $N_2$ and suspended in $CH_2Cl_2$ (30 mL). In a separate flask, ethylmagnesium bromide (3M solution in ether, 4.5 mL, 13.5 mmol) was added to a solution of 6-(4-fluorophenyl)indole (2.38 g, 11.3 mmol), prepared as described in WO 93/01813, in $CH_2Cl_2$ (56 mL). After 15 min, $ZnCl_2$ (1.0M solution in ether, 13.5 mL, 13.5 mmol) was added and the clear, dark brown solution was stirred for 20 min at ambient temperature. The 6-(4-fluorophenyl)indolylzinc solution was then transferred via cannula to the acid chloride suspension and the resulting light-brown suspension was stirred for 20 hours at ambient temperature. The reaction mixture was quenched with $H_2O$ (20 mL) and filtered. The filtrate layers were separated and the aqueous layer was extracted with $CH_2Cl_2$ (3×50 mL). The combined organic layers were washed with saturated aqueous $NaHCO_3$, dried over $MgSO_4$, filtered, and concentrated in vacuo to give a solid. The filter cake was stirred with methanol and filtered again. The filtrate was extracted with $CH_2Cl_2$ (4×50 mL), and the combined organic layers were washed with saturated aqueous $NaHCO_3$, dried over $MgSO_4$, filtered, and concentrated in vacuo to give additional solid. The combined solids were purified by chromatography on silica gel (2%, then 5%, then 10% methanol/$CH_2Cl_2$ to give 6-(4-fluorophenyl)- 3-{4-[(1H-2-methylbenzimidazolyl)methyl]benzoyl}indole (539 mg) as a red solid. $^1$H NMR (DMSO-d6, 300 MHz) δ2.57 (s, 3H), 5.61 (s, 2H), 7.15–7.25 (m, 2H), 7.25–7.35 (m, 3H), 7.5–7.6 (m, 6H), 7.97 (d, 1H, J=3.0 Hz), 8.28 (d, 1H, J=8.4 Hz), 12.16 (br s, 1H). MS (DCI/$NH_3$) m/e 460 (M+H)$^+$. Anal calcd for $C_{30}H_{22}FN_3O \cdot 0.6H_2O$: C, 76.61; H, 4.97; N, 8.93. Found: C, 76.72; H, 4.90; N, 8.95.

EXAMPLE 2

Preparation of
1-N,N-Dimethylcarbamoyl-6-(4-fluorophenyl)-3-{4-[(1H-2-methylbenzimidazolyl)methyl]benzoyl}indole To a solution of 6-(4-fluorophenyl)-3-{4-[(1H-2-methylbenzimidazolyl)methyl]benzoyl)indole (200 mg, 0.44 mmol), prepared as in Example 1, in 1:1 THF/DMF (8.0 mL) at 0° C. was added KOH (61 mg, 1.09 mmol). The reaction mixture was stirred for 10 min and dimethylcarbamoyl chloride (60.3 μL, 0.65 mmol) was added via syringe. Stirring was continued for 40 min and then the reaction mixture was partitioned between H$_2$O (20 mL) and ethyl acetate (20 mL). The aqueous phase was extracted twice with ethyl acetate. The combined organic layers were washed with brine, dried over MgSO$_4$, filtered, and concentrated in vacuo. Pure 6-(4-fluorophenyl)-3-{4-[1H-2-methylbenzimidazolyl)methyl]benzoyl}indole-1-carboxylic acid dimethylamide (200 mg) was obtained by chromatography on silica gel (5% methanol/CH$_2$Cl$_2$). $^1$H NMR (DMSO-d6, 300 MHz) δ2.56 (s, 3H), 3.02 (s, 6H), 5.62 (s, 2H), 7.15–7.25 (m, 2H), 7.25–7.35 (m, 4H), 7.5–7.6 (m, 2H), 7.64 (dd, 1H, J=8.4,1.8 Hz), 7.7–7.78 (m, 2H), 7.8–7.9 (m, 3H), 8.15 (s, 1H), 8.30 (d, 1H, J=8.4 Hz). MS (DCI/NH$_3$) m/e 531 (M+H)$^+$. Anal calcd for C$_{33}$H$_{27}$FN$_4$O$_2$.0.4H$_2$O: C, 73.70; H, 5.21; N, 10.42. Found: C, 73.70; H, 5.30; N, 10.40.

EXAMPLE 3

Preparation of
6-(4-Fluorophenyl)-3-{4-[(1H-2-methylimidazo-
[4.5-c]pyrid- 1-yl)methyl]benzoyl}indole Step 1: 1H-2-Methylimidazo[4,5-c]pyridine.

The desired compound was prepared according to the method of Example 1, step 1, except substituting 3,4-diaminopyridine for 1,2-diaminobenzene.

Step 2: Methyl 4-(1H-2-methylimidazo[4,5-c]pyrid-1-ylmethyl)benzoate.

To a solution under N$_2$ of 1H-2-methylimidazo[4,5-c]pyridine (600 mg, 4.51 mmol), prepared as in step 1, in THF (33 mL) and DMF (11 mL) was added NaH (130 mg, 5.41 mmol) in a single portion. The resulting brown suspension was stirred for one hour at ambient temperature, then cooled to 0° C. and a solution of methyl 4-(bromomethyl)benzoate (1.03 g, 4.51 mmol) in THF (5 mL) was added via syringe. The cold bath was then removed and the reaction mixture stirred for 17 hours at ambient temperature. The reaction mixture was partitioned between pH 7 buffer (40 mL), and ethyl acetate (40 mL). The aqueous phase was extracted with ethyl acetate (2×30 mL), and the combined organic layers were washed with H$_2$O (5×30 mL); dried over MgSO$_4$, filtered, and concentrated in vacuo to give a mixture of predominately two products. Chromatography on silica gel gave methyl 4-(1H-2methylimidazo[4,5-c]pyrid-1-ylmethyl)benzoate (150 mg) and methyl 4-(3H-2-methylimidazo[4,5-c]pyrid-3-ylmethyl)benzoate (95 mg). The original aqueous phase was concentrated in vacuo to give a brown solid which was taken up in methanol, dried over MgSO$_4$, filtered, and re-concentrated in vacuo. Chromatography on silica gel gave methyl 4-(5H-2-methylimidazo[4,5-c]pyrid-5-ylmethyl)benzoate (435 mg).

Step 3: 6-(4-Fluorophenyl)-3-{4-1 (1H-2-methylimidazo[4,5-c]pyrid-1-yl)methyl]benzoyl}indole.

The desired compound was prepared according to the method of Example 1, steps 3 and 4, except substituting 4-(1H-2-methylimidazo[4,5-c]pyrid-1-ylmethyl)benzoate, prepared as in step 2, for methyl 4-(2-methylbenzimidazol-1-ylmethyl)benzoate. $^1$H NMR (DMSO-d6, 300 MHz) δ2.60 (s, 3H), 5.65 (s, 2H), 7.25–7.35 (m, 4H), 7.52 (dd, 1H, J=8.4,1.5 Hz), 7.64 (d, 1H, J=8.7 Hz), 7.7–7.8 (m, 3H), 7.80 (d, 1H, J=8.1 Hz), 7.97 (s, 1H), 8.28 (d, 1H, J=8.4 Hz), 8.32 (d, 1H, J=5.4 Hz), 8.87 (s, 1H), 12.15 (br s, 1H). MS (FAB) m/e 461 (M+1)$^+$. Anal calcd for C$_{29}$H$_{21}$FN$_4$O. 1.2H$_2$O: C, 72.25; H, 4.89; N, 11.62. Found: C, 72.26; H, 4.72; N, 11.67.

EXAMPLE 4

Preparation of
1-N,N-Dimethylcarbamoyl-6-(4-fluorophenyl)-3-
{4-[(1H-2-methylimidazo[4.5-c]pyrid-1-yl)methyl]-
benzoyl}indole Step 1: 6-(4-fluorophenyl)indole-1-carboxylic acid dimethylamide.

To a 0° C. solution of 6-(4-fluorophenyl)indole (2.00 g, 9.48 mmol), prepared as described in WO 93/01813, in THF (50 mL) was added KOH (2.7 g, 47.4 mmol) in a single portion and the cold bath was removed. After stirring for 15 min at ambient temperature, dimethylcarbamoyl chloride (1.3 mL, 14.2 mmol) was added via syringe and the resulting brown suspension was stirred for 4 hours at ambient temperature. The reaction mixture was poured into a mixture of ethyl acetate and saturated aqueous NH$_4$Cl and the layers were separated. The aqueous phase was extracted twice with ethyl acetate. The combined organic layers were dried over MgSO$_4$, filtered, and concentrated in vacuo to afford 6-(4-fluorophenyl)indole-1-carboxylic acid dimethylamide as a brown solid which was used without further purification.

Step 2: 6-(4-Fluorophenyl)-3-(4-chloromethylbenzoyl)indole-1-carboxylic acid dimethylamide.

To a solution of 4-(chloromethyl)benzoyl chloride (804 mg, 4.26 mmol) in CH$_2$Cl$_2$ (21 mL) was added AlCl$_3$ (850 mg, 6.39 mmol) in a single portion, and the yellow solution was stirred for 15 min at ambient temperature. A solution of 6-(4 -fluorophenyl)indole-1-carboxylic acid dimethylamide (1.00 g, 3.55 mmol), prepared as in step 1, in CH$_2$Cl$_2$ was added dropwise and the dark solution was stirred for 2 hours at ambient temperature. Additional AlCl$_3$ (0.24 g, 1.78 mmol) was added and the reaction mixture was stirred for 0.5 hours. The reaction mixture was poured into a separatory funnel containing ice water and CH$_2$Cl$_2$. The layers were separated and the aqueous phase was extracted three times with CH$_2$Cl$_2$. The combined organic layers were washed with saturated aqueous NaHCO$_3$, dried over MgSO$_4$, filtered, and concentrated in vacuo. Pure 6-(4-fluorophenyl)-3-(4 -chloromethylbenzoyl)indole-1-carboxylic acid dimethylamide (294 mg) was obtained by chromatography on silica gel (25%, then 50% ethyl acetate/hexanes).

Step 3: 1-N,N-Dimethylcarbamoyl-6-(4-fluorophenyl)-3-{4-[(1H-2 -methylimidazo[4.5-c]pyrid-1-yl)methyl] benzoyl}indole.

To a solution of imidazo[4,5-c]pyridine (407 mg, 3.06 mmol) in THF (15 mL) and 1,3-dimethyl-3,4,5,6-tetrahydro-2-1H-pyrimidinone (5 mL) was added NaH (110 mg, 4.59 mmol) in a single portion and the resulting solution was stirred for 1 hour at ambient temperature. In a separate flask, NaBr (630 mg, 6.11 mmol) was added to a solution of 6-(4-fluorophenyl)-3-(4-chloromethylbenzoyl)indole-1-carboxylic acid dimethylamide (1.33 g, 3.06 mmol), prepared as in step 2, in THF (15 mL) and 1,3-dimethyl-3,4,5,6-tetrahydro-2-1H-pyrimidinone (5 mL). The resulting yellow suspension was stirred for 1 hour at ambient temperature, after which the imidazopyridine solution was added dropwise via syringe. The reaction mixture was stirred for 3 hours at ambient temperature and then was partitioned between brine and ethyl acetate. The layers were separated and the aqueous phase was extracted twice with ethyl acetate. The combined organic layers were washed twice with brine, dried over MgSO$_4$, filtered, and concentrated in vacuo. Chromatography on silica gel (2%, then 4% methanol/CH$_2$Cl$_2$) provided 1-N,N-dimethylcarbamoyl-6-(4 -fluorophenyl)-3-{4-[(1H-2-methylimidazo[4.5-c]pyrid-1- yl)methyl]benzoyl}indole. (228 mg). mp 257°–259° C. $^1$H NMR (DMSO-d6, 300 MHz) δ2.59 (s, 3H), 3.03 (s, 6H), 5.67 (s, 2H), 7.25–7.35 (m, 4H), 7.6–7.7 (m, 2H), 7.7–7.8 (m, 2H), 7.8–7.9 (m, 3H), 8.15 (s, 1H), 8.30 (d, 1H, J=8.4 Hz), 8.3 1 (d, 1H, J=5.7 Hz), 8.87 (s, 1H). MS (DCI/NH$_3$) m/e 532 (M+H)$^+$. Anal calcd for $C_{32}H_{26}FN_5O_2$.0.8H$_2$O: C, 70.39; H, 5.09; N, 12.83. Found: C, 70.38; H, 5.39; N, 12.82.

EXAMPLE 5

Preparation of
1-N,N-Dimethylcarbamoyl-6-(4-fluorophenyl)-3-
{4-[(1H-2-methylimidazo[4.5-c]pyrid-1-yl)methyl]-
benzoyl }indole hydrochloride.

To a 0° C. solution of 1-N,N-dimethylcarbamoyl-6-(4-fluorophenyl)-3-{4-[(1H-2-methylimidazo[4.5-c]pyrid-1-yl)methyl]benzoyl}indole (50 mg, 0.09 mmol), prepared as in Example 4, in CH$_2$Cl$_2$ (3 mL) was added 2 mL of 4N HCl in dioxane. The resulting yellow solution, which also contained a small amount of yellow oil, was stirred for 15 min at 0° C. and then was concentrated in vacuo. CH$_2$Cl$_2$ (2 mL) was added to the oily residue and the mixture was sonicated until a fine suspension was obtained. The suspension was diluted with ether and filtered to give 42 mg of 1-N,N-dimethylcarbamoyl- 6-(4-fluorophenyl)-3-{4-[(1H-2-methylimidazo[4.5-c]pyrid-1-yl)methyl]benzoyl}indole hydrochloride as a yellow solid. mp 275°–278° C. $^1$H NMR (D$_3$COD, 300 MHz) δ2.79 (s, 3H), 3.11 (s, 6H), 5.84 (s, 2H), 7.15–7.25 (m, 2H), 7.40 (apparent d, 2H, J=8.1 Hz), 7.61 (dd, 1H, J=8.4,2.3 Hz), 7.65–7.75 (m, 2H), 7.75–7.80 (narrow m, 1H), 7.85–7.90 (m, 2H), 7.99 (s, 1H), 8.19 (d, 1H, J=6.3 Hz), 8.34 (d, 1H, J=8.1 Hz), 8.58 (d, 1H, J=6.3 Hz), 9.26 (s, 1H). Anal calcd for $C_{32}H_{27}FN_5O_2Cl$. 0.6H$_2$O: C, 66.40; H, 4.91; N, 12.10. Found: C, 66.40; H, 5.00; N, 12.01.

EXAMPLE 6

Preparation of
6-(4-Fluorophenyl)-3-{4-[(3H-2-methylimidazo[4.5-c]-
pyrid- 3-yl)methyl]benzoyl}indole.

Step 1: Potassium 4-(3H-2-methylimidazo[4,5-c]pyrid-3-ylmethyl)benzoate.

Hydrolysis of methyl 4-(3H-2-methylimidazo[4,5-c]pyrid-3-ylmethyl)benzoate, prepared as in Example 3, step 2, with aqueous KOH in methanol was accomplished as described in Example 1, step 3. After complete consumption of starting material, the reaction mixture was partitioned between H$_2$O and ethyl acetate. The aqueous phase was washed twice with ethyl acetate and concentrated in vacuo. Lyophilization of the crude product gave potassium 4-(3H-2-methylimidazo[4,5 -c]pyrid-3-ylmethyl)benzoate.
Step 2: 6-(4-Fluorophenyl)-3-{4-[(3H-2-methylimidazo [4.5-c]pyrid-3-yl)methyl]benzoyl}indole.

To a suspension of potassium 4-(3H-2-methylimidazo[4,5-c]pyrid-3-ylmethyl)benzoate (3.50 mg, 1.15 mmol), prepared as in step 1, in THF (6 mL) was added DMF (179 μL, 2.3 mmol) and oxalyl chloride (200 μL, 2.30 mmol). The reddish suspension was stirred at ambient temperature for 1.5 hours after gas evolution ceased. The reaction mixture was concentrated in vacuo to give a tan paste which was suspended in CH$_2$Cl$_2$ (6 mL). A solution of 6-(4 -fluorophenyl)indolylzinc (2.30 mmol), prepared as described in Example 1, step 4, was added via cannula and the resulting tan suspension was stirred for 17 hours at ambient temperature. The reaction mixture was quenched with H$_2$O (50 mL) and the layers were separated. The aqueous phase was extracted with CH$_2$Cl$_2$ (2×50 mL) and ethyl acetate (4×50 mL). The combined organic layers were dried over MgSO$_4$, filtered, and concentrated in vacuo. Chromatography on silica gel (2%, then 5%, then 7% methanol/CH$_2$Cl$_2$) gave 79 mg of 6-(4-fluorophenyl)-3-{4-[(3H-2 -methylimidazo[4.5-c]pyrid-3-yl)methyl ]benzoyl}indole. $^1$H NMR (DMSO-d6, 300 MHz) δ2.59 (s, 3H), 5.64 (s, 2H), 7.2–7.3 (m, 4H), 7.45–7.55 (m, 1H), 7.63 (dd, 1H, J=5.4, 1.1 Hz), 7.75–7.80 (m, 2H), 7.91 (s, 1H), 8.2–8.3 (m, 1H), 831 (d, 1H, J=5.4 Hz), 8.87 (s, 1H), 12.08 (br s, 1H). MS (FAB) m/e 461 (M+1)$^+$.

EXAMPLE 7

Preparation of
1-N,N-Dimethylcarbamoyl-6-(4-fluorophenyl)-3-
{4-[(3H-2-methylimidazo[4.5-c]pyrid-3-yl)methyl]-
benzoyl}indole The desired compound was prepared according to the method of Example 2, except substituting 6-(4-fluorophenyl)-3-{4-[(3H-2-methylimidazo[4.5-c]pyrid-3 -yl)methyl]benzoyl}indole, prepared as in Example 6, for 6-(4-fluorophenyl)-3-{4-[(1H-2-methylbenzimidazolyl)methyl]benzoyl}indole. $^1$H NMR (DMSO-d6, 300 MHz) δ2.63 (s, 3H), 3.03 (s, 6H), 5.73 (s, 2H), 7.25–7.40 (m, 4H), 7.59 (dd, 1H, J=5.7,1.0 Hz), 7.65 (dd, 1H, J=8.1,1.5 Hz), 7.7–7.8 (m, 2H), 7.8–7.9 (m, 3H), 8.16 (s, 1H), 8.30 (d, J=8.1 Hz), 8.31 (d, 1H, J=5.7 Hz), 8.97 (s, 1H). MS (DCI/NH$_3$) m/e 532 (M+H)$^+$. Anal calcd for $C_{32}H_{26}FN_5O_2$.0.9H$_2$O: C, 70.16; H, 5.11; N, 12.78. Found C, 70.29; H, 5.28; N, 12.27.

EXAMPLE 8

Preparation of
1-N,N-Dimethylcarbamoyl-6-(4-fluorophenyl)-3-
[4-(5H-2-methylimidazo[4.5-c]pyrid-5-ylmethyl)-
benzoyl]indole Step 1: 6-(4-Fluorophenyl)-3-[4-(5H-2-methylimidazo [4.5-c]pyrid-5-ylmethyl)benzoyl]indole.

The desired compound was prepared according to the method of Example 6, except substituting 4-(5H-2-methylimidazo[4,5-c]pyrid-5-ylmethyl)benzoate, prepared as in Example 3, step 2, for methyl 4-(3H-2-methylimidazo[4,5-c]pyrid-3 -ylmethyl)benzoate.

Step 2:
1-N,N-Dimethylcarbamoyl-6-(4-fluorophenyl)-3-[4-
(5H-2
-methylimidazo[4.5-c]pyrid-5-ylmethyl)benzoyl]indole The desired compound was prepared according to the method of Example 2, except substituting 6-(4-fluorophenyl)-3-[4-(5H-2-methylimidazo[4.5-c]pyrid-5 -ylmethyl)benzoyl]indole, prepared as in step 1, for 6-(4-fluorophenyl)-3-{4-[(1H-2 -methylbenzimidazolyl)methyl]benzoyl}indole. $^1$H NMR (DMSO-d6, 300 MHz) δ2.52 (s, 3H), 3.02 (s, 6H), 5.77 (s, 2H), 7.25–7.35 (m, 2H), 7.57 (apparent d, 2H, J=8.4 Hz), 7.6–7.7 (m, 2H), 7.7–7.8 (m, 2H), 7.80–7.85 (narrow m, 1H), 7.89 (apparent d, 2H, J=8.4 Hz), 8.16 (s, 1H), 8.21 (dd, 1H, J=6.9,1.8 Hz), 8.31 (d, 1H, 8.4 Hz), 9.00 (d, 1H, J=1.2 Hz). MS (DCI/NH$_3$) m/e 532 (M+H)$^+$.

EXAMPLE 9

Preparation of
6-(4-Fluorophenyl)-3-[4-(1H-2-methylimidazo[4.5-c]-pyrid-1-yl)benzoyl]indole Step 1: 4-(N-3-nitropyrid-4-ylamino)benzonitrile.

To a solution under $N_2$ of 3-nitro-4-chloropyridine (4.63 g, 29.2 mmol), prepared as described by Wright, G. C., *J. Heterocyclic Chem.* 1976, 13, 601, and Kruger, S. and Mann, F. G., *J. Chem. Soc.* 2 1955, 758, in absolute ethanol (100 mL) was added 4-aminobenzonitrile (3.45 g, 29.2 mmol) and the resulting purple-brown solution was stirred for 17 hours at ambient temperature, during which time it became a green-brown suspension. The reaction mixture was poured into cold 10% aqueous $NH_4OH$ and filtered. The solid was suspended in ethanol (75 mL) and heated for 10 min on the steam bath. The suspension was cooled to ambient temperature and filtered to give 4-(N-3-nitropyrid-4-ylamino)benzonitrile as a bright-yellow solid.

Step 2: 4-(N-3-Aminopyrid-4-ylamino)benzonitrile.

Catalytic hydrogenation (2 atm H2, 10% Pd/C) of 4-(N-3-nitropyrid-4-ylamino)benzonitrile (6.17 g) in 1:1 methanol/$CH_2Cl_2$ gave 4-(N-3-aminopyrid-4-ylamino)benzonitrile.

Step 3: 4-(1H-2-Methylimidazo[4,5-c]pyrid-1-yl)benzonitrile.

A mixture of 4-(N-3-aminopyrid-4-ylamino)benzonitrile (5.20 g, 24.7 mmol), prepared as in step 2, acetic anhydride (16 mL, 169 mmol), and acetic acid (16 mL) was warmed to 95° C. and stirred for 2 hours. The reaction mixture was cooled to ambient temperature and concentrated in vacuo. The residue was azeotroped with benzene to give a brown solid. The brown solid was mixed with 10% aqueous $NH_4Cl$ and extracted with $CH_2Cl_2$ (3×75 mL). The combined organic extracts were dried over $MgSO_4$, filtered, and concentrated in vacuo to give 4-(1H-2-methylimidazo[4,5-c]pyrid-1-yl)benzonitrile (6.38 g) as a yellow solid which was used without further purification.

Step 4: Methyl 4-(1H-2-methylimidazo]4,5-c]pyrid-1-yl)benzoate.

HCl gas was bubbled for 10 minutes into a flask containing 100 mL of methanol and cooled in an ice/acetone bath, during which time the solution temperature rose to 37° C. The solution temperature was allowed to come down to −5° C. and a solution of 4-(1H-2-methylimidazo[4,5-c]pyrid-1-yl)benzonitrile (5.30 g, 22.6 mmol) in methanol (50 mL) was added dropwise over 15 min. The reaction was warmed slowly to ambient temperature and stirred for 65 hours. The milky white reaction mixture was cooled in an ice/water bath and $H_2O$ (100 mL) was added dropwise. The resulting clear-yellow suspension was stirred for 3 hours at ambient temperature and again cooled in an ice/water bath. Solid $Na_2CO_3$ was added until a pH of 8 was achieved and the white suspension was warmed to ambient temperature. Water was added until a clear solution was obtained and the solution was extracted with $CH_2Cl_2$ (3×600 mL). The combined organic extracts were dried over $Na_2SO_4$, filtered, and concentrated in vacuo to give methyl 4-(1H-2-methylimidazo[4,5-c]pyrid-1-yl)benzoate (5.19 g) as a yellow-white solid.

Step 5: 6-(4-Fluorophenyl)-3-[4-(1H-2-methylimidazo[4.5-c]pyrid-1-yl)benzoyl]indole.

The desired compound was prepared according to the method of Example 1, steps 3 and 4, except substituting 4-(1H-2-methylimidazo[4,5-c]pyrid-1-yl)benzoate for methyl 4-(1H-2-methylbenzimidazol-1-ylmethyl)benzoate. $^1$H NMR (DMSO-d6, 300 MHz) δ2.66 (s, 3H), 7.65 (d, 1H, J=1.5 Hz), 7.69 (d, 1H, J=1.5 Hz), 7.82–7.91 (c, 3H), 8.05 (bs, 1H), 8.25 (s, 1H), 8.28 (s, 1H), 8.36 (s, 1H), 8.55 (d, 1H), J=6 Hz), 8.69–8.80 (c, 5H), 9.24 (s,1H). IR (KBr) 3140, 1600, 1560, 1500, 1470, 1450, 1430, 1400, 1380, 13250, 1300, 1250, 12230, 1200, 890, 850, 810, 710. MS (DCI/$NH_3$) m/e 447 (M+H)$^+$, 281, 238, 212, 130, 117 cm$^{-1}$. Anal calcd for $C_{28}H_{22}FN_4O_{2.5}$: C, 71.02; H, 4.68; N, 11.84. Found: C, 70.86; H, 4.65; N, 12.26.

EXAMPLE 10

Preparation of
1-N,N-Dimethylcarbamoyl-6-(4-fluorophenyl)-3-[4-(1H-2-methylimidazo[4.5-c]pyrid-1-yl)benzoyl]-indole The desired compound was prepared according to the method of Example 2, except substituting 6-(4-fluorophenyl)-3-[4-(1H-2-methylimidazo[4.5-c]pyrid- 1-yl)benzoyl]indole, prepared as in Example 9, for 6-(4-fluorophenyl)-3-{4-[(1H-2-methylbenzimidazolyl)methyl]benzoyl}indole, and using $K_2CO_3$/DMSO instead of KOH/THF,DMF. mp 307.0°–307.5° C. $^1$H NMR (DMSO-d6, 300 MHz) δ2.59 (s, 3H), 3.10 (s, 6H), 7.30–7.40 (c, 2H), 7.61–7.72 (c, 2H), 7.73–7.88 (c, 5H), 8.05–8.16 (c, 2H), 8.30–8.41 (c, 2H), 8.96 (s, 1H), 9.08 (bd, 1H, J=10.5 Hz). IR (KBr) 1700, 1640, 1600, 1520, 1480, 1440, 1390, 1220, 1180, 1090, 1020, 990, 920 cm$^{-1}$. MS (DCI/$NH_3$) m/e 518 (M+H)$^+$.

EXAMPLE 11

Preparation of
6-(4-Fluorophenyl)-3-{3-[(1H-2-methylimidazo-[4.5-c]pyrid-1-yl)methyl]benzoyl}indole Step 1: Methyl 3-(1H-2-methylimidazo[4,5-c]-pyrid-1-yl)methyl)benzoate.

To a solution of 1H -2-methylimidazo[4,5-c]pyridine (3.00 g, 22.5 mmol), prepared as in Example 3, step 1, in THF (165 mL) was added DMF (55 mL) and NaH (95%, 650 mg, 27.0 mmol). The resulting brown suspension was stirred for 1 hour at ambient temperature, then cooled in an ice bath and a solution of methyl 3-(bromomethyl)benzoate (5.18 g, 22.6 mmol) in THF (25 mL) was added dropwise over 10 min. The reaction mixture was stirred for 15 min at 0° C., then the cold bath was removed and stirring was continued at ambient temperature for 17 hours. The reaction mixture was poured into $H_2O$ (200 mL) and the aqueous phase was extracted with ethyl acetate (3×250 mL). The combined organic layers were dried over $Na_2SO_4$, filtered, and concentrated in vacuo to give 3.95 g of gummy solid. Chromatography on silica gel (2%, then 4%, then 10% methanol/$CH_2Cl_2$) gave methyl 3-(1H-2-methylimidazo[4,5-c]pyrid-1-ylmethyl)benzoate (620 mg), methyl 3-(3H-2-methylimidazo[4,5-c]pyrid-3-ylmethyl)benzoate (790 mg), and methyl 3-(5H-2-methylimidazo[4,5-c]pyrid-5-ylmethyl)benzoate (1.50 g).

Step 2: 6-(4-Fluorophenyl)-3-{3-[(1H-2-methylimidazo[4.5-c]pyrid-1-yl)methyl]benzoyl}indole.

The desired compound was prepared according to the method of Example 1, steps 3 and 4, except substituting methyl 3-(1H-2-methylimidazo[4,5-c]pyrid-1-ylmethyl)benzoate, prepared as in step 1, for 4-(1H-2-methylbenzimidazol-1-ylmethyl)benzoate. mp 194.4°–196.4° C. $^1$H NMR (DMSO-d6, 300 MHz) δ2.60 (s, 3H), 5.65 (s, 2H), 7.27–7.38 (c, 3H), 7.49–7.56 (c, 2H), 7.70–7.79 (c, 4H), 7.89 (d, 1H,J=3 Hz), 8.24 (d, 1H, J=9 Hz), 8.30 (d, J=6

Hz), 8.85 (bs, 1H), 12.16 (bs, 1H). IR (KBr) 3160, 2940, 1610, 1580, 1510, 1450, 1400, 1370, 1290, 1240, 1180, 1160, 1040, 920, 900, 840, 810. MS(DCI/NH$_3$)m/e 461(M+H)$^+$, 212, 134 cm$^{-1}$. Anal calcd. for $C_{29}H_{21}FN_4O.1.25 H_2O$: C, 72.11; H, 4.9; N, 11.6. Found: C, 72.01; H, 5.17; N, 11.27.

EXAMPLE 12

Preparation of
1-N,N-Dimethylcarbamoyl-6-(4-fluorophenyl)-3-{3-[(1H-2-methylimidazo[4.5-c]pyrid-1-yl)methyl]-benzoyl}indole To a solution under N$_2$ of 6-(4-fluorophenyl)-3-{3-[(1H-2-methylimidazo[4.5-c]pyridyl)methyl]benzoyl}indole (921 mg, 2.00 mmol), prepared as in Example 11, in DMSO (2.0 mL), was added K$_2$CO$_3$ (138 mg, 1.00 mmol) and the resulting dark-yellow suspension was stirred for 30 min at ambient temperature. N,N-dimethylcarbamoyl chloride (36.7 μL, 4.00 mmol) was added and stirring was continued for 17 hours. The reaction was quenched with saturated aqueous NH$_4$Cl (0.60 mL), stirred for 30 min, and concentrated to dryness in vacuo. The residue was partitioned between saturated aqueous NH$_4$Cl and CH$_2$Cl$_2$. A small amount of brine was added and the layers were separated. The aqueous phase was extracted with CH$_2$Cl$_2$. The combined organic layers were dried over Na$_2$SO$_4$, filtered, and concentrated in vacuo. Chromatography on silica gel (3% methanol/CH$_2$Cl$_2$) gave 1-N,N-dimethylcarbamoyl-6-(4-fluorophenyl)-3-{3-[(1H-2-methylimidazo[4.5-c]pyrid-1-yl)methyl]benzoyl}indole (89 mg, 84%). mp. 244.5°–245.5° C. $^1$H NMR (DMSO-d6, 300 MHz) δ2.58 (s, 3H), 3.03 (s, 6H), 5.65 (bs, 2H), 7.32 (t, 2H, J=7.5 Hz), 7.40 (bd, 1H, J=7.5 Hz), 7.56 (bt, 1H, J=7.5 Hz), 7.59–7.67 (c, 3H), 7.73–7.83 (c, 4H), 8.02 (s, 1H), 8.24–8.31 (c, 2H), 8.85 (bs, 1H). IR (KBr) 3440, 1700, 1630, 1610, 1580, 1550, 1510, 1480, 1430, 1390, 1230, 1180, 820 cm$^{-1}$. MS (DCI/NH$_3$) m/e 532 (M+H)$^+$, 134, 106. Anal calcd for $C_{32}H_{27}FN_5O_2.2H_2O$: C, 67.7; H, 5.32; N, 12.34. Found C, 67.78; H, 4.93; N, 12.18.

EXAMPLE 13

Preparation of
3-{4-[(1H-2-Methylimidazo[4.5-c]pyrid-1-yl)methyl]-benzoyl}indole Step 1: potassium 4-(1H-2-methylimidazo[4,5-c]pyrid-1-ylmethyl)benzoate.

The desired compound was prepared as described in Example 6, step 1, except substituting methyl 4-(1H-2-methylimidazo[4,5-c]pyrid-1-ylmethyl)benzoate, prepared as in Example 3, step 2, for 4-(3H-2-methylimidazo[4,5-c]pyrid-3-ylmethyl)benzoate.
Step 2: 6-3-{4-[(1H-2-Methylimidazo[4.5-c]pyrid-1-yl)methyl]benzoyl}indole.

The desired compound was prepared according to the method of Example 6, step 2, except substituting potassium 4-(1H-2-methylimidazo[4,5-c]pyrid-1-ylmethyl)benzoate, prepared as in step 1, for potassium 4-(3H-2-methylimidazo [4,5-c] pyrid-3-ylmethyl)benzoate, and preparing the indolylzinc reagent from indole instead of 6-(4-fluorophenyl)indole. $^1$H NMR (DMSO-d6, 300 MHz) δ2.59 (s, 3H), 5.64 (s, 2H), 7.2–7.3 (m, 4H), 7.45–7.55 (m, 1H), 7.63 (dd, 1H, J=5.4, 1.1 Hz), 7.75–7.80 (m, 2H), 7.91 (s, 1H), 8.2–8.3 (m, 1H), 8.31 (d, 1H, J=5.4 Hz), 8.87 (s, 1H), 12.08 (br s, 1H). MS (FAB) m/e 367 (M+1)$^+$.

EXAMPLE 14

Preparation of
1-N,N-Dimethylcarbamoyl-3-{4-[(1H-2-methylimidazo-[4.5-c]pyrid-1 -yl)methyl]benzoyl}indole.

The desired compound was prepared according to the method of Example 2, except substituting 3-[4-(1H-2-methylimidazo[4.5-c]pyrid-1-ylmethyl)benzoyl]indole, prepared as in Example 13, for 6-(4-fluorophenyl)-3-{4-[(1H-2-methylbenzimidazolyl)methyl]benzoyl}indole. $^1$H NMR (DMSO-d6, 300 MHz) δ 2.59 (s, 3H), 3.00 (s, 6H), 5.66 (s, 2H), 7.25–7.45 (m, 4H), 7.6–7.7 (m, 2H), 7.8–7.9 (m, 2H), 8.10 (s, 1H), 8.2–8.3 (m, 1H), 8.31 (d, 1H, J=5.7 Hz), 8.87 (s, 1H). MS (FAB) m/e 438 (M+1)$^+$. Anal calcd for $C_{26}H_{23}N_5O_2.0.7H_2O$: C, 69.38; H, 5.46; N, 15.56. Found: C, 69.69; H, 5.60; N, 14.96.

EXAMPLE 15

Preparation of
3-[4-(5H-2-Methylimidazo[4.5-c]pyrid-5,ylmethyl)-benzoyl]indole

The desired compound was prepared according to the method of Example 1, steps 3 and 4, except substituting methyl 4-(5H-2-methylimidazo[4,5-c]pyrid-5-ylmethyl)benzoate, prepared as in Example 3, step 2, for methyl 4-(1H-2-methylbenzimidazol-1-ylmethyl)benzoate, and substituting indolylzinc for 6-(4-fluorophenyl)indolylzinc. $^1$H NMR (DMSO-d6, 300 MHz) δ2.55 (s, 3H), 5.81 (s, 2H), 7.2–7.3 (m, 2H), 7.50–7.55 (m, 1H), 7.56 (d, 2H, J=8.1 Hz), 7.71 (d, 1H, J=6.6 Hz), 7.81 (d, 2H, J=8.7 Hz), 7.91 (d, 1H, J=3.0 Hz), 8.2–8.3 (m, 1H), 8.32 (dd, 1H, J=6.6, 1.5 Hz), 12.21 (br s, 1H). MS (DCI/NH$_3$) m/e 367 (M+H)$^+$.

EXAMPLE 16

Preparation of
1-N,N-Dimethylcarbamoyl-3-[4-(5H-2-methylimidazo-[4.5-c]pyrid-5 -ylmethyl)benzoyl]indole The desired compound was prepared according to the method of Example 2, except substituting 3-[4-(5H-2-methylimidazo[4.5-c]pyrid-5-ylmethyl)benzoyl]indole, prepared as in Example 15, for 6-(4-fluorophenyl)-3-{4-[(1H-2-methylbenzimidazolyl)methyl]benzoyl}indole. $^1$H NMR (DMSO-d6, 300 MHz) δ2.52 (s, 3H), 3.00 (s, 6H), 5.76 (s, 2H), 7.3–7.4 (m, 2H), 7.5–7.65 (m, 4H), 7.8–7.9 (m, 2H), 8.11 (s, 1H), 8.15–8.30 (m, 2H), 8.99 (s, 1H). MS (DCI/NH$_3$)m/e 438(M+H)$^+$.

EXAMPLE 17

Preparation of
3-{3-[(1H-2-Methylimidazo[4.5-c]pyrid-1-yl)methyl]-benzoyl}indole The desired compound was prepared according to the method of Example 1, steps 3 and 4, except substituting methyl 3-(1H-2-methylimidazo[4,5-c]pyrid-1-ylmethyl)benzoate, prepared as in Example 11, step 1, for 4-(1H-2-methylbenzimidazol-1-ylmethyl)benzoate, and preparing the indolylzinc reagent from indole instead of 6-(4-fluorophenyl)indole. mp 246.1°–247.3° C. $^1$H NMR (DMSO-d6, 300 MHz) δ2.60 (s, 3H), 5.64 (s, 2H), 7.19–7.30 (c, 2H), 7.32(bd, 1H, J=7.5 Hz), 7.48–7.54 (c, 2H), 7.57 (bs, 1H), 7.62 (dd, 1H, J=6,1 Hz), 7.72 (bd, 1 H,J=7.5 Hz), 7.83 (s, 1H), 8.18–8.22 (c, 1H), 8.30 (d, 1H, J=6 Hz), 8.85 (s, 1H), 12.06 (bs, 1H). IR (KBr) 1610, 1580, 1520, 1490, 1440, 1390, 1370, 1340, 1290, 1180, 1170, 1150, 1030, 890, 830, 750 cm$^{-1}$. MS (DCI/NH$_3$) m/e 367 (M+H)$^+$, 118.

EXAMPLE 18

Preparation of 1-N,N-Dimethylcarbamoyl-3-{3-[(1H-2-methylimidazo-[4.5-c]pyrid-1-yl)methyl]benzoyl}indole The desired compound was prepared according to the method of Example 2, except substituting 3-{3-[(1H-2-methylimidazo[4.5-c]pyrid-1-yl)methyl]benzoyl}indole, prepared as in Example 17, for 6-(4-fluorophenyl)-3-{4-[(1H-2-methylbenzimidazolyl)methyl]benzoyl}indole. mp 192°–194° C. $^1$H NMR (DMSO-d6, 300 MHz) δ2.59 (s, 3H), 3.01 (s, 6H), 5.64 (s, 2H), 7.32–7.43 (c, 3H), 7.51–7.66 (c, 4H), 7.79 (bd, 1H, J=7.5 Hz), 7.98 (s, 1H), 8.21–8.32 (c, 2H), 8.85 (bs, 1H). IR (KBr) 3440, 1700, 1630, 1610, 1580, 1530, 1480, 1450, 1390, 1230, 1180, 1160, 1080, 1030, 760 cm$^{-1}$. MS (DCI/NH$_3$) m/e 438 (M+H)$^+$, 296, 118.

EXAMPLE 19

Preparation of 3-{3-[(3H-2-Methylimidazo[4.5-c]pyrid-3-yl)methyl]benzoyl}indole The desired compound was prepared according to the method of Example 17, except substituting methyl 3-(3H-2-methylimidazo[4,5-c]pyrid-3-ylmethyl)benzoate, prepared as in Example 11, step 1, for methyl 3-(1H-2-methylimidazo[4,5-c]pyrid-1-ylmethyl)benzoate. mp 210°–212° C. $^1$H NMR (DMSO-d6, 300 MHz) δ2.63 (s, 3H), 5.71 (s, 2H), 7.20–7.30 (c, 2H), 7.37 (bd, 1H, J=7.5 Hz), 7.49–7.59 (c, 3H), 7.60 (bs, 1H), 7.72 (bd, 1H, J=7.5 Hz), 7.84 (s, 1H), 8.19–8.25 (c, 1H), 8.30 (d, 1H, J=6 Hz), 8.88 (s, 1H), 12.09 (bs, 1H). IR (KBr) 1610, 1580, 1520, 1510, 1470, 1460, 1450, 1400, 1370, 1310, 1230, 1170, 830, 750 cm$^{-1}$. MS (DCI/NH$_3$) m/e 367 (M+H)$^+$, 134, 118. Anal calcd for C$_{23}$H$_{19.5}$N$_4$O$_{1.75}$: C, 72.7; H, 5.17; N, 14.75. Found: C, 72.38; H, 4.87; N, 14.66.

EXAMPLE 20

Preparation of 1-N,N-Dimethylcarbamoyl-3-{3-[(3H-2-methylimidazo[4.5-c]pyrid-3-yl)methyl]benzoyl}indole The desired compound was prepared according to the method of Example 2, except substituting 3-{3-[(3H-2-methylimidazo[4.5-c]pyrid-3-yl)methyl]benzoyl}indole, prepared as in Example 19, for 6-(4-fluorophenyl)-3-{4-[(1H-2-methylbenzimidazolyl)methyl]benzoyl}indole. mp 134°–136° C. $^1$H NMR (DMSO-d6, 300 MHz) δ2.63 (s, 3H), 3.02 (s, 6H), 5.70 (s, 2H), 7.32–7.44 (c, 3H), 7.52–7.58 (c, 2H), 7.64 (d, 1H, J=4.5 Hz), 7.68 (s, 1H), 7.79 (d, 1H, J=4.5 Hz), 8.01 (s, 1H), 8.24 (d, 1H, J=4.5 Hz), 8.29 (d, 1H, J=3.0 Hz), 8.86 (s, 1H). IR (KBr) 1700, 1630, 1610, 1580, 1530, 1505, 1450, 1390, 1310, 1230, 1190, 1180, 1080, 830, 780 cm$^{-1}$. MS (DCI/NH$_3$) m/e 438 (M+H)$^+$. Anal calcd for C$_{26}$H$_{26}$FN$_5$O$_{3.5}$: C, 67.22; H, 5.64; N, 15.08. Found: C, 67.25; H, 5.25; N, 14.89.

EXAMPLE 21

Preparation of 3-{4-[(1H-2-Methylimidazo[4.5-c]pyrid-1-yl)]benzoyl}indole

The desired compound was prepared according to the method of Example 9, except preparing the indolylzinc reagent from indole instead of 6-(4-fluorophenyl)indole. mp 239.5°–240.5° C. $^1$H NMR (DMSO-d6, 300 MHz) δ2.58 (s, 3H), 7.26–7.32 (c, 2H), 7.34 (dd, 1H, J=1, 6 Hz), 7.53–7.58 (c, 1H), 7.72–7.80 (c, 2H), 8.01–8.07 (c, 2H), 8.07–8.11 (c, 1H), 8.29–8.93 (c, 1H), 8.95 (d, 1H), J=6 Hz), 8.95 (s, 1H), 12.17 (bs, 1H). IR (KBr) 3160, 1600, 1575, 1565, 1510, 1490, 1430, 1380, 1210, 895 cm$^{-1}$. MS (DCI/NH$_3$) m/e 353 (M+H)$^+$, 281, 253, 130, 118.

EXAMPLE 22

Preparation of 1-N,N-Dimethylcarbamoyl-3-{4-[(1H-2-methylimidazo[4.5-c]pyrid-1-yl)]benzoyl}indole The desired compound was prepared according to the method of Example 2, except substituting 3-{4-[(1H-2-methylimidazo[4.5-c]pyrid-1-yl)]benzoyl}indole, prepared as in Example 21, for 6-(4-fluorophenyl)-3-{4-[(1H-2-methylbenzimidazolyl)methyl]benzoyl}indole. mp 241.1°–241.7° C. $^1$H NMR (DMSO-d6, 300 MHz) δ2.58 (s, 3H), 3.06 (s, 6H), 7.35 (dd, 1H, J=1.5, 6 Hz), 7.39–7.45 (c, 2H), 7.64–7.69 (c, 1H), 7.76–7.83 (c, 2H), 8.08–8.14 (c, 2H), 8.28 (s, 1H), 8.32–8.39 (c, 2H), 8.96 (bs, 1H). MS (DCI/NH$_3$) m/e 424 (M+H)$^+$.

EXAMPLE 23

Preparation of 1-N,N-Dimethylcarbamoyl-6-(4-fluorophenyl)-3-]-(3H-2-methylimidazo[4.5-c]pyrid-3-yl)methylcarbonyl]indole Step 1: 1-Chloro-2-[6-(4-fluorophenyl)indol-3-yl]ethanone.

A solution under N$_2$ of 6-(4-fluorophenyl)indole (10.0 g, 47.4 mmol), prepared as described in WO 93/01813, in dioxane (36 mL) and pyridine (5.8 mL, 71.8 mmol) was heated to 60° C. and a solution of chloroacetyl chloride (5.7 mL, 71.1 mmol) in dioxane (12.5 mL) was added dropwise over 1 hour. The reaction mixture was stirred for 1 hour at 60° C., then cooled to ambient temperature and poured into a mixture of H$_2$O (200 mL) and ether (50 mL). The resulting orange precipitate was filtered and dried. Recrystallization from ethanol, followed by rinsing with cold ether gave 1-chloro-2-[6-(4-fluorophenyl)indol-3-yl]ethanone (2.8 g) as an orange solid.

Step 2: 1-Chloro-2-[1-N,N-dimethycarbamoyl-6-(4-fluorophenyl)indol-3-yl]ethanone.

The desired compound was prepared according to the method of Example 2, except substituting 1-chloro-2-[6-(4-fluorophenyl)indol-3-yl]ethanone, prepared as in step 1, for 6-(4-fluorophenyl)-3-{4-[(1H-2-methylbenzimidazolyl)methyl]benzoyl}-indole.

Step 3: 1-N,N-Dimethylcarbamoyl-6-(4-fluorophenyl)-3-[(3H-2-methylimidazo[4.5-c]pyrid-3-yl)methylcarbonyl]indole To a solution under N$_2$ of 1H-2-methylimidazo[4,5-c]pyridine (372 mg, 2.80 mmol), prepared as in Example 3, step 1, in a mixture of THF (13.2 mL) and 1,3-dimethyl-3, 4,5,6-tetrahydro-2(1H)-pyrimidinole (DMPU, 4.4 mL) was added NaH (81 mg, 3.36 mmol) and the resulting yellow suspension was stirred for 50 min at ambient temperature. In a separate flask, a mixture of 1-chloro-2-[1-N,N-dimethylcarbamoyl-6-(4-fluorophenyl)indol-3-yl]ethanone (1.00 g, 2.80 mmol), prepared as in step 2, and NaBr (577 mg, 5.60 mmol) in THF (13.2 mL) was cooled to 0° C. The imidazopyridine/NaH suspension was then added via syringe, and the orange solution was warmed slowly to ambient temperature and stirred for 17 hours. The reaction mixture was partitioned between $H_2O$ (75 mL) and ethyl acetate (75 mL). The layers were separated and the aqueous phase was washed with ethyl acetate (2×75 mL), and the combined organic extracts were washed with $H_2O$ (2×75 mL). The combined aqueous extracts were extracted twice with ethyl acetate. The combined organic layers were dried over $MgSO_4$, filtered, and concentrated in vacuo. Chromatography on silica gel (8% methanol/$CH_2Cl_2$) gave 1-N,N-dimethylcarbamoyl-6-(4-fluorophenyl)-3-[(3H-2-methylimidazo[4.5-c]pyrid-3-yl)methylcarbonyl]indole (92.6 mg). $^1$H NMR (DMSO-d6, 300 MHz) δ2.54 (s, 3H), 3.15 (s, 6H), 5.99 (s, 2H), 7.25–7.35 (m, 2H), 7.58 (d, 1H, J=5.4 Hz), 7.64 (dd, 1H, J=8.1, 1.2 Hz), 7.7–7.8 (m, 2H), 7.87 (s, 1H), 8.19 (d, 1H, J=8.1 Hz), 8.30 (d, 1H, J=5.4 Hz), 8.84 (s, 1H), 8.95 (s, 1H). MS (DCI/$NH_3$) m/e 456 (M+H)$^+$. Anal calcd for $C_{26}H_{22}FN_5O_2 \cdot 1.7H_2O$: C, 64.24; H, 5.27; N, 14.41. Found: C, 64.58; H, 5.20; N, 13.81.

EXAMPLE 24

Preparation of
1-N,N-Dimethylcarbamoyl-6-(4-fluorophenyl)-3-[(1H-2-methylimidazo[4.5-c]pyrid-1-yl)methylcarbonyl]indole.

The desired compound (58.3 mg) was obtained from the chromatography described in Example 23. $^1$HNMR(DMSO-d6, 300MHz) δ2.52 (s, 3H), 3.15 (s, 6H), 5.93 (s, 2H), 7.25–7.35 (m, 2H), 7.56 (d, 1H, J=5.4 Hz), 7.63 (d, 1H, J=9.3 Hz), 7.7–7.8 (m, 2H), 7.89 (s, 1H), 8.19 (d, 1H, J=8.4 Hz), 8.28 (d, 1H, 5.7 Hz), 8.86 (s, 1H), 8.95 (s, 1H). MS (DCI/$NH_3$) m/e 456 (M+H)$^+$. Anal calcd for $C_{26}H_{22}FN_5O_2 \cdot 2H_2O$: C, 63.53; H, 5.33; N, 14.25. Found: C, 63.62; H, 5.04; N, 13.93.

EXAMPLE 25

Preparation of
1-N,N-Dimethylcarbamoyl-3-[(3H-2-methylimidazo-[4.5-c]pyrid-3-yl)methylcarbonyl]indole The desired compound was prepared according to the method of Example 23, except substituting indole for 6-(4-fluorophenyl)indole and separating the isomers by chromatography on silica gel using 5% methanol/$CH_2Cl_2$ instead of 8% methanol/$CH_2Cl_2$. $^1$H NMR (DMSO-d6, 300 MHz) δ2.52 (s, 3H), 3.12 (s, 6H), 5.97 (s, 2H), 7.3–7.45 (m, 2H), 7.55–7.60 (m, 1H), 7.65–7.70 (m, 1H), 8.14 (d, 1H, J=7.8 Hz), 8.29 (dd, 1H, J=5.4,1.2 Hz), 8.23 (s, 1H), 8.92 (s, 1H). MS (DCI/$NH_3$) m/e 362 (M+H)$^+$.

EXAMPLE 26

Preparation of
1-N,N-Dimethylcarbamoyl-3-[(1H-2-methylimidazo-[4.5-c]pyrid-1-yl)methylcarbonyl]indole The desired compound was obtained in the chromatography described in Example 25. $^1$H NMR (DMSO-d6, 500 MHz) δ2.52 (s, 3H), 3.12 (s, 6H), 5.90 (s, 2H), 7.30–7.45 (m, 2H), 7.54 (dd, 1H, J=5.4,1.2 Hz), 7.67 (d, 1H, 8.1 Hz) 8.14 (d, 1H, J=7.2 Hz), 8.27 (d, 1H, J=5.4 Hz), 8.85 (s, 1H), 8.91 (s, 1H). MS (FAB) m/e 362 (M+1)$^+$. Anal calcd for $C_{20}H_{19}N_5O_2 \cdot 1.1H_2O$: C, 63.01; H, 5.61; N, 18.37. Found: C, 63.25; H, 5.61; N, 18.03.

EXAMPLE 27

Preparation of
1-N,N-Dimethylcarbamoyl-3-{4-[(3H-2-methylimidazo[4.5-b]pyrid-3-yl)methyl]benzoyl}indole Step 1: 1H-2-Methylimidazo[4.5-b]pyridine.

A solution of 2,3-diaminopyridine (10.0 g, 91.7 mmol) in acetic anhydride (83.4 mL, 888 mmol) was heated at 140° C. for 18.5 hours. The black solution was then cooled to ambient temperature and stirred for 17 hours. The reaction mixture was cooled in an ice bath and a solution of NaOH (70.8 g, 1.77 mol) in $H_2O$ (200 mL) was added dropwise to bring the reaction to pH 9. The reaction mixture was poured into ethyl acetate (200 mL) and the layers were separated. The organic phase was washed with $H_2O$ (2×100 mL), dried over $MgSO_4$, filtered, and concentrated in vacuo. The aqueous phase was transferred to a continuous extraction vessel and extracted with ethyl acetate for 17 hours. The resulting ethyl acetate solution was as combined with the product from above and concentrated in vacuo. Chromatography on silica gel (10% methanol/$CH_2Cl_2$ gave 5.07 g of 1H-2-methylimidazo[4,5-b]pyridine.

Step 2: Methyl 4-(3 H-2-methylimidazo[4.5-b]pyrid-3-ylmethyl)benzoate.

To a solution under $N_2$ of 1H-2-methylimidazo[4,5-b]pyridine (3.00 g, 22.6 mmol), prepared as in step 1, in THF (113 mL) and DMF (25 mL) was added NaH (758 mg, 31.6 mmol). The resulting suspension was stirred for 1 hour at ambient temperature, then cooled to 0° C. and a solution of methyl (4-bromomethyl)benzoate (6.20 g, 27.1 mmol) in THF (30 mL) was added via cannula. The cold bath was removed and the reaction mixture was stirred for 70 hours at ambient temperature. The reaction mixture was partitioned between $H_2O$ (100 mL) and ethyl acetate (200 mL). The organic phase was extracted with $H_2O$ (75 mL), and the combined aqueous phases were extracted with ethyl acetate (3×150 mL). The combined organic phases were dried over $MgSO_4$, filtered, and concentrated in vacuo. Chromatography on silica gel (2%, then 5%, then 7% methanol/$CH_2Cl_2$) gave methyl 4-(3H-2-methylimidazo[4.5-b]pyrid-3-ylmethyl)benzoate (2.89 g), methyl 4-(1H-2-methylimidazol[4,5-b]pyrid-1-ylmethyl)benzoate (1.36 g), and methyl 4-(4H-2-methylimidazo[4.5-b]pyrid-4-ylmethyl)benzoate (1.16 g).

Step 3: 3-{4-[(3H-2-Methylimidazo[4.5-b]pyrid-3-yl)methyl]benzoyl}indole.

The desired compound was prepared according to the method of Example 15, except substituting methyl 3-(3H-2-methylimidazo[4.5-b]pyrid-3-ylmethyl)benzoate, prepared as in step 2, for methyl 4-(5H-2-methylimidazo[4,5-c]pyrid-5-ylmethyl)benzoate.

Step 4: 1-N,N-Dimethylcarbamoyl-3-{4-[(3H-2-methylimidazo[4.5-b]pyrid-3-yl)methyl]benzoyl}indole.

The desired compound was prepared according to the method of Example 2, except substituting 3-{4-[(3H-2-methylimidazo[4.5-b]pyrid-1-yl)methyl]benzoyl}indole, prepared as in step 3, for 6-(4-fluorophenyl)-3-{4-[(1H-2-methylbenzimidazolyl)methyl]benzoyl}indole. $^1$H NMR (DMSO-d6, 300 MHz) δ 2.57 (s, 3H), 3.00 (s, 6H), 5.63 (s, 2H), 7.28 (dd, 1H, J=8.1,5.1 Hz), 7.3–7.4 (m, 4H), 7.6–7.7 (m, 1H), 7.83 (apparent d, 2H, J=7.8 Hz), 8.00 (dd, 1H, J=7.8, 1.2 Hz), 8.11 (s, 1H), 8.2–8.3 (m, 1H), 8.30–8.35 (m, 1H). MS (DCI/NH₃) m/e 438 (M+H)⁺.

EXAMPLE 28

Preparation of
1-N,N-Dimethylcarbamoyl-3-{4-[(1H-2-methylimidazo[4.5-b]pyrid-1-yl)methyl]benzoyl}indole The desired compound was prepared according to the method of Example 27, except substituting methyl 4-(1H-2-methylimidazo[4,5-b]pyrid-1-ylmethyl)benzoate, prepared as in Example 27, step 2, for methyl 4-(3H-2-methylimidazo[4,5-b]pyrid-3-ylmethyl)benzoate. ¹H NMR (DMSO-d6, 300 MHz) δ2.61 (s, 3H), 3.00 (s, 6H), 5.66 (s, 2H), 7.22 (dd, 1H, J=8.1, 4.8 Hz), 7.30–7.45 (m, 4H), 7.63 (d, 1H, J=8.1 Hz), 7.84 (apparent d, 2H, J=8.1 Hz), 7.98 (d, 1H, J=8.1 Hz), 8.10 (s, 1H), 8.25–8.30 (m, 1H), 8.35–8.40 (m, 1H). MS (DCI/NH₃) m/e 438 (M+H)⁺. Anal calcd for $C_{26}H_{23}N_5O_2 \cdot 1.9H_2O$: C, 66.20; H, 5.73; N, 14.85. Found: C, 66.49; H, 5.46; N, 14.34.

EXAMPLE 29

Preparation of
1-N,N-Dimethylcarbamoyl-3-{4-[1H-2-trifluoromethylimidazo[4.5-c]pyrid-1-yl)methyl]benzoyl}indole Step 1: 4-(N-tert-Butoxycarbonylaminomethyl)benzoic acid.

To a solution of 4-aminomethylbenzoic acid (11.1 g, 73.4 mmol) in 1N aqueous NaOH (100 mL) was added THF (100 mL) and di-tert-butyldicarbonate (16.8 g, 77.1 mmol). The reaction mixture was stirred for 2 hours at ambient temperature, then acidified to pH 2 and extracted 3 times with ethyl acetate. The combined organic layers were dried over MgSO₄, filtered, and concentrated in vacuo to give 4-(N-tert-butoxycarbonylaminomethyl)benzoic acid (18.3 g) as white crystals which was used without further purification.
Step 2: 3-[4-(N-tert-Butoxycarbonylaminomethyl)benzoyl] indole.

To a 0° C. solution of 4-(N-tert-butoxycarbonylaminomethyl)benzoic acid (5.07 g, 20.2 mmol) in CHCl₃ was added DMF (200 µL) and oxalyl chloride (1.94 mL, 22.2 mmol). The cold bath was removed and the reaction mixture was stirred for 2 hours at ambient temperature, after which it was concentrated in vacuo. The residue was taken up in CH₂Cl₂ and added to a solution of indolylzinc (50.5 mmol, prepared as described in Example 1, step 4, except substituting indole for 6-(4-fluorophenyl)indole). The reaction mixture was stirred for 16 hours at ambient temperature, then quenched with saturated aqueous NH₄Cl and partitioned between CH₂Cl₂ and saturated aqueous NH₄Cl. The solids were filtered off and rinsed with CH₂Cl₂. The layers were separated and the organic phase was dried over MgSO₄, filtered, and concentrated in vacuo. Pure 3-[4-(N-tert-butoxycarbonylaminomethyl)benzoyl]indole (3.10 g) was obtained by chromatography on silica gel (60% ether/hexanes, then 60% ethyl acetate/hexanes).
Step 3: 1-N,N-Dimethylcarbamoyl-3-[4-(N-tert-butoxycarbonylaminomethyl)benzoyl]indole.

Sodium hydride (60% dispersion in mineral oil, 251 mg, 6.29 mmol) was washed twice with hexanes and added to a solution of 3-[4-(N-tert-butoxycarbonylaminomethyl)benzoyl]indole (1.00 g, 2.86 mmol), prepared as in step 2, in THF (40 mL). After stirring for 10 min, dimethylcarbamoyl chloride (315 µL, 3.43 mmol) was added and the reaction mixture was stirred for 10 min. The reaction mixture was poured into saturated aqueous NH₄Cl and extracted three times with ethyl acetate. The combined organic layers were dried over MgSO₄, filtered, and concentrated in vacuo. Chromatography on silica gel gave 1-N,N-dimethylcarbamoyl-3-[4-(N-tert-butoxycarbonylaminomethyl)benzoyl]indole (870 mg, 72%).
Step 4: 1-N,N-Dimethylcarbamoyl-3-(4-aminomethylbenzoyl)indole.

To a solution of 1-N,N-dimethylcarbamoyl-3-[4-(N-tert-butoxycarbonylaminomethyl)benzoyl]indole (870 mg, 2.07 mmol), prepared as in step 3, in ethyl acetate (10 mL) was added 3N aqueous HCl (2 mL). The reaction mixture was stirred for 17 hours at ambient temperature, and an additional 4 mL of 3N aqueous HCl was added. The reaction mixture was stirred for a further 10 hours and then was adjusted to pH 1 and extracted three times with ethyl acetate. The combined organic extracts were washed with H₂O, and the aqueous layers were combined, adjusted to pH 12, and extracted three times with CH₂Cl₂. The CH₂Cl₂ extracts were combined, dried over Na₂SO₄, filtered, and concentrated in vacuo to give 620 mg of 1-N,N-dimethylcarbamoyl-3-(4-aminomethylbenzoyl)indole which was used without further purification.
Step 5: 1-N,N-Dimethylcarbamoyl-3-[4-(N-3-nitropyridin-4-yl)aminomethylbenzoyl]indole.

To a solution of 1-N,N-dimethylcarbamoyl-3-(4-aminomethylbenzoyl)indole (0.620 g, 1.93 mmol), prepared as in step 4, in THF (10 mL) was added triethylamine (403 µL, 2.90 mmol) and 3-nitro-4-chloropyridine (0.300 g, 1.93 mmol), prepared as described by Wright, G. C., *J. Heterocyclic Chem.* 1976, 13, 601, and Kruger, S. and Mann, F. G., *J. Chem. Soc.* 2 1955, 758. The reaction mixture was heated for 17 hours at 45° C., then additional 3-nitro-4-chloropyridine (40 mg) was added and heating was continued for 2 hours at which all to the starting material was consumed. The reaction mixture was poured into a mixture of saturated aqueous NH₄Cl and brine and the aqueous phase was extracted twice with CH₂Cl₂. The combined organic layers were dried over MgSO₄, filtered, and concentrated in vacuo. Chromatography on silica gel (60% ethyl acetate/hexanes, then 10% methanol/CH₂Cl₂) gave 1-N,N-dimethylcarbamoyl-3-[4-(N-3-nitropyridin-4-yl)aminomethylbenzoyl]indole. (903 mg).
Step 6: 1-N,N-Dimethylcarbamoyl-3-[4-(N-3-aminopyridin-4-yl)aminomethylbenzoyl]indole.

A mixture of 1-N,N-dimethylcarbamoyl-3-[4-(N-3-nitropyridin-4-yl)aminomethylbenzoyl]indole (141 mg), prepared as in step 5, and 10% palladium on activated carbon (40 mg) in 5:1 ethanol/CH₂Cl₂ (10 mL) was stirred under 1 atmosphere of hydrogen for 4 hours. The reaction mixture was filtered through a pad of celite and the filtrate was concentrated in vacuo to give 131 mg of 1-N,N-dimethylcarbamoyl-3-[4-(N-3-aminopyridin-4-yl)aminomethylbenzoyl]indole which was used without further purification.
Step 7: 1-N,N-Dimethylcarbamoyl-3-{4-[1H-2-trifluoromethylimidazo[4.5-c]pyrid-1-yl)methyl]benzoyl}indole.

A mixture of 1-N,N-dimethylcarbamoyl-3-[4-(N-3-aminopyridin-4-yl)aminomethylbenzoyl]indole (131 mg), prepared as in step 6, trifluroacetic anhydride (1.0 mL), and trifluoroacetic acid (0.5 mL) was heated at 45° C. for 17 hours. The reaction mixture was cooled to ambient temperature and concentrated in vacuo. Chromatography on silica gel (ethyl acetate) gave 1-N,N-dimethylcarbamoyl-3-{4-[1H-2-trifluoromethylimidazo[4.5-c]pyrid-1-yl)methyl]benzoyl}indole (107 mg, 68% yield for steps 4 and 5). ¹H NMR (DMSO-d6, 300 MHz) δ2.99 (s, 6H), 5.89 (s, 2H), 7.30 (d, 2H, J=8.7 Hz), 7.32–7.42 (m, 2H), 7.61–7.63 (m, 1H), 7.84 (d. 2H, J=8.7 Hz), 7.85–7.88 (m,1H), 8.08 (s, 1H), 8.23–8.26 (m, 1H), 8.58 (d, 1H, J=6 Hz). MS (DCI/NH$_3$) m/e 492 (M+H)$^+$, 409, 306. Anal calcd for C$_{26}$H$_{20}$F$_3$N$_5$O$_2$.1.25 CF$_3$CO$_2$H: C, 53.99; H, 3.37; N, 11.04. Found: C, 53.76; H, 3.55; N, 11.10.

EXAMPLE 30

Preparation of
1-N,N-Dimethylcarbamoyl-6-3-{4-[1H-imidazo[4.5-c]-pyrid-1-yl)methyl]benzoyl}indole.

To a solution of 1-N,N-dimethylcarbamoyl-3-[4-(N-3-aminopyridin-4-yl)aminomethylbenzoyl]indole (44.9 mg, 0.11 mmol), prepared as in Example 29, step 5, in acetic acid (1.5 mL) was added ethyl (ethoxymethylene)cyanoacetate (27.6 mg, 0.16 mmol). The reaction mixture was heated at 90° C. for 4 hours, then cooled to ambient temperature and concentrated in vacuo. 1-N,N-dimethylcarbamoyl-6-3-{4-[1H-imidazo[4.5-c]pyrid-1-yl)methyl]benzoyl}indole (15.6 mg) was isolated by thin layer chromatography (10% methanol/CH$_2$Cl$_2$). $^1$H NMR (DMSO-d6, 300 MHz) δ 9.19 (s, 1H), 8.47 (d, 1H, J=5.7 Hz), 8.38 (m, 1H), 8.11 (s, 1H), 7.86 (2 H, d, J=8.4 Hz), 7.73 (s, 1H), 7.53 (m, 1H), 7.40 (m, 2H), 7.31 (m, 3H), 5.49 (s, 2H), 3.08 (s, 6H). MS (DCI/NH$_3$) m/e 424 (M+H)$^+$, 306, 120.

EXAMPLE 31

Preparation of
1-N,N-Dimethylcarbamoyl-3-{4-[1H-2-(2-propyl)-imidazo[4.5-c]pyrid-1-yl)methyl]benzoyl}indole Step 1: 1-N,N-Dimethylcarbamoyl-3-[4-(N-3-(2-propyl)aminopyridin-4-yl)-N-(2 -propyl)aminomethylbenzoyl]indole.

The desired compound (66.4 mg) was prepared according to the method of Example 29, step 6, except substituting isobutyric anhydride and isobutyric acid for trifluoroacetic anhydride and trifluoroacetic acid.
Step 2: 1-N,N-Dimethylcarbamoyl-3-{4-[1H-2-(2-propyl)imidazo[4.5-c]pyrid-1 -yl)methyl]benzoyl}indole-1-carboxylic acid dimethylamide.

A solution of 1-N,N-dimethylcarbamoyl-3-[4-(N-3-(2-propyl)aminopyridin-4-yl)-N-(2-propyl)aminomethylbenzoyl]indole (62.5 mg) in trifluoroacetic acid (1.0 mL) was heated at 70° C. for 17 hours. The reaction mixture was cooled to ambient temperature and concentrated in vacuo. 1-N,N-dimethylcarbamoyl-3-{4-[1H-2-(2-propyl)imidazo[4.5-c]pyrid-1-yl)methyl]benzoyl}indole (50.6 mg) was obtained by thin layer chromatography (7% methanol/CH$_2$Cl$_2$). $^1$H NMR (DMSO-d6, 300 MHz) δ1.31 (d, 6H, J=6.8 Hz), 3.01 (s, 6H), 3.47 (m, 1H), 5.92 (2H, s), 7.31 (d, 2H, J=8.4 Hz), 7.32–7.42 (m, 2H), 7.62 (d, 1H, J=7.5 Hz), 7.86 (d, 2H, J=8.4 Hz), 8.04 (s, 1H), 8.23 (d, 1H, J=7.5 Hz), 8.29 (d, 1H, J=6.4 Hz), 8.69 (d, 1H, J=6.4 Hz), 9.49 (s, 1H). MS (DCI/NH$_3$) m/e 466 (M+H)$^+$, 162. Anal calcd for C$_{28}$H$_{27}$N$_5$O$_2$.2.25H$_2$O: C, 66.45; H, 6.24; N, 12.73. Found: C, 66.80; H, 6.27; N, 13.84.

EXAMPLE 32

Preparation of
1-N,N-Dimethylcarbamoyl-3-{4-[1H-2-phenyl-imidazo[4.5-c]pyrid-1 -yl)methyl]benzoyl}indole.

To a solution of 1-N,N-dimethylcarbamoyl-3-[4-(N-3-aminopyridin-4-yl)aminomethylbenzoyl]indole (38 mg), prepared as in Example 29, step 5, in CH$_2$Cl$_2$ was added triethylamine and benzoyl chloride. The reaction mixture was stirred for 20 hours at ambient temperature and was then partitioned between CH$_2$Cl$_2$ and saturated aqueous NaHCO$_3$. The organic phase was dried over MgSO$_4$, filtered, and concentrated in vacuo. Pure 1-N,N-dimethylcarbamoyl-3-{4-[1H-2-phenylimidazo[4.5-c]pyrid-1-yl)methyl]benzoyl}indole (21 mg, 41% ) was obtained by thin layer chromatography (10% methanol/CH$_2$Cl$_2$). $^1$H NMR (CDCl$_3$, 300 MHz) δ3.09 (s, 6H), 5.58 (s, 2H), 7.20 (d, 2H, J=8.5 Hz), 7.24 (d, 1H, J=6 Hz), 7.36–7.44 (m, 2H), 7.50–7.58 (m, 4H), 7.71 (dd, 2H, J=7.8, 2.2 Hz), 7.79 (s, 1H), 7.85 (d, 2H, J=8.5 Hz), 8.38–8.41 (m, 1H), 8.46 (d, 1H, J=5.4 Hz), 9.21 (s, 1H). MS (DCI/NH$_3$) m/e 500 (M+H)$^+$, 318.

EXAMPLE 33

Preparation of
1-N,N-Dimethylcarbamoyl-3-{4-[1H-2-ethylimidazo-[4.5-c]pyrid-1-yl)methyl]benzoyl}indole.

The desired compound (66.4 mg) was prepared according to the method of Example 29, step 6, except substituting propionic anhydride and propionic acid for trifluoroacetic anhydride and trifluoroacetic acid. $^1$H NMR (DMSO-d6, 300 MHz) δ1.32 (t, 3H, J=7.5 Hz), 2.91 (q, 2H, J=7.5 Hz), 2.99 (s, 6H), 5.66 (s, 2H), 7.28 (d, 2H, J=8.1 Hz), 7.32–7.42 (m, 2H), 7.62 (d, 2H, J=6 Hz), 7.83 (d, 2H, J=8.1 Hz), 8.09 (s, 1H), 8.25 (dd, 1H, J=6.3, 2.1 Hz), 8.31 (d, 1H, J=6.3 Hz), 8.91 (s, 1H). MS (DCI/NH$_3$) m/e 452 (M+H)$^+$, 306. Anal calcd for C$_{27}$H$_{25}$N$_5$O$_2$.1H$_2$O: C, 69.06; H, 5.79; N, 14.91. Found: C, 69.07; H, 5.71; N, 14.76.

EXAMPLE 34

Preparation of
1-N,N-Dimethylcarbamoyl-3-{3-[(5H-2-methyl-imidazo[4.5-c]pyrid-5 -yl)methyl]benzoyl}indole.

The desired compound was prepared according to the method of Example 17, except substituting methyl 3-(5H-2-methylimidazo[4,5-c]pyrid-5-ylmethyl)benzoate, prepared as in Example 11, step 1, for methyl 3-(1H-2-methylimidazo[4,5-c]pyrid-1 -yl)methyl)benzoate. mp 230°–232° C. $^1$H NMR (DMSO-d6, 300 MHz) δ2.50 (s, 3H), 5.75 (s, 2H), 7.20–7.30 (c, 2H), 7.50–7.60 (c, 4H), 7.76 (d, 1H, J=4.5 Hz), 7.88 (s, 1H), 7.91(d, 1H, J=1.5 Hz), 8.20–8.23 (c, 2H), 9.00(s, 1H), 12.10 (bs,1H). IR (KBr) 1630, 1580, 1530, 1500, 1445, 1370, 1320, 1235, 1180, 1150 cm$^{-1}$. MS (DCI/NH$_3$) m/e 367 (M+H)$^+$, 134, 118.

EXAMPLE 35

Preparation of
1-N,N-Dimethylcarbamoyl-3-{3-[(5H-2-methylimidazo-[4.5-c]pyrid-5 -yl)methyl]benzoyl}indole The desired compound was prepared according to the method of Example 2, except substituting 3-{3-[(5H-2-methylimidazo[4.5-c]pyrid-5-yl)methyl]benzoyl}indole, prepared as in Example 34, for 6-(4-fluorophenyl)-3-{4-[(1H-2-methylbenzimidazolyl)methyl]benzoyl}indole. mp 194.4°–196.4° C. $^1$H NMR (DMSO-d6, 300 MHz) δ3.01 (s, 6H), 5.74 (s, 2H), 7.38 (dm, 2H, J=7.5, 1.5 Hz), 7.55–7.62 (c, 2H), 7.62–7.71 (c, 2H), 7.83 (dt, 1H, J=1, 7.5 Hz), 7.92 (bs, 1H), 8.07 (s, 1H), 8.19–8.28 (c, 2H), 9.00 (bs, 1H). IR (KBr) 1690, 1630, 1600, 1580, 1530, 1470, 1450, 1390, 1310, 1230, 1190, 1170, 1120, 1080 cm$^{-1}$. MS (DCI/NH$_3$)

m/e 438 (M+H)⁺. Anal calcd for C₂₆H₂₈N₅O₄.₅: C, 64.71; H, 5.85; N, 14.52. Found: C, 64.59; H, 5.45; N, 14.30.

EXAMPLE 36

Preparation of
1-N,N-dDimethylcarbamoyl-6-(4-fluorophenyl)-3-[(3H-2-methylimidazo[4.5-c]pyrid-3-yl)pent-5-ylcarbonyl]indole Step 1: 6-Bromo-1-[6-(4-fluorophenyl)-1-N,N-dimethylcarbamoylindol-3-yl]hexanone.

To a solution of 6-bromohexanoyl chloride (596 μL, 3.9 mmol) in CH₂Cl₂ was added AlCl₃ (1.00 g, 7.8 mmol) in a single portion and the reaction mixture was stirred for 1 hour at ambient temperature. A solution of 6-(4-fluorophenyl)-1-N,N-dimethylcarbamoylindole (1.00 g, 3.55 mmol), prepared as in Example 4, step 1, in CH₂Cl₂ (5 mL) was added dropwise and the solution was stirred for 1 hour at ambient temperature. The reaction mixture was partitioned between H₂O and CH₂Cl₂. The layers were separated and the aqueous phase was extracted twice with CH₂Cl₂. The combined organic layers were washed with saturated aqueous NaHCO₃, dried over MgSO₄, filtered, and concentrated in vacuo. Chromatography as on silica gel (CH₂Cl₂) gave 6-chloro-1-[6-(4-fluorophenyl)-1-N,N-dimethylcarbamoylindol-3-yl]hexanone (1.57 g) as an off-white solid.

Step 2: 1-N,N-Dimethylcarbamoyl-6-(4-fluorophenyl)-3-[(3H-2-methylimidazo[4.5-c]pyrid-3-yl)pent-5-ylcarbonyl]indole.

The desired compounds were prepared according to the method of Example 23, step 2, except substituting 6-chloro-1-[6-(4-fluorophenyl)-1-N,N-dimethylcarbamoylindol-3-yl]hexanone, prepared as in step 1, for 1-chloro-2-[1-N,N-dimethycarbamoyl-6-(4-fluorophenyl)indol-3-yl]ethanone. Chromatography on silica gel (2%, then 3%, then 4%, then 15% methanol/CH₂Cl₂) gave 1-N,N-dimethylcarbamoyl-6-(4-fluorophenyl)-3-[(3H-2-methylimidazo[4.5-c]pyrid-3-yl)pent-5-ylcarbonyl]indole (137 mg). ¹H NMR (DMSO-d6, 300 MHz) δ1.35–1.45 (m, 2H), 1.65–1.75 (m, 2H), 1.75–1.85 (m, 2H); 2.59 (s, 3H), 2.92 (t, 2H, J= 7.4 Hz), 3.07 (s, 6H), 4.29 (t, 2H, J=7.4 Hz), 7.25–7.35 (m, 2H), 7.50 (dd, 1H, J=5.4, 1.0 Hz), 7.59 (dd, 1H, J=8.4, 1.8 Hz), 7.7–7.8 (m, 4H), 8.25–8.35 (m, 2H), 8.58 (d, 1H, J=1.0 Hz). MS (DCI/NH₃) m/e 512 (M+H)⁺.

EXAMPLE 37

Preparation of
1-N,N-Dimethylcarbamoyl-6-(4-fluorophenyl)-3-[(1H-2-methylimidazo[4.5-c]pyrid-1-yl)pent-5-ylcarbonyl]indole.

The desired compound (184 mg) was obtained from the chromatography described in Example 36, step 2. ¹H NMR (DMSO-d6, 300 MHz) δ1.30–1.45 (m, 2H), 1.65–1.85 (m, 4H), 2.58 (s, 3H), 2.91 (t, 2H, J=7.4 Hz), 3.06 (s, 6H), 4.22 (t, 2H, J=7.4 Hz), 7.25–7.35 (m, 2H), 7.5–7.6 (m, 2H), 7.7–7.8 (m, 3H), 8.2–8.3 (m, 2H), 8.58 (s, 1H), 8.78 (d, 1H, J=1.0 Hz). MS (DCI/NH₃) m/e 512 (M+H)⁺. Anal calcd for C₃₀H₃₀FN₅O₂.0.8H₂O: C, 68.50; H, 6.05; N, 13.31. Found: C, 68.52; H, 5.99; N, 13.26.

EXAMPLE 38

Preparation of
1-N,N-Dimethylcarbamoyl-6-(4-fluorophenyl)-3-[(5H-2-methylimidazo[4.5-c]pyrid-5-yl)pent-5-ylcarbonyl]indole The desired compound (431 mg) was obtained in the chromatography described in Example 36, step 2. ¹H NMR (DMSO-d6, 300 MHz) δ1.3–1.4 (m, 2H), 1.65–1.75 (m, 2H), 1.9–2.0 (m, 2H), 2.51 (s, 1H), 2.93 (t, 2H, J=7.4 Hz), 3.07 (s, 6H), 4.42 (t, 2H, 7.1 Hz), 7.2–7.3 (m, 2H), 7.5–7.6 (m, 2H), 7.7–7.8 (m, 3H), 8.05 (dd, 1H, J=6.7, 1.3 Hz), 8.28 (d, 1H, J=8.4 Hz), 8.58 (s, 1H), 8.78 (d, 1H, J=1.3 Hz). MS (DCI/NH₃) m/e 512 (M+H)⁺.

EXAMPLE 39

Preparation of
1-N,N-Dimethylcarbamoyl-6-(4-fluorophenoxy)-3-{4-[(3H-2-methylimidazo[4.5-c]pyrid-3-yl)methyl]benzoyl}indole The desired compound was prepared according to the method of Example 4, except substituting 6-(4-fluorophenoxy)indole for 6-(4-fluorophenyl)indole. Chromatography on silica gel (2%, then 3%, then 4% methanol/CH₂Cl₂) gave 1-N,N-dimethylcarbamoyl-6-(4-fluorophenoxy)-3-{4-[(3H-2-methylimidazo[4.5-c]pyrid-3-yl)methyl]benzoyl}indole. ¹H NMR (DMSO-d6, 300 MHz) δ2.62 (s, 3H), 2.97 (s, 6H), 5.72 (s, 2H), 7.05–7.15 (m, 3H), 7.2–7.3 (m, 3H), 7.35 (apparent d, 2H, J=8.4 Hz), 7.59 (dd, 1H, J=5.4, 1.2 Hz), 7.85 (apparent d, 2H, J=8.4 Hz), 8.08 (s, 1H), 8.23 (d, 1H, J=8.7 Hz), 8.31 (d, 1H, J=5.7 Hz), 8.90 (d, 1H, 1.2 Hz). MS (DCI/NH₃) m/e 548 (M+H)⁺.

EXAMPLE 40

Preparation of
1-N,N-Dimethylcarbamoyl-6-(4-fluorophenoxy)-3-{4-[(1H-2-methylimidazo[4.5-c]pyrid-1-yl)methyl]benzoyl}indole The desired compound was obtained in the chromatography described in Example 39. ¹H NMR (DMSO-d6, 300 MHz) δ2.59 (s, 3H), 2.97 (s, 6H), 5.66 (s, 2H), 7.05–7.10 (m, 3H), 7.2–7.3 (m, 3H), 7.30 (apparent d, 2H, J=8.4 Hz), 7.63 (dd, 1H, J=5.7, 1.0 Hz), 7.84 (apparent d, 2H, J=8.4 Hz), 8.08 (s, 1H), 8.23 (d, 1H, J=8.4 Hz), 8.31 (d, 1H, J=5.7 Hz), 8.87 (s, 1H). MS (DCI/NH₃) m/e 548 (M+H)⁺. Anal calcd for C₃₂H₂₆N₅O₃F: C, 67.52; H, 5.03; N, 12.30. Found: C, 67.57; H, 4.79; N, 12.01.

EXAMPLE 41

Preparation of
1-N,N-Dimethylcarbamoyl-6-phenylmethyl-3-{4-[(3H-2-methylimidazol[4.5-c]pyrid-3-yl)methyl]benzoyl}indole The desired compound was prepared according to the method of Example 4, except substituting 6-phenylmethylindole for 6-(4-fluorophenyl)indole. 1-N,N-dimethylcarbamoyl-6-phenylmethyl-3-{4-[(3H-2-methylimidazo[4.5-c]pyrid-3-yl)methyl]benzoyl}indole was isolated by chromatography on silica gel (3%, then 4%, then 5% methanol/CH₂Cl₂). ¹H NMR (DMSO-d6, 300 MHz) δ2.62 (s, 3H), 2.98 (s, 6H), 4.08 (s, 2H), 5.71 (s, 2H), 7.1–7.3 (m, 6H), 7.33 (apparent d, 2H, J= 7.8 Hz), 7.49 (s, 1H), 7.58 (dd, 1H, J=5.4, 1.0 Hz), 7.83 (apparent d, 2H, J=8.7 Hz), 8.04 (s, 1H), 8.14 (d, 1H, J=8.1 Hz), 8.3 1 (d, 1H, J=5.4 Hz), 8.88 (d, 1H, J=1.0 Hz). MS (DCI/NH₃) m/e 528 (M+H)⁺.

EXAMPLE 42

Preparation of
1-N,N-Dimethylcarbamoyl-6-phenylmethyl-3-
{4-[(1H-2-methylimidazo[4.5-c]pyrid-1-yl)methyl]-
benzoyl}indole The desired compound was isolated in the chromatography described in Example 41. $^1$H NMR (DMSO-d6, 300 MHz) δ2.58 (s, 3H), 2.98 (s, 6H), 4.08 (s, 2H), 5.65 (s, 2H), 7.15–7.30 (m, 8H), 7.49 (s, 1H), 7.62 (dd, 1H, J=5.4, 1.2 Hz), 7.82 (apparent d, 2H, J=8.1 Hz), 8.03 (s, 1H), 8.14 (d, 1H, J=8.1 Hz), 8.31 (d, 1H, J=5.4 Hz), 8.86 (d, 1H, J=1.0 Hz). MS (DCI/NH$_3$) m/e 528 (M+H)$^+$.

EXAMPLE 43

Preparation of
1-N,N-Dimethylcarbamoyl-4-methoxycarbonyl-3-
{4-[(3H-2-methylimidazo[4.5-c]pyrid-3-yl)methyl]-
benzoyl}indole Step 1: 4-methoxycarbonylindole.

To a 0° C. solution of indole-4-carboxylic acid (1.00 g, 6.21 mmol) in ether (60 mL) was added diazomethane (0.3M solution in ether, 24.8 mL, 7.45 mmol) and the reaction mixture was stirred for 0.5 hours at 0° C. An additional 20 mL of diazomethane solution was then added and stirring was continued for 1 hour at 0° C. The reaction mixture was quenched with formic acid (1.0 mL) and concentrated in vacuo to give 4-methoxycarbonylindole (1.1 g) as an off white powder.

Step 2: 1-N,N-Dimethylcarbamoyl-4-methoxycarbonyl-3-
{4-[(3H-2-methylimidazo[4.5c]pyrid-3-yl)methyl]
benzoyl}indole.

The desired compound was prepared according to the method of Example 4, except substituting 4-methoxycarbonylindole, prepared as in step 1, for 6-(4-fluorphenylindole). 1-N,N-dimethylcarbamoyl-4-methoxycarbonyl-3-{4-[(3H-2-methylimidazo[4.5-c]pyrid-3-yl)methyl]benzoyl}indole was isolated by chromatography on silica gel (3%, then 5%, then 6% methanol/CH$_2$Cl$_2$). $^1$H NMR (DMSO-d6, 300 MHz) δ2.60 (s, 3H), 3.02 (s, 6H), 3.47 (s, 3H), 5.70 (s, 2H), 7.32 (apparent d, 2H, J=8.1 Hz), 7.4–7.5 (m, 1H), 7.56 (dd, 1H, J=2.1, 1.0 Hz), 7.56–7.58 (m, 1H), 7.85 (apparent d, 2H, J=8.1 Hz), 7.86 (dd, 1H, J=8.1, 1.2 Hz), 8.11 (s, 1H), 8.30 (d, 1H, J=5.7 Hz), 8.86 (d, 1H, J=1.0 Hz). MS (DCI/NH$_3$) m/e 496 (M+H)$^+$. Anal calcd for C$_{28}$H$_{25}$N$_5$O$_4$.1.8 H$_2$O: C, 63.70; H, 5.46; N, 13.26. Found: C. 63.68; H, 5.12; N, 12.95.

EXAMPLE 44

Preparation of
1-N,N-Dimethylcarbamoyl-4-methoxycarbonyl-3-
{4-[(1H-2-methylimidazol[
4.5-c]pyrid-1-yl)methyl]benzoyl}indole The desired compound was isolated in the chromatography described in Example 43. $^1$H NMR (DMSO-d6, 300 MHz) δ2.57 (s, 3H), 3.02 (s, 6H), 3.47 (s, 3H), 5.64 (s, 2H), 7.28 (apparent d, 2H, J=8.4 Hz), 7.4–7.5 (m, 1H), 7.55–7.60 (m, 2H), 7.84 (apparent d, 2H, J=8.4 Hz), 7.86 (dd, 1H, J=8.4, 1.2 Hz), 8.10 (s, 1H), 8.30 (d, 1H, J=5.7 Hz), 8.86 (d, 1H, J=1.0 Hz). MS (DCI/NH$_3$) m/e 496 (M+H)$^+$. Anal calcd for C$_{28}$H$_{25}$N$_5$O$_4$.1.9 H$_2$O: C, 63.48; H, 5.48; N, 13.22. Found: C. 63.69; H, 5.08; N, 12.73.

EXAMPLE 45

Preparation of
1-N,N-Dimethylcarbamoyl-5-phenylmethoxy-3-
{4-[(1H-2-methylimidazo[4.5-c]pyrid-1-yl)methyl]-
benzoyl}indole The desired compound is prepared according to the method of Example 4, except substituting 5-benzyloxyindole for 6-(4-fluorophenyl)indole.

EXAMPLE 46

Preparation of
1-N,N-Dimethylcarbamoyl-6-(4-methoxyphenyl)-3-
{4-[(1H-2-methylimidazo[4.5-c]pyrid-1-yl)methyl]-
benzoyl}indole The desired compound is prepared according to the method of Example 4, except substituting 6-(4-methoxyphenyl)indole, prepared as described in WO 93/01813, for 6-(4-fluorophenyl)indole.

EXAMPLE 47

Preparation of
1-N,N-Dimethylcarbamoyl-6-(pyrid-3-yl)-3-
{4-[(1H-2-methylimidazo[4.5-c]pyrid-1-yl)methyl]-
benzoyl}indole The desired compound is prepared according to the method of Example 4, except substituting 6-(pyrid-3-yl)indole, prepared as described in WO 93/01813, for 6-(4-fluorophenyl)indole.

EXAMPLE 48

Preparation of
1-N,N-Dimethylcarbamoyl-6-bromo-3-{4-[(1H-2-
methylimidazo[4.5-c]pyrid-1-yl)methyl]benzoyl}indole The desired compound is prepared according to the method of Example 4, except substituting 6-bromoindole for 6-(4-fluorophenyl)indole.

EXAMPLE 49

Preparation of
1-N,N-Dimethylcarbamoyl-6-chloro-3-{4-[(1H-2-
methylimidazo[4.5-c]pyrid-1-yl)methyl]benzoyl}indole The desired compound is prepared according to the method of Example 4, except substituting 6-chloroindole for 6-(4-fluorophenyl)indole.

EXAMPLE 50

Preparation of
1-N,N-Dimethylcarbamoyl-5-methoxy-3-
{4-[(1H-2-methylimidazo[
4.5-c]pyrid-1-yl)methyl]benzoyl}indole The desired compound is prepared according to the method of Example 4, except substituting 5-methoxyindole for 6-(4-fluorophenyl)indole.

EXAMPLE 51

Preparation of
1-N,N-Dimethylcarbamoyl-6-(4-fluorophenyl)-3-
{5-[(1H-2-methylimidazo[4.5-c]pyrid-1-yl)methyl]-
thien-2-oyl}indole Step 1: 5-Methyl-2-carboxymethylthiophene.

The desired compound was prepared according to the method of Example 43, step 1, except substituting 5-methyl-2-thiophenecarboxylic acid for indole-4-carboxylic acid.

Step 2: 5-Bromomethyl-2-carboxymethylthiophene.

To a solution of N-bromosuccinimide (5.94 g, 33 mmol) in hexanes (16 mL) was added 5-methyl-2-carboxymethylthiophene (5.0 g, 32 mmol), prepared as in step 1, followed by 1 drop of perchloric acid. The reaction mixture was stirred for 22 hours at ambinet temperature and then partitioned between ethyl acetate and saturated aqueous HaHSO$_3$ solution. The organic phase was dried over Na$_2$SO$_4$, filtered, and concentrated in vacuo to give 6.17 g of 5-bromomethyl-2-carboxymethylthiophene as a yellow oil.

Step 3: 5-[(1H-2-Methylimidazo[4.5-c]pyrid-1-yl)methyl]-2-carboxymethylthiophene.

To a solution of 1H-2-methylimidazo[4,5-c]pyridine (2.00 g, 15 mmol), prepared as in Example 3, step 1, in DMSO (150 mL) was added potassium tert-butoxide (1.7 g, 17 mmol) and the reaction mixture was stirred until all of the base dissolved (~15 min). After a further 5 min, 5-bromomethyl-2-carboxymethylthiophene (4.0 g, 17 mmol), prepared as in step 2, was added. The reaction mixture was stirred for 2 hours at ambient temperature and then partitioned between ethyl acetate (2 L), and 1:1 pH 7 buffer/brine (1 L). The organic phase was dried over MgSO$_4$, filtered, and concentrated in vacuo. Chromatography on silica gel (3%, then 4%, then 5% methanol/CH$_2$Cl$_2$) gave 5-[(1H-2-methylimidazo[4.5-c]pyrid-1-yl)methyl]-2-carboxymethylthiophene.

Step 4: 5-[(1H-2-Methylimidazo[4.5-c]pyrid-1-yl)methyl]-2-thiophenecarboxylic acid.

To a solution of 5-[(1H-2-methylimidazo[4.5-c]pyrid-1-yl)methyl]-2-carboxymethylthiophene (0.360 g, 1.25 mmol) in THF (15 mL) and H$_2$O (2 mL) was added lithium hydroxide hydrate (0.114 g, 2.70 mmol). The reaction mixture was stirred for 6 hours at ambient temperature and then quenched with 4N HCl/dioxane (1 mL) and partioned between ethyl acetate and H$_2$O. The aqueous phase was extracted with CH$_2$Cl$_2$. The combined organic layers were dried over MgSO$_4$, filtered, and concentrated in vacuo to give 5-[(1H-2-methylimidazo[4.5-c]pyrid-1-yl)methyl]-2-thiophenecarboxylic acid (0.46 g) as an oil.

Step 5: 6-(4-Fluorophenyl)-3-{5-(1H-2-methylimidazo[4.5-c]pyrid-1-yl)methyl]thien-2-oyl}indole.

The desired compound was prepared according to the method of Example 1, step 4, except substituting 5-[(1H-2-methylimidazo[4.5-c]pyrid-1-yl)methyl]-2 -thiophenecarboxylic acid, prepared as in step 4, for 4-(1H-2-methylbenzimidazol-1-ylmethyl)benzoic acid.

Step 6: 1-N,N-dimethylcarbamoyl-6-(4-fluorophenyl)-3-{5-[(1H-2-methylimidazo[4.5-c]pyrid-1-yl)methyl]thien-2-oyl}indole.

The desired compound was prepared according to the method of Example 2, except substituting 6-(4-fluorophenyl)-3-{5-[(1H-2-methylimidazo[4.5-c]pyrid-1 -yl)methyl]thien-2-oyl}indole, prepared as in step 5, for 6-(4-fluorophenyl)-3-{4-[(1H-2-methylbenzimidazolyl)methyl]benzoyl}indole. mp 200–203 C. $^1$H NMR (CDCl$_3$, 300 MHz) δ9.06 (s, 1H), 8.44 (d, 1H J=5.6 Hz), 8.32 (d, 1H, J= 8.5 Hz), 7.94 (s, 1H), 7.71 (d, 1H, J=1.5 Hz), 7.64 (d, 1H, J=3.6 Hz), 7.58 (m, 3H), 7.32 (d, 1H, J=4.5 Hz), 7.14 (t, 2H, J=8.8 Hz), 6.92 (d, 1H, J=3.3 Hz), 5.54 (s, 2H), 3.12 (s, 6H), 2.73 (s, 3H). MS (DCI/NH$_3$) m/e 538 (M+H)$^+$, 205.

EXAMPLE 52

Preparation of
1-N,N-Dimethylcarbamoyl-6-(4-fluorophenyl)-3-
{5-[(1H-2-methylimidazo[4.5-c]pyrid-1-yl)methyl]-
fur-2-oyl}indole Step 1: 5-hydroxymethyl-2-carboethoxyfuran.

A solution of 5-acetoxymethyl-2-ethoxycarbonylfuran (Maybridge Chemical Co., Ltd., Tintagel, Cornwall, UK., 0.54 g, 2.5 mmol) and K$_2$CO$_3$ (0.352 g, 2.6 mmol) in 5:1THF/H$_2$O (30 mL), was stirred for 17 hours at ambient temperature. The reaction mixture was concentrated in vacuo and the residue partitioned between CH$_2$Cl$_2$ and saturated aqueous NaHCO$_3$. The organic phase was dried over MgSO$_4$, filtered, and concentrated in vacuo to give 5-hydroxymethyl-2-carboethoxyfuran (0.32 g) as a yellow liquid which was used without further purification.

Step 2: 5-Methanesulfonyloxymethyl-2-carboethoxyfuran.

To a 0° C. solution of 5-hydroxymethyl-2-carboethoxyfuran (2.94 g, 17.3 mmol), prepared as in step 1, in CH$_2$Cl$_2$ (50 mL) was added 2,6-lutidine (2.50 mL, 21.5 mmol) and methanesulfonyl chloride (1.50 mL, 19.0 mmol). The reaction mixture was stirred for 40 min at 0° C., then the cold bath was removed and stirring was continued for 2 hours. The reaction mixture was extracted with 1N aqueous HCl and saturated aqueous NaHCO$_3$, and the organic phase was dried over MgSO$_4$, filtered, and concentrated in vacuo to give 5-methanesulfonyloxymethyl-2-carboethoxyfuran (4.0 g) as a yellow oil which was used without further purification.

Step 3: 5-Azidomethyl-2-carboxyethylfuran.

To a suspension of NaN$_3$ (1.3 g, 20 mmol) in CH$_3$CN (50 mL) was added the 5-methanesulfonyloxymethyl-2-carboethoxyfuran (4.0 g, 16 mmol) obtained in step 2, and the suspension was warmed to 60° C. and heated for 68 hours. The reaction mixture was cooled to ambient temperature and extracted with saturated aqueous NaHCO$_3$ and CH$_2$Cl$_2$. The aqueous phase was extracted with ethyl acetate. The combined organic layers were dried over MgSO$_4$, filtered, and concentrated in vacuo to give 5-azidomethyl-2-carboxyethylfuran (3.6 g) as an orange oil.

Step 4: 5-Aminomethyl-2-carboxyethylfuran.

Treatment of a solution in ethanol (50 mL) at ambient temperature of 5-azidomethyl-2-carboxyethylfuran (585 mg, 3.00 mmol), prepared as in step 3, with Raney nickel 2800 and 4 atmospheres of H$_2$ for 24 hours, followed by filtration of the reaction mixture and concentration in vacuo gave 5-aminomethyl-2-carboxyethylfuran (0.50 g) as a yellow oil.

Step 5: 5-[N-(3-Nitropyrid-4-yl)aminomethyl]-2-carboxyethylfuran.

The desired compound was prepared by heating a solution in CH$_3$CN of 5-aminomethyl-2-carboxyethylfuran with 4-ethoxy-3-nitropyridine.

Step 6: 5-[N-(3-aminopyrid-4-yl)aminomethyl]-2-carboxyethylfuran.

The desired compound was prepared by reduction of 5-[N-(3-nitropyrid-4-yl)aminomethyl]-2-carboxyethylfuran, prepared as in step 5, with tin(II) chloride.

Step 7: 5-[(1H-2-Methylimidazo[4.5-c]pyrid-1-yl)methyl[-2-ethoxycarbonylfuran.

The desired compound was prepared by reaction of 5-[N-(3-aminopyrid-4-yl)aminomethyl]-2-carboxyethylfuran, prepared as in step 6, with acetic anhydride and acetic acid as described in Example 3, step 1.

Step 8: 1-N,N-Dimethylcarbamoyl-6-(4-fluorophenyl)-3-{5-[(1H-2-methylimidazo[4.5-c]pyrid-1-yl)methyl]fur-2-oyl}indole.

The desired compound was prepared according to the method of Example 51, steps 4–6, except substituting 5-[(1H-2-methylimidazo[4.5-c]pyrid-1-yl)methyl]-2-ethoxycarbonylfuran, prepared as in step 7, for 5-[(1H-2-methylimidazo[4.5-c]pyrid-1-yl)methyl]-2-carboxymethylthiophene. $^1$H NMR (CDCl$_3$, 300 MHz) $\delta$9.03 (s, 1H), 8.44 (d, 1H J=6 Hz), 8.32 (d, 1H, J=8 Hz), 8.04 (s, 1H), 7.71 (d, 1H, J=2 Hz), 7.64 (d, 1H, J=4 Hz), 7.58 (m, 2H), 7.32 (d, 1H, J=4.5 Hz), 7.14 (t, 2H, J=8.8 Hz), 6.82 (d, 1H, J=3 Hz), 6.52 (d, 1H, J=3 Hz), 5.45 (s, 2H), 3.07 (s, 6H), 2.73 (s, 3H). MS (DCI/NH$_3$) m/e 522 (M+H)$^+$, 171.

EXAMPLE 53

Preparation of
1-N,N-Dimethylcarbamoyl-6-(4-fluorophenyl)-3-{4-[(3H-2-methylimidazo[4.5-c]pyrid-3-yl)methyl]-thiazo-2-oyl}indole Step 1: 4-Chloromethyl-2-ethoxycarbonylthiazole.

A mixture of ethyl thiooxamate (1.0 g, 7.5 mmol) and 1,3-dichloroacetone (1.0 g, 8.3 mmol) in ethanol (25 mL) was heated at reflux for 15 hours. The reaction mixture was cooled to ambient temperature and concentrated in vacuo. The residue was partitioned between CH$_2$Cl$_2$ and saturated aqueous NaHCO$_3$. The organic phase was washed with brine, dried over MgSO$_4$, filtered, and concentrated in vacuo to give an orange oil. 4-chloromethyl-2-ethoxycarbonylthiazole was obtained as a yellow oil by chromatography on silica gel (10% ether/hexanes).

Step 2: Potassium 4-chlormethyl-2-thiazocarboxylate.

To a solution of 4-chloromethyl-2-ethoxycarbonylthiazole (354 mg, 1.73 mmol), prepared as in step 1, in ethanol (10 mL) was added KOH (116 mg, 2.07 mmol). The reaction mixture was stirred for 1 hour at ambient temperature, then concentrated in vacuo and azeotroped twice with THF to give potassium 4-chlormethyl-2-thiazocarboxylate.

Step 3: 4-Chloromethyl-2-thiazocarbonyl chloride.

The desired compound is prepared by treatment of a suspension of potassium 4-chlormethyl-2-thiazocarboxylate in THF/DMF with oxalyl chloride.

Step 4: 1-N,N-Dimethylcarbamoyl-6-(4-fluorophenyl)-3-{4-[(3H-2-methylimidazo[4.5-c]pyrid-3-yl)methyl]thiazo-2-oyl}indole.

The desired compound is prepared according to the method of Example 4, except substituting 4-chloromethyl-2-thiazocarbonyl chloride, prepared as in step 3, for 4-chloromethyl benzoyl chloride.

EXAMPLE 54

Preparation of
1-N,N-Dimethylcarbamoyl-6-(4-fluorophenyl)-3-{4-[(1H-2-methylimidazo[4.5-c]pyrid-1-yl)methyl]-thiazo-2-oyl}indole.

The desired compound is isolated by chromatography on silica gel from the mixture of products formed in Example 53, step 4.

EXAMPLE 55

Preparation of
1-N,N-Dimethylcarbamoyl-6-(4-fluorophenyl)-3-{4-[(1H-2-methylimidazo[4.5-c]pyrid-1-yl)methyl]-benzoyloxime}indole The desired compound is prepared by reaction of 1-N,N-dimethylcarbamoyl-6-(4-fluorophenyl)-3-{4-[(1H-2-methylimidazo[4.5-c]pyrid-1-yl)methyl]benzoyl}indole, prepared as in Example 4, with hydroxylamine hydrochloride and pyridine in ethanol as described in WO 93/01813.

EXAMPLE 56

Preparation of
1-N,N-Dimethylcarbamoyl-6-(4-fluorophenyl)-3-{4-[(1H-2-methylimidazo[4.5-c]pyrid-1-yl)methyl]-benzoylhydrazone}indole The desired compound is prepared by treatment of 1-N,N-dimethylcarbamoyl-6-(4-fluorophenyl)-3-{4-[(1H-2-methylimidazo[4.5-c]pyrid-1-yl)methyl]benzoyl}indole, prepared as in Example 4, with hydrazine as described in WO 93/01813.

EXAMPLE 57

Preparation of
1-N,N-Dimethylcarbamoyl-3-{4-[(1H-2-methyl-imidazo[4.5-c]pyrid-1-yl)methyl]phenylsulfonyl}indole Step 1: 3-(4-methylthiophenyl)indole.

To a −10° C. solution of indole (5.85 g, 50 mmol) in CH$_2$Cl$_2$ (50 mL) was added triethylamine (7.0 mL, 50 mmol). In a separate flask a solution of p-tolyldisulfide (6.16 g, 25 mmol) in CH$_2$Cl$_2$ (50 mL) was cooled to −20° C. and sulfuryl chloride (2.0 mL, 25 mmol) was added over 10 min. The cold bath was removed and the reaction mixture was stirred for 1 hour and then was added to the indole/triethylamine solution over 15 min. The resulting solution was warmed to ambient temperature and stirred for 17 hours. The reaction mixture was washed with H$_2$O and brine, dried over MgSO$_4$, filtered, and concentrated in vacuo. The residue was taken up in toluene and filtered through a plug of silica gel. The filtrate was diluted with an equal volume of hexanes and the resulting solid was collected to give 4.43 g of the desired material. The mother liquors were concentrated in vacuo and the residue was purified by chromatography on silica gel (10% ethyl acetate/hexanes). The material from the chromatography was combined with the original solid and recrystallized from toluene/hexanes to give 7.41 g (62% yield) of 3-(4-methylthiophenyl)indole. mp 125°–126.4° C.

Step 2: 1-Phenylsulfonyl-3-(4-methylthiophenyl)indole.

To a solution of 3-(4-methylthiophenyl)indole (7.34 g, 30.7 mmol), prepared as in step 1, in dimethoxyethane (75 mL) was added powdered KOH (85%, 7.01 g, 125 mmol) and benzenesulfonyl chloride (4.25 mL, 33.3 mmol). A white precipitate formed immediately and the reaction mixture became quite warm. The reaction mixture was stirred for 1 hour during which time it cooled to ambient temperature. Water (50 mL) was added and the mixture was extracted with ethyl acetate. The organic phase was washed with H$_2$O and brine, dried over Na$_2$SO$_4$, filtered, and concentrated in vacuo. 1-phenylsulfonyl-3-(4-methylthiophenyl)indole (8.89 g, 76% yield) was obtained by chromatography on silica gel (10%, then 20% ethyl acetate/hexanes).

Step 3: 1-Phenylsulfonyl-3-(4-methylphenylsulfonyl)indole.

To a solution of 1-phenylsulfonyl-3-(4-methylthiophenyl)indole (8.89 g, 23.4 mmol) in glacial acetic acid (15 mL) was added 30% $H_2O_2$ solution (2.45 g, 72 mmol) and the resulting 2-phase mixture was heated at reflux for 30 min during which time it became a solid mass. The reaction mixture was cooled to ambient temperature and diluted with $H_2O$ and ethyl acetate and the solid was filtered off. The filtrate layers were separated and the organic phase was washed with saturated aqueous $NaHCO_3$, $H_2O$, and brine, dried over $Na_2SO_4$, filtered, and concentrated in vacuo. The residue was triturated with ethyl acetate/ether and the resulting solid was combined with the solid obtained above and recrystallized from ethyl acetate to give 8.15 g of 1-phenylsulfonyl-3-(4-methylphenylsulfonyl)indole. mp 188.9°–189.7° C.

Step 4: 1-Phenylsulfonyl-3-[(4-bromomethyl)phenylsulfonyl]indole.

To a suspension of 1-phenylsulfonyl-3-(4-methylphenylsulfonyl)indole (7.33 g, 17.8 mmol) and N-bromosuccinimide (3.20 g, 17.9 mmol) in $CCl_4$ (750 mL) was added benzoyl peroxide (100 mg, 0.40 mmol) and the reaction mixture was warmed to reflux, during which time it became homogenous. The reaction mixture was heated for 3 hours at reflux, cooled to ambient temperature, stirred for 17 hours, and concentrated in vacuo. Pure (1.14 g, mp 194°–195.5° C.), and 75% pure (3.74 g) 1-phenylsulfonyl-3-[(4-bromomethyl)phenylsulfonyl]indole was obtained by chromatography on silica gel (20%, then 30%, then 50% $CH_2Cl_2$/toluene) followed by recrystallization from toluene/hexanes.

Step 5: 1-Phenylsulfonyl-3-[(4-(di-tert-butoxycarbonyl)aminomethyl)phenylsulfonyl]indole.

To a suspension in DMF (10 mL) of potassium bis(tert-butoxycarbonyl)amide (1.78 g, 6.99 mmol), prepared as described by Allan, R. D., et al, *J. Chem. Soc. Perkin Trans.* I, 1983, 2983, was added a solution of 1-phenylsulfonyl-3-[(4-bromomethyl)phenylsulfonyl]indole (2.8 g, 5.7 mmol), prepared as in step 4, in DMF (12 mL). The reaction mixture was heated at 50° C. for 2 hours, then cooled to ambient temperature and diluted with ethyl acetate (20 mL). The suspension was filtered and the filtrate concentrated in vacuo. The residue was taken up in ethyl acetate and washed with 1N aqueous $NaHSO_4$, $H_2O$, 5% aqueous $NaHCO_3$, $H_2O$, and brine, dried over $Na_2SO_4$, filtered, and concentrated in vacuo. Chromatography on silica gel (1:1 toluene/$CH_2Cl_2$, then $CH_2Cl_2$, then 5% ethyl acetate/$CH_2Cl_2$), followed by recrystallization from toluene/hexanes gave 1-phenylsulfonyl-3-[(4 -(di-tert-butoxycarbonyl)aminomethyl)phenylsulfonyl]indole (3.10 g, 85% yield). mp 175.5°–177° C.

Step 6: 1-Phenylsulfonyl-3-[(4-aminomethyl)phenylsulfonyl]indole.

A mixture of 1-phenylsulfonyl-3-[(4-(di-tert-butoxycarbonyl)aminomethyl)phenylsulfonyl]indole (3.00 g, 4.79 mmol), prepared as in step 5, $CH_2Cl_2$ (5 mL), and trifluoroacetic acid (5 mL) was stirred for 45 min at ambient temperature. The reaction mixture was concentrated in vacuo and the residue partitioned between ethyl acetate (150 mL) and 1M aqueous $Na_2CO_3$. The aqueous phase was extracted twice with ethyl acetate. The combined organic layers were washed with $H_2O$ and brine, and concentrated in vacuo to give 1-phenylsulfonyl-3-[(4-aminomethyl)phenylsulfonyl]indole (2.10 g) which was used without further purification.

Step 7: 3-[(4-(N-3-Nitropyrid-4-yl)aminomethyl)phenylsulfonyl]indole.

A solution of 1-phenylsulfonyl-3-[(4-aminomethyl)phenylsulfonyl]indole (2.10 g, 4.79 mmol), prepared in step 6, and 4-ethoxy-3-nitropyridine (0.894 g, 5.31 mmol) in ethanol (20 mL) and triethylamine (1 mL) was heated at reflux for 70 hours. The reaction mixture was cooled to ambient temperature and diluted with ethyl acetate (250 mL). The organic phase was washed twice with $H_2O$ and once with brine. The combined aqueous washings were extracted with ethyl acetate. The combined organic as layers were dried over $Na_2SO_4$, filtered, and concentrated in vacuo. Chromatography on silica gel (ethyl acetate, then 0.2% ethanol/ethyl acetate) followed by recrystallization from ethyl acetate/ether gave 3-[(4-(N-3-nitropyrid-4-yl)aminomethyl)phenylsulfonyl]indole (350 mg, 23% yield). mp 97°–102° C.

Step 8: 3-{4-[(1H-2-Methylimidazo[4.5-c]pyrid-1-yl)methyl]phenylsulfonyl}indole.

A mixture of iron powder (140 mg), 3-[(4-(N-3-nitropyrid-4-yl)aminomethyl)phenylsulfonyl]indole (483 mg, 0.88 mmol), 1M aqueous $NH_4Cl$ (5 mL), and $CH_3CN$ (10 mL) was heated at reflux for 2 hours. The reaction mixture was filtered hot and the filter cake was rinsed with hot methanol. The filtrate was concentrated to a volume of ~2 mL. The liquid was decanted and the residue dried to give crude 3-[(4-(N-3-aminopyrid-4-yl)aminomethyl)phenylsulfonyl]indole (670 mg). To this material was added acetic acid (3 mL) and acetic anhydride (3 mL) and the mixture was heated at reflux for 2 hours. The reaction mixture was concentrated in vacuo and the residue partitioned between 4N aqueous $NH_4OH$ and ethyl acetate/$CH_2Cl_2$. The organic phase was washed with $H_2O$ and brine, dried over $Na_2SO_4$, filtered, and concentrated in vacuo. Chromatography on silica gel (7%, then 10% methanol/$CH_2Cl_2$) followed by recrystallization from methanol/$H_2O$ gave 3-{4-[(1H-2-methylimidazo[4.5-c]pyrid-1-yl)methyl]phenylsulfonyl}indole (327 mg). mp 291°–293° C.

Step 9: 1-N,N-Dimethylcarbamoyl-3-{4-[(1H-2-methylimidazo[4.5-c]pyrid-1-yl)methyl]phenylsulfonyl}indole.

The desired compound was prepared according to the method of Example 2, except substituting 3-{4-[(1H-2-methylimidazo[4.5-c]pyrid-1-yl)methyl] phenylsulfonyl}indole, prepared as in step 8, for 6-(4-fluorophenyl)-3-{4-[(1H-2-methylbenzimidazolyl)methyl] benzoyl}indole, and substituting 1,2-dimethoxyethane for THF/DMF. $^1$H NMR (CDCl$_3$, 300 MHz) δ2.54 (s, 3H), 3.09 (s, 6H), 5.36 (s, 2H), 7.10 (dd, 1H, J=6.0, 0.9 Hz), 7.12 (d, 2H, J=8.4 Hz), 7.29 (td, 1H, J=7.5, 1.5 Hz), 7.58 (dt, 1H, J=8.4, 2.4 Hz), 7.87 (dt, 1H, J=7.5, 2.4 Hz), 7.95 (t, 1H, J=1.8 Hz), 7.96 (s, 1H), 7.99 (t, 1H, J=1.8 Hz), 8.33 (d, 1H, J=6.0), 9.01 (s, 1H). MS (DCI/NH$_3$) m/e 474 (M+H)$^+$. Anal Calcd for $C_{25}H_{23}N_5O_3S \cdot 0.5H_2O$: C, 52.65; H, 5.26, N, 13.53. Found C, 62.29; H, 5.31; N, 13.71. S: calcd 6.19, found 6.22.

EXAMPLE 58

Preparation of
1-Methyl-3-{4-[(1H-2-methylimidazo[4.5-c]-pyrid-1-yl)methyl]phenylsulfonylamino}indole Step 1: 1-Methyl-3-[4-(azidomethyl)phenylsulfonylamino]indole.

A mixture of 4-azidomethylphenylsulfonyl azide (2.93 g, 12.3 mmol), prepared by reaction of p-toluenesulfonyl chloride with N-bromosuccinimide followed by sodium azide, and 1-methylindole was heated at 55° C. for 6 hours. Pure 1-methyl-3-[4-(azidomethyl)phenylsulfonylamino]indole was obtained by chromatography on silica gel (1:1 CH₂Cl₂/hexanes, then CH₂Cl₂, then 1.5% methanol/CH₂Cl₂).

Step 1: 1-Methyl-3-[4-(aminomethyl)phenylsulfonylamino]indole.

To a solution of 1-methyl-3-[4-(azidomethyl)phenylsulfonylamino]indole (674 mg, 1.97 mmol), prepared as in step 1, in 8:2 THF/H₂O (10 mL) was added triphenylphosphine (1.03 g, 3.9 mmol) and the reaction mixture was stirred for 17 hours at ambient temperature. The reaction mixture was concentrated in vacuo and the residue was partitioned between ethyl acetate and brine. The organic phase was dried over Na₂SO₄, filtered, and concentrated in vacuo to give 1-methyl-3-[4-(aminomethyl)phenylsulfonylamino]indole (1.68 g) as a yellow-orange foam.

Step 3: 1-Methyl-3-{4-[(1H-2-methylimidazo[4.5-c]pyrid-1-yl)methyl]phenylsulfonylamino}indole.

The desired compound is prepared according to the method of Example 52, steps 5–8, except substituting 1-methyl-3-[4-(aminomethyl)phenylsulfonylamino]indole, prepared as in step 2, for 5-aminomethyl-2-carboxyethylfuran.

EXAMPLE 59

Preparation of 1-p-Toluenesulfonyl-6-(4-fluorophenyl)-3-{4-[(1H-2-methylimidazo[4.5-c]pyridyl)methyl]benzoyl}-indole.

The desired compound was prepared according to the method of Example 4, except substituting p-toluenesulfonyl chloride for N,N-dimethylcarbamoyl chloride. ¹H NMR (DMSO-d6, 300 MHz) δ2.32 (s, 3H), 2.61 (s, 3H), 5.69 (s, 2H), 7.30–7.45 (m, 6H), 7.64 (dd, 1H, J=5.4, 1.2 Hz), 7.70 (dd, 1H, J=8.4, 1.8 Hz), 7.7–7.8 (m, 2H), 7.91 (apparent d, 2H, J=8.4 Hz), 8.05–8.10 (m, 3H), 8.21 (d, 1H, J=9.0 Hz), 8.27 (s, 1H), 8.33 (d, 1H, J=5.4 Hz), 8.88 (d, 1H, J=1.2 Hz). MS (DCI/NH₃) m/e 615 (M+H)⁺. Anal calcd for C₃₆H₂₇FN₄O₃S.1.4H₂O: C, 67.57 H, 4.69; N, 8.76. Found: C, 67.55; H, 4.51; N, 8.72.

EXAMPLE 60

Preparation of 1-(Morpholin-4-ylcarbonyl)-6-(4-fluorophenyl)-3-{-4-[(1H-2-methylimidazo[4.5-c]pyridyl)methyl]benzoyl}indole.

The desired compound was prepared according to the method of Example 2, except substituting 6-(4-fluorophenyl)-3-{4-[(1H-2-methylimidazo[4.5-c]pyrid-1-yl)methyl]benzoyl}indole for 6-(4-fluorophenyl)-3-{4-[(1H-2-methylbenzimidazolyl)methyl]benzoyl}indole, and substituting 4-morpholinecarbonyl chloride for N,N-dimethylcarbamoyl chloride. ¹H NMR (DMSO-d6, 300 MHz) δ 2.60 (s, 3H), 3.5–3.6 (m, 4H), 3.6–3.7 (m, 4H), 5.67 (s, 2H), 7.3–7.4 (m, 4H), 7.6–7.7 (m, 2H), 7.7–7.8 (m, 2H), 7.87 (apparent d, 2H, J=8.1 Hz), 7.85–7.90(narrow m, 1H), 8.12 (s, 1H), 8.30 (d, 1H, J=8.4 Hz), 8.32 (d, 1H, J=5.4 Hz), 8.87 (s, 1H). MS (DCI/NH₃) m/e 574 (M+H)⁺.

EXAMPLE 61

Preparation of 1-(N,N-Dimethylcarbamoylmethyl)-6-(4-fluorophenyl)-3-{4-[(1H-2-methylimidazo[4.5-c]pyridyl)methyl]benzoyl}indole.

The desired compound was prepared according to the method of Example 2, except substituting 6-(4-fluorophenyl)-3-{4-[(1H-2-methylimidazo[4.5-c]pyrid-1-yl)methyl]benzoyl}indole for 6-(4-fluorophenyl)-3-{4-[(1H-2-methylbenzimidazolyl)methyl]benzoyl}indole, and substituting N,N-dimethylchloroacetamide for N,N-dimethylcarbamoyl chloride. ¹H NMR (DMSO-d6, 300 MHz) δ2.60 (s, 3H), 2.84 (s, 3H), 3.09 (s, 3H), 5.76 (s, 2H), 7.25–7.35 (m, 4H), 7.56 (dd, 1H, J=8.4, 1.8 Hz), 7.76 (apparent d, 2H, J=8.4 Hz), 7.7–7.8 (m, 3H), 7.92 (s, 1H), 8.30 (d, 1H, J=8.1 Hz), 8.31 (d, 1H, J=5.4 Hz), 8.87 (s, 1H). MS (DCI/NH₃) m/e 546 (M+H)⁺.

The compounds represented in Table 3 are prepared from 6-(4-fluorophenyl)-3-{4-[(1H-2-methylimidazo[4.5-c]pyridyl)methyl]benzoyl}indole by the methods described in Examples 59–61 and WO 93/01813.

TABLE 3

| Example | R² |
|---|---|
| 62 | —CH₃ |
| 63 | ![structure: acetyl-O-tBu] |
| 64 | ![structure: C(O)OCH₃] |
| 65 | ![structure: C(O)O-phenyl] |
| 66 | ![structure: C(O)NH₂] |
| 67 | ![structure: C(O)NHCH₃] |
| 68 | ![structure: C(O)N(CH₃)phenyl] |
| 69 | ![structure: C(O)N(CH₃)CH₂CH₂N(CH₃)₂] |

TABLE 3-continued

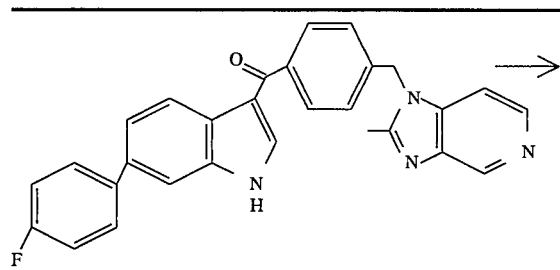

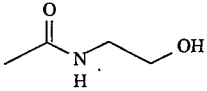

| Example | R² |
|---|---|
| 70 | 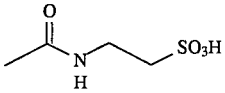 |
| 71 | 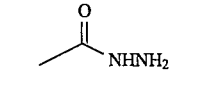 |
| 72 | 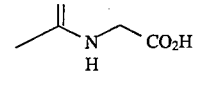 |
| 73 | 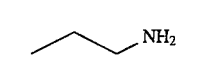 |
| 74 | 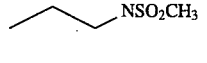 |
| 75 | 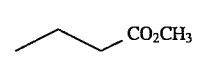 |
| 76 | 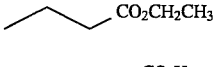 |
| 77 |  |
| 78 | 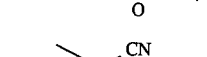 |
| 79 | 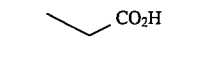 |
| 80 | 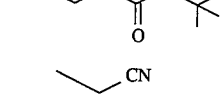 |
| 81 | 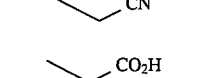 |
| 82 | 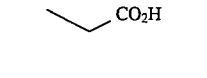 |
| 83 | 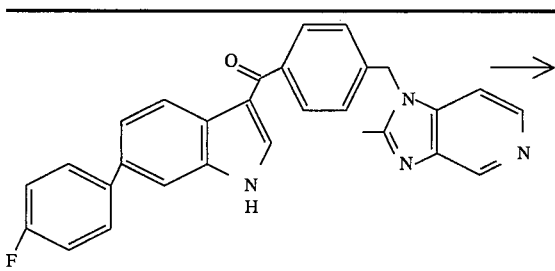 |

TABLE 3-continued

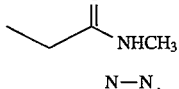

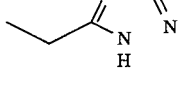

| Example | R² |
|---|---|
| 84 | 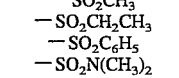 |
| 85 | (pictured above) |
| 86 | —SO$_2$CH$_3$ |
| 87 | —SO$_2$CH$_2$CH$_3$ |
| 88 | —SO$_2$C$_6$H$_5$ |
| 89 | —SO$_2$N(CH$_3$)$_2$ |

EXAMPLE 90

Preparation of 4,7-Dimethoxycarbonyl-3-{4-[(1H-2-methylimidazo-[4,5-c]pyrid-1-yl)methyl]benzoyl}indole Step 1: 4,7-Dimethoxycarbonylindole.

To a solution under N$_2$ of dimethyl nitroterephthlate (10.0 g, 41.8 mmol) in dry, freshly distilled THF (420 mL) at −45° to −40° C. was added vinylmagnesium bromide (1.0M in THF, 125 mL, 125 mmol) over 10 minutes and the reaction mixture was stirred for an additional 40 minutes. The reaction was quenched with saturated aqueous NH$_4$Cl and extracted twice with ether. The combined ether extracts were dried over Na$_2$SO$_4$, filtered, and concentrated in vacuo to give 11.9 g of orange oil and yellow granular solid. Chromatography on silca gel (3:1 hexane/ethyl acetate) gave 4,7-dimethoxycarbonylindole (1.90 g) as a bright-yellow waxy solid. Trituration of the mixed fractions with hexane-ethyl acetated gave an additional 0.66 g of product.

Step 2: 4,7-Dimethoxycarbonyl-3-(4-chloromethylbenzoyl)indole.

To a solution under N$_2$ of 4.7-dimethoxycarbonylindole (1.87 g, 8.02 mmol) in CH$_2$Cl$_2$ (135 mL) was added ethylmagnesium bromide (3.0M in ether, 2.70 mL, 8.10 mmol) over 5 minutes. The resulting red-orange suspension was stirred for 10 minutes at ambient temperature and ZnCl$_2$ (1.0M in ether, 24.1 mL, 24.1 mmol) was added quickly via syringe. After stirring for 20 minutes, during which time the reaction mixture turned to a light-green suspension, a solution of 4-chloromethylbenzoyl chloride in CH$_2$Cl$_2$ (35 mL) was added over 5 minutes. The reaction mixture was stirred for 3 days at ambient temperature and then was poured into saturated aqueous NH$_4$Cl. The layers were separated and the aqueous phase was extracted twice with CH$_2$Cl$_2$. The combined organic layers were washed with brine, dried over Na$_2$SO$_4$, filtered, and concentrated in vacuo to give a clear-orange oil (3.57 g). Chromatography on silica gel (99:1, then 97:3 CH$_2$Cl$_2$/acetone) gave a clear-yellow oil which partially crystallized on standing. Azeotroping with CH$_2$Cl$_2$ gave 4,7-dimethoxycarbonyl-3-(4-chloromethylbenzoyl)indole as a yellow solid (0.85 g, 28%).

Step 3: 4,7-Dimethoxycarbonyl-3-{4-[(1H-2-methylimidazo[4,5-c]pyrid-1-yl)methyl]benzoyl}indole.

To a 0° C. solution under N$_2$ of 1H-2-methylimidazo[4,5-c]pyridine, (0.32 g, 2.4 mmol) prepared as in Example 3, step 1, in THF (8.0 mL) and DMPU (1,3-dimethyl-3,4,5,6-tetrahydro-1H-pyridin-2-one, 2.75 mL) was added NaH (95%, 0.23 g, 2.2 mmol), and the mixture was stirred for 30 minutes. In a separate reaction vessel, NaBr (0.23 g, 2.2 mmol) was added to a solution of 4,7-dimethoxycarbonyl-3-(4-chloromethylbenzoyl)indole (0.83 g, 2.2 mmol) in THF (8.5 mL) and DMPU (1.75 mL). The sodium anion solution was then added to the indole/NaBr solution via cannula over 5 minutes, and the reaction mixture was stirred overnight at ambient temperature. The reaction mixture was partitioned between ethyl acetate and saturated aqueous NH$_4$Cl. The organic phase was washed with H$_2$O and brine, dried over Na$_2$SO$_4$, filtered, and concetrated in vacuo to give a viscous, clear-orange oil (1.1 g). Chromatography on silica gel (40:1, then 20:1, then 12:1 CHCl$_3$/methanol) gave a bright-yellow oil. Azeotroping with CH$_2$Cl$_2$ gave 4,7-dimethoxycarbonyl-3-{4-[(1H-2-methylimidazo[4,5-c]pyrid-1-yl)methyl]benzoyl)indole (40 mg) as a bright-yellow solid. $^1$H NMR (CDCl$_3$, 300 MHz) δ2.63 (s, 3H), 3.72 (s, 3H), 4.02 (s, 3H), 5.41 (s, 2H), 7.14 (d, 2H, J=8.5 Hz), 7.20 (d, 1H, J=5.5 Hz), 7.62 (d, 1H, J=7.7 Hz), 7.70 (d, 1H, J=2.9 Hz), 7.86 (d, 2H, J=8.5 Hz), 8.01 (d, 1H, J=8.1 Hz), 8.40 (d, 1H, J=4.8 Hz), 9.05 (s, 1H), 10.58 (s, 1H). MS (DCI/NH$_3$) m/e 483 (M+H)$^+$. IR (microscope) 1163 (s), 1198 (m), 1280 (s), 1433 (m), 1520 (m), 1610 (m), 1637 (m), 1721 (s), 2952 (w), 3362 (br) cm$^{-1}$. Anal calcd for C$_{27}$H$_{22}$N$_4$O$_5$ .0.35 H$_2$O. 0.65 CH$_2$Cl$_2$: C, 61.05; H, 4.45; N, 10.30. Found: C, 61.29; H, 4.53; N, 9.91.

EXAMPLE 91

Preparation of 4,7-Dimethyl-3-{4-[(1H-2-methylimidazo[4,5-c]pyrid-1-yl)methyl]benzoyl}indole The desired compound was prepared according to the method of Example 90, except substituting 4,7-dimethylindole, prepared as described by Dalton, et al., *Aust. J. Chem.*, 1968, 21, 2053, for 4,7-dimethoxycarbonylindole. mp 146°–151° C. $^1$H NMR (DMSO-d6, 500 MHz) δ2.45 (s, 3H), 2.52 (s, 3H), 2.59 (s, 3H), 5.63 (s, 2H), 6.85 (d, 1H, J=7.3 Hz), 6.94 (d, 1H, J=7.1 Hz), 7.27 (d, 2H, J=8.3 Hz), 7.59 (d, 1H, J=5.4 Hz), 7.60 (s, 1H), 7.80 (d, 2H, J=8.3 Hz), 8.30 (d, 1H, J=5.6 Hz), 8.86 (s, 1H), 11.85 (s, 1H). MS (DCI/NH$_3$) m/e 395 (M+H)$^+$. IR (microscope) 885 (m), 1222 (m), 1299 (m), 1350 (m), 1391 (m) cm$^{-1}$. Anal calcd for C$_{25}$H$_{22}$N$_4$O.1.2 H$_2$O: C, 72.17; H, 5.91; N, 13.46. Found: C, 72.06, H, 5.64; N, 13.55.

EXAMPLE 92

Preparation of 4,7-Dimethyl-3-{4-[(3H-2-methylimidazo[4,5-c]pyrid-3-yl)methyl]benzoyl}indole The desired compound was separated by chromatography (30:1, then 20:1, then 14:1, then 11:1, then 10:1 CHCl$_3$, methanol) from the 1H isomer prepared in Example 91. mp 219°–225° C. $^1$H NMR (DMSO-d6, 500 MHz) δ2.46 (s, 3H), 2.53 (s, 3H), 2.62 (s, 3H), 5.70 (s, 2H), 6.85 (d, 1H, J=7.3 Hz), 6.94 (d, 1H, J= 7.3 Hz), 7.32 (d, 2H, J=8.3 Hz), 7.58 (dd, 1H, J=0.8, 5.5 Hz), 7.61 (s, 1H), 7.81 (d, 2H, J=8.3 Hz), 8.30 (d, 1H, J=5.4 Hz), 8.86 (d, 1H, J=0.7 Hz), 11.85 (s, 1H). MS (DCI/NH$_3$) m/e 395 (M+H)$^+$, 412 (M+NH$_4$)$^+$. IR cm$^{-1}$ (microscope) 881 (m), 1162 (m), 1215 (m), 1346 (s), 1381 (m). Anal calcd for C$_{25}$H$_{22}$N$_4$O.0.8 H$_2$O: C, 73.44; H, 5.82; N, 13.70. Found: C, 73.18; H, 5.50, N, 13.45.

EXAMPLE 93

Preparation of 7-Benzyloxy-3-{4-[(1H-2-methylimidazo[4,5-c]pyrid-1-yl)methyl] benzoyl}indole The desired compound was prepared according to the method of Example 90, except substituting 7-benzyloxyindole for 4,7-dimethoxycarbonylindole. $^1$H NMR (DMSO-d6, 300 MHz) δ2.59 (s, 3H), 5.30 (s, 2H), 5.63 (s, 2H), 6.93 (d, 1H, J=7.7 Hz), 7.13 (t, 1H, J=7.9 Hz), 7.28 (d, 2H, J=8.1 Hz), 7.32–7.46 (c, 3H), 7.54–7.60 (c, 2H), 7.62 (d, 1H, J=5.1 Hz), 7.71 (d, 1H, J=2.2 Hz), 7.76 (d, 2H), J=8.5 Hz), 7.80 (d, 1H, J=8.1 Hz), 8.30 (d, 1H, J=5.2 Hz), 8.87 (s, 1H), 12.24 (d, 1H, J=2.6 Hz). MS (DCI/NH$_3$) m/e 473 (M+H)$^+$. IR, cm$^{-1}$ (microscope) 738 (m), 1219 (m), 1248 (m), 1278 (m), 1436 (s). Anal calcd for C$_{30}$H$_{24}$N$_4$O$_2$.1.2 H$_2$O: C, 72.92; H, 5.38; N, 11.34. Found: C, 72.97; H, 5.30; N, 11.05.

EXAMPLE 94

Preparation of 7-(4-Fluorophenyl)-3-{4-[(1H-2-methylimidazo-[4,5-c]pyrid-1 -yl)methyl]benzoyl}indole The desired compound was prepared according to the method of Example 90, except substituting 7-(4-fluorophenyl)indole, prepared as described by Carrera, G. M., and Sheppard, G. S., *Synlett*, 1994, 93, for 4,7-dimethoxycarbonylindole. $^1$H NMR (DMSO-d6, 300 MHz) δ2.59 (s, 3H), 5.64 (s, 2H), 7.26 (dd, 1H, J=1.3, 7.2 Hz), 7.30 (d, 2H, J=8.1 Hz), 7.33 (t, 1H, J=7.6 Hz), 7.37 (t, 2H, J(F-Hortho, Hortho-Hmeta)=9.0 Hz), 7.61 (dd, 1H, J=1.1, 5.5 Hz), 7.64 (dd, 2H, J(F-Hmeta, Hortho-Hmeta)=5.5, 8.8 Hz), 7.76 (d, 1H, J=3 Hz), 7.78 (d, 2H, J=8.5 Hz), 8.26 (dd, 1H, J=1.1, 7.7 Hz), 8.30 (d, 1H, J=5.5 Hz), 8.86 (s, 1H), 11.90 (d, 1H, J=2.6 Hz). MS (DCI/NH$_3$) m/e 461 (M+H)$^+$. IR, cm$^{-1}$ (microscope) 800 (m), 1174 (m), 1225 (s), 1374 (m), 1395 (m). Anal calcd for C$_{29}$H$_{24}$N$_4$OF.0.75 H$_2$O: C, 73.48; H, 4.78; N, 11.82. Found: C, 73.60; H, 4.38; N, 11.79.

EXAMPLE 95

Preparation of 6-(4-Fluorophenyl)-3-{N-[3-(1H-2-methylimidazo-[4,5-c]pyrid-1 -yl)propyl]sarcosyl}indole-1-carboxylic acid dimethyl amide Step 1: N-tert-butoxycarbonyl-3-bromopropylamine.

To a 0° C. solution of 3-bromopropylamine hydrobromide (10.0 g, 45.7 mmol) in 1:1 aqueous dioxane was added triethylamine (12.8 mL, 91.8 mmol), di-tert-butyldicarbonate (20.2 g, 92.6 mmol), and saturated aqueous NaHCO$_3$ (3 mL). The cold bath was removed and the reaction mixture was stirred for 3.5 hours. The reaction mixture was extracted three times with ethyl acetate. The combined organic extracts were washed with 10% aqueous citric acid and brine, dried over Na$_2$SO$_4$, filtered, and concentrated in vacuo. Chromatography on silica gel (10:1, then 6:1, then 3:1 hexane, ethyl acetate) gave N-tert-butoxycarbonyl-3-bromopropylamine (21.1 g, 79%) as a clear yellow oil.

Step 2: 1-(3-N-tert-Butoxycarbonylaminoprop-1-yl)-1H-2-methylimidazo[4,5-c]pyridine.

To a solution under N$_2$ of 1H-2-methylimidazo[4,5-c]pyridine, (2.00 g, 15.0 mmol) prepared as in Example 3, step 1, in THF (35 mL) and DMF (2.0 mL) was added NaH (95%, 0.42 g, 16.6 mmol) over 15 minutes and the reaction mixture was stirred for 80 minutes. The resulting suspension was cooled in an ice-water bath and a solution of N-tert-butoxy-3-bromopropylamine (3.93 g, 16.5 mmol), prepared as in step 1, in THF (5.0 mL) was added via cannula. The cold bath was removed, DMF (20 mL) was added to make a homogenous solution, and the reaction mixture was stirred overnight at ambient temperature. The reaction mixture was diluted with ethyl acetate and poured into water. The layers were separated and the organic phase was washed with ethyl acetate. The aqueous phase was extracted with ethyl acetate. The combined organic extracts were dried over Na$_2$SO$_4$, filtered, and concentrated in vacuo to give 5.5 g of a dark oil. Chromatography on silica gel (20:1, then 10:1 CHCl$_3$, methanol) gave 1-(3-N-tert-butoxycarbonylaminoprop-1-yl)-1H-2-methylimidazo[4,5-c]pyridine (0.58 g) which was contaminated with 8–10% of the 3H isomer.

Step 3: 1-(3-Aminoprop-1-yl)-1H-2-methylimidazo[4,5-c]pyridine.

To a 0° C. solution of 1-(3-N-tert-butoxycarbonylaminoprop-1-yl)-1H-2-methylimidazo[4,5-c]pyridine (0.33 g, 1.1 mmol), prepared as in step 2, in CH$_2$Cl$_2$ (8.8 mL) was added dropwise trifluoroacetic acid (2.20 mL, 28.6 mmol). The cold bath was removed and the reaction mixture was stirred for 20 minutes. The reaction mixture was carefully added to saturated aqueous NaHCO$_3$ (20 mL). The acidic aqueous phase (pH=2) was taken to pH=12–13 with 15% aqueous NaOH. The layers were combined and added to a liquid-liquid continuous extractor and extracted into CH$_2$Cl$_2$ for 18 hours. Concentration in vacuo gave 1-(3-aminoprop-1-yl)-1H-2-methylimidazo[4,5-c]pyridine (0.27 g).

Step 4: 1-(3-N-Formylaminoprop-1-yl)-1H-2-methylimidazopyridine.

The desired compound was prepared by reaction of the 1-(3-aminoprop-1-yl)-1H-2-methylimidazo[4,5-c]pyridine (0.27 g, 1.1 mmol) prepared in step 3 with ethyl formate according to the method of DeCosta et al., *J. Med. Chem.*, 1994, 37, 314. Distillazation was replaced by chromatography on silica gel (10:1 CHCl$_3$, methanol+1% of 29% aqueous NH$_4$OH, then 7:1 CHCl$_3$, methanol+1% of 29% aqueous NH$_4$OH) gave 1-(3-N-formylaminoprop-1-yl)-1H-2-methylimidazopyridine (0.23 g, 96% yield from step 3).

Step 5: 1-(3-N-Methylaminoprop-yl)-1H-2-methylimidazopyridine.

The desired compound (0.21 g) was prepared by reduction of 1-(3-N-formylaminoprop-1-yl)-1H-2-methylimidazopyridine (0.21 g, 0.96 mmol), prepared as in step 4, with LAH according to the method of DeCosta et al., *J. Med. Chem.*, 1992, 35, 38, except substituting DME for THF to give 1-(3-N-methylaminoprop-1-yl)-1H-2-methylimidazopyridine as a bright yellow oil which was used without further purification.

Step 6: 6-(4-Fluorophenyl)-3-{N-[3-(1H-2-methylimidazo[4.5-c]pyrid-1-yl)propyl]sarcosyl}indole.

To a solution under N$_2$ of the 1-(3-N-methylaminoprop-1-yl)-1H-2-methylimidazopyridine (0.21 g) prepared in step 5 and N,N-diisopropylethylamine (0.52 mL, 3.0 mmol) in DMF (1 mL) was added a solution in 1:1 DMF,THF (6 mL) of 3-chloroacetyl-6-(4-fluorophenyl)indole (0.18 g, 0.62 mmol), prepared as in Example 23, step 1, and the reaction mixture was stirred overnight at ambient temperature. The reaction mixture was diluted with ethyl acetate and extracted twice with aqueous 1N NaOH. The organic phase was dried over Na$_2$SO$_4$, filtered, and concentrated in vacuo to give a clear orange foam. Chromatography on silica gel (50:1 CHCl$_3$, methanol+0.5% NH$_4$OH, then 20:1 CHCl$_3$, methanol+0.5% NH$_4$OH, then 10:1 CHCl$_3$, methanol+0.5% NH$_4$OH) to give 6-(4-fluorophenyl)-3-{N-[3-(1H-2-methylimidazo[4.5-c]pyrid-1-yl)propyl]sarcosyl}indole (21 mg) as an orange, oily foam.

Step 7: 6-(4-Fluorophenyl)-3-{N-[3-(1H-2-methylimidazo[4.5-c]pyrid-1 -yl)propyl]sarcosyl}indole-1-carboxylic acid dimethyl amide.

The desired compound was prepared as an 85:15 mixture of the 1H and 3H isomers by reaction of 6-(4-fluorophenyl)-3-{3-[N-methyl-N-methylcarbonyl-(1H-2-methylimidazo[4,5-c]pyrid-1-yl)amino]prop-1-yl]indole, prepared as in step 6, with KOH and N,N-dimethylcarbamoyl chloride in THF/DMF as described in Example 2. $^1$H NMR (DMSO-d6, 300 MHz) δ1.96 (quintet, 2H, J=7.0 Hz), 2.32 (s, 3H), 2.47–2.56 (c, 2H), 2.59 (s, 3H), 3.05 (s, 6H), 3.76 (s, 2H), 4.25 (t, 2H, J=7.2 Hz), 7.30 (t, 2H, J(F-Hortho, Hortho-Hmeta)=8.8 Hz), 7.57 (dd, 1H, J=0.7, 5.5 Hz), 7.60 (dd, 1H, J=1.5, 8.5 Hz), 7.74 (dd, 2H, J(F-Hmeta, Hortho-Hmeta)= 5.5, 8.8 Hz), 7.79 (d, 1H, J=1.1 Hz), 8.24 (d, 1H, J=5.5 Hz), 8.30 (d, 1H, J=8.1 Hz), 8.66 (s, 1H), 8.78 (s, 1H). MS (DCI/NH3) m/e 527 (M+H)+. IR, cm$^{-1}$ (microscope) 822 (m), 1160 (m), 1177 (m), 1391 (s), 1480(m). Anal calcd for C$_{30}$H$_{31}$N$_6$O$_2$F.0.6 H$_2$O.0.2 Et$_2$O: C, 66.99; H, 6.24; N, 15.22. Found: C, 67.22; H, 6.00; N, 14.87.

EXAMPLE 96

Preparation of 1-N,N-Dimethylcarbamoyl-4-methoxycarbonyl-3-(3-fluoro-4-[(1H-2-methylimidazo[4,5-c]pyrid-1-yl)-methyl]benzoyl}indole Step 1: 4-methoxycarbonyl-3-(3-fluoro-4-methylbenzoyl}indole.

The desired compound was prepared according to the method of Example 90, step 2, except substituting 4-methoxycarbonylindole for 4,7-dimethoxycarbonylindole, and substituting 3-fluoro-4-methylbenzoyl chloride, prepared by reaction of 3-fluoro-4-methylbenzoic acid with thionyl chloride, for 4-chloromethylbenzoyl chloride.

Step 2: 1-N,N-Dimethylcarbamoyl-4-methoxycarbonyl-3-(3-fluoro-4-methylbenzoyl)indole.

The desired compound was prepared by reaction of 4-methoxycarbonyl-3-(3-fluoro-4-methylbenzoyl)indole, prepared as in step 1, with KOH and N,N-dimethylcarbamoyl chloride in THF as described in Example 2.

Step 3: 1-N,N-Dimethylcarbamoyl-4-methoxycarbonyl-3-(3-fluoro4-bromomethylbenzoyl)indole.

The desired compound was prepared by heating a solution in CCl$_4$ of N,N-dimethylcarbamoyl-4-methoxycarbonyl-3-(3-fluoro-4-methylbenzoyl)indole, prepared as in step 2, N-bromosuccinimide, and catalytic AIBN.

Step 4: 1-N,N-Dimethylcarbamoyl-4-methoxycarbonyl-3-{3-fluoro-4-[(1H-2-methylimidazo[4,5-c]pyrid-1-yl)methyl]benzoyl}indole.

The desired compound was prepared according to the method of Example 90, step 3, except substituting N,N-dimethylcarbamoyl-4-methoxycarbonyl-3-(3-fluoro-4-bromomethylbenzoyl)indole, prepared as in step 3, for 4,7-dimethoxycarbonyl-3-(4-chloromethylbenzoyl)indole. $^1$H NMR (DMSO-d6, 300 MHz) δ8.86 (s, 1H), 8.31–8.29 (d, 1H, J=4.4 Hz), 8.19 (s, 1H), 7.88–7.85 (d, 1H, J=8.5 Hz), 7.71–7.69 (d, 1H, J=4.4 Hz), 7.66–7.63 (d, 1H, J=4.4 Hz), 7.59–7.56 (d, 1H, J=4.4 Hz), 7.49–7.46 (d, 1H, J=8.1 Hz), 7.16–7.10 (t, 1H, J=7.8 Hz), 5.69 (s, 2H), 3.51 (s, 3H), 3.34 (s, 6H), 2.62 (s, 3H). MS (DCI/NH$_3$) m/e 514 (M+H)$^+$. Anal calcd for $C_{28}H_{24}FN_5O_4 \cdot 0.5$ $CH_2Cl_2$: C, 61.56; H, 4.53; N, 12.13. Found: C, 61.55; H, 4.51; N, 12.28.

EXAMPLE 97

Preparation of 1-N,N-Dimethylcarbamoyl-6-benzyloxy-3-{4-[(1H-2-methylimidazo[4,5-c]pyrid-1-yl)methyl]benzoyl}indole The desired compound was prepared according to the method of Example 90, except substituting 6-benzyloxyindole for 4-methoxycarbonylindole. $^1$H NMR (DMSO-d6, 300 MHz) δ8.86 (s, 1H), 8.31–8.29 (d, 1H, J 5.1 Hz), 8.13–8.10 (d, 1H, J=8.8 Hz), 7.95 (s, 1H), 7.83–7.80 (d, 2H, J=5.0 Hz), 7.50–7.47 (d, 2H, J=5.0 Hz), 7.43–7.37 (t, 1H, J=6.9 Hz), 7.35–7.33 (d, 2H, J=5.5 Hz), 7.30–7.26 (d, 2H, J=7.8 Hz), 7.18 (s, 1H), 7.09–7.06 (d, 1H, J=5.5 Hz), 5.56 (s, 2H), 5.17 (s, 2H), 2.95 (s, 6H), 2.59 (s, 3H). MS (DCI/NH$_3$) m/e 544 (M+H)$^+$. Anal calcd for $C_{33}H_{29}N_5O_3 \cdot 1.5$ $H_2O$: C, 69.45; H, 5.65; N, 12.27. Found: C, 69.45; H, 5.57; N, 11.64.

EXAMPLE 98

Preparation of 1-N,N-Dimethylcarbamoyl-4-methoxycarbonyl-3-{5-[(1H-2-methylimidazo[4,5-c]pyrid-1-yl)methyl]-thien-2-oyl}indole Step 1: 1-N,N-Dimethylcarbamoyl-4-methoxycarbonyl-3-(5-bromomethylthien-2-oyl)indole.

The desired compound was prepared according to the method of Example 96, steps 1–3, except substituting 5-methylthiophene-2-carboxylic acid for 3-fluoro-4-methylbenzoic acid.

Step 2: 1-N,N-Dimethylcarbamoyl-4-methoxycarbonyl-3-(5-azidomethylthien-2-oyl)indole.

To a solution of 1-N,N-dimethylcarbamoyl-4-methoxycarbonyl-3-(5-bromomethylthien-2-oyl)indole (2.8 g, 6.2 mmol), prepared as in step 1, in CH$_3$CN (10 mL) was added sodium azide (0.77 g, 11.8 mmol) and benzyltrimethylammonium chloride (0.10 g, 0.40 mmol). The reaction mixture was stirred for 3.5 hours at ambient temperature and then was partitioned between CH$_2$Cl$_2$ and saturated aqueous NaHCO$_3$. The organic phase was washed with brine, dried over MgSO$_4$, filtered, and concentrated in vacuo to give 1-N,N-dimethylcarbamoyl-4-methoxycarbonyl-3-(5-azidomethylthien-2-oyl)indole (2.18 g) as a yellow foam which was used without further purification.

Step 3: 1-N,N-Dimethylcarbamoyl-4-methoxycarbonyl-3-(5-aminomethylthien-2-oyl)indole.

To a solution of SnCl$_2$ (4.73 g, 25 mmol) in methanol (70 mL) was added in 2-mL portions a solution in methanol (30 mL) of the 1-N,N-dimethylcarbamoyl-4-methoxycarbonyl-3-(5-azidomethylthien-2-oyl)indole prepared in step 2. The reaction mixture was stirred at ambient temperature for 5 hours and then was concentrated in vacuo. The residue was partitioned between CH$_2$Cl$_2$ and saturated aqueous NaHCO$_3$. The organic phase was dried over MgSO$_4$, filtered, and concentrated in vacuo to give a yellow foam (1.60 g). Chromatography on silica gel (1% triethylamine, 99% CH$_2$Cl$_2$, then 1% triethylamine, 3% methanol, 94% CH$_2$Cl$_2$) gave 1-N,N-dimethylcarbamoyl-4-methoxycarbonyl-3-(5-aminomethylthien-2-oyl)indole (0.95 g) as a tan foam.

Step 4: 1-N,N-Dimethylcarbamoyl-4-methoxycarbonyl-3-[5-(N-3-nitropyridin-4 -yl)aminomethylthien-2-oyl]indole.

To a solution of 1-N,N-dimethylcarbamoyl4-methoxycarbonyl-3-(5-aminomethylthien-2-oyl)indole (0.896 g, 2.33 mmol) in CH$_3$CN (5 mL) was added 4-ethoxy-3-nitropyridine (0.428 g, 2.55 mmol) and the reaction mixture was heated at reflux for 17 hours, then the solvent was removed in vacuo and the residue heated at 100° C. for 2 hours. The reaction mixture was then put under high vacuum to give 1-N,N-dimethylcarbamoyl-4-methoxycarbonyl-3-[5-(N-3-nitropyridin-4-yl)aminomethylthien-2-oyl]indole as a brown foam which was used without further purification.

Step 5: 1-N,N-Dimethylcarbamoyl-4-methoxycarbonyl-3-[5-(N-3-aminopyridin-4-yl)aminomethylthien-2-oyl]indole.

To a solution of SnCl$_2$ in methanol (30 mL) was added in 2 mL portions a solution in 2:1 methanol, CH$_2$Cl$_2$ of the 3-[5-(N-3-nitropyridin4-yl)aminomethylthien-2-oyl]indole prepared in step 4 (1.18 g), and the reaction mixture was stirred for 3 hours at ambient temperature. The reaction mixture was partitioned between CH$_2$Cl$_2$ and saturated aqueous NaHCO$_3$. The resulting emulsion was filtered after which layers formed. The layers were separated and the organic phase was dried over MgSO$_4$, filtered, and concentrated in vacuo to give 1-N,N-dimethylcarbamoyl-4-methoxycarbonyl-3-[5-(N-3-aminopyridin-4-yl)aminomethylthien-2-oyl]indole (1.73 g) which was used without further purification.

Step 6: 1-N,N-Dimethylcarbamoyl-methoxycarbonyl-3-{5-(1H-2-methylimidazo[4,5-c]pyrid-1-yl)methyl]thien-2-oyl}indole.

A mixture of the 1-N,N-dimethylcarbamoyl-4-methoxycarbonyl-3-[5-(N-3-aminopyridin-4-yl)aminomethylthien-2-oyl]indole prepared in step 5, acetic acid (20 mL), and acetic anhydride (20 mL) were stirred overnight at reflux. The reaction mixture was cooled to ambient temperature, quenched by dropwise addition of methanol (30 mL), and concentrated in vacuo. The residue was partitioned between saturated aqueous NaHCO3 and CH$_2$Cl$_2$. The organic phase was dried over MgSO$_4$, filtered, and concentrated in vacuo to give 0.83 g of red-brown gum. Chromatography on silica gel (99:1 CH$_2$Cl$_2$, triethylamine, then 97:2:1 CH$_2$Cl$_2$, methanol, triethylamine) gave 1-N,N-dimethylcarbamoyl-methoxycarbonyl-3-{5-[(1H-2-methylimidazo[4,5-c]pyrid-1-yl)methyl]thien-2-oyl}indole (0.14 g) as a brown solid.

Step 7: 1-N,N-Dimethylcarbamoyl-methoxycarbonyl-3-{5-[(1H-2-methylimidazo[4,5-c]pyrid-1-yl)methyl]thien-2-oyl}indole hydrochloride.

A solution of 1-N,N-dimethylcarbamoyl-methoxycarbonyl-3-{5-[(1H-2-methylimidazo[4,5-c]pyrid-1-yl)methyl]thien-2-oyl}indole (0.125 g), prepared in step 6, in THF was swirled with activated carbon and filtered. To the filtrate was added 4M HCl/dioxane (0.07 mL). 1-N,N-dimethylcarbamoyl-methoxycarbonyl-3-{5-[(1H-2-methylimidazo[4,5-c]pyrid-1-yl)methyl]thien-2-oyl}indole hydrochloride (71 mg) was isolated as a light brown powder by filtration. $^1$H NMR (DMSO-d6, 300 MHz) δ8.84 (s, 1H), 8.36 (d, 1H, J=6 Hz), 8.30 (s, 1H), 7.97 (dd, 1H, J=1,9 Hz), 7.73 (dd, 1H, J=1, 6 Hz), 7.68 (d, 1H, J=5 Hz), 7.57 (dd, 1H, J=1, 7 Hz), 7.46 (m, 1H), 7.22 (d, 1H, J=5 Hz), 5.84 (s, 2H), 3.54 (s, 3H), 3.04 (s, 6H), 2.68 (s, 3H). MS (DCI/NH$_3$) m/e 502 (M+H)$^+$, 371, 151. IR cm$^{-1}$ (microscope) 3400 (br), 2970, 2950, 2600, 1700, 1640, 1515, 1485. Anal calcd for $C_{25}H_{23}N_5O_4S \cdot HCl \cdot C_4H_{10}O \cdot 1.5\ H_2O$: C, 56.37; H, 5.83; N, 10.96. Found: C, 56.22; H, 6.05; N, 11.08.

EXAMPLE 99

Preparation of
1-N,N-Dimethylcarbamoyl-6-(4-fluorophenyl)-3-{4-[(1H-2-methylimidazo[4.5-c]pyrid-1-yl)methyl]-phenylaminocarbonyl}indole hydrochloride Step 1: 4-(1H-2-Methylimidazo[4,5-c]pyrid-1-ylmethyl)nitrobenzene.

To a suspension in CH$_3$CN (700 mL) of 1H-2-methylimidazo[4,5-c]pyridine (5.04 g, 37.9 mmol), prepared as in Example 3, step 1, was added tris[2-(2-methoxyethoxy)ethyl]amine (1.3 mL, 4.1 mmol) and KOH (10.6 g, 190 mmol). The suspension was stirred at ambient temperature for 90 minutes and then 4-nitrobenzyl bromide (8.23 g, 38.1 mmol) was added and stirring was continued for 2 hours. The reaction mixture was partitioned between ethyl acetate and pH 7 buffer. The organic phase was dried over MgSO$_4$, filtered, and concentrated in vacuo. Chromatography on silica gel (5% methanol/CH$_2$Cl$_2$) gave 4-(1H-2-methylimidazo[4,5-c]pyrid-1 -ylmethyl)nitrobenzene (1.07 g) as a tan solid.

Step 2: 4-(1H-2-Methylimidazo[4,5-c]pyrid-1-ylmethyl)aniline.

A suspension of 4-(1H-2-methylimidazo[4,5-c]pyrid-1-ylmethyl)nitrobenzene (1.04 g, 3.9 mmol), prepared as in step 1, and SnCl$_2$ (3.25 g, 19.9 mmol) in 8:2 ethyl acetate, methanol (100 mL) was stirred vigorously for two hours at ambient temperature. The reaction mixture poured into 1N aqueous NaOH and extracted twice with ethyl acetate and and once with CH$_2$Cl$_2$. The combined organic layers were dried over MgSO$_4$, filtered, and concentrated in vacuo to give 0.91 g of an orange foam. The foam was dissolved in 30 mL of methanol and SnCl$_2$ (3.7 g) was added. After stirring for 3 hours, the reaction was worked up as above to give 0.79 g of 4-(1H-2-methylimidazo[4,5-c]pyrid-1-ylmethyl)aniline as an orange oil.

Step 3: 6-(4-Fluorophenyl)indole-2-carboxaldehyde.

The desired compound was prepared by Vilsmeier formylation of 6-(4-fluorophenyl)indole using DMF and oxalyl chloride.

Step 4: 1-N,N-Dimethylcarbamoyl-6-(4-Fluorophenyl)indole-2-carboxaldehyde.

The desired compound was prepared by reaction of 6-(4-fluorophenyl)indole-2-carboxaldehyde with KOH and N,N-dimethylcarbamoyl chloride in THF/DMF as described in Example 2.

Step 5: 6-(4-Fluorophenyl)indole-2-carboxylic acid.

To a solution in THF (25 mL) and tert-butyl alcohol (70 mL) of 1-N,N-dimethylcarbamoyl-6-(4-fluorophenyl)indole-2-carboxaldehyde, prepared as in step 4, was added 2-methyl-2-butene (2M in THF, 8 mL, 16 mmol), followed by a solution of NaClO$_2$ (1.2 g, 13 mmol) and NaH$_2$PO$_4$ (2.4 g, 17 mmol) in H$_2$O (20 mL). After stirring overnight at ambient temperature, a solution of NaClO$_2$ (0.25 g) and NaH$_2$PO$_4$ (0.50 g) in H$_2$O (10 mL) was added and the reaction mixture was stirred for 2 hours. The organic solvents were stripped off in vacuo and the residue was extracted with ether. The aqueous phase was taken to pH 3 with concentrated HCl, the water was decanted, and the residue was taken up in ethyl acetate. The ethyl acetate solution was dried over MgSO$_4$, filtered, and concentrated in vacuo to give a dark-brown oil (0.53 g) . The oil was dissolved in THF and treated with activated carbon. Filtration and concentration in vacuo gave 6-(4-fluorophenyl)indole-2-carboxylic acid (0.426 g, 93%) as a red solid.

Step 6: 1-N,N-Dimethylcarbamoyl-6-(4-fluorophenyl)-3-{4-[(1H-2-methylimidazo[4.5-c]-pyrid-1-yl)methyl] phenylaminocarbonyl}indole.

To a solution in THF (6 mL) of 6-(4-fluorophenyl)indole-2-carboxylic acid (0.103 g, 0.32 mmol), prepared as in step 5, was added diisopropylethylamine (0.10 mL, 0.57 mmol) and bis(2-oxo-3-oxazolidinyl)phosphinic chloride (0.095 g, 0.37 mmol), and the reaction mixture was stirred at ambient temperature for 15 minutes. A solution of 4-(1H-2-methylimidazo[4,5-c]pyrid-1-ylmethyl)aniline (0.108 g, 0.45 mmol), prepared as in step 2, in THF (4 mL) was added and the reaction mixture was stirred for 15 hours at ambient temperature. The reaction mixture was partitioned between CH$_2$Cl$_2$ and saturated aqueous NaHCO$_3$. The organic phase was dried over Na$_2$SO$_4$, filtered, and concentrated in vacuo to give a tan solid (0.165 g). Chromatography on silica gel (7% methanol, ethyl acetate) gave a mixture of desired compound and starting aniline. Gradient elution on the HPLC (5% to 90% acetonitrile/H$_2$O with 1% trifluoroacetic acid) gave 1-N,N-dimethylcarbamoyl-6-(4-fluorophenyl)-3-{4-[(1H-2-methylimidazo[4.5-c]pyrid-1-yl)methyl] phenylaminocarbonyl}indole (13 mg).

Step 7: 1-N,N-Dimethylcarbamoyl-6-(4-fluorophenyl)-3-{4-[(1H-2-methylimidazo[4.5-c]pyrid-1-yl)methyl] phenylaminocarbonyl}indole hydrochloride.

The desired compound was prepared by treating a solution of 1-N,N-dimethylcarbamoyl-6-(4-fluorophenyl)-3-{4-[(1H-2-methylimidazo[4.5-c]pyrid-1-yl)methyl] phenylaminocarbonyl}indole, prepared as in step 6, in CH$_2$Cl$_2$/CDCl$_3$ with 4N HCl/dioxane. $^1$H NMR (CDCl$_3$, 300 MHz) δ8.97 (s, 1H), 8.38 (d, 1H, J=6 Hz), 8.06 (d, 1H, J=7 Hz), 7.97 (s, 1H), 7.92 (s, 1H), 7.70 (s, 1H), 7.59 (d, 2H, J=7 Hz), 7.53 (m, 2H), 7.46 (m, 1H), 7.09 (m, 2H), 6.99 (d, 2H, J=7 Hz), 5.27 (s, 2H, 3.05 (s, 6H), 2.59 (s, 3H). MS (DCI/NH$_3$) m/e 547 (M+H)$^+$.

EXAMPLE 100

Preparation of
1-N,N-Dimethylcarbamoyl-5-(4-fluorophenyl)-3-{4-[(1H-2-methylimidazo[4.5-c]pyrid-1-yl)methyl]-benzoyl}indole.

The desired compound was prepared according to the method of Example 4, except substituting 5-(4-fluorophenyl)indole for 6-(4-fluorophenyl)indole, and using KI instead of NaBr in step 3. mp 198°–203° C. $^1$H NMR (CDCl$_3$, 300 MHz) δ2.63 (s, 3H), 3.10 (s, 6H), 5.41 (s, 2H), 7.12 (d, 1H, J=8.4 Hz), 7.15 (t, 2H, J=8.4 Hz), 7.20 (d, 1H, J=6.0 Hz), 7.58 (d, 2H, J=1.5 Hz), 7.61 (d, 1H, J=5.1 Hz), 7.64 (d, 1H, J=5.1 Hz), 7.76 (s, 1H), 7.83 (d, 2H, J=8.4 Hz), 8.38 (d, 1H, J=6.0 Hz), 8.57 (t, 1H, J=1.3 Hz), 9.06 (s, 1H). MS (DCI/NH$_3$) m/e 532 (M+H)$^+$. Anal calcd for $C_{32}H_{26}N_5O_2F \cdot 0.3\ C_4H_8O_2$: C, 71.46; H, 5.13; N, 12.55. Found: C, 71.58; H, 5.17; N, 12.77.

EXAMPLE 101

Preparation of
1-N,N-Dimethylcarbamoyl-6-(4-fluorophenyl)3-{4-[(1H-2-methylimidazo[4.5-c]pyrid-1-yl)methyl]-phenylsulfonyl}indole Step 1: 3-(4-Methylthiophenyl)-6-(4-fluorophenyl)indole.

The desired compound was prepared according to the method of Example 57, step 1, except substituting 6-(4-fluorophenyl)indole for indole.

Step 2: 1-tert-Butoxycarbonyl-3:(4-methylthiophenyl)-6-(4-fluorophenyl)indole.

To a suspension in CH$_3$CN (40 mL) of 3-(4-methylthiophenyl)-6-(4-fluorophenyl)indole (6.75 g, 20.2 mmol), prepared as in step 1, was added di-tert-butyldicarbonate (4.94 g, 22.6 mmol) and 4-dimethylaminopyridine (250 mg, 2.05 mmol). The reaction mixture was stirred for 15 minutes at ambient temperature during which time significant gas evolution occurred and the reaction mixture became a clear solution. The solvent was removed in vacuo and the residue was taken up in ethyl acetate. The ethyl acetate solution was washed with H$_2$O, 1M aqueous NaHSO$_4$, H$_2$O, and brine, dried over Na$_2$SO$_4$, filtered, and concentrated in vacuo. Chromatography on silica gel (1% then 2% ethyl acetate/hexane), followed by crystallization from ether/hexane gave 1-tert-butoxycarbonyl-3-(4-methylthiophenyl)-6-(4-fluorophenyl)indole (8.05 g, 92% yield). mp 123.7°–124.4° C.

Step 3: 1-tert-Butoxycarbonyl-3-(4-methylphenylsulfonyl)-6-(4-fluorophenyl)indole.

To a 0° C. solution in CH$_2$Cl$_2$ (200 mL) of 1-tert-butoxycarbonyl-3-(4-methylthiophenyl)-6-(4-fluorophenyl)indole (8.03 g, 18.5 mmol), prepared as in step 1, was added 3-chloroperbenzoic acid (80%, 8.2 g, 38 mmol). The cold bath was removed and the reaction mixture was stirred for 1 hour. Aqueous 2N Na$_2$CO$_3$ (50 mL) was added and the layers separated. The organic phase was washed with H$_2$O, dried over Na$_2$SO$_4$, filtered, and concentrated in vacuo. Chromatography on silica gel (10%, then 20% ethyl acetate/hexane), followed by crystallization from ether/hexane gave 1-tert-butoxycarbonyl-3-(4-methylphenylsulfonyl)-6-(4-fluorophenyl)indol (5.99 g), mp 134.6°–135.3° C.

Step 4: 1-N,N-Dimethylcarbamoyl-6-(4-fluorophenyl)3-{4-[(1H-2-methylimidazo[4.5-c]pyrid-1-yl)methyl]phenylsulfonyl}indole.

The desired compound was prepared according to the method of Example 56, steps 4–9, except substituting 1-tert-butoxycarbonyl-3-(4-methylphenylsulfonyl)-6-(4-fluorophenyl)indol, prepared as in step 3, for 1-phenysulfonyl-3-[(4-bromomethyl)phenylsulfonyl]indole. $^1$H NMR (CDCl$_3$, 300 MHz) δ2.54 (s, 3H), 3.13 (s, 6H), 5.37 (s, 2H), 7.11 (d, 2H, J=8.4 Hz), 7.13 (d, 2H, J=8.4 Hz), 7.14 (d, 1H, J=8.4 Hz), 7.47–7.58 (c, 3H), 7.75 (d, 1H, J=1.5 Hz), 7.92 (d, 1H, J=8.4 Hz), 8.00 (d, 2H, J=8.4 Hz), 8.35 (d, 1H, J=3.6 Hz), 9.03 (s, 1H). MS (DCI/NH$_3$) m/e 568 (M+H)$^+$. Anal calcd for C$_{31}$H$_{26}$N$_5$O$_3$SF.0.40 ethyl acetate: C, 64.95; H, 4.88; N, 11.62. Found: C, 64.85; H, 4.73; N, 11.72.

EXAMPLE 102

Preparation of
1-N,N-Dimethylcarbamoyl-4-bromo-3-{4-[(1H-2-methylimidazo[4.5-c]pyrid-1-yl)methyl]benzoyl}indole Step 1: 1-N,N-Dimethylcarbamoyl-4-bromo-3-(4-chloromethylbenzoyl)indole.

The desired compound was prepared according to the method of Example 4, steps 1 and 2, except substituting 4-bromoindole for 6-(4-fluorophenyl)indole.

Step 2: 1-N,N-Dimethylcarbamoyl-4-bromo-3-(4-azidomethylbenzoyl)indole.

To a solution in DMF (40 mL) of 1-N,N-dimethylcarbamoyl-4-bromo-3-(4-chloromethylbenzoyl)indole (12.54 g, 31 mmol), prepared as in Step 1, was added sodium azide (2.15 g, 33 mmol). The reaction mixture was stirred for 3 hours at ambient temperature and then was diluted with H$_2$O and extracted twice with ethyl acetate. The combined organic extracts were washed twice with H$_2$O, once with brine, dried over Na$_2$SO$_4$, filtered, and concentrated in vacuo to give 1-N,N-dimethylcarbamoyl-4-bromo-3-(4-azidomethylbenzoyl)indole (16.0 g) which was used without further purification.

Step 3: 1-N,N-Dimethylcarbamoyl-4-bromo-3-(4-aminomethylbenzoyl)indole.

To a solution of the 1-N,N-dimethylcarbamoyl-4-bromo-3-(4-azidomethylbenzoyl)indole prepared in step 2 (16.0 g) in THF (60 mL) was added triphenylphosphine (8.7 g, 33 mmol) and H$_2$O (30 mL) and the reaction mixture was stirred overnight at ambient temperature. The reaction mixture was evaporated to dryness and the residue was dissolved in THF (100 mL). 4N HCl/dioxane (8 mL) was added followed by ether (100 mL) to form a gummy solid which was left standing overnight. The liquid was decanted and the solid was dissolved in H$_2$O. The aqueous solution was extracted with ethyl acetate. The ethyl acetate extract was discarded and the aqueous phase was made basic with aqueous 2N Na$_2$CO$_3$ and as extracted three times with ethyl acetate. The combined organic extracts were washed with H$_2$O and brine, dried over Na$_2$SO$_4$, filtered, and concentrated in vacuo to give 1-N,N-dimethylcarbamoyl-4-bromo-3-(4-aminomethylbenzoyl)indole (13.65 g) which was used without further purification.

Step 4: 1-N,N-Dimethylcarbamoyl-4-bromo-3-(4-(N-3-nitropyridin-4-yl)aminomethylbenzoyl)indole.

A mixture of the 1-N,N-dimethylcarbamoyl-4-bromo-3-(4-aminomethylbenzoyl)indole prepared in step 3 (13.65 g) and 4-ethoxy-3-nitropyridine (5.10 g, 30.3 mmol) in CH$_3$CN (50 mL) was heated at reflux for 50 hours during which time 46 mL of solvent distilled out. To the thick residue was added toluene (50 mL) and the mixture was heated at a rate such that 21 mL of solvent distilled off over 2 hours. The reaction mixture was cooled to ambient temperature and diluted with ethyl acetate (30 mL). The solution was placed directly on a silica gel column and eluted with 50%, then 80% ethyl acetate/toluene to give 1-N,N-dimethylcarbamoyl-4-bromo-3-(4-(N-3-nitropyridin-4-yl)aminomethylbenzoyl)indole (6.76 g), mp 173.5°–174.5° C. after crystallization from ethyl acetate/ether.

Step 5: 1-N,N-Dimethylcarbamoyl-4-bromo-3-{4-[(1H-2-methylimidazo[4.5-c]pyrid-1-yl)methyl]benzoyl}indole.

The desired compound (4.72 g), was prepared according to the method of Example 57, step 8, except substituting 1-N,N-dimethylcarbamoyl-4-bromo-3-(4-(N-3-nitropyridin-4-yl)aminomethylbenzoyl)indole, prepared as in step 4, for 3-[(4-(N-3-nitropyrid-4-yl)aminomethyl)phenylsulfonyl]indole and crystallization from CH$_2$Cl$_2$/ethyl acetate. mp 232.5°–234 ° C. $^1$H NMR (DMSO-d6, 300 MHz) δ2.56 (s, 3H), 3.01 (s, 6H), 5.63 (s, 2H), 7.27 (d, 2H, J=8.4 Hz), 7.28 (t, 1H, J=8.4 Hz), 7.47 (dd, 1H, J=8.4, 0.3 Hz), 7.57 (dd, 1H, J=5.7, 0.3 Hz), 7.69 (dd, 1H, J=8.4, 0.3 Hz), 7.86 (d, 2H, J=8.4 Hz), 8.03 (s, 1H), 8.38 (d, 1H, J=5.7 Hz), 8.84 (d, 1H, J=0.3 Hz). MS (DCI/NH$_3$) m/e 516, 518 (M+H)$^+$. Anal calcd for C$_{26}$H$_{22}$N$_5$O$_2$Br: C, 60.47; H, 4.29; N, 13.56. Found: C, 60.21; H, 4.29; N, 13.38.

EXAMPLE 103

Preparation of
1-N,N-Dimethylcarbamoyl-4-acetyl-3-{4-[(1H-2-methylimidazo[4.5-c]pyrid-1-yl)methyl]benzoyl}indole To a 20-mL pressure bottle were added 1-N,N-dimethylcarbamoyl-4-bromo-3-{4-[(1H-2-methylimidazo[4.5-c]pyrid-1-yl)methyl]benzoyl}indole (212 mg, 0.41 mmol), prepared as in Example 102, tetrakis(triphenylphosphine)palladium(0) (27 mg, 0.023 mmol), butyl vinyl ether (208 mg, 2.1 mmol), triethylamine (87 mg, 0.86 mmol), and dioxane (5 mL). The bottle was flushed thoroughly with $N_2$, sealed, and heated at 130° C. for 24 hours. The reaction mixture was cooled to ambient temperature and placed directly on a silica gel column eluting with 7% methanol, $CH_2Cl_2$ to give 193 mg of the intermediate enol ether. The enol ether was stirred for 30 minutes in 90% trifluoroacetic acid. The reaction mixture was diluted with $H_2O$ and concentrated in vacuo. The residue was partioned between 5% aqueous $NaHCO_3$ and $CH_2Cl_2$. The organic phase was washed with $H_2O$ and brine, dried over $Na_2SO_4$, filtered, and concentrated in vacuo. 1-N,N-dimethylcarbamoyl-4-acetyl-3-{4-[(1H-2-methylimidazo[4.5-c]pyrid-1-yl)methyl]benzoyl)indole (131 mg) was obtained by chromatography on silica gel (8% methanol/$CH_2Cl_2$). $^1$H NMR (DMSO-d6, 300 MHz) δ2.40 (s, 3H), 2.58 (s, 3H), 3.03 (s, 6H), 5.64 (s, 2H), 7.27 (d, 2H, J=8.4 Hz), 7.45 (dd, 1H, J=7.8, 8.1 Hz), 7.57 (dd, 1H, J=7.8, 0.6 Hz), 7.59 (d, 1H, J=6.6 Hz), 7.84 (d, 2H, J=8.4 Hz), 7.84 (dd, 1H, J=8.1, 0.6 Hz), 8.09 (s, 1H), 8.30 (d, 1H, J=6.6 Hz), 8.87 (s, 1H). MS (DCI/$NH_3$) m/e 480 (M+H)$^+$. Anal calcd for $C_{28}H_{25}N_5O_3$.1.4 $H_2O$: C, 66.63; H, 5.55; N, 13.87. Found: C, 66.75; H, 5.70; N, 13.87.

EXAMPLE 104

Preparation of
1-N,N-Dimethylcarbamoyl-4-(fur-2-yl)-3-{4-[(1H-2-methylimidazo[4.5-c]pyrid-1-yl)methyl]benzoyl}indole.

To a 20-mL pressure bottle were added tri(n-butyl)-(fur-2-yl)stannane (160 mg, 0.45 mmol), 1-N,N-dimethylcarbamoyl-4-bromo-3-{4-[(1H-2-methylimidazo[4.5-c]pyrid-1-yl)methyl]benzoyl}indole (153 mg, 0.30 mmol), prepared as in Example 102, tetrakis(triphenylphosphine)palladium(0) (21 mg, 0.018 mmol), and dioxane (5 mL). The bottle was flushed thoroughly with $N_2$, sealed, and heated –at 115° C. for 2.5 hours. The reaction mixture was cooled to ambient temperature, filtered, and concentrated in vacuo. The residue was chromatographed on silica gel (7% methanol, $CH_2Cl_2$). The resulting material was taken up in ethyl acetate, and the solution was warmed, diluted with ether, filtered, and concentrated in vacuo. Chromatography on silica gel twice (5% methanol/$CH_2Cl_2$) gave pure 1-N,N-dimethylcarbamoyl-4-(fur-2-yl)-3-{4-[(1H-2-methylimidazo[4.5-c]pyrid-1-yl)methyl]benzoyl}indole (94 mg). $^1$H NMR (DMSO-d6, 300 MHz) δ2.53 (s, 3H), 3.03 (s, 6H), 5.57 (s, 2H), 6.17 (dd, 1H, J=3.9, 3.6 Hz), 6.36 (dd, 1H, J=3.9, 0.9Hz), 7.13 (d, 2H, J=8.7 Hz), 7.26 (dd, 1H, J=2.4, 0.9 Hz), 7.34 (dd, 1H, J=8.4, 2.1 Hz), 7.39 (t, 1H, J=8.4 Hz), 7.57 (dd, 1H, J=6.3, 1.2 Hz), 7.66 (dd, 1H, J=8.4, 2.1 Hz), 7.67 (d, 2H, J=8.7 Hz), 8.01 (s, 1H), 8.31 (d, 1H, J= 6.3 Hz), 8.86 (s, 1H). MS (DCI/$NH_3$) m/c 504 (M+H)$^+$. Anal calcd for $C_{30}H_{25}N_5 O_3$. 0.2 ethyl acetate.0.2 $H_2O$: C, 70.49; H, 5.19; N, 13.35. Found: C, 70.30; H, 5.10; N, 13.30.

EXAMPLE 105

Preparation of
1-N,N-Dimethylcarbamoyl-4-(benzo[b]fur-2-yl)-3-{4-[(1H-2-methylimidazo[4.5-c]pyrid-1-yl)methyl]benzoyl}indole The desired compound was prepared according to the method of Example 104, except substituting tri(n-butyl)-(benzo[b]fur-2-yl)stannane for tri(n-butyl)-(fur-2-yl)stannane. $^1$H NMR (DMSO-d6, 300 MHz) δ2.49 (s, 3H), 3.07 (s, 6H), 5.47 (s, 2H), 6.87 (s, 1H), 6.91 (dd, 1H, J=7.8, 1.2 Hz), 6.98 (d, 2H, J=8.7 Hz), 7.04 (dd, 1H, J=6.0, 1.2 Hz), 7.08 (td, 1H, J=6.0, 1.2 Hz), 7.33 (dt, 1H, J=9.3, 1.2 Hz), 7.47 (t, 1H, J=7.8 Hz),7.50 (dd, 1H, J=6.0, 1.2 Hz), 7.55 (dd, 1H, J=6.6, 1.2 Hz), 7.58 (d, 2H, J=8.7 Hz), 7.78 (dd, 1H, J=9.3, 1.2 Hz), 8.10 (s, 1H), 8.32 (d, 1H, J=6.6 Hz), 8.87 (s, 1H). Anal calcd for $C_{34}H_{27}N_5O_3$.0.4 ethyl acetate. 0.5 $H_2O$: C, 71.52; H, 5.26; N, 11.71. Found: C, 71.43; H, 5.35; N, 11.67.

EXAMPLE 106

Preparation of
1-N,N-Dimethylcarbamoyl-4-(trimethylsilylethynyl)-3r{4-[(1H-2-methylimidazo[4.5-c]pyrid-1-yl)methyl]benzoyl}indole The desired compound was prepared by heating a mixture of trimethyl-(trimethysilylethynyl)stannane (58 mg, 0.232 mmol), 1-N,N-dimethylcarbamoyl-4-bromo-3-{4-[(1H-2-methylimidazo[4.5-c]pyrid-1-yl)methyl]benzoyl}indole (100 mg 0.194 mmol), prepared as in Example 102, tetrakis(triphenylphosphine)palladium(0) (16 mg), and toluene (7 mL) were heated in a pressure bottle at 120° C. for 4 hours as s described in Example 103. The reaction mixture was cooled to ambient temperature, filtered, and concentrated in vacuo. Chromatography on silica gel ($CH_2Cl_2$, then 5% methanol/$CH_2Cl_2$ gave 1-N,N-dimethylcarbamoyl-4-(trimethylsilylethynyl)-3-{4-[(1H-2-methylimidazo[4.5-c]pyrid-1-yl)methyl]benzoyl}indole (58 mg). $^1$H NMR (DMSO-d6, 300 MHz) δ0.00 (s, 9H), 2.60 (s, 3H), 3.05 (s, 6H), 5.68 (s, 2H), 7.33 (d, 2H, J=9 Hz), 7.37–7.40 (m, 1H), 7.62 (d, 1H, J=6 Hz), 7.70–7.78 (m, 1H), 7.90 (d, 2H, J=9 Hz), 8.04 (s, 1H), 8.33 (d, 1H, J=6 Hz), 8.88 (s, 1H). MS (DCI/$NH_3$) m/e 534 (M+H)$^+$. Anal calcd for $C_{31}H_{31}N_5O_2Si$. 0.75 $H_2O$: C, 67.83; H, 5.94; N, 12.41. Found: C, 68.04; H, 5.98; N, 12.79.

EXAMPLE 107

Preparation of
1-N,N-Dimethylcarbamoyl-4-ethynyl-3-{4-[(1H-2-methylimidazo[4.5-c]pyrid-1-yl)methyl]benzoyl}indole To a solution in 40:20 THF/$CH_3CN$ of 1-N,N-dimethylcarbamoyl-4-(trimethylsilylethynyl)-3-{4-[(1H-2-methylimidazo[4.5-c]pyrid-1-yl)methyl]benzoyl}indole (0.39 g, 0.73 mmol), prepared as in Example 106, was added CsF (0.56 g, 3.66 mmol) and the reaction mixture was stirred for 16 hours at ambient temperature. The reaction mixture was filtered and the filtrate was washed with brine, dried over $MgSO_4$, filtered, and concentrated in vacuo to give 1-N,N-dimethylcarbamoyl-4-ethynyl-3-{4-[(1H-2-methylimidazo [4.5-c]pyrid-1-yl)methyl]benzoyl}indole (0.29 g). $^1$H NMR (DMSO-d6, 300 MHz) δ2.55 (s, 3H), 3.00 (s, 6H), 4.04 (s, 1H), 5.64 (s, 2H), 7.25 (d, 2H, J=9 Hz), 7.30–7.42 (m, 2H), 7.58 (d, 1H, J=6 Hz), 7.73 (d, 1H, J=9 Hz), 7.85 (d, 2H, J=9 Hz), 8.04 (s, 1H), 8.29 (d, 1H, J=6 Hz), 8.86 (s, 1H). MS (DCI/$NH_3$) m/e 462 (M+H)$^+$. Anal calcd for $C_{28}H_{23}N_5O_2$.2.0$H_2O$: C, 67.21;H, 5.20;N, 13.53. Found: C, 67.59; H, 5.46: N, 14.07.

EXAMPLE 108

Preparation of
4-(4-Fluorophenyl)-3-{4-[(1H-2-methylimidazo-[4.5-c]pyrid-1 -yl)methyl]benzoyl}indole To a solution in DMF (6 mL) of 1-N,N-dimethylcarbamoyl-4-bromo-3-{4-[(1H-2-methylimidazo[4.5-c]pyrid-1-yl)methyl]benzoyl}indole (200 mg, 0.38 mmol), prepared as in Example 102, was added tetrakis(triphenylphosphine)palladium(0) (22 mg) and the solution was stirred for 30 minutes. A solution of 4-fluorophenylboronic acid (80 mg, 0.57 mmol) in DMF (2 mL) was added, followed by saturated aqueous $NaHCO_3$ (4 mL). The reaction mixture was stirred at 90° C. for 4 hours and 40° C. for 48 hours. Additonal tetrakis(triphenylphosphine)palladium(0) (22 mg) was added and the reaction mixture was stirred at 115° C. for 4 hours. The reaction mixture was cooled to ambient temperature, diluted with $H_2O$, and extracted three times with ethyl acetate. The combined organic layers were dried over $MgSO_4$, filtered, and concentrated in vacuo. Chromatography on silica gel (5% methanol/$CH_2Cl_2$ gave 4-(4-fluorophenyl)-3-{4-[(1H-2-methylimidazo[4.5-c]pyrid-1-yl)methyl]benzoyl}indole as a white solid (111 mg). $^1$H NMR (DMSO-d6, 300 MHz) δ2.60 (s, 3H), 3.04 (s, 6H), 5.58 (s, 2H), 6.85 (t, 2H, J=9 Hz), 7.05–7.13 (m, 5H), 7.43 (t, 1H, J=9 Hz), 7.50 (d, 2H, J=9 Hz), 7.60 (d, 1H, J=6 Hz), 7.68 (d, 1H, J=9 Hz), 8.01 (s, 1H), 8.30 (bs, 1H), 8.88 (bs, 1H). MS (DCI/$NH_3$) m/e 532 (M+H)$^+$. Anal calcd for $C_{32}H_{26}N_5O_2F$: 0.75 $H_2O$: C, 70.51; H, 5.08; N, 12.84. Found: C, 70.23; H, 5.16; N, 12.54.

EXAMPLE 109

Preparation of
1-N,N-Dimethylcarbamoyl-4-chloro-3-{4-[(1H-2-methylimidazo[4.5-c]pyrid-1-yl)methyl]benzoyl}indole Step 1: 4-Chloro-3-(4-chloromethylbenzoyl)indole.

The desired compound was prepared according to the method of Example 90, step 2, except substituting 4-chloroindole for 4,7-dimethoxycarbonylindole.

Step 2: 1-N,N-Dimethylcarbomoyl-4-chloro-3-(4-chloromethylbenzoyl)indole.

The desired compound was prepared by reaction of 4-chloro-3-(4-chloromethylbenzoyl)indole, prepared as in step 1, with KOH and N,N-dimethylcarbamoyl chloride in THF/DMF as described in Example 2.

Preparation of
1N,N-Dimethylcarbamoyl-4-chloro-3-{4-[(1H-2-methylimidazo[4.5-c]pyrid-1-yl)methyl]benzoyl}indole The desired compound was prepared according to the method of Example 90, step 3, except substituting 1-N,N-dimethylcarbomoyl-4-chloro-3-(4-chloromethylbenzoyl)indole, prepared as in step 2, for 4,7-dimethoxycarbonyl-3-(4-chloromethylbenzoyl)indole. $^1$H NMR (DMSO-d6, 300 MHz) δ2.56 (s, 3H), 3.01 (s, 6H), 5.65 (s, 2H), 7.28 (d, 2H, J=8.4 Hz), 7.25–7.40 (m, 2H), 7.59 (dd, 1H, J=6.0, 1.2 Hz), 7.65 (dd, 1H, J=7.8, 1.2 Hz), 7.86 (d, 2H, J=8.1 Hz), 8.05 (s, 1H), 8.29 (d, 1H, J=5.4 Hz), 8.85 (s, 1H). MS (DCI/$NH_3$) m/e 472 (M+H)$^+$. Anal calcd for $C_{26}H_{22}ClN_5O_2$.1.3 $H_2O$: C, 63.04; H, 5.01; N, 14.14. Found: C, 62.92; H, 4.62; N, 13.97.

EXAMPLE 110

Preparation of
1-N,N-Dimethylcarbamoyl-4-fluoro-3-{4-[(1H-2-methylimidazo[4.5-c]pyrid-1-yl)methyl]benzoyl}indole The desired compound was prepared according to the method of Example 109, except substituting 4-fluoroindole for 4-chloroindole. $^1$H NMR (DMSO-d6, 300 MHz) δ2.57 (s, 3H), 3.00 (s, 6H), 5.66 (s, 2H), 7.08 (dd, 1H, J=11.1, 6.9 Hz) 7.29 (d, 2H, J=8.4 Hz), 7.37 (dr, 1H, J=8.1, 5.1 Hz), 7.46 (d, 1H, J=7.8 Hz), 7.62 (dd, 1H, J=5.7, 1.0 Hz), 7.86 (d, 2H, J=8.7 Hz), 8.04 (s, 1H), 8.31 (d, 1H, J=5.4 Hz), 8.87 (s, 1H). MS (DCI/$NH_3$) m/e 456 (M+H)$^+$. Anal calcd for $c_{26}H_{22}FN_5O_2$.0.2 ethyl acetate. 0.8 $H_2O$: C, 66.03; H, 5.21; N, 1437 . Found: C, 66.16; H, 5.27; N, 14.08.

EXAMPLE 111

Preparation of
1-N,N-dimethylcarbamoyl-2-methyl-3-{4-[(1H-2-methylimidazo[4.5-c]pyrid-1-yl)methyl]benzoyl}indole The desired compound was prepared according to the method of Example 109, except substituting 2-methylindole for 4-chloroindole. $^1$H NMR (DMSO-d6, 300 MHz) δ2.35 (s, 3H), 2.57 (s, 3H), 5.64 (s, 2H), 6.99 (dt, 1H, J=8.1, 1.0 Hz), 7.11 (dt, 1H, J=8.1, 1.0 Hz), 7.2–7.3 (m, 3H), 7.38 (d, 1H, J=8.1 Hz), 7.58 (d, 2H, J=8.1 Hz), 7.55–7.65 (m, 1H), 8.31 (d, 1H, J=5.4 Hz), 8.86 (s, 1H). MS (DCI/$NH_3$) m/e 381 (M+H)$^+$. Anal calcd for $C_{24}H_{20}N_4O$.0.4 $H_2O$: C, 74.36; H, 5.41; N, 14.45. Found: C, 74.25; H, 5.35; N, 14.4.

EXAMPLE 112

Preparation of
1,4-di-N,N-Dimethylcarbamoyl-3-{4-[(1H-2-methylimidazo[4.5-c]pyrid-1-yl)methyl]benzoyl}indole The desired compound was prepared according to the method of Example 109, except substituting 4-N,N-dimethylcarbamoylindole for 4-chloroindole. $^1$H NMR (DMSO-d6, 300 MHz) δ2.58 (s, 3H), 2.76 (s, 3H), 2.82 (s, 3H), 3.01 (s, 6H), 5.65 (s, 2H), 7.15 (dd, 1H, J=7.2, 1 Hz), 7.28 (apparent d, 2H, J=8.4 Hz), 7.35–7.45 (m, 1H), 7.62 (d, 1H, J=5.4 Hz), 7.67 (apparent d, 2H, J=8.4 Hz), 8.04 (s, 1H) 8.30 (d, 1H, J=5.4 Hz), 8.86 (s, 1H). MS (DCI/$NH_3$) m/e 509 (M+H)$^+$. Anal calcd for $C_{29}H_{28}N_6O_3$.1.4 $H_2O$: C, 65.52; H, 5.82; N, 15.74. Found: C, 65.59; H, 6.02; N, 14.58.

EXAMPLE 113

Preparation of
1-N,N-Dimethylcarabamoyl-5-methoxycarbonyl-3-{4-[(1H-2-methylimidazo[4.5-c]pyrid1-yl)methyl]benzoyl}indole The desired compound was prepared according to the method of Example 109, except substituting 5-methoxycarbonylindole for 4-chloroindole. $^1$H NMR (DMSO-d6, 300 MHz) δ2.65 (s, 3H), 3.08 (s, 6H), 3.96 (s, 3H), 5.44 (s, 2H), 7.19 (d, 2H, J=8.1 Hz), 7.29 (d, 1H, J=5.7 Hz), 7.57 (d, 1H, J=9.0 Hz), 7.78 (s, 1H), 7.84 (d, 2H, J=8.1 Hz), 8.11 (dd, 1H, J=9.0, 1.5 Hz), 8.42 (d, 1H, J=5.7 Hz), 9.05 (d, 1H, J=1.5 Hz), 9.06 (s, 1H). MS (DCI/$NH_3$) m/e 513 (M+$NH_4$)$^+$. Anal calcd for $C_{28}H_{25}N_5O_4$. 0.7 EtOAc: C, 66.39; H, 5.54; N, 12.57. Found: C, 66.36; H, 5.20; N, 12.47.

EXAMPLE 114

Preparation of
1-N,N-Dimethylcarbamoyl-4-methoxycarbonyl-6-(4-fluorophenyl)-3-{4-[(1H-2-methylimidazo[4.5-c]-pyrid-1-yl)-methyl]benzoyl}indole The desired compound was prepared according to the method of Example 109, except substituting 4-methoxycarbonyl-6-(4-fluorophenyl)indole for 4-chloroindole. $^1$H NMR (DMSO-d6, 300 MHz) δ2.57 (s, 3H), 3.04 (s, 6H), 3.48 (s, 3H), 5.64 (s, 2H), 7.25–7.35 (m, 4H), 7.59 (d, 1H, J=6.4 Hz), 7.75–7.80 (m, 3H), 7.85 (apparent d, 2H, J=8.1 Hz), 8.04 (d, 1H, J=1.7 Hz), 8.14 (s, 1H), 8.30 (d, 1H, J=5.2 Hz), 8.85 (s, 1H). MS (DCI/NH$_3$) m/e 590 (M+H)$^+$. Anal calcd for C$_{34}$H$_{28}$N$_5$O$_4$F. 1.4 H$_2$O: C, 66.42; H, 5.05; N, 11.39. Found: C, 66.41; H, 4.96; N, 10.91.

EXAMPLE 115

Preparation of 4-Methoxycarbonyl-3-{4-[(1H-2-methylimidazo-[4.5-c]pyrid-1 -yl)methyl]benzoyl}indole To a 0° C. solution in methanol (4 mL) of 1-N,N-dimethylcarbamoyl-4-methoxycarbonyl-3-{4-[(1H-2-methylimidazo[4.5-c]pyrid-1-yl)methyl]benzoyl}indole, (164 mg, 0.33 mmol), prepared as in Example 44, was added aqueous 1N NaOH (0.9 mL, 0.9 mmol) and the reaction mixture was stirred for 1 hour. The reaction mixture was partitioned between CH$_2$Cl$_2$ and saturated aqueous NH$_4$Cl. The aqueous phase was acidified with 1N aqueous HCl and extracted 4 times with CH$_2$Cl$_2$. The combined organic layers were dried over MgSO$_4$, filtered, and concentrated in vacuo to give 4-methoxycarbonyl-3-{4-[(1H-2-methylimidazo[4.5-c]pyrid-1-yl)methyl]benzoyl}indole (140 mg) as a white solid. $^1$H NMR (DMSO-d6,300 MHz) δ2.58 (s, 3H), 3.51 (s, 3H), 5.63 (s, 2H), 7.2–7.35 (m, 3H), 7.40 (dd, 1H, J=7.3, 1.1 Hz), 7.60 (dd, 1H, J=5.5, 1.1 Hz), 7.69 (dd, 1H, J=8.1, 1.1 Hz), 7.79 (apparent d, 2H, J=8.1 Hz), 7.89 (s, 1H), 8.30 (d, 1H, J=5.6 Hz), 8.86 (s, 1H), 12.17 (br s, 1H). MS (DCI/NH$_3$) m/e 425 (M+H)$^+$.

EXAMPLE 116

Preparation of 4-Methoxycarbonyl-1-(pyrrolidin-1-ylcarbonyl)-3-{4-[(1H-2-methylimidazo[4.5-c]pyrid-1-yl)methyl]-benzoyl}indole To a 0° C. solution in 1:1THF/DMF (2 mL) of 4-methoxycarbonyl-3-{4-[(1H-2-methylimidazo[4.5-c]pyrid-1-yl-)methyl]benzoyl}indole (111 mg, 0.26 mmol), prepared as in Example 115 was added NaH (9.0 mg, 0.39 mmol). After 5 minutes, 1-pyrrolidine carbonyl chloride (42 mg, 0.31 mmol) was added and the yellow suspension was stirred for 1 hour at 0° C. The reaction mixture was partitioned between ethyl acetate and brine. The aqueous phase was extracted twice with ethyl acetate. The combined organic layers were washed twice with H$_2$O, dried over MgSO$_4$, filtered, and concentrated in vacuo. Chromatography on silica gel gave 4-methoxycarbonyl-1-(pyrrolidin-1-ylcarbonyl)3-{4-[(1H-2-methylimidazo[4.5-c]pyrid-1-yl)methyl]benzoyl}indole (101 mg) as a white solid. $^1$H NMR (DMSO-d6, 300 MHz) δ1.7–1.8 (br m, 4H), 2.57 (s, 3H), 3.46 (s, 3H), 3.5–3.6 (br m, 4H), 5.64 (s, 2H), 7.28 (apparent d, 2H, J=8.4 Hz), 7.4–7.5 (m, 1H), 7.55–7.65 (m, 2H), 7.85 (apparent d, 2H, J=8.4 Hz), 7.98 (dd, 1H, J=8.4, 1.2 Hz), 8.19 (s, 1H), 8.30 (d, 1H, J=5.4 Hz), 8.86 (s, 1H). MS (DCI/NH$_3$) m/e 522 (M+H)$^+$.

EXAMPLE 117

Preparation of 1-N,N-Dimethylcarbamoyl-4-benzyloxycarbonyl-3-{4-[(1H-2-methylimidazo[4.5-c]pyrid-1-yl)methyl]-benzoyl}indole The desired compound was prepared according to the method of Example 109, except substituting 4-benzyloxycarbonylindole for 4-chloroindole. 1H NMR (DMSO-d6, 300 MHz) δ2.6 (s, 3H), 3.01 (s, 6H), 5.01 (s, 2H), 5.67 (s, 2H), 7.0–7.2 (m, 5H), 7.29 (apparent d, 2H, J=8.1 Hz), 7.4–7.5 (m, 1H), 7.6–7.7 (m, 2H), 7.86 (apparent d, 2H, J=8.4 Hz), 8.10 (s, 1H), 8.31 (d, 1H, J=5.4 Hz), 8.87 (s, 1H). MS (DCI/NH$_3$) m/e 572 (M+H)$^+$. Anal calcd for C$_{34}$H$_{29}$N$_5$O$_4$1.1 H$_2$O: C, 69.05; H, 5.32; N, 11.84. Found: C, 69.27; H, 5.29; N, 11.26.

EXAMPLE 118

Preparation of 1-N,N-Dimethylcarbamoyl-3-{[(1H-2-methylimidazo-[4.5-c]pyrid-1-yl)methyl]benzoyl}indole-4-carboxylic acid The desired compound (46 mg) was prepared by hydrogenolysis (1 atm H$_2$, 10% palladium on carbon, 7:3 methanol, CH$_2$Cl$_2$) of 1-N,N-dimethylcarbamoyl-4-benzyloxycarbonyl-3-{4-[(1H-2-methylimidazo[4.5-c]pyrid-1yl)methyl]benzoyl}indole, prepared as in Example 117. $^1$H NMR (DMSO-d6, 300 MHz) δ2.55 (s, 3H), 3.02 (s, 6H), 5.62 (s, 2H), 7.25 (d, 2H, J=8.4 Hz), 7.4–7.5 (m, 1H), 7.55–7.65 (m, 2H), 7.81 (d, 2H, J=8.4 Hz), 7.8–7.9 (m, 1H), 8.03 (s, 1H), 8.30 (d, 1H, J=5.7 Hz), 8.85 (s, 1H), 12.62 (br s, 1H). MS (DCI/NH$_3$) m/e 482 (M+H)$^+$.

EXAMPLE 119

Preparation of 1-N,N-Dimethylcarbamoyl-4-(N-nonylcarbamoyl)-3-{4-[(1H-2-methylimidazo[4.5-c]pyrid-1-yl)methyl]-benzoyl}indole To a suspension of 1-N,N-dimethylcarbamoyl-3-{4-[(1H-2-methylimidazo[4.5-c]pyrid-1-yl)methyl]benzoyl}indole-4-carboxylic acid (100 mg, 0.21 mmol), prepared as in Example 118, was added 1-aminononane (46 μL, 0.25 mmol), and 1-(3-dimethylaminopropyl)-3-ethylcarbodiimide hydrochloride (48 mg, 0.25 mmol), and the resulting clear solution was stirred for 24 hours at ambient temperature. The reaction mixture was partitioned between CH$_2$Cl$_2$ and brine. The aqueous phase was extracted with CH$_2$Cl$_2$. The combined organic layers were dried over MgSO$_4$, filtered, and concentrated in vacuo. The residue was purified directly by reverse-phase HPLC (25–60% CH$_3$CN/H$_2$O with 0.1% trifluoroacetic acid) to give 1-N,N-dimethylcarbamoyl-4-(N-nonylcarbamoyl)-3-{4-[(1H-2-methylimidazo[4.5-c]pyrid-1-yl)methyl]benzoyl}indole (33 mg). $^1$H NMR (DMSO-d6, 300 MHz) δ0.85 (t, 3H, J=6.3 Hz), 1.1–1.3 (m, 14H), 2.57 (s, 3H), 2.82 (q, 2H, J=6.3 Hz), 3.01 (s, 6H), 5.62 (s, 2H), 7.25 (d, 2H, J=8.1 Hz), 7.29 (dd, 1H, J=7.5, 1.0 Hz), 7.3–7.4 (m, 1H), 7.61 (d, 1H, J=5.4 Hz), 7.71 (dd, 1H, J=8.1, 1.0 Hz), 7.77 (d, 2H, J=8.1 Hz), 7.97 (s, 1H), 8.16 (t, 1H, J=5.4 Hz), 8.30 (d, 1H, J=5.7 Hz), 8.86 (s, 1H). MS (DCI/NH$_3$) m/e 607 (M+H)$^+$.

EXAMPLE 120

Preparation of 1-N,N-Dimethylcarbamoyl-4-(dec-1-yloxycarbonyl)-3-{4-[(1H-2-methylimidazo[4.5-c]pyrid-1-yl)methyl]-benzoyl}indole To a solution in DMF (4 mL) of 1-N,N-dimethylcarbamoyl-3-{4-[(1H-2-methylimidazo[4.5-c]pyrid-1-yl)methyl]benzoyl}indole-4-carboxylic acid (200 mg, 0.42 mmol), prepared as in Example 118, was added NaHCO$_3$ (70 mg, 0.83 mmol) and decyl bromide (0.43 mL, 2.07 mmol). The resulting white suspension was stirred for 72 hours at ambient temperature and then partitioned between $CH_2Cl_2$ and brine. The aqueous phase was extracted twice with $CH_2Cl_2$. The combined organic layers were dried over $MgSO_4$, filtered, and concentrated in vacuo. Chromatography on silica gel (10% methanol/$CH_2Cl_2$) gave 1-N,N-dimethylcarbamoyl-4-(dec-1-yloxycarbonyl)-3-{4-[(1H-2-methylimidazo[4.5-c]pyrid-1-yl)methyl]benzoyl}indole (65 mg). $^1$H NMR (DMSO-d6, 300 MHz) δ0.83 (t, 3H, J=6.6 Hz), 1.0–1.35 (m, 16H), 2.57 (s, 3H), 3.02 (s, 6H), 3.90 (t, 2H, J=6.6 Hz), 5.64 (s, 2H), 7.30 (d, 2H, J=8.1 Hz), 7.4–7.5 (m, 1H), 7.5–7.6 (m, 2H), 7.86 (dd, 1H, J=8.1, 1.2 Hz), 7.88 (d, 2H, J=8.4 Hz), 8.10 (s, 5.7 Hz), 8.29 (d, 1H, J=5.7 Hz), 8.85 (s, 1 H). MS(DCI/$NH_3$) m/e 622 (M+H)$^+$. Anal calcd for $C_{37}H_{43}N_5O_4$. 0.4 $H_2O$: C, 70.65; H, 7.11; N, 10.90. Found: C, 70.65; H, 7.02; N, 11.13.

EXAMPLE 121

Preparation of 1-N,N-Dimethylcarbamoyl-4-methoxy-3-{4-[(1H-2-methylimidazo[4.5-c]pyrid-1-yl)methyl]benzoyl}indole The desired compound was prepared according to the method of Example 109, except substituting 4-methoxyindole for 4-chloroindole. $^1$H NMR (DMSO-d6, 300 MHz) δ2.6 (s, 3H), 3.03 (s, 6H), 3.49 (s, 3H), 5.63 (s, 2H), 6.7 (d, 1H, J=7.5 Hz), 7.18–7.3 (m, 4H), 7.63 (d, 1H, J=6 Hz), 7.74 (d, 2H, J=7.5 Hz), 7.85 (s, 1H), 8.31 (d, 1H, 1H, J=6 Hz), 8.88 (s, 1H). MS (DCI/$NH_3$) m/e 468 (M$^+$). Anal calcd for $C_{27}H_{25}N_5O_3$. 0.75 $H_2O$: C, 67.41; H, 5.55; N, 14.55. Found: C, 67.71; H, 5.34; N, 13.64.

EXAMPLE 122

Preparation of 1-N,N-Dimethylcarbamoyl-4-methyl-3-(4-[(1H-2-methylimidazo[4.5-c]pyrid-1-yl)methyl]benzoyl}indole The desired compound was prepared according to the method of Example 109, except substituting 4-methylindole for 4-chloroindole. $^1$H NMR (DMSO-d6, 300 MHz) δ2.57 (s, 3H), 2.96 (s, 6H), 5.64 (s, 2H), 7.05 (d, 1H, J=6 Hz), 7.25 (d, 1H, J=6 Hz), 7.27–7.32 (m, 2H), 7.45 (d, 1H, J=6 Hz), 7.58 (d, 1H, J=3 Hz), 7.83 (d, 1H, J=3 Hz), 7.85 (d, 2H, J=6 Hz), 8.30 (d, 1H, J=3 Hz), 8.84 (s, 1H). MS (DCI/$NH_3$) m/e 452 (M+H)$^+$. Anal calcd for $C_{27}H_{25}N_5O_2$. 0.5 $H_2O$: C, 70.56; H, 5.73; N, 14.73. Found: C, 70.41; H, 5.69; N, 15.20.

EXAMPLE 123

Preparation of 1-N,N-Dimethylcarbamoyl-4-methoxycarbonyl-3-[(1H-2-methylimidazo[4.5-c]pyrid-1-yl)hex-6-ylcarbonyl]indole The desired compound was prepared according to the method of Example 109, except substituting 4-methoxycarbonylindole for 4-chloroindole, and 7-bromoheptanoyl chloride for 4-bromomethylbenzoyl chloride. $^1$H NMR (DMSO-d6, 300 MHz) δ1.25–1.45 (m, 4H), 1.6–1.8 (m, 4H), 2.57 (s, 3H), 2.87 (t, 2H, J= 7.4 Hz), 3.05 (s, 3H), 3.73 (s, 3H), 4.20 (t, 2H, J=7.4 Hz), 7.4–7.45 (narrow m, 2H), 7.56 (dd, 1H, 1H, J=5.4, 0.6 Hz), 7.7–7.8 (complex m, 1H), 8.25 (d, 1H, J= 5.4 Hz), 8.59 (s, 1H), 8.79 (d, 1H, J=0.6 Hz). MS (DCI/$NH_3$) m/e 490 (M+H)$^+$. Anal calcd for $C_{27}H_{31}N_5O_4$. 0.6 $H_2O$: C, 64.81; H, 6.49; N, 14.00. Found: C, 64.91; H, 6.32; N, 13.92.

EXAMPLE 124

Preparation of 1-N,N-Dimethylcarbamoyl-4-methoxycarbonyl-3-{4-[(1H-2-methylbenzimidazolyl)methyl]benzoyl}-indole The desired compound was prepared according to the method of Example 109, except substituting 2-methylbenzimidazole for 1H-2-methylimidazo[4,5-c]pyridine. $^1$H NMR (DMSO-d6, 300 MHz) δ2.54 (s, 3H), 3.02 (s, 6H), 3.47 (s, 3H), 5.59 (s, 2H), 7.1–7.2 (m, 2H), 7.26 (d, 2H, J=8.1 Hz), 7.4–7.6 (m, 4H), 7.8–7.9 (m, 3H), 8.10 (s, 1H). MS (DCI/$NH_3$) m/e 495(M+H)$^+$.

EXAMPLE 125

Preparation of 4-Methoxycarbonyl-1-(pyrrolidin-1-ylcarbonyl)3-{4-[(1H-2-methylbenzimidazolyl)methyl]benzoyl}indole The desired compound was prepared according to the method of Example 109, except substituting 1-pyrrolidine carbonyl chloride for N,N-dimethylcarbamoyl chloride in step 2, and substituting 2-methylbenzimidazole for 1H-2-methylimidazo[4,5-c]pyridine in step 3. $^1$H NMR (DMSO-d6, 300 MHz) δ1.8–1.9 (m, 4H), 2.54 (s, 3H), 3.46 (s, 3H), 3.5–3.6 (m, 4H), 5.60 (s, 2H), 7.1–7.2 (complex m, 2H), 7.27 (d, 2H, J=8.4 Hz), 7.4–7.6 (m, 4H), 7.84 (d, 2H, J=8.1 Hz), 7.97 (dd, 1H, J=8.4, 1.2 Hz), 8.18 (s, 1H). MS (DCI/$NH_3$) m/e 521 (M+H)$^+$. Anal calcd for $C_{31}H_{28}N_4O_4$. 0.1 $H_2O$. 0.4 $CH_2Cl_2$: C, 67.79; H, 5.25; N, 10.07. Found: C, 67.70; H, 5.11; N, 9.97.

EXAMPLE 126

Preparation of 1-N,N-Dimethylcarbamoyl-4-methoxycarbonyl-3-]-(1H-2-methylimidazo[4.5-c]pyrid-1-yl)pent-5-ylcarbonyl]indole The desired compound was prepared according to the method of Example 109, except substituting 4-methoxycarbonylindole for 4-chloroindole, and 6-bromohexanoyl chloride for 4-bromomethylbenzoyl chloride. $^1$H NMR (DMSO-d6, 300 MHz) δ1.3–1.4 (m, 2H), 1.66 (quint, 2H, J=7.5 Hz), 1.77 (quint, 2H, J=7.5 Hz), 2.58 (s, 3H), 2.88 (t, 2H, J=7.2 Hz), 3.04 (s, 6H), 3.70 (s, 3H), 4.21 (t, 2H, J=7.2 Hz), 7.40–7.45 (m, 2H), 7.56 (dd, 1H, J=5.2, 1.1 Hz), 7.8–7.8 (m, 1H), 8.25 (d, 1H, J=5.7 Hz), 8.59 (s, 1H), 8.79 (s, 1H). MS (DCI/$NH_3$) m/e 476 (M+H)$^+$. Anal calcd for $C_{26}H_{29}N_5O_4$. 0.5 $H_2O$: C, 64.45; H, 6.24; N, 14.45. Found: C, 64.41; H, 5.99; N, 14.20.

EXAMPLE 127

Preparation of 1-N,N-Dimethylcarbamoylmethyl-4-methoxycarbonyl-3-[(1H-2-methylimidazo[4.5-c]pyrid-1-yl)methyl)-benzoyl]indole The desired compound was prepared according to the method of Example 109, except substituting 2-chloro-N,N-dimethylacetamide for N,N-dimethylcarbamoyl chloride in step 2, and 4-methoxycarbonylindole for 4-chloroindole in step 3. $^1$H NMR (DMSO-d6, 300 MHz) δ2.59 (s, 3H), 2.84 (s, 3H), 3.08 (s, 3H), 3.58 (s, 3H), 5.30 (s, 2H), 5.64 (s, 2H), 7.25–7.45 (m, 4H), 7.6–7.7 (m, 2H), 7.78 (apparent d, 2H, J=8.1 Hz), 7.86 (s, 1H), 8.3 1 (d, 1H, J=5.4 Hz), 8.86 (s, 1H). MS (DCI/NH$_3$) m/e 510 (M+H)$^+$. Anal calcd for C$_{29}$H$_{27}$N$_5$O$_4$.1.5 H$_2$O: C, 64.91; H, 5.64; N, 13.05. Found: C, 64.75; H, 5.64; N, 13.05.

EXAMPLE 128

Preparation of
1-N,N-Dimethylcarbamoyl-4-methoxycarbonyl-3-[(1H-2-methylimidazo[4.5-c]pyrid-1-yl)methyl)-benzoyl]indole The desired compound was prepared according to the method of Example 109, except substituting 4-methoxycarbonylindole for 4-chloroindole, and 5-iodopentanoyl chloride for 4-bromomethylbenzoyl chloride. $^1$H NMR (DMSO-d6, 300 MHz) δ1.59–1.70 (m, 2H), 1.75–1.85 (m, 2H), 2.60 (s, 3H), 2.95 (t, 2H, J=9 Hz), 3.04 (s, 3H), 3.60 (s, 3H), 4.28 (t, 2H, J=9 Hz), 7.42 (d, 2H, J=6 Hz), 7.62 (d, 1H, J=6 Hz), 7.74–7.80 (m, 1H), 8.26 (d, 1H, J=6 Hz), 8.60 (s, 1H), 8.80 (s, 1H). MS (DCI/NH$_3$) m/e 462 (M+). Anal calcd for C$_{25}$H$_{27}$N$_5$O$_4$. 1.0 H$_2$O: C, 62.63; H, 6.16; N, 14.00. Found: C, 62.61; H, 6.09; N, 14.60.

EXAMPLE 129

Preparation of
1-N,N-Dimethylcarbamoyl-4-methoxycarbonyl-3-{4-[(2-methyl-4-(3H)quinazolinone-3-yl)methyl]-benzoyl}indole Step 1: 1-N,N-Dimethylcarbamoyl-4-methoxycarbonyl-3-(4-chloromethylbenzoyl)indole.

The desired compound was prepared according to the method of Example 109, steps 1 and 2, except substituting 4-carboxymethylcarbonylindole for 4-chloroindole.

Step 2: 1-N,N-Dimethylcarbamoyl -4-methoxycarbonyl-3-{4-[(2-methyl-4-(3H)quinazolinone-3-yl)methyl]benzoyl}indole.

To a solution of 2-methyl-4-(3H)quinazolinone (120 mg, 0.75 mmol) in DMF (2 mL) was added lithium hexamethyldisilazide (1.0M in THF, 0.83 mL, 0.83 mmol) and a solution in DMF (2 mL) of 1-N,N-dimethylcarbamoyl-4-methoxycarbonyl-3-(4-chloromethylbenzoyl)indole (300 mg, 0.75 mmol), prepared as in step 1, and LiBr (65 mg). The clear-brown solution was stirred for 20 hours at ambient temperature and then was partitioned between saturated aqueous NH$_4$Cl and ethyl acetate. The aqueous phase was extracted twice with ethyl acetate. The combined organic layers were washed three times with H$_2$O, dried over MgSO$_4$, filtered, and concentrated in vacuo. Chromatography on silica gel (10%, then 20% acetone/CH$_2$Cl$_2$) and reverse phase HPLC (30–65% CH$_3$CN, H$_2$O with 0.1% trifluoroacetic acid) gave 1-N,N-dimethylcarbamoyl-4-methoxycarbonyl-3-{4-[(2-methyl-4-(3H)quinazolinone-3-yl)methyl]benzoyl}indole (203 mg). $^1$H NMR (DMS)-d6, 300 MHz) δ2.52 (s, 3H), 3.03 (s, 6H), 3.51 (s, 3H), 5.49 (s, 2H), 7.37 (d, 2H, J=8.1 Hz), 7.4–7.6 (m, 3H), 7.65 (d, 1H, J=8.1 Hz), 7.8–7.9 (m, 2H), 7.87 (d, 2H, J=8.1 Hz), 8.15 (s, 1H), 8.1–8.2 (m, 1H). MS (DCI/NH$_3$) m/e 523 (M+H)$^+$. Anal calcd for C$_{30}$H$_{26}$N$_4$O$_5$. 0.3 CH$_2$Cl$_2$: C, 66.41; H, 4.89; N, 10.22. Found: C, 66.32; H, 4.97, N, 9.73.

EXAMPLE 130

Preparation of
1-(2-Ethoxyethyl)-4-methoxycarbonyl-3-{4-[(1H-2-methylimidazo[4.5-c]pyrid-1-yl)methyl]benzoyl}indole To a solution in 1:1 THF, DMF (30 mL) of 4-methoxycarbonyl-3-{4-[(1H-2-methylimidazo[4.5-c]pyrid-1-yl)m-ethyl]benzoyl}indole (0.13 g, 0.31 mmol), prepared as in Example 115, was added NaH (95%, 9.3 mg, 0.37 mmol) and the reaction mixture was stirred for 15 minutes. Neat 2-bromoethyl ethyl ether (90%, 87 μL, 0.80 mmol) was added and stirring was continued for 48 hours. The reaction was quenched with saturated aqueous NH$_4$Cl and extracted twice with ethyl acetate. The combined organic extracts were dried over MgSO$_4$, filtered, and concentrated in vacuo. Chromatography on silica gel gave 1-(2-ethoxyethyl)-4-methoxycarbonyl-3-{4-[(1H-2-methylimidazo[4.5-c]pyrid-1-yl)methyl]benzoyl}indole (83 mg) as a white solid. $^1$H NMR (DMSO-d6, 300 MHz) δ0.95 (t, 3H, J=7.5 Hz), 2.58 (s, 3H), 3.35 (q, 2H, J=6 Hz), 3.55 (s, 3H), 3.68 (t, 2H, J=6 Hz), 4.45 (t, 2H, J= 6 Hz), 5.65 (s, 2H), 7.28(d, 2H, J=9 Hz), 7.34–7.45 (m, 2H), 7.63 (dd, 1H, J=2, 6 Hz), 7.80 (d, 2H, J=9 Hz), 7.85 (dd, 1H, J=2, 8 Hz), 7.94 (s, 1H), 8.33 (d, 1H, J=6 Hz), 8.87(s,1H). MS (DCI/NH$_3$) m/e 497 (M+H)$^+$. Anal calcd for C$_{29}$H$_{28}$N$_4$O$_4$. 0.5 H$_2$O:C, 68.89; H, 5.78; N, 11.08. Found: C, 68.97; H, 5.64; N, 10.82.

EXAMPLE 131

Preparation of
1-N,N-Dimethylsulfamoyl-4-methoxycarbonyl-3-{4-[(1H-2-methylimidazo[4.5-c]pyrid-1-yl)methyl]-benzoyl}indole The desired compound was prepared according to the method of Example 130, except substituting N,N-dimethylsulfamoyl chloride for 2-bromoethyl ethyl ether. $^1$H NMR (DMSO-d6, 300 MHz) δ2.57 (s, 3H), 2.88 (s, 6H), 3.44 (s, 3H), 5.65 (s, 2H), 7.28 (d, 2H, J=9 Hz), 7.53 (d, 1H, J=9 Hz), 7.60 (d, 1H, J=6 Hz), 7.68 (d, 1H, J=8 Hz), 7.85 (d, 2H, J=9 Hz), 8.08(s, 1H), 8.20 (d, 1H, J=8 Hz), 8.30 (d, 1H, J=6 Hz), 8.87(s, 1H). MS (DCI/NH$_3$) m/e 532 (M+). Anal calcd for C$_{27}$H$_{25}$N$_5$O$_5$S. 0.25 H$_2$O: C, 60.49; H, 4.79; N, 13.06. Found: C, 60.69; H, 5.09; N, 12.87.

EXAMPLE 132

Preparation of
1-iso-Propyl-4-methoxycarbonyl-3-{4-[(1H-2-methylimidazo[4.5-c]pyrid-1-yl)methyl]benzoyl}indole The desired compound was prepared according to the method of Example 130, except substituting 1-iodo-2-methylpropane for 2-bromoethyl ethyl ether. $^1$H NMR (DMSO-d6, 300 MHz) δ0.84 (d, 6H, J=6 Hz), 2.08–2.2 (m, 1H), 2.60 (s, 3H), 3.54 (s, 3H), 4.13 (d, 2H, J=7 Hz), 5.63 (s, 2H), 7.28 (d, 2H, J=9 Hz), 7.3–7.45 (m, 2H), 7.63 (d, 1H, J=6 Hz), 7.80 (d, 2H, J=9 Hz), 7.85 (d, 1H, J=9 Hz), 7.98 (s, 1H), 8.33 (d, 1H, J=6 Hz), 8.87(s, 1H). MS (DCI/NH$_3$) m/e 481 (M+H)$^+$. Anal calcd for C$_{29}$H$_{28}$N$_4$O$_3$. 0.75 H$_2$O: C, 70.49; H, 6.01; N, 11.33. Found: C, 70.48; H, 5.85; N, 11.54.

EXAMPLE 133

Preparation of
1-Methoxycarbonylmethyl-4-methoxycarbonyl-3-{4-[(1H-2-methylimidazo[4.5-c]pyrid-1-yl)methyl]-benzoyl}indole The desired compound was prepared according to the method of Example 130, except substituting methyl bromoacetate for 2-bromoethyl ethyl ether. $^1$H NMR (DMSO-d6, 300 MHz) δ2.60 (s, 3H), 3.55 (s, 3H), 3.68 (s, 3H), 5.30 (s, 2H), 5.65 (s, 2H), 7.28 (d, 1H, J=9 Hz), 7.31–7.40 (m, 1H), 7.45 (d, 1H, J=9 Hz), 7.62 (d, 1H, J=6 Hz), 7.77–7.81(m, 3H), 7.99 (s, 1H), 8.3 1 (d, 1H, J=6 Hz), 8.87 (s, 1H). MS (DCI/NH$_3$) m/e 497 (M+H)$^+$. Anal calcd for C$_{28}$H$_{24}$N$_4$O$_5$. 0.25 H$_2$O: C, 67.12; H, 4.92; N, 11.18. Found: C, 67.17; H, 5.05; N, 10.79.

EXAMPLE 134

Preparation of
1-(2-Propanesulfonyl)-4-methoxycarbonyl-3-{4-[(1H-2-methylimidazo[4.5-c]pyrid-1-yl)methyl]-benzoyl}indole The desired compound was prepared according to the method of Example 130, except substituting 2-propanesulfonyl chloride for 2-bromoethyl ethyl ether. $^1$H NMR (DMSO-d6, 300 MHz) δ1.25 (d, 6H, J=6 Hz), 2.58 (s, 3H), 3.43 (s, 3H), 3.97–4.08 (m, 1H), 5.65 (s, 2H), 7.28 (d, 2H, J=9 Hz), 7.55–7.60 (m, 2H), 7.70 (d, 1H, J=8 Hz), 7.84 (d, 2H, J=9 Hz), 8.04 (s, 1H), 8.18 (d, 1H, J=9 Hz), 8.30 (d, 1H, J=6 Hz), 8.88(s, 1H). MS (DCI/NH$_3$) 531 (M$^+$). Anal calcd for C$_{28}$H$_{26}$N$_4$O$_5$S. 0.5 H$_2$O: C, 62.32; H, 5.04; N, 10.38. Found: C, 62.55; H, 5.02; N, 10.12.

EXAMPLE 135

Preparation of
1-(1-Pinacolyl)4-methoxycarbonyl-3-{4-[(1H-2-methylimidazo[4.5-c]pyrid-1-yl)methyl]benzoyl}indole The desired compound was prepared according to the method of Example 130, except substituting 1-chloropinacolone for 2-bromoethyl ethyl ether. mp 122°–127° C. $^1$H NMR (DMSO-d6, 300 MHz) δ1.23 (s, 9H), 2.60 (s, 3H), 3.58 (s, 3H), 5.57 (s, 2H), 5.65 (s,2H), 7.30 (d, 2H, J=9 Hz), 7.35 (d, 1H, J=9 Hz), 7.43 (d, 1H, J= 6 Hz), 7.54 (d, 1H, J=9 Hz), 7.62 (d, 1H, J=6 Hz), 7.80 (d, 2H, J=9 Hz), 7.88 (s, 1H), 8.30 (bs, 1H), 8.87 (bs, 1H). MS (DCI/NH$_3$) m/e 523 (M$^+$). Anal calcd for C$_{31}$H$_{30}$N$_4$O$_4$. 0.75 H$_2$O: C, 69.45; H, 5.92; N, 10.45. Found: C, 69.45; H, 6.17; N, 10.14.

EXAMPLE 136

Preparation of
1-Carbamoyl-4-methoxycarbonyl-3-{4-[(1H-2-methylimidazo[4.5-c]pyrid-1-yl)methyl]benzoyl}indole Step 1; 1-(4-Nitrophenoxycarbonyl)-4-methoxycarbonyl-3-{4-[(1H-2-methylimidazo[4.5-c]pyrid-1-yl)methyl]benzoyl}indole.

The desired compound was prepared by addition of NaH and 4-nitrophenyl chloroformate to a solution in DMF of 4-methoxycarbonyl-3-{4-[(1H-2-methylimidazo[4.5-c]pyrid-1-yl)methyl]benzoyl}indole, prepared as in Example 115.
Step 2: 1-Carbamoyl-4-methoxycarbonyl-3-{4-[(1H-2-methylimidazo[4.5-c]pyrid-1 -yl)methyl]benzoyl}indole.

Liquid ammonia (10 drops) was condensed into a –78° C. solution in THF (12 mL) of 1-(4-nitrophenoxycarbonyl)-4-methoxycarbonyl-3-{4-[(1H-2-methylimidazo[4.5-c]pyrid-1-yl)methyl]benzoyl}indole (259 mg), prepared as in step 1. The resulting clear-yellow solution was stirred for 20 minutes at –78° C., then saturated aqueous NH$_4$Cl was added and the reaction mixture was warmed to ambient temperature and extracted with ethyl acetate. The organic phase was dried over MgSO$_4$, filtered, and concentrated in vacuo to give 32 mg of 1-carbamoyl-4-methoxycarbonyl-3-{4-[(1H-2-methylimidazo[4.5-c]pyrid-1-yl)methyl]benzoyl}indole as a white solid. $^1$H NMR (DMSO-d6, 300 MHz) δ2.58 (s, 3H), 3.45 (s, 3H), 5.65 (s, 2H), 7.29 (d, 2H, J=9 Hz), 7.45 (t, 1H, J=9 Hz), 7.58(t,2H,J=6 Hz), 8.3–7.9(m,4H), 8.3(d, 1H,J=6 Hz), 8.34(s,1H), 8.55 1H, J= 3, 9 Hz), 8.86 (s, 1H). MS (FAB) m/e 468 (M+H)$^+$.

EXAMPLE 137

Preparation of
1-N-Methylcarbamoyl-4-methoxycarbonyl-3-{4-[(1H-2-methylimidazo[4.5-c]pyrid-1-yl)methyl]-benzoyl}indole The desired compound was prepared according to the method of Example 136, except substituting methylamine for ammonia. $^1$H NMR (DMSO-d6, 300 MHz) δ2.60 (s, 3H), 2.82 (d, 3H, J=6 Hz), 3.46 (s, 3H), 5.65 (s, 2H), 7.30 (d, 2H, J=9 Hz), 7.48 (t, 1H, J=9 Hz), 7.59 (dd, 1H, J=3, 9 Hz), 7.61 (d, 1H, J=6 Hz), 7.87 (d, 2H, J=9 Hz), 8.28 (s, 1H), 8.31 (d, 1H, J=6 Hz), 8.44 (d, 1H, J= 6 Hz), 8.52 (dd, 1H, J=3, 9 Hz), 8.90 (bs, 1H). MS (DCI/NH$_3$) m/e 425.

EXAMPLE 138

Preparation of
1-(2-Ethoxyethyl)-4-chloro-3-{4-[(1H-2-methyl-imidazo[4.5-c]pyrid-1-yl)methyl] benzoyl}indole Step 1: 4-Chloro-3-{4-[(1H-2-methylimidazo[4,5-c]pyrid-1-yl)methyl]benzoyl}indole.

The desired compound was prepared according to the method of Example 90, except substituting 4-chloroindole for 4,7-dimethoxycarbonylindole.
Step 2: 1-(2-Ethoxyethyl)-4-chloro-3-{4-[(1H-2-methylimidazo[4.5-c]pyrid-1 -yl)methyl]benzoyl}indole.

The desired compound was prepared according to the method of Example 130, except substituting 4-chloro-3-{4-[(1H-2-methylimidazo[4.5-c]pyrid-1-yl)methyl] benzoyl}indole, prepared as in step 1, for 4-methoxycarbonyl-3-{4-[(1H-2-methylimidazo[4.5-c]pyrid-1-yl)methyl] benzoyl}indole. $^1$H NMR (DMSO-d6, 300 MHz) δ0.95 (t, 3H, J=9 Hz), 2.57 (s, 3H), 3.2–3.3 (m, 2H), 3.68 (t, 2H, J= 6 Hz), 4.4 (t, 2H, J=6 Hz), 5.65 (s, 2H), 7.2–7.31 (m, 4H), 7.6 (d, 1H, J=6 Hz), 7.65 (d, 1H, J=9 Hz),7.8 (d, 2H, J=9 Hz), 7.84 (s, 1H), 8.3 (d, 1H, J=6 Hz), 7.86 (s, 1H). MS (DCI/NH$_3$) m/e 473 (M+H)$^+$. Anal calcd for C$_{27}$H$_{25}$ClN$_4$O$_2$. 0.75 H$_2$O: C, 66.66; H, 5.49; N, 11.51. Found: C, 66.95; H, 5.33; N, 11.60.

EXAMPLE 139

Preparation of
1-N,N-Dimethylcarbamoyl-4-methoxycarbonyl-3-{3-methoxy-4-[(1H-2-methylimidazo[4.5-c]pyrid-1-yl)methyl]benzoyl}indole The desired compound was prepared according to the method of Example 96, except substituting 3-methoxy-4-bromomethylbenzoic acid for 4-chloromethylbenzoic acid. Chromatography on silica gel (CH$_2$C$_2$, then 2% methanol/CH$_2$Cl$_2$) gave 1-N,N-dimethylcarbamoyl-4-methoxycarbonyl-3-(3-methoxy-4-[(1H-2-methylimidazo[4.5-c]pyrid-1-yl)methyl]benzoyl}indole (120 mg). $^1$H NMR (DMSO-d6, 300 MHz) δ8.84 (s, 1H), 8.28–8.26 (d, 1H, J=5.5 Hz), 8.17 (s, 1H), 7.87–7.85 (d, 1H, J=8.1 Hz), 7.57–7.51 (m, 3H), 7.48–7.45 (d, 1H, J=8.1 Hz), 7.41–7.38 (d, 1H, J=7.4 Hz), 5.52 (s, 2H), 3.87 (s, 3H), 3.51 (s, 3H), 3.03 (s, 6H), 2.57 (s, 3H). MS (DCI/NH$_3$) m/e 526 (M+H)$^+$. IR (KBr) 3450, 1700, 1395, 1320, 1300, 1200, 750 cm$^{-1}$. Anal calcd for $C_{29}H_{27}N_5O_5$. 1.0 $H_2O$: C, 64.07; H, 5.37; N, 12.88. Found: C, 63.91; H, 5.30; N, 12.59.

EXAMPLE 140

Preparation of
1-N,N-Dimethylcarbamoyl-4-methoxycarbonyl-3-{3-methoxy-4-[(3-H2-methylimidazo[4.5-c]pyrid-3-yl)-methyl]benzoyl}indole The desired compound (230 mg) was isolated from the chromatography described in Example 139. $^1$H NMR (DMSO-d6, 300 MHz) δ8.80 (s, 1H), 8.29–8.27 (d, 1H, J=5.5 Hz), 8.17 (s, 1H), 7.88–7.85 (d, 1H, J=8.5 Hz), 7.56–7.51 (t, 1H, J=5.4 Hz), 7.48–7.45 (d, 1H, J=5.4 Hz), 7.43–7.41 (d, 1H, J=7.5 Hz), 5.58 (s, 2H), 3.87 (s, 3H), 3.51 (s, 3H), 3.03 (s, 6H), 2.60 (s, 3H). MS (DCI/NH$_3$) m/e 526 (M+H)$^+$. Anal calcd for $C_{29}H_{27}N_5O_5$. 0.25 $H_2O$: C, 65.71; H, 5.22; N, 13.21. Found: C, 65.95; H, 5.15; N, 13.53.

EXAMPLE 141

Preparation of
1-N,N-Dimethylcarbamoyl-4-methoxycarbonyl-3-{4-[(1H-2-methylimidazo[4.5-c]pyrid-1-yl)methyl]-phenylsulfonyl}indole Step 1: 3-(4-Methylthiophenyl)-4-methoxycarbonylindole.

The desired compound was prepared according to the method of Example 57, step 1, except substituting 4-methoxycarbonylindole for indole.
Step 2: 1N,N-Dimethylcarbamoyl-3-(4-methylthiophenyl)-4-methoxycarbonylindole.

The desired compound was prepared by reaction of 3-(4-methylthiophenyl)-4-methoxycarbonylindole with KOH and N,N-dimethylcarbamoyl chloride as described in Example 2.
Step 3: 1-N,N-Dimethylcarbamoyl-3-(4-methylphenyl[sulfonyl)4-methoxycarbonylindole.

To a solution in acetic acid (50 mL) of 1-N,N-dimethylcarbamoyl-3-(4-methylthiophenyl)-4-methoxycarbonylindole (3.5 g, 9.5 mmol), prepared as in step 2, was added OXONE (potassium peroxymonosulfate, 6.2 g, 10 mmol) and the reaction mixture was stirred for 14 hours at ambient temperature. NaIO$_4$ (1.5 g) was added and the reaction was stirred for 4 hours and then quenched with saturated aqueous Na$_2$SO$_3$. Solid Na$_2$SO$_3$ was added to the reddish reaction mixture until it remained bright yellow in color. The reaction mixture was diluted with H$_2$O, made basic with saturated aqueous Na$_2$CO$_3$, and extracted three times with CH$_2$Cl$_2$. The combined organic extracts were washed with saturated aqueous Na$_2$CO$_3$ and brine, dried over MgSO$_4$, filtered, and concentrated in vacuo. Chromatography on silica gel (3%, then 20% methanol/CH$_2$Cl$_2$) gave 1.2 g of impure material which was chromatographed again (CH$_2$Cl$_2$) to give 1-N,N-dimethylcarbamoyl-3-(4-methylphenylsulfonyl)-4-methoxycarbonylindole (0.52 g).
Step 4: 1-N,N-Dimethylcarbamoyl-3-[(4-bromomethyl)phenylsulfonyl]-4-methoxycarbonylindole.

To a solution in CCl$_4$ (50 mL) of 1-N,N-dimethylcarbamoyl-3-(4-methylphenylsulfonyl)-4-methoxycarbonylindole (1.9 g, 4.7 mmol), prepared as in step 3, was added N-bromosuccinimide (0.85 g, 4.8 mmol) and catalytic benzoyl peroxide. The reaction mixture was stirred at reflux for 14 hours, then cooled to ambient temperature and concentrated in vacuo. Chromatography on silica gel (1%, then 3% methanol/CH$_2$Cl$_2$) gave 1-N,N-dimethylcarbamoyl-3-[(4-bromomethyl)phenylsulfonyl]-4-methoxycarbonylindole (1.5 g) of sufficient purity to use in the next step.
Step 5: 1-N,N-Dimethylcarbamoyl-4-methoxycarbonyl-3-{4-[(1H-2-methylimidazo[4.5-c]pyrid-1-yl)methyl]phenylsulfonyl}indole.

The desired compound was prepared according to the method of Example 90, step 3, except substituting 1-N,N-dimethylcarbamoyl-3-[(4-bromomethyl)phenylsulfonyl]-4-methoxycarbonylindole, prepared as in step 4, for 4,7-dimethoxycarbonyl-3-(4-chloromethylbenzoyl)indole. Chromatography on silica gel (1%, then 2% methanol/CH$_2$Cl$_2$) gave 1-N,N-dimethylcarbamoyl-4-methoxycarbonyl-3-{4-[(1H-2-methylimidazo[4.5-c]pyrid-1-yl)methyl]phenylsulfonyl}indole (180 mg). $^1$H NMR (DMSO-d6, 300 MHz) δ8.83 (s, 1H), 8.56 (s, 1H), 8.27–8.25 (d, 1H, J=5.5 Hz), 7.88–7.83 (m, 4H), 7.54–7.52 (d, 1H, J=5.5 Hz), 7.47–7.45 (d, 2H, J=5.1 Hz), 7.3 1–7.28 (d, 2H, J=8.5 Hz), 5.63 (s, 2H), 3.51 (s, 3H), 3.02 (s, 6H), 2.56 (s, 3H). MS (DCI/NH$_3$) m/e 532 (M+H)$^+$. IR (KBr) 3950, 1700, 1600, 1400, 1290 cm$^{-1}$. Anal calcd for $C_{27}H_{25}N_5O_5S$. 1.75 $H_2O$: C, 57.13; H, 5.14; N, 12.33. Found: C, 57.09; H, 4.63; N, 11.76.

EXAMPLE 142

Preparation of
1-N,N-Dimethylcarbamoyl-4-methoxycarbonyl-3-{4-[(1H-2-methylimidazo[4.5-c]pyrid-1-yl)methyl]-phenylsulfonyl}indole The desired compound (130 mg) was isolated from the chromatography described in Example 141. $^1$H NMR (DMSO-d6, 300 MHz) δ8.56 (s, 1H), 8.29–8.27 (d, 1H, J=5.8 Hz), 7.89–7.86 (d, 1H, J=8.5 Hz), 7.84–7.81(d, 1H, J=5.5 Hz), 7.56–7.54 (d, 1H, J=5.5 Hz), 7.48–7.45 (d, 2H, J=8.0 Hz), 7.36–7.3 (d, 2H, J=8.5Hz), 5.69 (s, 2H), 3.51 (s, 3H), 3.02 (s, 6H), 2.56 (s, 3H). MS (DCI/NH$_3$) m/e 532 (M+H)$^+$. Anal calcd for $C_{27}H_{25}N_5O_5S$. 1.75 $H_2O$: C, 57.59; H, 5.10; N, 12.43. Found: C, 57.57; H, 4.75; N, 13.05.

EXAMPLE 143

Preparation of 1-N,N-Dimethylcarbamoyl-4-ethynyl-3-{4-[(1H-2-methylimidazo[4.5-c]-pyrid-1-yl)methyl]benzoyl}indole The desired compound was prepared by catalytic hydrogenolysis (1 atm. H2, 10% palladium on carbon, ethanol) of 1-N,N-dimethylcarbamoyl-4-ethynyl-3-{4-[(1H-2-methylimidazo[4.5-c]pyrid-1-yl)methyl]benzoyl)indole, prepared as in Example 107. $^1$H NMR (DMSO-d6, 300 MHz) δ1.02 (t, 3H, J=9 Hz), 2.58 (s, 3H), 2.98 (bs, 8H), 5.65 (s, 2H), 7.13 (d, 1H, J=9 Hz), 7.28–7.33 (m, 3H), 7.47 (d, 1H, J=9 Hz), 7.60 (d, 1H, J=6 Hz), 7.85–7.90 (m, 3H), 8.30 (m, 3H), 8.86 (s, 1H). MS (DCI/NH$_3$) m/e 466 (M+H)$^+$. Anal calcd for $C_{28}H_{27}N_5O_2$. 0.75 $H_2O$. C, 70.54; H, 6.03; N, 14.27. Found: C, 70.20; H, 5.99; N, 14.61.

EXAMPLE 144

Preparation of
1-N,N-Dimethylcarbamoyl-4-hydroxy-3-{4-[(1H-2-methylimidazo[4.5-c]pyrid-1-yl)methyl]benzoyl}indole To a solution in CH$_2$Cl$_2$ (10 mL) at −78° C. of 1-N,N-dimethylcarbamoyl-4-methoxy-3-{4-[(1H-2-methylimidazo[4.5-c]pyrid-1-yl)methyl]benzoyl}indole (94 mg, 0.20 mmol), prepared as in Example 121, was added BBr3 (1.0M in CH$_2$Cl$_2$, 240 μL, 0.24 mmol), and the reaction mixture was stirred for 30 minutes at −78° C. The cold bath was removed and the reaction mixture was stirred overnight at ambient temperature. The reaction was quenched by addition of H$_2$O (5 mL) and the resulting slightly turbid yellow solution was extracted with CH$_2$Cl$_2$. The organic phase was washed with brine, dried over MgSO$_4$, filtered, and concentrated in vacuo. The is resulting yellow solid was dissolved in acetone (15 mL) and aqueous 1M HCl (5 mL) was added. The solution was shaken for 5–10 minutes, neutralized with saturated aqueous NaHCO$_3$, and extracted twice with ethyl acetate. The combined organic extracts were washed with brine, dried over MgSO$_4$, filtered, and concentrated in vacuo to give 1-N,N-dimethylcarbamoyl-4-hydroxy-3-{4-[(1H-2-methylimidazo[4.5-c]pyrid-1-yl)methyl]benzoyl}indole (48 mg) as an amorphous yellow solid. mp 99°–108° C. $^1$H NMR (DMSO-d6, 300 MHz) δ2.60 (s, 3H), 2.98 (s, 6H), 5.68 (s, 2H), 6.68 (d, 1H, J=9 Hz), 7.03 (d, 1H, J=9 Hz), 7.25 (d, 1H, J=9 Hz), 7.28– 7.36 (m, 2H), 7.64 (d, 1H, J=6 Hz), 7.86 (d, 2H, J=9 Hz), 8.15 (s, 1H), 8.34 (bs, 1H), 8.88 (bs, 1H). MS (DCI/NH$_3$) m/e 454(M$^+$).

EXAMPLE 145

Preparation of
1N,N-Dimethylcarbamoyl-6-bromo-4-methoxycarbonyl-3-{4-[(1H-2-methylimidazo[4.5-c]pyrid-1-yl)methyl]benzoyl}indole.

Step 1: 1-N,N-Dimethylcarbamoyl-6-bromo-4-methoxycarbonyl-3-(4-(N-3-nitropyridin-4-yl)aminomethylbenzoyl)indole.

The desired compound was prepared according to the method of Example 102, steps 1–4, except substituting 6-bromo-4-methoxycarbonylindole for 4-bromoindole.

Step 2: 1-N,N-Dimethylcarbamoyl-6-bromo-4-methoxycarbonyl-3-(4-(N-3-aminopyridin-4-yl)aminomethylbenzoyl)indole.

The desired compound was prepared by catalytic hydrogenolysis (4 atm H2, Raney nickel, THF) of 1-N,N-dimethylcarbamoyl-6-bromo-4-methoxycarbonyl-3-(4-(N-3-nitropyridin-4-yl)aminomethylbenzoyl)indole, prepared as in step 1.

Step 3: 1-N,N-Dimethylcarbamoyl-6-bromo-4-methoxycarbonyl-3-{4-[(1H-2-methylimidazo[4.5-c]pyrid-1-yl)methyl]benzoyl}indole.

The desired compound was prepared by heating a solution of 1-N,N-dimethylcarbamoyl-6-bromo-4-methoxycarbonyl-3-(4-(N-3-aminopyridin-4yl)aminomethylbenzoyl)indole (2.53 g), prepared as in step 2, in acetic acid (20 mL) and acetic anhydride (20 mL) as described in Example 57, step 8. $^1$H NMR (DMSO-d6, 300 MHz) δ2.57 (s, 3H), 3.01 (s, 6H), 3.50 (s, 3H), 5.64 (s, 2H), 7.28 (d, 2H, J=8.4 Hz), 7.59 (dd, 1H, J=5.7, 0.6 Hz), 7.67 (d, 1H, J=2.1 Hz), 7.84 (d, 2H, J=8.4 Hz), 8.07 (d, 1H, J=2.1 Hz), 8.17 (s, 1H), 8.30 (d, 1H, J=5.7 Hz), 8.86 (s, 1H). MS (DCI/NH$_3$) m/e 576 (M+H)$^+$, 574. Anal calcd for C$_{28}$H$_{24}$N$_5$O$_4$ Br . 0.4 ethyl acetate: C, 58.31; H, 4.50; N, 11.49. Found: C, 58.44; H, 4.35; N, 11.21.

EXAMPLE 146

Preparation of
1-N,N-Dimethylcarbamoyl-6-(benzo[b]fur-2-yl)-4-methoxycarbonyl-3-{4-[(1H-2-methylimidazo[4.5-c]pyrid-1yl)methyl]benzoyl}indole.

The desired compound was prepared according to the method of Example 105, except substituting 1-N,N-dimethylcarbamoyl-6-bromo-4-methoxycarbonyl-3-{4-[(1H-2-methylimidazo[4.5-c]pyrid-1-yl)methyl]benzoyl}indole, prepared as in Example 145, for 1-N,N-dimethylcarbamoyl-4-bromo-3-{4-[(1H-2-methylimidazo[4.5-c]pyrid-1-yl)methyl]benzoyl}indole. $^1$H NMR (DMSO-d6, 300 MHz) δ2.57 (s, 3H), 3.07 (s, 6H), 3.53 (s, 3H), 5.66 (s, 2H), 7.29 (t, 1H, J=8.4 Hz), 7.30 (d, 2H, J=8.7 Hz), 7.35 (t, 1H, J=8.4 Hz), 7.62 (d, 1H, J=5.4 Hz), 7.63 (s, 1H), 7.67 (d, 1H, J=8.4 Hz), 7.69 (d, 1H, J=8.4 Hz), 7.88 (d, 2H, J=8.7 Hz), 8.11 (d, 1H, J=1.5 Hz), 8.23 (s, 1H), 8.32 (d, 1H, J=5.4 Hz), 8.35 (d, 1H, J=1.5 Hz), 8.87 (s, 1H). MS (DCI/NH$_3$) m/e 612 (M+H)$^+$. Anal calcd for C$_{36}$H$_{29}$N$_5$O$_3$. 0.4 ethyl acetate. 0.4 H$_2$O: C, 69.04; H, 5.08; N, 10.71. Found: C, 69.25; H, 4.94; N, 10.69.

EXAMPLE 147

Preparation of
1N,N-Dimethylcarbamoyl-6-(fur-2-yl)-4-methoxycarbonyl-3-{4-[(1H-2-methylimidazo[4.5-c]-pyrid-1-yl)methyl]benzoyl}indole The desired compound was prepared according to the method of Example 104, except substituting 1-N,N-dimethylcarbamoyl-6-bromo-4-methoxycarbonyl-3-{4-[(1H-2-methylimidazo[4.5-c]pyrid-1-yl)methyl]benzoyl}indole, prepared as in Example 145, for 1-N,N-dimethylcarbamoyl-4-bromo-3-{4-[(1H-2-methylimidazo[4.5-c]pyrid-1-yl)methyl]benzoyl}indole. $^1$H NMR (DMSO-d6, 300 MHz) δ2.58 (s, 3H), 3.06 (s, 6H), 3.51 (s, 3H), 5.65 (s, 2H), 6.63 (dd, 1H, J=2.4, 3.6 Hz), 7.11 (d, 1H, J=3.6 Hz), 7.29 (d, 2H, J=8.4 Hz), 7.60 (d, 1H, J=6.3 Hz), 7.79 (d, 1H, J=1.2 Hz), 7.87 (d, 2H, J=8.4 Hz), 7.89 (d, 1H, J=1.2 Hz), 8.10 (d, 1H, J=2.4 Hz), 8.14 (s, 1H), 8.30 (d, 1H, J=6.3 Hz), 8.86 (s, 1H). MS (DCI/NH$_3$) m/e 562 (M+H)$^+$. Anal calcd for C$_{32}$H$_{27}$N$_5$O$_5$. 0.5 ethyl acetate. 0.1 H$_2$O: C, 67.23; H, 5.18; N, 11.53. Found: C, 67.24; H, 5.03; N, 11.57.

EXAMPLE 148

Preparation of
1-N,N-Dimethylcarbamoyl-4-(N,N-dimethylaminocarbonyloxy)-3-{4-[(1H-2-methylimidazo[4.5-c]pyrid-1-yl)methyl]benzoyl}indole Step 1: 1-N,N-Dimethylcarbamoyl-4-(N,N-dimethylaminocarbonyloxy)indole.

The desired compound was prepared by treating 4-hydroxyindole with 2 equivalents of NaH and 2 equivalents of dimethylcarbamyl chloride according to the method of Example 130.

Step. 2: 1-N,N-Dimethylcarbamoyl-4-(N,N-dimethylaminocarbonyloxy)-3-(4-chloromethylbenzoyl)indole.

The desired compound was prepared according to the method of Example 4, step 2, except substituting 1-N,N-dimethylcarbamoyl-4-(N,N-dimethylaminocarbonyloxy)indole, prepared as in step 1, for 6-(4-fluorophenyl)indole-1-carboxylic acid diamide.

Step 3: 1-N,N-Dimethylcarbamoyl-4-(N,N-dimethylaminocarbonyloxy)-3-{4-[(1H-2-methylimidazo[4.5-c]pyrid-1-yl)methyl]benzoyl}indole.

The desired compound was prepared according to the method of Example 102, steps 2–5, except substituting 1N,N-dimethylcarbamoyl-4-(N,N-dimethylaminocarbonyloxy)-3-(4-chloromethylbenzoyl)indole, prepared as in step 2, for 1-N,N-dimethylcarbamoyl-4-bromo-3-(4-chloromethylbenzoyl)indole. $^1$H NMR (DMSO-d6, 300 MHz) δ2.58 (s, 3H), 2.70 (s, 3H), 2.85 (s, 3H), 3.0 (s, 6H), 5.65 (s, 2H), 6.96 (d, 1H, J=8 Hz), 7.28 (d, 2H, J=9 Hz), 7.30–7.38 (m,1H), 7.50 (d, 1H, J=9 Hz), 7.60(d, 1H, J=6 Hz), 7.80 (d, 2H, J=9 Hz), 7.94 (s, 1H), 8.30 (d, 1H, J=6 Hz), 8.87(s, 1H). MS (DCI/NH$_3$) m/e 525 (M+). Anal calcd for C$_{29}$H$_{28}$N$_6$O$_4$. 1.0 H$_2$O: C, 64.19; H, 5.57; N, 15.48. Found: C, 64.40; H, 5.33; N, 15.38.

EXAMPLE 149

Preparation of 1-N,N-Dimethylcarbamoyl-4-(N,N-dimethylaminocarbonylamino)-3-{4-[(1H-2-methylimidazo[4.5-c]-pyrid-1-yl)methyl]benzoyl}indole.

Step 1: 1-N,N-Dimethylcarbamoyl-4-(N,N-dimethylaminocarbonylamino)indole.

To a solution of 4-aminoindole (1.0 g, 7.6 mmol) in THF (30 mL) at −78° C. was added lithium hexamethyldisilazide (1.0M in THF, 7.6 mL, 7.6 mmol). The reaction mixture was stirred for 5 minutes at −78° C. and N,N-dimethylcarbamyl chloride (0.74 mL, 8.0 mmol) was added. The cold bath was removed and the reaction mixture was stirred for 80 minutes. The reaction mixture was cooled back to −78° C. and lithium hexamethyldisilazide (1.0M in THF, 7.6 mL, 7.6 mmol) was added. The reaction mixture was stirred for 10 minutes at −78° C. and N,N-dimethylcarbamyl chloride (0.74 mL, 8.0 mmol) was added. The reaction mixture was stirred for 15 minutes at −78° C., the cold bath was removed and the reaction mixture was warmed to ambient temperature. The reaction was quenched with saturated aqueous NH$_4$Cl and the mixture was extracted twice with ethyl acetate. The combined organic layers were washed with brine, dried over MgSO$_4$, filtered, and concentrated in vacuo. Chromatography on silica gel (ethyl acetate) gave 1-N,N-dimethylcarbamoyl-4-(N,N-dimethylaminocarbonylamino)indole (0.96 g).

Step 2: 1-N,N-Dimethylcarbamoyl-4-(N,N-dimethylaminocarbonylamino)-3-{4-[( 1H-2-methylimidazo[4.5-c]pyrid-1-yl)methyl]benzoyl}indole.

The desired compound was prepared according to the method of Example 4, steps 2 and 3, except substituting 1-N,N-dimethylcarbamoyl-4-(N,N-dimethylaminocarbonylamino)indole, prepared as in step 1, for 6-(4-fluorophenyl)indole-1-carboxylic acid diamide. $^1$H NMR (DMSO-d6, 300 MHz) δ 2.58 (s, 3H), 2.93 (s, 6H), 3.00 (s, 6H), 5.63 (s, 2H), 7.13 (d, 1H, J=6 Hz), 7.28–7.33 (m, 3H), 7.60 (d, 1H, J=3 Hz), 7.83 (d, 2H, J=6 Hz), 7.97 (s, 1H), 8.03 (d, 1H, J=6 Hz), 8.30 (d, 1H, J=3 Hz), 8.85 (s, 1H), 10.34 (s, 1H). MS (DCI/NH$_3$) m/e 524 (M+H)$^+$. Anal calcd for C$_{29}$H$_{29}$N$_7$O$_3$. 1.75 H$_2$O: C, 62.74; H, 5.90; N, 17.66. Found: C, 62.70; H, 5.57; N, 16.04.

EXAMPLE 150

Preparation of 1-N,N-Dimethylcarbamoyl-4-Cyano-3-{4-[(1H-2-methylimidazo[4.5-c]pyrid-1-yl)methyl]benzoyl}indole hydrochloride.

Step 1: 1H-1-(4-Bromobenzyl)-2-methylimidazo[4.5-c]pyridine.

The desired compound was prepared according to the method of Example 57, steps 7 and 8, except substituting 4-bromobenzylamine for 1-phenylsulfonyl-3-[(4-aminomethyl)phenylsulfonyl]indole.

Step 2: 1H-1-(4-Trimethylstannylbenzyl)-2-methylimidazo[4.5-c]pyridine.

To a solution under N$_2$ of 1H-1-(4-bromobenzyl)-2-methylimidazo[4.5-c]pyridine (3.48 g, 11.5 mmol), prepared as in step 1, and hexamethylditin (7.73 g, 23.6 mmol) in dimethoxyethane (150 mL) was added tetrakis(triphenylphosphine) palladium(0) (660 mg, 0.57 mmol) and the reaction mixture was stirred at reflux for 3.5 hours. The reaction mixture was cooled to ambient temperature and filtered. The titrate was concentrated in vacuo and taken up in ethyl acetate. The ethyl acetate solution was washed twice with pH 7 buffer and once with brine. The combined aqueous washings were extracted twice with ethyl acetate. The combined organic extracts were dried over Na$_2$SO$_4$, filtered, and concentrated in vacuo. Chromatography on silica gel (4% methanol/CHCl$_3$) followed by trituration with hexane gave 1H-1-(4-trimethylstannylbenzyl)-2-methylimidazo[4.5-c]pyridine (3.74 g) as soft crystals, mp 123°–126° C.

Step 3: 1-N,N-Dimethylcarbamoyl-4-cyano-3-{4-[(1H-2-methylimidazo[4.5-c]pyrid-1-yl)methyl]benzoyl}indole hydrochloride.

To a solution of 1-N,N-dimethylcarbamoyl-4-cyanoindole-3-carbonyl chloride (prepared by treatment of 566 mg of 1-N,N-dimethylcarbamoyl-4-cyanoindole-3-carboxylic acid with thionyl chloride) in THF (20 mL) was added allylpalladium chloride dimer (52 mg, 0.14 mmol) and 1H-1-(4-trimethylstannylbenzyl)-2-methylimidazo[4.5-c] pyridine (850 mg, 2.2 mmol), prepared as in step 2. The reaction mixture was heated at reflux for 4 hours, and then was cooled to ambient temperature, diluted with CH$_2$Cl$_2$, and filtered. The filtrate was washed with 5% aqueous NaHCO$_3$, H$_2$O, and brine. The combined aqueous washings were extracted with CH$_2$Cl$_2$. The combined organic extracts were dried over Na$_2$SO$_4$, filtered, and concentrated in vacuo. The crude material was chromatographed three times (twice with 4–8% methanol/CHCl$_3$; then 7% methanol/CH$_2$Cl$_2$). The material obtained after the chromatographies was dissolved in THF (3 mL) and 2 drops of 4N HCl/dioxane was added. The resulting fine solid was filtered and washed with ether to give 1-N,N-dimethylcarbamoyl-4-cyano-3-{4-[(1H-2-methylimidazo[4.5-c]pyrid-1-yl)methyl]benzoyl}indole hydrochloride (13 mg). mp 179°–181° C. $^1$H NMR (DMSO-d6, 300 MHz) δ2.70 (s, 3H), 3.01 (s, 6H), 5.88 (s, 2H), 7.39 (d, 2H, J=8.1 Hz), 7.56 (t, 1H, J=8.1 Hz), 7.84 (dd, 1H, J=8.1, 1.2 Hz), 7.94 (d, 2H, J=8.1 Hz), 8.02 (dd, 1H, J=8.1, 1.2 Hz), 8.27 (s, 1H), 8.32 (d, 1H, J=6.3 Hz), 8.68 (d, 1H, J=6.3 Hz), 9.44 (s, 1H). MS (DCI/NH$_3$) m/e 463 (M+H)$^+$. Anal calcd for C$_{27}$H$_{23}$N$_6$O$_2$Cl. 1.4 H$_2$O: C, 61.87; H, 4.96; N, 16.03. Found: C, 61.89; H, 4.84; N, 16.00.

EXAMPLE 151

Preparation of 1-N,N-Dimethylcarbamoyl-4-methoxycarbonyl-3-{4-(1H-2-methylimidazo[4.5-c]pyrid-1-yl)methyl]-benzyl}indole.

Step 1: 4-Methoxycarbonyl-3-[(4-chloromethyl)benzyl] indole.

To a 0° C. solution of trifluoroacetic acid (0.65 mL, 8.6 mmol) and triethylsilane (2.7 mL, 17 mmol) in CH$_2$Cl$_2$ (17 mL) was added dropwise a solution of 4-methoxycarbonylindole (1.0 g, 5.7 mmol) and 4-chloromethylbenzaldehyde (0.97 g, 6.3 mmol) in CH$_2$Cl$_2$ (29 mL). The reaction mixture was stirred for 1 hour at 0° C. and 20 hours at ambient temperature and then was partitioned between CH$_2$Cl$_2$ and saturated aqueous NaHCO$_3$. The aqueous phase was extracted with CH$_2$Cl$_2$. The combined organic layers were washed with saturated aqueous NaHCO$_3$, dried over MgSO$_4$, filtered, and concentrated in vacuo. Chromatography on silica gel (25% hexane/CH$_2$Cl$_2$, then CH$_2$Cl$_2$) gave 4-methoxycarbonyl-3-[(4-chloromethyl)benzyl]indole (1.06 g).

Step 2: 1-N,N-Dimethylcarbamoyl-4-methoxycarbonyl-3-[(4-chloromethyl)benzyl]indole.

The desired compound was prepared according to the method of Example 130, except substituting 4-methoxycarbonyl-3-[(4-chloromethyl)benzyl]indole, prepared as in step 1, for 4-methoxycarbonyl-3-{4-[(1H-2-methylimidazo[4,5-c]pyrid-1-yl)methyl]benzoyl}indole, and substituting N,N-dimethylcarbamyl chloride for 2-bromoethyl ethyl ether.

Step 3: 1-N,N-Dimethylcarbamoyl-4-methoxycarbonyl-3-{4-[(1H-2-methylimidazo[4,5-c]pyrid-1-yl)methyl] benozyl}indole.

The desired compound was prepared according to the method of Example 90, step 3, except substituting 1-N,N-dimethylcarbamoyl-4-methoxycarbonyl-3-[(4-chloromethyl)benzyl]indole, prepared as in step 2 for 4,7-dimethoxycarbonyl-3-(4-chloromethylbenzoyl)indole. $^1$H NMR (DMSO-d6, 300 MHz) δ2.52 (s, 3H), 3.00 (s, 6H), 3.56 (s, 3H), 4.13 (s, 2H), 5.43 (s, 2H), 7.03 (s, 4H), 7.2–7.3 (m, 1H), 7.43 (dd, 1H, J=7.5, 1.2 Hz), 7.50–7.55 (m, 2H), 7.83 (dd, 1H, J=8.1, 1.2 Hz) 8.25 (d, 1H, J=5.4 Hz), 8.81 (d, 1H, J=1.2 Hz). MS (DCI/NH$_3$) m/e 482 (M+H)$^+$.

EXAMPLE 152

Preparation of 1-N,N-Dimethylcarbamoyl-4-chloro-3-{4-[(1H-2-methylimidazo[4,5-b]pyrid-1-yl)methyl]benzoyl}indole The desired compound was prepared according to the method of Example 109, except substituting 1H-2-methylimidazo[4,5-b]pyridine, prepared as is Example 27, step 1, for 1H-2-methylimidazo[4,5-c]pyridine. $^1$H NMR (DMSO-d6, 300 MHz) δ2.59 (s, 3H), 3.00 (s, 3H), 5.65 (s, 2H), 7.18–7.22 (m, 1H), 7.25–7.40 (m, 4H), 7.65 (d, 1H, J=9 Hz), 7.86 (d, 2H, J=9 Hz), 7.93 (d, 1H, J=9 Hz), 8.05 (s, 1H), 8.35 (d, 1H, J=6 Hz). MS (DCI/NH$_3$) 472 (M$^+$).

EXAMPLE 153

Preparation of 1-N,N-Dimethylcarbamoyl-4-methoxycarbonyl-3-{4-[(3H-2-methylimidazo[4,5-b]pyrid-3-yl)methyl]benzoyl}indole The desired compound was prepared according to the method of Example 43, except substituting 1H-2-methylimidazo[4,5-b]pyridine, prepared as is Example 27, step 1, for 1H-2-methylimidazo[4,5-c]pyridine. 1-N,N-dimethylcarbamoyl-4-methoxycarbonyl-3-{4-[(3H-2-methylimidazo[4,5-b]pyrid-3-yl)methyl]benzoyl}indole (286 mg) was isolated by chromatography on silica gel (CH$_2$Cl$_2$, then 2%, then 4%, then 5% methanol/CH$_2$Cl$_2$). $^1$H NMR (DMSO-d6, 300 MHz) δ2.55 (s, 3H), 3.02 (s, 6H), 3.48 (s, 3H), 5.62 (s, 2H), 7.27 (dd, 1H, J=8.1, 4.8 Hz), 7.34 (apparent d, 2H, J=8.1 Hz), 7.4–7.5 (m, 1H), 7.56 (dd, 1H, J=7.2, 1.2 Hz), 7.85 (apparent d, 2H, J=8.4 Hz), 7.86 (dd, 1H, J=8.4, 1.2 Hz), 8.00 (dd, 1H, J=8.1, 1.5 Hz), 8.12 (s, 1H), 8.31 (dd, 1H, J=5.1, 1.5 Hz). MS (DCI/NH$_3$) m/e 496 (M+H)$^+$. Anal calcd for C$_{28}$H$_{25}$N$_5$O$_4$. 0.8 H$_2$O: C, 65.95; H, 5.26; N, 13.73. Found: C, 65.63; H, 4.86; N, 13.47.

EXAMPLE 154

Preparation of 1-N,N-Dimethylcarbamoyl-4-methoxycarbonyl-3-{4-[(1H-2-methylimidazo[4,5-b]pyrid-1-yl)methyl]benzoyl}indole The desired compound (45 mg) was isolated from the chromatography described in Example 153. $^1$H NMR (DMSO-d6, 300 MHz) δ2.59 (s, 3H), 3.02 (s, 6H), 3.47 (s, 3H), 5.65 (s, 2H), 7.21 (dd, 1H, J=8.1, 4.8 Hz), 7.29 (apparent d, 2H, J=8.1 Hz), 7.4–7.5 (m, 1H), 7.57 (dd, 1H, J=7.5, 1.0 Hz), 7.85 (apparent d, 2H, J=8.4 Hz), 7.86 (dd, 1H, J=8.1, 1.2 Hz), 7.95 (dd, 1H, J=8.1, 1.5 Hz), 8.11 (s, 1H), 8.36 (dd, 1H, J=4.8, 1.5 Hz). MS (DCI/NH$_3$) m/e 496 (M+H)$^+$. Anal calcd for C$_{28}$H$_{25}$N$_5$O$_4$. 1.0 H$_2$O: C, 65.49; H, 5.30; N, 13.64. Found: C, 65.45; H, 5.06; N, 13.50.

EXAMPLE 155

Preparation of 1-N,N-Dimethylcarbamoyl-4-methoxycarbonyl-3-{4-[(5H-2-methylimidazo[4,5-c]pyrid-5-yl)methyl]benzoyl}indole The desired compound was prepared according to the method of Example 43. 1-N,N-dimethylcarbamoyl-4-methoxycarbonyl-3-{4-[(5H-2-methylimidazo[4,5-c]pyrid-5-yl)methyl]benzoyl}indole (143 mg) was isolated by chromatography on silica gel (5%, then 10%, then 12% methanol/CH$_2$Cl$_2$). $^1$H NMR (DMSO-d6, 300 MHz) δ2.51 (s, 3H), 3.02 (s, 6H), 3.46 (s, 3H), 5.76 (s, 2H), 7.4–7.65 (m, 3H), 7.54 (d, 2H, J=8.1 Hz), 7.87 (dd, 1H, J=9.3, 1.2 Hz), 7.90 (d, 2H, J=8.1 Hz), 8.13 (s, 1H), 8.18 (dd, 1H, J=6.9, 1.8 Hz), 8.97 (d, 1H, J=1.5 Hz). MS (DCI/NH$_3$) m/e 496 (M+H)$^+$. Anal calcd for C$_{28}$H$_{25}$N$_5$O$_4$. 1.6 H$_2$O: C, 64.14; H, 5.42; N, 13.36. Found: C, 64.17; H, 5.03; N, 13.36.

EXAMPLE 156

Preparation of 1-N,N-Dimethylcarbamoyl-4-methoxycarbonyl-3-{4-[1-(1H-2-methylimidazo[4,5-c]pyrid-1-yl)eth-1-yl]benzoyl}indole Step 1: 1-N,N-Dimethylcarbamoyl-4-methoxycarbonyl-3-(4-acetylbenzoyl)indole.

To a solution in dichloroethane (10 mL) of 4-acetylbenzoyl chloride (3.0 mmol), prepared by treatment of 4-acetylbenzoic acid with oxalyl chloride, was added AlCl$_3$ (1.2 g, 9.0 mmol) and the brown solution was heated at 50° C. for 10 minutes. 1-N,N-dimethoxycarbonyl-4-methoxycarbonylindole (738 mg, 3.0 mmol) was added and the reaction mixture was heated at 65° C. for 8 hours. The reaction mixture was cooled to ambient temperature and poured into aqueous 3N HCl. The aqueous phase was extracted three times with CH$_2$Cl$_2$. The combined organic extracts were washed with aqueous 1N NaOH and brine, dried over MgSO$_4$, filtered, and concentrated in vacuo. Chromatography on silica gel (40% to 80% ethyl acetate/hexane) gave 1-N,N-dimethylcarbamoyl-4-methoxycarbonyl-3-[(4-acetyl)benzoyl]indole (620 mg).

Step 2: 1-N,N-Dimethylcarbamoyl-4-methoxycarbonyl-3-[4-(1-hydroxyethyl)benzoyl]indole.

To a solution in 3:1 ethanol-CH$_2$Cl$_2$ (8 mL) of 1-N,N-dimethylcarbamoyl-4-methoxycarbonyl-3-[(4-acetyl)benzoyl]indole (260 mg, 0.663 mmol), prepared as in step 1, was added NaBH$_4$ (28.2 mg, 0.742 mmol) in portions. After 5 minutes, the reaction was quenched with saturated aqueous NH$_4$Cl and concentrated in vacuo. The residue was taken up in CH$_2$Cl$_2$ and washed with brine. The aqueous phase was extracted with CH$_2$Cl$_2$. The combined organic layers were dried over MgSO$_4$, filtered, and concentrated in vacuo to give a yellow oil (260 mg) which was used without further purification.

Step 3: 1-N,N-Dimethylcarbamoyl-4-methoxycarbonyl-3-[4-(1-methanesulfonyloxyethyl)benzoyl]indole.

To a 0° C. solution in CH$_2$Cl$_2$ (10 mL) of the 1-N,N-dimethylcarbamoyl-4-methoxycarbonyl-3-[4-(1-hydroxyethyl)benzoyl]indole prepared in step 2 (260 mg) was added triethylamine (138 μL, 0.99 mmol) and methanesulfonyl chloride (61.3 μL, 0.79 mmol) and the reaction mixture was stirred for 20 minutes. The cold bath was removed and stirring was continued for 10 minutes. The reaction mixture was poured into a mixture of brine and saturated aqueous NaHCO$_3$ and extracted three times with CH$_2$Cl$_2$. The combined organic extracts were dried over MgSO$_4$, filtered, and concentrated in vacuo to give 1-N,N-dimethylcarbamoyl-4-methoxycarbonyl-3-[4-(1-methanesulfonyloxyethyl)benzoyl]indole which was used without further purification.

Step 4: 1-N,N-Dimethylcarbamoyl-4-methoxycarbonyl-3-[4-(1-azidoethyl)benzoyl]indole.

To a solution in DMF (8 mL) of the 1-N,N-dimethylcarbamoyl-4-methoxycarbonyl-3-[4-(1-methanesulfonyloxyethyl)benzoyl]indole prepared in step 3 was added sodium azide (429 mg, 6.6 mmol) and the reaction mixture was heated at 60° C. for 1 hour. The reaction mixture was poured into brine and the aqueous phase was extracted three times with ethyl acetate. The combined organic extracts were as washed with brine, dried over MgSO$_4$, filtered, and concentrated in vacuo. Chromatography on silica gel (40–60% ethyl acetate/hexane) gave 1-N,N-dimethylcarbamoyl-4-methoxycarbonyl-3-[4-(1-azidoethyl)benzoyl]indole (250 mg).

Step 5: 1-N,N-Dimethylcarbamoyl-4-methoxycarbonyl-3-{4-[1-(1H-2-methylimidazo[4,5-c]pyrid-1-yl)eth-1-yl]benzoyl}indole.

The desired compound was prepared according to the method of Example 29, steps 5 and 6, except substituting 1-N,N-dimethylcarbamoyl-4-methoxycarbonyl-3-[4-(1-azidoethyl)benzoyl]indole, prepared as in step 4, for 1-N,N-dimethylcarbamoyl-3-(4-aminomethylbenzoyl)indole. $^1$H NMR (DMSO-d6, 300 MHz) δ1.97 (d, 3H, J=6.9 Hz), 2.64 (s, 3H), 3.03 (s, 6H), 3.46 (s, 3H), 6.07 (q, 1H, J=6.9 Hz), 7.26 (dd, 1H, J=0.9, 5.7 Hz), 7.43 (d, 2H, J=8.1 Hz), 7.46 (t, 1H, J=8.4 Hz), 7.58 (dd, 1H, J=1.2, 7.5 Hz), 7.86 (d, 2H, J=8.1 Hz), 7.88 (dd, 1H, J=0.6, 7.5 Hz), 8.12 (s, 1H), 8.17 (d, 1H, J=5.7 Hz), 8.83 (s, 1H). MS (DCI/NH$_3$) m/e 511 (M+2)$^+$, 510 (M+1)$^+$, 378, 277, 205.

EXAMPLE 157

Preparation of
1-N,N-Dimethylcarbamoyl-4-methoxycarbonyl-3-{4-[1-(1H-imidazo[4,5-c]pyrid-1-yl)eth-1-yl]-benzoyl}indole The desired compound was prepared according to the method of Example 30, except substituting 1-N,N-dimethylcarbamoyl-4-methoxycarbonyl-3-[4-(1-(N-3-aminopyridin-4-yl)ethyl)benzoyl]indole, prepared as in Example 156, for 1-N,N-dimethylcarbamoyl-3-[4-(N-3-aminopyridin-4-yl)aminomethylbenzoyl]indole. $^1$H NMR (DMSO-d6, 300 MHz) δ2.3 (d, 3H, J=6.9 Hz), 3.1 (s, 6H), 3.43 (s, 3H), 6.04 (q, 1H, J=6.9 Hz), 7.45 (t, 1H, J=8.4 Hz), 7.51–7.57 (m, 3H), 7.84–7.89 (m, 3H), 8.11 (s, 1H), 8.30 (d, 1H, J=5.2 Hz), 8.79 (s, 1H), 8.99 (s, 1H). MS (DCI/NH$_3$) m/e 496 (M+H)$^+$, 378, 167.

EXAMPLE 158

Preparation of
1-N,N-Dimethylcarbamoyl-4-methoxycarbonyl-3-{4-[(1H-2-methyl-5- and 6-chlorobenzimidazolyl)methyl]benzoyl}indole Step 1: 5-chloro-1,2-phenylenediamine.

To a suspension in diethyl ether (50 mL) of 5-chloro-2-nitroaniline (2.70 g, 15.6 mmol) was added zinc powder (10.2 g, 156 mmol) in portions. The reaction mixture was filtered and concentrated in vacuo to give 5-chloro-2-aminoaniline which as was used without further purification.

Step 2: 5, and 6-Chloro-2-methylbenzimidazole.

The 5-chloro-1,2-phenylenediamine prepared in step 1 was dissolved in acetic acid (10 mL) and the solution was heated at 95° C. for 4 hours. The reaction mixture was then cooled in an ice bath and taken to pH=8–9 with concentrated NH$_4$OH. The resulting precipitate was filtered, washed with H$_2$O, and dried in a vacuum oven to give a mixture of 5- and 6-chloro-2-methylbenzimidazole (2.25 g).

Step 3: 1-N,N-Dimethylcarbamoyl -4-methoxycarbonyl-3-{4-[(1H-2-methyl-5- and 6-chlorobenzimidazolyl)methyl]benzoyl}indole Sodium hydride (60% oil dispersion, 22.5 mg, 0.563 mmol) was washed three times with hexane and suspended in DMF (3 mL). A mixture of mixture of 5and 6-chloro-2-methylbenzimidazole (75 mg, 0.450 mmol), prepared as in step 1,was added, the reaction mixture was stirred for 5 minutes, and LiBr (20 mg) and 1-N,N-dimethylcarbamoyl-4-methoxycarbonyl-3-(4-chloromethylbenzoyl)indole (150 mg, 0.373 mmol) were added. The reaction mixture was stirred for 7.5 hours at ambient temperature and then was poured into H$_2$O and extracted three times with ethyl acetate. The combined organic layers were washed with brine, dried over MgSO$_4$, filtered, and concentrated in vacuo. Chromatography on silica gel (60% ethyl acetate/hexane, then 10% methanol/CH$_2$Cl$_2$), followed by HPLC (20–70% CH$_3$CN/H$_2$O) gave a mixture of 1-N,N-dimethylcarbamoyl-4-methoxycarbonyl-3-{4-[1H-2-methyl-5- and 6-chlorobenzimidazolyl)methyl]benzoyl}indole in about a 1:1 ratio of Cl regioisomers. $^1$H NMR (DMSO-d6, 300 MHz) δ2.52 (s, 3H), 2.54 (s, 3H), 3.02 (s, 6H), 3.02 (s, 6H), 3.27 (s, 3H), 3.28 (s, 3H), 5.62 (s, 2H), 5.62 (s, 2H), 7.18–7.22 (m, 1H), 7.18–7.22(m, 1H), 7.25 (d, 2H, J=8.4 Hz), 7.25 (d, 2H, J=8.4 Hz), 7.43 (t, 1H, J=8.7 Hz), 7.43 (t, 1H, J=8.7 Hz), 7.52–7.58 )m, 2H), 7.52–7.58 (m, 2H), 7.62 (d, 1H, J=2.6 Hz), 7.68 (d, 1H, J=2.6 Hz), 7.82–7.88 (m, 3H), 7.82–7.88 (m, 3H), 8.09 (s, 1H), 8.10 (s, 1H). MS (DCI/NH$_3$) m/e 529 (M+H)$^+$, 364, 182, 167. Anal calcd for C$_{29}$H$_{25}$ClN$_4$O$_4$.0.75 CH$_3$OH. 0.25 CF$_3$CO$_2$H: C, 62.47; H, 4.89; N, 9.63. Found: C, 62.43; H, 4.86; N, 9.59.

EXAMPLE 159

Preparation of
1-N,N-Dimethylcarbamoyl-4-chloro-3-{4-[(1H-2-methyl-5- and 6-chlorobenzimidazoyl)methyl]benzoyl}indole.

The desired compound was prepared as a mixture of chlorine regiosiomers according to the method of Example 158, except substituting 1-N,N-dimethylcarbamoyl-4-chloro-3-(4-chloromethylbenzoyl)indole, prepared as in Example 109, step 2, for 1-N,N-dimethylcarbamoyl-4-methoxycarbonyl-3-(4-chloromethylbenzoyl)indole. $^1$H NMR (DMSO-d6, 300 MHz) δ2.51 (s, 3H), 2.52 (s, 3H), 3.0 (s, 6H), 3.0 (s, 6H), 5.62 (s, 2H), 5.62 (s, 2H), 7.17–7.39 (m, 0.5H), 7.17–7.39 (m, 0.5H), 7.52 (d, 1H, J=8.6 Hz), 7.57 (d, 1H, J=8.6 Hz), 7.62–7.67 (m, 2H), 7.62–7.67 (m, 2H), 7.85 (d, 2H, J=8.4 Hz), 7.87 (d, 2H, J=8.4 Hz), 8.04 (s, 1H), 8.05 (s, 1H). MS (DCI/NH$_3$) m/e 505 (M+H)$^+$, 140, 167.

EXAMPLE 160

Preparation of
1-(2-Ethoxyethyl)-4-methoxycarbonyl-3-{4-[(1H-2-methyl-5- and 6
-chlorobenzimidazolyl)methyl]benzoyl}indole.

Step 1: 1-(2-Ethoxyethyl)-4-methoxycarbonylindole.

The desired compound was prepared according to the method of Example 130, except substituting 4-methoxycarbonylindole, prepared as in Example 43, step 1, for 4-methoxycarbonyl-3-{4-[(1H-2-methylimidazo[4.5-c]pyrid-1-yl)methyl]benzoyl}indole.

Step 2: 1-(2-Ethoxyethyl)-4-methoxycarbonyl-3-(4-chloromethylbenzoyl)indole.

The desired compound was prepared according to the method of Example 4, step 2, except substituting 1-(2-ethoxyethyl)-4-methoxycarbonylindole, prepared as in step 1, for 6-(4-fluorophenyl)indole-1-carboxylic acid dimethylamide.

Step 3: 1-(2-Ethoxyethyl)-4-methoxycarbonyl-3-{4-[(1H-2-methyl-5- and 6 -chlorobenzimidazolyl)methyl]benzoyl}indole.

The desired compound was prepared as a mixture of chlorine regiosiomers according to the method of Example 158, except substituting 1-(2-ethoxyethyl)-4-methoxycarbonyl-3-(4-chloromethylbenzoyl)indole, prepared as in step 2, for 1-N,N-dimethylcarbamoyl-4-methoxycarbonyl-3-(4-chloromethyl benzoyl)indole. $^1$H NMR (DMSO-d6, 300 MHz) δ0.97 (t, 3H, J=7.4 Hz), 0.97 (t, 3H, J=7.4 Hz), 2.53 (s, 3H), 2.56 (s. 3H), 3.35 (q, 2H, J=7.4 Hz), 3.35 (q, 2H, J=7.4 Hz), 3.55 (s, 3H). 3.56 (s, 3H), 3.69 (t, 2H, J=5.8 Hz), 3.69 (t, 2H, J=5.8 Hz), 4.44 (t, 2H, J=5.8 Hz), 4.44 (t, 2H, J=5.8 Hz), 5.61 (s, 2H), 5.61 (s, 2H), 7.18–7.27 (m, 3H), 7.18–7.27 (m, 3H), 7.33–7.43 (m, 2H), 7.33–7.43 (m, 2H), 7.57 (t, 1H, J=8.7 Hz), 7.57 (t, 1H, J=8.7 Hz), 7.63 (d, 1H, J=2.4 Hz), 7.70 (d, 1H, J=2.5 Hz), 7.80 (dd, 2H, J=6.5, 8.8 Hz), 7.80 (dd, 2H, J=6.5, 8.8 Hz), 7.85 (dd, 1H, J=1.2, 8.8 Hz), 7.85 (dd, 1H, J=1.2, 8.8 Hz), 7.92 (s, 1H), 7.93 (s, 1H). MS (DCI/NH$_3$) m/e 530 (M+H)$^+$, 365, 248, 181,169. Anal calcd for C$_{30}$H$_{28}$ClN$_3$O$_4$. 0.475 H$_2$O: C, 66.78; H, 5.41; N, 7.80. Found: C, 66.81; H, 5.36; N, 7.88.

EXAMPLE 161

Preparation of
1-(Pyrrolidin-1-ylcarbonyl)-4-methoxycarbonyl-3-{4-[(1H-2-methyl-5- and 6-chlorobenzimidazolyl)methyl]benzoyl}indole The desired compound was prepared as a mixture of chlorine regiosiomers according to the method of Example 160, except substituting 1-pyrrolidine carbonyl chloride, for 2-bromoethyl ethyl ether. $^1$H NMR (DMSO-d6, 300 MHz) δ1.87 (bs, 2H), 1.87 (bs, 2H), 2.52 (s, 3H), 2.54 (s, 3H), 3.30 (s, 3H), 3.47 (s, 3H), 3.52 (bs, 2H), 3.52 (bs, 2H), 5.61 (s, 2H), 5.61 (s, 2H), 7.18–7.23 (m, 1H), 7.18–7.23 (m, 1H), 7.26 (d, 2H, J=8.4 Hz), 7.44 (t, 1H, J=8.0 Hz), 7.44 (t, 1H, J=8.0 Hz), 7.52 –7.59 (m, 2H), 7.52 –7.59 (m, 2H), 7.63 (d, 1H, J=2.0 Hz), 7.68 (d, 1H, J=2.0 Hz), 7.83 (d, 2H, J=8.4 Hz), 7.85 (d, 2H, J=8.4 Hz), 7.98 (d, 1 H, J=8.0 Hz), 7.98 (d, 1H, J=8.0 Hz), 8.18 (s, 1H), 8.19 (s, 1H). MS (DCI/NH$_3$) m/e 555 (M+H)$^+$, 169. Anal calcd for C$_{31}$H$_{27}$ClN$_4$O$_4$. 0.8 H$_2$O. 0.2 DMF: C, 65.01; H, 5.17; N, 10.06. Found: C, 64.95; H, 4.91; N, 10.00.

EXAMPLE 162

Preparation of
1-N,N-Dimethylcarbamoyl-4-methoxycarbonyl-3-{4-[(1H-2-(trifluoromethyl)benzimidazolyl)methyl]benzoyl}indole Step 1: 1H-2-(Trifluoromethyl)benzimidazole.

A mixture of 1,2-diaminobenzene (1.0 g), trifluoroacetic acid (1 mL) and trifluoroacetic anhydride (1 mL) was heated at 60° C. for 10 hours. The reaction mixture was then cooled in an ice bath and taken to pH=7–8 with concentrated NH$_4$OH. The resulting white solid was filtered and recrystallized from ethanol to give 400 mg of 1H-2-(trifluoromethyl)benzimidazole as colorless crystals.

Step 2: 1-N,N-Dimethylcarbamoyl-4-methoxycarbonyl-3-{4-[(1H-2 -(trifluoromethyl)benzimidazolyl)methyl] benzoyl}indole.

The desired compound was prepared according to the method of Example 158, step 3, except substituting 1H-2-(trifluoromethyl)benzimidazole, prepared as in step 1, for 5- and 6-chloro-2-methylbenzimidazole. $^1$H NMR (CDCl$_3$, 300 MHz) δ3.11 (s, 6H), 3.53 (s, 3H), 5.61 (s, 2H), 7.17 (d, 2H, J=8.4 Hz), 7.27–7.30 (m, 1 H), 7.39–7.45 (m, 3H), 7.69 (s, 1H), 7.73 (d, 1H, J=7.6 Hz), 7.82–7.86 (m, 3H), 7.91–7.95 (m, 1H). MS (DCI/NH$_3$) m/e 550 (M+2)$^+$, 549 (M+H)$^+$, 364, 204, 187.

EXAMPLE 163

Preparation of
1-N,N-Dimethylcarbamoyl-4-methoxycarbonyl-3-{4-[(1H-2-methyl-5- and 6-methylbenzimidazolyl)methyl]benzoyl}indole Step 1: 5- and 6-Methyl-2-methylbenzimidole.

A mixture of 3,4-diaminotoluene (1.0 g), acetic anhydride (1.5 mL) and acetic acid (2.0 mL) was heated at 85° C. for 12 hours. The reaction mixture was cooled in an ice bath and taken to pH=8 with concentrated NH$_4$OH. The resulting solid was filtered and dried in a vacuum oven to give 1.2 g of 5- and 6-methyl-2-methylbenzimidole as light-brown crystals.

Step 2: 1-N,N-Dimethylcarbamoyl-4-methoxycarbonyl-3-{4-[(1H-2-methyl-5- and 6-methylbenzimidazolyl)methyl] benzoyl}indole.

The desired compound was prepared as a mixture of methyl regioisomers according to the method of example 158, step 3, except substituting 5- and 6-methyl-2-methylbenzimidazole, prepared as in step 1, for 5- and 6-chloro-2-methylbenzimidazole. $^1$H NMR (DMSO-d6, 300 MHz) δ2.39 (s, 3H), 2.39 (s, 3H), 2.50 (s, 3H), 2.50 (s, 3H), 3.02 (s, 6H), 3.02 (s, 6H), 3.47 (s, 3H), 3.47 (s, 3H), 5.55 (s, 2H), 5.55 (s, 2H), 6.98–7.00 (m, 1H), 6.98–7.00 (m, 1H), 7.24 (d, 2H, J=8.8 Hz), 7.24 (d, 2H, J=8.8 Hz), 7.29 (s, 1H), 7.35 (s, 1H), 7.36 (d, 1H, J= 8.4 Hz), 7.44 (d, 1H, J=8.4 Hz), 7.45 (t, 1H, J=8.4 Hz), 7.45 (t, 1H, J=8.4 Hz), 7.56 (d, 1H, J=8.4 Hz), 7.56 (d, 1H, J=8.4 Hz),7.82–7.88 (m, 3H), 7.82–7.88 (m, 3H), 8.11 (s, 1H), 8.12 (s, 1H). MS (DCI/NH$_3$) m/e 509 (M+H)$^+$, 364.

EXAMPLE 164

Preparation of
1-N,N-Dimethylcarbamoyl-4-methoxycarbonyl-3-
{4-[(1H-2-methyl-4- and and
7-methylbenzimidazolyl)methyl]benzoyl}indole The desired compound was prepared as a mixture of methyl regioisomers according to the method of Example 163, except substituting 2,3-diaminotoluene for 3,4-diaminotoluene. $^1$H NMR (DMSO-d6, 300 MHz) δ2.39 (s, 3H), 2.39 (s, 3H), 2.50 (s, 3H), 2.50 (s, 3H), 3.02 (s, 6H), 3.02 (s, 6H), 3.48 (s, 3H), 3.48 (s, 3H), 5.56 (s, 2H), 5.56 (s, 2H), 6.99 (d, 1H, J=8.6 Hz), 6.99 (d, 1H, J=8.6 Hz), 7.24 (d, 2H, J=8.4 Hz), 7.24 (d, 2H, J=8.4 Hz), 7.29 (s, 1H), 7.55 (d, 1H, J=7.8 Hz), 7.56 (s, 1H), 7.44 (d, 1H, J=7.9 Hz), 7.45 (t, 1H, J=8.0 Hz), 7.45 (t, 1H, J=8.0 Hz), 7.57 (d, 1H, J=8.0 Hz), 7.57 (d, 1H, J=8.0 Hz), 7.82–7.88 (m, 3H), 7.82–7.88 (m, 3H), 8.11 (s, 1H), 8.12 (s, 1H). MS (DCI/NH$_3$) m/e 509 (M+H)$^+$, 161. Anal calcd for $C_{30}H_{28}N_4O_4 \cdot 0.6$ H$_2$O. 0.3 EtOH; C, 68.86; H, 5.96; N, 10.49. Found: C, 68.93; H, 5.98; N, 10.17.

EXAMPLE 165

Preparation of 1-N,N-Dimethylcarbamoyl
-4-methoxycarbonyl-3-{4-[(1H-2-methyl-5- and
6-fluorobenzimidazolyl)methyl]benzoyl}indole The desired compound was prepared as a mixture of fluorine regioisomers according to the method of Example 158, except substituting 4-fluoro-2-nitroaniline for 5-chloro-2-nitroaniline. $^1$H NMR (DMSO-d6, 300 MHz) δ2.51 (s, 3H), 2.54 (s, 3H), 3.02 (s, 6H), 3.02 (s, 6H), 3.48 (s, 3H), 3.48 (s, 3H), 5.59 (s, 2H), 5.61 (s, 2H), 7.02 (dt, 1H, J=2.4, 10.2 Hz), 7.04 (dt, 1H, J=2.4, 10.2 Hz), 7.27 (d, 2H, J=8.4Hz), 7.27 (d, 2H, J=8.4 Hz),7.38 (dd, 1H, J=2.7, 10.2 Hz), 7.45 (t, 1H, J=8.0 Hz), 7.45 (t, 1H, J=8.0 Hz), 7.45 (dd, 1H, J=2.7, 10.1 Hz), 7.51 (dd, 1H, J=5.1, 9.2 Hz), 7.56 (dd, 1H, J=5.0, 9.2 Hz), 7.56 (d, 1H, J=8.0 Hz), 7.56 (d, 1H, J=8.0 Hz), 7.83–7.88 (m, 3H), 8.11 (s, 1H), 8.14 (s, 1H). MS (DCI/NH$_3$) m/e 513 (M+H)$^+$. Anal calcd for $C_{29}H_{25}FN_4O_4 \cdot 0.2$ H$_2$O: C, 65.69; H, 4.89; N, 10.50. Found: C, 65.53; H, 4.89; N, 10.51.

EXAMPLE 166

Preparation of
1-N,N-Dimethylcarbamoyl-4-methoxycarbonyl-3-
{4-[(1H-2-methyl-5- and
6-nitrobenzimidazolyl)methyl]benzoyl}indole The desired compound was prepared as a mixture of nitro regioisomers according to the method of Example 158, step 3, except substituting 5-nitro-2-methylbenzimidazole for 6-chloro-2-methylbenzimidazole. $^1$H NMR (DMSO-d6, 300 MHz) δ2.60 (s, 3H), 2.61 (s, 3H), 3.02 (s, 6H), 3.02 (s, 6H), 3,46 (s, 3H), 3.47 (s, 3H), 5.73 (s, 2H), 5.80 (s, 2H), 7.29 (d, 2H, J=8.7 Hz), 7.29 (d, 2H, J=8.2 Hz), 7.45 (t, 1H, J=8.7 Hz), 7.45 (t, 1H, J=8.7 Hz), 7.55–7.58 (m, 1H), 7.55–7.58 (m, 1H), 7.78 (d, 1H, J=8.7 Hz), 7.78 (d, 1H, J=8.7 Hz), 7.83–7.88 (m, 3H), 7.83–7.88 (m, 3H), 8.10–8.17 (m, 2H), 8.10–8.17 (m, 2H), 8.47 (d, 1H, J=2.6 Hz), 8.60 (d, 1H, J=2.6 Hz). MS (DCI/NH$_3$) m/e 540 (M+H)$^+$, 178.

EXAMPLE 167

Preparation of
1-N,N-Dimethylcarbamoyl-4-methoxycarbonyl-3-
{4-[(1H-2-methyl-5,6
-dichlorobenzimidazolyl)methyl] benzoyl}indole The desired compound was prepared according to the method of Example 158, steps 2 and 3, except substituting 4,5-dichloro-1,2-phenylenediamine for 5-chloro-1,2-phenylenediamine. $^1$H NMR (DMSO-d6, 300 MHz) δ2.52 (s, 3H), 3.02 (s, 6H), 3.48 (s, 3H), 6.63 (s, 2H), 7.25 (d, 2H, J=8.4 Hz), 7.45 (t, 1H, J= 7.8 Hz), 7.57 (dd, 1H, J=7.8, 0.6 HZ), 7.85 (d, 2H, J=8.4 Hz), 7.86 (s, 1H), 7.87 (dd, 1H, J=0.6, 7.8 Hz), 7.95 (s, 1H), 8.12 (s, 1H). MS (DCI/NH$_3$) m/e 563 (M+H)$^+$.

EXAMPLE 168

Preparation of
1-N,N-Dimethylcarbamoyl-4-methoxycarbonyl-3-
{4-[(1H-2-methyl-5- and
6-methoxycarbonyl]benzimidazolyl)methyl]benzoyl}-
indole The desired compound was prepared as a mixture of ester regioisomers according to the method of Example 158, steps 2 and 3, except substituting methyl 3,4-diaminobenzoate for 5-chloro-1,2-phenylenediamine. $^1$H NMR (DMSO-d6, 300 MHz) δ2.57 (s, 3H), 2.58 (s, 3H), 3.02 (s, 6H), 3.02 (s, 6H), 3.47 (s, 3H), 3.48 (s, 3H), 3.84 (s, 3H), 3.86 (s, 3H), 5.67 (s, 2H), 5.73 (s, 2H), 7.23 (d, 2 H, J=8.4 Hz), 7.27 (d, 2H, J=8.4 Hz), 7.45 (t, 1H, J=8.0 Hz), 7.45 (t, 1H, J=8.0 Hz), 7.56 (d, 1H, J=8.0 Hz), 7.56 (d, 1H, J=8.0 Hz), 7.64 (d, 1H, J=9.5 Hz), 7.68 (d, 1H, J=9.5 Hz), 7.81–7.88 (m, 4H), 7.81–7.88 (m, 4H), 8.11(s, 1H), 8.12 (s, 1H), 8.15 (d, 1H, J=1.8 Hz), 8.18 (d, 1H, J=1.8 Hz). MS (DCI/NH$_3$) m/e 553 (M+H)$^+$, 364, 191.

EXAMPLE 169

Preparation of
1-(Pyrrolidin-1-ylcarbonyl)-4-methoxycarbonyl-3-
{4-[(1H-2-methyl-5- and
6-methoxycarbonylbenzimidazolyl)methyl]benzoyl}-
indole The desired compound was prepared as a mixture of ester regioisomers according to the method of Example 160, except substituting 1-pyrrolidine carbonyl chloride, for 2-bromoethyl ethyl ether in step 1, and substituting 5- and 6-methoxycarbonyl-2-methylbenzimidazole, prepared as in Example 168, for 5- and 6-chloro-2-methylbenzimidazole in step 3. $^1$H NMR (DMSO-d6, 300 MHz) δ1.87 (bs, 4H), 1.87 (bs, 4H), 2.58 (s, 3H), 2.58 (s, 3H), 3.37 (s, 3H), 3.37 (s, 3H), 3.51 (bs, 4H), 3.51 (bs, 4H), 3.84 (s, 3H), 3.86 (s, 3H), 5.66 (s, 2H), 5.74 (s, 2H), 7.24 (d, 2H, J=8.4 Hz), 7.28 (d, 2H, J=8.4 Hz), 7.44 (t, 1H, J=8.0 Hz), 7.63 (t, 1H, J=8.0 Hz), 7.56 (d, 1H, J=8.0 Hz), 7.56 (d, 1H, J=8.0 Hz), 7.63 (d, 1H, J=8.6 Hz), 7.67 (d, 1H, J=8.4 Hz), 7.82–7.84 (m, 3H), 7.82–7.84 (m, 3H), 7.98 (d, 1H, J=8.0 Hz), 7.98 (d, 1H, J=8.0 Hz), 8.14 (s, 1H), 8.18 (s, 1H), 8.18 (s, 1H), 8.19 (s, 1H). MS (DCI/NH$_3$) m/e 579 (M+H)$^+$, 390, 280, 191. Anal calcd for $C_{33}H_{30}N_4O_6 \cdot 0.6$ H$_2$O: C, 66.43; H, 5.40; N, 9.39. Found: C, 66.45; H, 5.39; N, 9.39.

EXAMPLE 170

Preparation of
1-(Pyrrolidin-1-ylcarbonyl)-4-methoxycarbonyl-3-
{4-[(1H-2-methyl-5- and
6-methylbenzimidazolyl)methyl]benzoyl}indole.

The desired compound was prepared as a mixture of methyl regioiosmers according to the method of Example 169, except substituting 5- and 6-methyl-2-methylbenzimidole, prepared as in Example 163, step 1, for 5- and 6-methoxycarbonyl-2-methylbenzimidazole. $^1$H NMR (DMSO-d6, 300 MHz) δ1.86 (bs, 2H), 1.8 ,(bs, 2H), 2.40 (s, 3H), 2.50 (s, 3H), 3.3 1 (s, 3H), 3.47 (s, 3H), 3.51 (bs, 2H), 3.51 (bs, 2H), 5.56 (s, 2H), 5.56 (s, 2H), 6.99 (d, 1H, J=8.4 Hz), 6.99 (d, 1H, J=8.4 Hz), 7.24 (d, 2H, J=8.4 Hz), 7.24 (d, 2H, J=8.4 Hz), 7.28 (s, 1H), 7.34 (d, 1H, J=8.4 Hz), 7.36 (s, 1H), 7.43 (t, 1H, J=8.0 Hz), 7.43 (t, 1H, J=8.0 Hz), 7.43 (d, 1H, J=8.4 Hz), 7.56 (d, 1H, J=8.0 Hz), 7.56 (d, 1 H, J= 8.0 Hz), 7.73 (d, 2H, J=8.4 Hz), 7.74 (d, 2H, J=8.4 Hz), 7.98 (d, 1H, J=8.0 Hz), 7.98 (d, 1H, J=8.0 Hz), 8.18 (s, 1H), 8.19 (s, 1H). MS (DCI/NH$_3$) m/e 535 (M+H)$^+$, 390. Anal calcd for C$_{32}$H$_{30}$N$_4$O$_4$. 0.6 H$_2$O. 0.2 Ac$_2$O: C, 69.99; H, 5.87; N, 9.95. Found: C, 69.92; H, 5.79; N, 9.88.

EXAMPLE 171

Preparation of
1-N,N-Dimethylcarbamoyl-4-methoxycarbonyl-3-
{4-[(3H-2,4,6-trimethylimidazo[4.5-c]pyrid-3-yl)-
methyl]benzoyl}indole Step 1: 1-N,N-Dimethylcarbamoyl-4-methoxycarbonyl-3-(4-aminomethylbenzoyl)indole.

The desired compound was prepared according to the method of Example 102, steps 1–3, except substituting 4-methoxycarbonylindole, prepared as in Example 43, step 1, for 4-bromoindole.

Step 2: 1-N,N-Dimethylcarbamoyl-4-bromo-3-(4-(N-3-nitro-2,6-dimethylpyridin-4 -yl)aminomethylbenzoyl)indole.

A mixture of 1-N,N-dimethylcarbamoyl-4-methoxycarbonyl-3-(4-aminomethylbenzoyl)indole (150 mg, 0.393 mmol), triethylamine (60.1 µL, 0.432 mmol), and 3-nitro-4-chloro-2,6-dimethylpyridine (110 mg, 0.589 mmol) in THF (5 mL) was heated at 60° C. for 160 hours. The reaction mixture was cooled to ambient temperature and concentrated in vacuo. The residue was purified by chromatography on silica gel (ethyl acetate) to give 128 mg of 1-N,N-dimethylcarbamoyl-4-bromo-3-(4-(N-3-nitro-2,6-dimethylpyridin-4-yl)aminomethylbenzoyl)indole.

Step 3: 1-N,N-Dimethylcarbamoyl-4-methoxycarbonyl-3-{4-[(3H-2,4,6-trimethylimidazo[4.5-c]pyrid-3-yl) methyl]benzoyl}indole.

The desired compound was prepared according to the method of Example 57, step 8, except substituting 1-N,N-dimethylcarbamoyl-4-bromo-3-(4-(N-3-nitro-2,6-dimethylpyridin-4-yl)aminomethylbenzoyl)indole, prepared as in step 2, for 3-[(4-(N-3-nitropyrid-4-yl)aminomethyl)phenylsulfonyl]indole. $^1$H NMR (DMSO-d6, 300 MHz) δ2.47 (s, 3H), 2.51 (s, 3H), 2.62 (s, 3H), 3.02 (s, 6H), 3.47 (s, 3H), 5.56 (s, 2H), 7.22 (s, 1H), 7.24 (d, 2H, J=8.4 Hz), 7.45 (t, 1H, J=8.6 Hz), 7.56 (dd, 1H, J=8.6, 1.5 Hz), 7.83 (d, 2H, J=8.4 Hz), 7.87 (1H, dd, J=8.6, 1.5 Hz), 8.11 (s, 1H). MS (DCI/NH$_3$) m/e 584 (M+H+HOAc)$^+$, 524 (M+H)$^+$, 453, 364. Anal calcd for C$_{30}$H$_{29}$N$_5$O$_4$.0.4 H$_2$O.0,4 HOAc: C, 65.93; H, 5.63; N, 12.48. Found: C, 65.86; H, 5.61; N, 12.38.

EXAMPLE 172

Preparation of
1-(Pyrrolidin-1-ylcarbonyl)-4-methoxycarbonyl-3-
{4-[(1H-5-trifluoromethyl-2-methylmethyl-
benzimidazolyl)methyl]benzoyl}indole The desired compound was prepared according to the method of Example 171, except substituting 4-chloro-3-nitrobenzotrifluoride for 3-nitro-4-chloro-2,6-dimethylpyridine. $^1$H NMR (DMSO-d6, 300 MHz) δ2.59 (s, 3H), 3.02 (s, 6H), 3.47 (s, 3H), 5.68 (s, 2H), 7.28 (d, 2H, J=8.7 Hz), 7.45 (dd, 1H, J=7.6, 8.8 Hz), 7.53 (dd, 1H, J=1.6, 9.0 Hz), 7.57 (dd, 1H, J=1.8, 7.6 Hz), 7.73 (d, 1H, J=9.0 Hz), 7.83 (d, 2H, J=8.7 Hz), 7.86 (dd, J=1.6, 8.7 Hz), 7.93 (s, 1H), 1H, 8.10 (s, 1H). MS (DCI/NH$_3$) m/e 563 (M+H)$^+$, 364, 278, 201.

EXAMPLE 173

Preparation of
1-N,N-Dimethylcarbamoyl-4-methoxycarbonyl-3-
{4-[(5-oxide-1H-2-methylimidazo[4.5-c]pyrid-1-yl)-
methyl]benzoyl}indole To a 0° C. solution in CH$_2$Cl$_2$ (2 mL) of 1-N,N-dimethylcarbamoyl-4-methoxycarbonyl-3-{4-[(1H-2-methylimidazo[4.5-c]pyrid-1-yl)methyl]benzoyl}indole (25 mg, 0.045 mmol), prepared as in Example 44, was added 3-chloroperbenzoic acid (80%, 12.5 mg, 0.045 mmol). The reaction mixture was stirred for 1 hour at 0° C. and then was partitioned between CH$_2$Cl$_2$ and saturated aqueous NaHCO$_3$/NaHSO$_3$. The organic phase was dried over MgSO$_4$, filtered, and concentrated in vacuo. Pure 1-N,N-dimethylcarbamoyl-4-methoxycarbonyl-3-{4-[(5-oxide-1H-2-methylimidazo[4.5-c]pyrid-1-yl)methyl] benzoyl}indole was obtained by HPLC (20–40% CH$_3$CN/H$_2$O). $^1$H NMR (DMSO-d6, 300 MHz) δ2.55 (s, 3H), 3.02 (s, 6H), 3.48 (s, 3H), 5.65 (s, 2H), 7.31 (d, 2H, J=8.4 Hz), 7.46 (t, 1H, J=8.0 Hz), 7.57 (d, 1H, J=8.0 Hz), 7.85 (d, 2H, J=8.4 Hz), 7.87 (d, 1H, J=7.6 Hz), 8.11 (s, 1H), 8.12 (dd, 1H, J=7.6, 2.2 Hz), 8.68 (d, 1H, J=2.2 Hz). MS (DCI/NH$_3$) m/e 512 (M+H)$^+$, 496, 364.

EXAMPLE 174

Preparation of
1-N,N-Dimethylcarbamoyl-4-methoxycarbonyl-3-
{4-[(4-chloro-1H-2
-methylimidazo[4.5-c]pyrid-1-yl)methyl]benzoyl}-
indole A mixture of 1-N,N-dimethylcarbamoyl-4-methoxycarbonyl-3-{4-[(5-oxide-1H-2-methylimidazo[4.5-c]pyrid-1-yl)methyl]benzoyl}indole (60 mg), prepared as in Example 173, and POCl$_3$ (1 mL) was heated at 100° C. for 1 hour. The reaction mixture was cooled to ambient temperature and partitioned between CH$_2$Cl$_2$ and saturated aqueous NaHCO$_3$. The organic phase was washed with saturated aqueous NaHCO$_3$, dried over MgSO$_4$, filtered, and concentrated in vacuo. The residue was purified by chromatography on silica gel (2% methanol/CH$_2$Cl$_2$) to give 1-N,N-dimethylcarbamoyl-4-methoxycarbonyl-3-{4-[(4-chloro-1H-2-methylimidazo[4.5-c]pyrid-1-yl)methyl]benzoyl}indole (34 mg). $^1$H NMR (DMSO-d6, 300 MHz) δ 2.60 (s, 3H), 3.01 (s, 6H), 3.47 (s, 3H), 5.68 (s, 2H), 7.29 (d, 2H, J=8.4 Hz), 7.45 (t, 1H, J=8.6 Hz), 7.57 (d, 1H, J=8.6 Hz), 7.68 (d, 1H, J=6.0 Hz), 7.84 (d, 2H, J=8.4 Hz), 7.87 (d, 1H, J=8.6 Hz), 8.11 (s, 1H), 8.12 (d, 1H, J=6.0 Hz). MS (DCI/NH$_3$) m/e 530

(M+H)⁺, 364. Anal calcd for $C_{28}H_{24}ClN_4O_5$ . 0.5 $H_2O$ . 0.375 HCl: C, 61.28; H, 4.74; N, 12.29. Found: C, 61.29; H, 4.67; N, 12.29.

EXAMPLE 175

Preparation of
1-N,N-Dimethylcarbamoyl-4-methoxycarbonyl-3-
{4-[(1,5-H-2-methylimidazo[4.5-c]pyrid-4-one-1-yl)-
methyl]benzoyl}indole A mixture of 1-N,N-dimethylcarbamoyl-4-methoxycarbonyl-3-{4-[(5-oxide-1H-2-methylimidazo[4.5-c]pyrid-1-yl)methyl]benzoyl}indole (61 mg), prepared as in Example 173, acetic anhydride (1 mL) was heated at 130° C. for 6 hours. The reaction mixture was cooled to ambient temperature and concentrated in vacuo. The residue was purified by chromatography on silica gel (5%, then 8% methanol/$CH_2Cl_2$) to give 1-N,N-dimethylcarbamoyl-4-methoxycarbonyl-3-{4-[(1,5-H-2-methylimidazo[4.5-c]pyrid-4 -one-1-yl)methyl]benzoyl}indole (42 mg). ¹H NMR (DMSO-d6, 300 MHz) δ2.42 (s, 3H), 3.03 (s, 6H), 3.49 (s, 3H), 5.51 (s, 2H), 6.57 (d, 1H, J=6.7 Hz), 7.13 (t, 1H, J=6.7 Hz), 7.24 (d, 2H, J=8.4 Hz), 7.46 (t, 1H, J=8.6 Hz), 7.57 (d, 1H, J=8.6 Hz), 7.86 (d, 2H, J=8.4 Hz), 7.87 (d, 1H, J=8.6 Hz), 8.12 (s, 1H), 11.14 (d, 1H, J=6.7 Hz). MS (DCI/$NH_3$) m/e 512 (M+H)⁺, 441, 365, 264, 250, 236, 178.

EXAMPLE 176

Preparation of
1-N,N-Dimethylcarbamoyl-4-ethoxycarbonyl-3-
{4-[(1H-2-methylimidazo[4.5-c]pyrid-1-yl)methyl]-
benzoyl}indole To a solution in DMF (4 mL) of 1-N,N-dimethylcarbamoyl-3-{4-[(1H-2-methylimidazo[4.5-c]pyrid-1-yl)methyl]benzoyl}indole-4-carboxylic acid (200 mg, 0.42 mmol), prepared as in Example 118 was added $NaHCO_3$ (70 mg, 0.83 mmol) and bromoethane (62 μL, 0.83 mmol). The reaction vessel was sealed and heated at 40° C. for 1.5 hours. The reaction mixture was cooled to ambient temperature and partitioned between $CH_2Cl_2$ and brine. The aqueous phase was extracted three times with $CH_2Cl_2$. The combined organic layers were dried over $MgSO_4$, filtered, and concentrated in vacuo. The residue was purified by chromatography on silica gel (5%, then 15% methanol/$CH_2Cl_2$) to give 1-N,N-dimethylcarbamoyl-4-ethoxycarbonyl-3-{4-[(1H-2-methylimidazo[4.5-c]pyrid-1-yl)methyl]benzoyl}indole (53 mg). ¹H NMR (DMSO-d6, 300 MHz) δ0.92 (t, 3H, J=7.4 Hz), 2.57 (s, 3H), 3.02 (s, 6H), 3.95 (q, 2H, J=7.0 Hz), 5.65 (s, 2H), 7.30 (d, 2H, J=7.8 Hz), 7.4–7.5 (m, 1H), 7.5–7.6 (m, 2H), 7.87 (d, 2H, J=8.1 Hz), 7.8–7.9 (m, 1H), 8.10 (s, 1H), 8.30 (d, 1H, J=5.7 Hz), 8.86 (s, 1H). MS (DCI/$NH_3$) m/e 572 (M+H)⁺. Anal calcd for $C_{29}H_{27}N_5O_4$. 0.3 $Et_2O$. 0.5 $H_2O$: C, 66.41; H, 5.83; N, 12.82. Found: C, 66.42; H, 5.59; N, 12.66.

EXAMPLE 177

Preparation of
1-N,N-Dimethylcarbamoyl-4-(2-propyloxycarbonyl)-
3-{4-[(1H-2-methylimidazo[4.5-c]pyrid-1-yl)methyl]-
benzoyl}indole Step 1: 4-(2-propyloxycarbonyl)indole.

The desired compound was prepared according to the method of Example 176, except substituting indole-4-carboxylic acid for 1-N,N-dimethylcarbamoyl-3-{4-[(1H-2-methylimidazo[4.5-c]pyrid-1-yl)methyl]benzoyl}indole-4-carboxylic acid, and substituting 2-bromopropane for bromoethane.

Step 2: 1-N,N-Dimethylcarbamoyl-4-(2-propyloxycarbonyl)-3-{4-[(1H-2-methylimidazo[4.5-c]pyrid-1-yl)methyl]benzoyl}indole.

The desired compound was prepared according to the method of Example 109, except substituting 4-(2-propyloxycarbonyl)indole, prepared as in step 1, for 4-chloroindole. ¹H NMR (DMSO-d6, 300 MHz) δ1.02 (d, 6H, J=6.3 Hz), 2.57 (s, 3H), 3.02 (s, 6H), 4.86 (apparent quint, 1H, J=6.3 Hz), 5.64 (s, 2H), 7.30 (d, 2H, J=8.1 Hz), 7.4–7.5 (m, 1H), 7.54–7.64 (m, 2H), 7.8–7.9 (m, 3H), 8.08 (s, 1H), 8.30 (d, J=5.7 Hz), 8.86 (s, 1H). MS (DCI/$NH_3$) m/e 524 (M+H)⁺. Anal calcd for $C_{30}H_{29}N_5O_4$. 1.2 $H_2O$: C, 66.09; H, 5.80; N, 12.85. Found: C, 66.31; H, 5.57; N, 12.47.

EXAMPLE 178

Preparation of
1-N,N-Dimethylcarbamoyl-4-methoxycarbonyl-3-
{4-[(1H-2-methylnaphtho[2,3-d]imidazol-1-yl)-
methyl]benzoyl}indole Step 1: 1H-2-Methylnaphtho[2,3-d]imidazole.

The desired compound was prepared according to the method of Example 158, step 2, except substituting 2,3-diaminonaphthalene for 5-chloro-1,2-phenylenediamine.

Step 2: 4-Methoxycarbonyl-3-{4-[(1H-2-methylnaphtho[2,3-d]imidazol-1-yl)methyl]benzoyl}indole.

The desired compound was prepared according to the method of Example 90, except substituting 4-methoxycarbonylindole, prepared as in Example 43, step 1, for 4,7-dimethoxycarbonylindole, and substituting 1H-2-methylnaphtho[2,3-d]imidazole, prepared as in step 1, for 1H-2-methylimidazo[4,5-c]pyridine.

Step 3: 1-N,N-Dimethylcarbamoyl-4-methoxycarbonyl-3-{4-[(1H-2-methylnaphtho[2,3-d]imidazol-1-yl)methyl]benzoyl}indole.

To a 0° C. ,solution in THF (5 mL) of 4-methoxycarbonyl-3-{4-[(1H-2-methylnaphtho[2,3-d]imidazol-1-yl)methyl]benzoyl}indole (38 mg, 0.098 mmol), prepared as in step 2, was added NaH (95%, 3.00 mg, 0.118 mmol). After 10 minutes, dimethylcarbamyl chloride (11.5 μL, 0.137 mmol) was added and the reaction mixture was stirred for 15 minutes, then the cold bath was removed and stirring was continued for 15 minutes. The reaction mixture was quenched with saturated aqueous $NH_4Cl$ and extracted with ethyl acetate. The organic phase was washed with brine, dried over $MgSO_4$, filtered, and concentrated in vacuo. Chromatography on silica gel ($CH_2Cl_2$, then 5% methanol/$CH_2Cl_2$) gave 1-N,N-dimethylcarbamoyl-4 -methoxycarbonyl-3-{4-[(1H-2-methylnaphtho[2,3-d]imidazol-1-yl)methyl]benzoyl}indole (21 mg) as an amorphous solid. ¹H NMR (DMSO-d6, 300 MHz) δ2.64 (s, 3H), 3.02 (s, 6H), 3.45 (s, 3H), 5.70 (s, 2H), 7.30 (d, 2H, J=9 Hz), 7.35–7.44 (m, 3H), 7.55 (d, 1H, J=7 Hz), 7.84 (d, 3H, J=9 Hz) 7.90–8.05 (m, 3H), 8.10 (d, 2H, J=7 Hz). MS (DCI/$NH_3$) m/e 545 (M⁺). Anal calcd for $C_{33}H_{28}N_4O_4$. 0.5 $H_2O$: C, 71.59; H, 5.28; N, 10.12. Found: C, 71.32; H, 5.36; N, 9.70.

EXAMPLE 179

Preparation of
1-N,N-dimethylcarbamoyl-4-(N,N-dimethylamino-
carbonyloxy)-3-{3-fluoro-4-[(1H-2-methylimidazo-
[4,5-c]pyrid-1-yl)methyl]benzoyl}indole The desired compound was prepared according to the method of example 96, steps 1, 2, 3, and 4, except substituting 4-(N,N-dimethylaminocarbonyloxy)indole for 4,7-dimethoxycarbonylindole. $^1$H NMR (DMSO-d6, 300 MHz) δ2.59 (s, 3H), 2.73 (s, 3H), 2.91 (s, 3H), 3.00 (s, 6H), 5.69 (s, 2H), 6.97–7.00 (d, 1H, J=8.8 Hz), 7.13 (t, 1H), 7.33–7.38 (t, 1H, J=8.5 Hz), 7.49–7.52 (d, 1H, J=8.1Hz), 7.59– 7.67 (m, 3H), 8.02 (s, 1H), 8.29–8.31 (d, 1H, J=8.0 Hz), 8.86 (s, 1H). MS (DCI/NH3) m/z =543(M+1)$^+$. Anal calcd for $C_{29}H_{27}FO4N_6$: C, 63.14;H, 5.11 ;N, 15.23. Found C, 63.01;H, 5.39;N, 13.75.

EXAMPLE 180

Preparation of
1-N,N-dimethylcarbamoyl-4-ethynyl-3-{3-fluoro-4-[(1H-2-methylimidazo-[4,5-c]pyrid-1-yl)methyl]-benzoyl}indole.

Step 1: 1-N,N-dimethylcarbamoyl-4-bromo-3-{3-fluoro-4-[(1H-2-methylimidazo[4,5-c]pyrid-1-yl)methyl]benzoyl}indole.

The desired compound was prepared according to the method of example 96, steps 1, 2, 3, and 4, except substituting except substituting 4-bromoindole for 4,7-dimethoxycarbonylindole.

Step 2: 1-N,N-dimethyl carbamoyl-4-(trimethylsilylethynyl)-3-{3-fluoro-4-[(1H-2-methylimidazo-[4,5-c]pyrid-1-yl)methyl]benzoyl}indole.

The desired compound was prepared according to example 106 except substituting 1-N,N-dimethyl carbamoyl-4-bromo-3-{3-fluoro-4-[(1H-2-methylimidazo-[4,5-c]pyrid-1-yl)methyl]benzoyl}indole for 1-N,N-dimethylcarbamoyl-4-bromo-3-{-4-[(1H-2-methylimidazo-[4,5-c]pyrid-1-yl)methyl]benzoyl)indole.

Step 3: 1-N,N-dimethylcarbamoyl-4-ethynyl-3-{3-fluoro4-[(1H-2-methylimidazo-[4,5-c]pyrid-1-yl)methyl]benzoyl}indole.

The desired compound was prepared according to example 107 except substituting 1-N,N-dimethylcarbamoyl-4-(trimethylsilylethynyl)-3-{3-fluoro-4-[(1H-2-methylimidazo-[4,5-c]pyrid-1-yl)methyl ]benzoyl)indole for 1-N,N-dimethylcarbamoyl-4-(trimethylsilylethynyl)-3-{4-[(1H-2-methylimidazo-[4,5-c]pyrid-1-yl)methyl]benzoyl)indole.
$^1$H NMR (DMSO-d6, 300 MHz): δ2.57 (s, 3H), 3.01 (s, 6H), 4.07 (s, 1H), 5.69 (s, 2H), 7.05–7.15 (m, 1H), 7.30–7.45 (m, 2H), 7.55–7.75 (m, 4H), 8.18 (s, 1H), 8.29 (d, J=5.7 Hz, 1H), 8.85 (s, 1H). MS (DCI/NH$_3$) m/e 480 (M+1)$^+$. Anal calcd for $C_{28}H_{22}N_5O_2F.0.1 CH_2Cl_2$: C, 69.16; H, 4.59; N, 14.35. Found: C, 69.28; H, 4.43; N, 13.79.

We claim:
1. A compound of formula

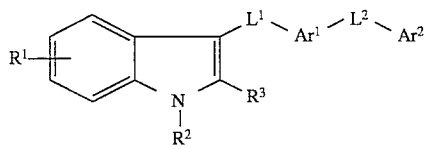

or a pharmaceutically acceptable salt thereof wherein
R$^1$ is one or more groups independently selected from the group consisting of
hydrogen,
halogen,
hydroxy,
cyano,
alkyl of one to six carbon atoms,
alkynyl of two to four carbon atoms,
alkoxy of one to six carbon atoms,
alkanoyl of one to seven carbon atoms,
—COOR$^6$, wherein R$^6$ is hydrogen, alkyl of one to ten carbon atoms, or phenylalkyl wherein the alkyl portion is of one to four carbon atoms,
unsubstituted phenyl,
phenyl, substituted with
alkyl of one to six carbon atoms,
alkoxy of one to six carbon atoms,
halogen,
—NR$^4$R$^5$, where R$^4$ and R$^5$ are independently selected from hydrogen and alkyl of one to six carbon atoms, or R$^4$ and R$^5$ together with the nitrogen atom to which they are attached form a pyrrolidinyl, piperidinyl, piperazinyl, or morpholinyl ring,
—COOR$^6$,
—C(O)NR$^4$R$^5$, or
—SO$_2$NR$^4$R$^5$,
—C(O)NR$^4$R$^5$,
—OC(O)NR$^4$R$^5$,
—NHC(O)NR$^4$R$^5$,
2- or 3-furyl,
2- or 3-thienyl,
2-, 4-, or 5-thiazolyl
2-, 3-, or 4-pyridyl,
2-, or 4-pyrimidyl,
phenylalkyl in which the alkyl portion is of one to six carbon atoms,
phenylalkyl, in which the alkyl portion is of one to six carbon atoms and the phenyl moiety is substituted with
halogen,
alkyl of from one to six carbon atoms, or
alkoxy of from one to six carbon atoms,
unsubstituted benzoyl,
benzoyl substituted with
halogen,
alkyl of from one to six carbon atoms, or
alkoxy of from one to six carbon atoms,
unsubstituted phenoxy,
phenoxy substituted with
halogen,
alkyl of from one to six carbon atoms, or
alkoxy of from one to six carbon atoms,
unsubstituted phenylalkyloxy, in which the alkyl portion is of one to six carbon atoms,
phenylalkyloxy in which the alkyl portion is of one to six carbon atoms and the phenyl moiety is substituted with
halogen,
alkyl of from one to six carbon atoms, or
alkoxy of from one to six carbon atoms, and
unsubstituted phenylalkanoyl, in which the alkanoyl portion is of one to seven carbon atoms,
phenylalkanoyl, in which the alkanoyl portion is of one to seven carbon atoms and the phenyl moiety is substituted with;
halogen,
alkyl of one to six carbon atoms, or
alkoxy of one to six carbon atoms;
R$^2$ is selected from the group consisting of
hydrogen,
alkyl of one to six carbon atoms;
—(CH$_2$)$_p$COOR$^6$, where p 0, 1, 2, 3, or 4,
—(CH$_2$)$_q$NR$^4$R$^5$, where q 2, 3, or 4,
—(CH$_2$)$_p$COR$^6$ —$(CH_2)_qOR^6$,
—$(CH_2)_pSO_2R^6$,
—$(CH_2)_pSO_2NR^4R^5$,
—$(CH_2)_pCONR^7R^8$, where $R^7$ and $R^8$ are independently selected from the group consisting of
  hydrogen,
  alkyl of one to six carbon atoms,
  —$(CH_2)_rCOOR^6$, where r is 1, 2, 3, or 4,
  —$(CH_2)_rNR^4R^5$,
  —$(CH_2)_rOH$,
  —$(CH_2)_rSO_2R^6$, and
  —$(CH_2)_rSO_2NR^4R^5$,
—$(CH_2)_pCN$
—$(CH_2)_p$-1H-tetrazol-5-yl
—$CONHNH_2$, and;
unsubstituted phenylalkyl wherein the alkyl portion is of one to four carbon atoms, and
phenylakyl wherein the alkyl portion is of one to four carbon atoms and the phenyl moiety is substituted with
  halogen,
  alkyl of from one to six carbon atoms, or
  alkoxy of from one to six carbon atoms; or
$R^7$ and R, taken together with the nitrogen atom to which they are attached, for a pyrrolidinyl or morpholinyl ring;
$R^3$ is selected from the group consisting of hydrogen and alkyl of one to six carbon atoms;
$L^1$ is selected from the group consisting of
  >C=O,

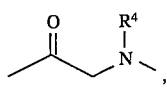

>C=$NNR^9R^{10}$, where $R^9$ and $R^{10}$ are independently selected from
  hydrogen,
  alkyl of one to six carbon atoms,
  alkoxycarbonyl of from one to six carbon atoms,
  aminocarbonyl,
  alkylaminocarbonyl of one to six carbon atoms,
  dialkylaminocarbonyl in which the alkyl groups are independently of one to six carbon atoms,
  alkanoyl of one to six carbon atoms,
  unsubstituted phenyl, and
  phenyl substituted with
    halogen,
    alkyl of from one to six carbon atoms, or
    alkoxy of from one to six carbon atoms; and
>C=$NOR^9$,
>$S(O)_n$, wherein n is 1 or 2, and
—$NHSO_2$—;
$Ar^1$ is a radical of formula

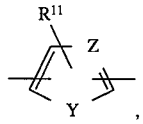

where Y is O, S, or —CH=CH—, Z is N or CH, and $R^{11}$ is selected from the group consisting of
  hydrogen,
  alkyl of one to six carbon atoms,
  alkenyl of two to six carbon atoms,
  alkoxy of one to six carbon atoms, and
  halogen;

$L^2$ is selected from the group consisting of
  a valence bond,
  unsubstituted straight-chain alkylene of one to six carbon atoms,
  straight-chain alkylene of one to six carbon atoms substituted with one or more groups selected from
    alkyl of one to six carbon atoms,
    alkenyl of two to six carbon atoms,
    alkoxycarbonyl of one to six carbon atoms,
    alkoxy of one to six carbon atoms,
    alkylthio of one to six carbon atoms,
    alkoxyalkyl in which the two alkyl portions each are of one to six carbon atoms,
    alkylthioalkyl in which the alkoxy and alkyl portions are independently of one to six carbon atoms,
  unsubstituted phenylalkyl wherein the alkyl portion is of one to six carbon atoms,
  phenylalkyl wherein the alkyl portion is of one to six carbon atoms, and the phenyl ring is substituted with alkyl of one to six carbon atoms, haloalkyl of one to six carbon atoms, alkoxy of one to six carbon atoms, hydroxy, or halogen,
  unsubstituted thiophenyl, and
  thiophenyl substituted with alkyl of one to six carbon atoms, haloalkyl of one to six carbon atoms, alkoxy of one to six carbon atoms, hydroxy, or halogen,
with the proviso that $L^2$ is unsubstituted alkylene or alkylene substituted alkyl when $Ar^1$ is a valence bond;
$Ar^2$ is selected from the group consisting of

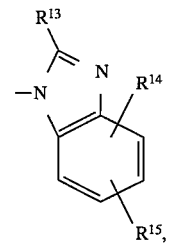

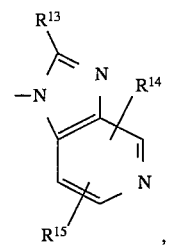

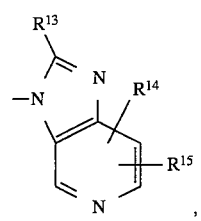

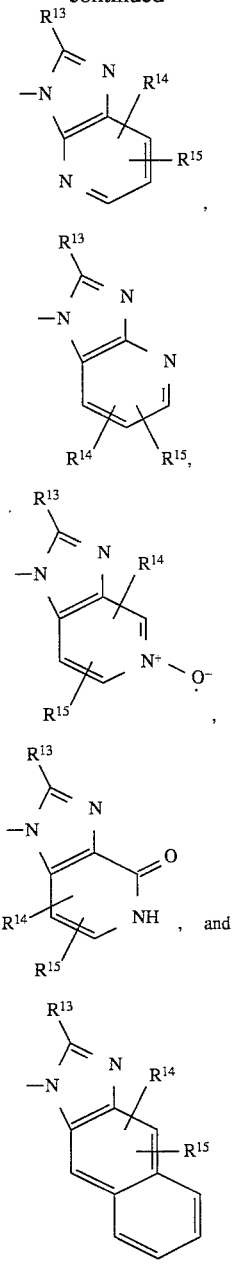

where $R^{13}$ is selected from the group consisting of
alkyl of one to six carbon atoms,
alkenyl of two to six carbon atoms,
alkoxy of one to six carbon atoms,
alkylthio of one to six carbon atoms,
alkoxyalkyl in which the alkoxy and alkyl portions are independently of one to six carbon atoms,
alkylthioalkyl in which the alkyl portions each independently of one to six carbon atoms,
haloalkyl of one to six carbon atoms, unsubstituted phenylalkyl wherein the alkyl portion is of one to six carbon atoms,
phenylalkyl wherein the alkyl portion io of one to six carbon atoms and the phenyl is substituted with
alkyl of one to six carbon atoms,
haloalkyl of one to six carbon atoms,
alkoxy of one to six carbon atoms,
hydroxy, or
halogen,
cycloalkyl of three to eight carbon atoms,
unsubstituted thiophenyl, and
thiophenyl substituted with
alkyl of one to six carbon atoms,
haloalkyl of one to six carbon atoms,
alkoxy of one to six carbon atoms,
hydroxy, or
halogen, and
$R^{14}$ and $R^{15}$ are independently selected from the group consisting of
hydrogen,
alkyl of one to six carbon atoms,
alkenyl of two to six carbon atoms,
halogen,
cyano,
carboxyl,
alkoxycarbonyl of two to six carbon atoms,
aminocarbonyl,
alkylaminocarbonyl of two to six carbon atoms,
dialkylaminocarbonyl in which the alkyl groups are independently of one to six carbon atoms,
alkanoyl,
hydroxyalkyl,
haloalkyl,
alkoxy of one to six carbon atoms,
alkylthio of one to six carbon atoms,
alkylsulfinyl of one to six carbon atoms,
alkylsulfonyl of one to six carbon atoms,
amino,
alkonylamino, of one to six carbon atoms, and
nitro, or
$R^{14}$ and $R^{15}$, together with the carbon atoms to which they are attached define a phenyl ring or 5- to 7-membered cycloalkylene ring.

2. A compound as defined by claim 1, or the pharmaceutically acceptable salt thereof wherein
$R^1$ is one or more groups independently selected from the group consisting of
hydrogen,
halogen,
alkyl of one to six carbon atoms,
alkynyl of two to four carbon atoms,
alkoxy of one to six carbon atoms,
—COOR$^6$, wherein $R^6$ is hydrogen, alkyl of one to ten carbon atoms, or phenylalkyl wherein the alkyl portion is of one to four carbon atoms,
—OC(O)NR$^4$R$^5$, wherein $R^4$ and $R^5$ are independently selected from hydrogen and alkyl of one to six carbon atoms, or $R^4$ and $R^5$ together with the nitrogen atom to which they are attached form a pyrrolidinyl, piperidinyl, piperazinyl, or morpholinyl ring,
phenyl,
phenyl, optionally substituted with alkyl of one to six carbon atoms, alkoxy of one to six carbon atoms, or halogen,
phenylalkyl wherein the alkyl portion is of one to four carbon atoms,
phenylalkyl wherein the alkyl portion is of one to four carbon atoms, and the phenyl moiety is substituted with
halogen,
alkyl of one to six carbon atoms, or
alkoxy of one to six carbon atoms,
phenoxy, and
phenoxy substituted with
halogen, alkyl of one to six carbon atoms, or
alkoxy of one to six carbon atoms;
$R^3$ is hydrogen;
$L^1$ is >C=O or —SO$_2$—;
$Ar^1$ is

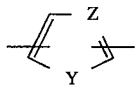

wherein
Y is O, S, or —CH=CH—,
Z is N or CH;
$L^2$ is straight chain alkylene of one to six carbon atoms; and
$Ar^2$ is selected from the group consisting of

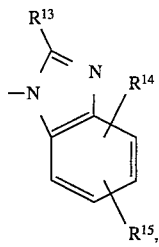

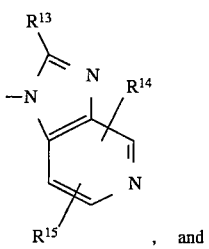, and

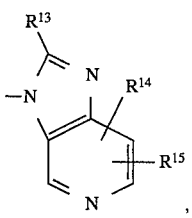

wherein $R^{13}$ is methyl and $R^{14}$ and $R^{15}$ are hydrogen.

3. A compound as defined by claim 2, or the pharmaceutically acceptable salt thereof wherein $Ar^1$ is selected from the group consisting of
unsubstituted phenyl and
phenyl substituted with
alkyl of one to six carbon atoms,
alkoxy of one to six carbon atoms, or
halogen.

4. A compound as defined by claim 3, or the pharmaceutically acceptable salt thereof wherein
$R^1$ is one or more groups independently selected from the group consisting of
hydrogen,
alkyl of one to six carbon atoms,
alkynyl of two to four carbon atoms,
—COOR$^6$, wherein R$^6$ is hydrogen, alkyl of one to ten carbon atoms, or phenylalkyl wherein the alkyl portion is of one to four carbon atoms,
—OC(O)NR$^4$R$^5$, wherein R$^4$ and R$^5$ are independently selected from hydrogen and alkyl of one to six carbon atoms, or R$^4$ and R$^5$ together with the nitrogen atom to which they are attached form a pyrrolidinyl, piperidinyl, piperazinyl, or morpholinyl ring,
phenylmethyl,
4-fluorophenyl, and
4-fluorophenoxy;
$R^2$ is —C(O)N(CH$_3$)$_2$ or —(CH$_2$)$_q$OR$^6$ where q is 1, 2, 3, or 4, and
$L^1$ is >C=O or —SO$_2$—.

5. A compound as defined by claim 4, or the pharmaceutically acceptable salt thereof wherein $L^2$ is methylene.

6. A compound as defined by claim 4, or the pharmaceutically acceptable salt thereof wherein $L^2$ is a valence bond.

7. A compound as defined by claim 1 selected from the group consisting of:
6-(4-fluorophenyl)-3-{4-[(1H-2-ethylbenzimidazolyl)methyl]benzoyl}indole,
1-N,N-dimethylcarbamoyl-6-(4-fluorophenyl)-3-{4-[(1H-2-methylbenzimidazolyl)methyl]benzoyl}indole,
6-(4-fluorophenyl)-3-{4-[(1H-2-methylimidazo[4.5-c]pyrid-1-yl)methyl]benzoyl}indole,
1-N,N-dimethylcarbamoyl-6-(4-fluorophenyl)-3-{4-[(1H-2-methylimidazo[4.5-c]pyrid-1-yl)methyl]benzoyl}indole,
1-N,N-dimethylcarbamoyl-6-(4-fluorophenyl)-3-{4-[(1H-2-methylimidazo[ 4.5-c]pyrid-1-yl)methyl]benzoyl}indole hydrochloride,
6-(4-fluorophenyl)-3-{4-[(3H-2-methylimidazo[4.5-c]pyrid-3-yl)methyl]benzoyl}indole,
1-N,N-dimethylcarbamoyl-6-(4-fluorophenyl)-3-{4-[(3H-2-methylimidazo[4.5-c]pyrid-3-yl)methyl]benzoyl}indole,
6-(4-fluorophenyl)-3-[4-(1H-2-methylimidazo[4.5-c]pyridyl)benzoyl]indole,
1-N,N-dimethylcarbamoyl-6-(4-fluorophenyl)-3-[4-(1H-2-methylimidazo[4.5-c]pyrid-1-yl)benzoyl]indole,
6-(4-fluorophenyl)-3-{3-[(1H-2-methylimidazo[4.5-c]pyridyl)methyl]benzoyl}indole,
1-N,N-dimethylcarbamoyl-6-(4-fluorophenyl)-3-{3-[(1H-2-methylimidazo[4.5-c]pyridyl)methyl]benzoyl}indole,
3-{4-[(1H-2-methylimidazo[4.5-c]pyrid-1-yl)methyl]benzoyl}indole,
1-N,N-dimethylcarbamoyl-3-{4-[(1H-2-methylimidazo[4.5-c]pyridyl)methyl]benzoyl}indole,
3-{3-[(1H-2-methylimidazo[4.5-c]pyridyl)methyl]benzoyl}indole,
1-N,N-dimethylcarbamoyl-3-{3-[(1H-2-methylimidazo[4.5-c]pyrid-1-yl)methyl]benzoyl}indole,
3-{3-[(3H-2-methylimidazo[4.5-c]pyridyl)methyl]benzoyl}indole,
1-N,N-dimethylcarbamoyl-3-{3-[(3H-2-methylimidazo[4.5-c]pyridyl)methyl]benzoyl}indole,
3-{4-[(1H-2-methylimidazo[4.5-c]pyrid-1-yl)]benzoyl}indole,
1-N,N-dimethylcarbamoyl-3-{4-[(1H-2-methylimidazo[4.5-c]pyrid-1-yl)benzoyl} indole,
1-N,N-dimethylcarbamoyl-6-(4-fluorophenyl)-3-[(3H-2-methylimidazo[4.5-c]pyrid-3-yl)methylcarbonyl]indole,
1-N,N-dimethylcarbamoyl-6-(4-fluorophenyl)-3-[(1H-2-methylimidazo[4.5-c]pyrid-1-yl)methylcarbonyl]indole,
1-N,N-dimethylcarbamoyl-3-[(3H-2-methylimidazo[4.5-c]pyrid-3-yl)methylcarbonyl]indole,
1-N,N-dimethylcarbamoyl-3-[(1H-2-methylimidazo[4.5-c]pyrid-1-yl)methylcarbonyl] indole,
1-N,N-dimethylcarbamoyl-3-{4-[(3 H-2-methylimidazo[4.5-b]pyrid-3-yl)methyl] benzoyl}indole,
1-N,N-dimethylcarbamoyl-3-{4-[(1H-2-methylimidazo[4.5-b]pyrid-1-yl)methyl] benzoyl}indole,
1-N,N-dimethylcarbamoyl-3-{4-[1H-2-trifluoromethylimidazo[4.5-c]pyrid-1 -yl)methyl]benzoyl}indole, 1-N,N-dimethylcarbamoyl-3-{4-[1H-imidazo[4.5-c]pyrid-1-yl)methyl]benzoyl}indole,
1N,N-dimethylcarbamoyl-3-{4-[1H-2-(2-propyl)imidazo[4.5-c]pyrid-1-yl)methyl]benzoyl}indole,
1-N,N-dimethylcarbamoyl-3-{4-[1H-2-phenylimidazo[4.5-c]pyrid-1-yl)methyl]benzoyl}indole,
1-N,N-dimethylcarbamoyl-3-{4-[1H-2-ethylimidazo[4.5-c]pyrid-1-yl)methyl]benzoyl}indole,
1-p-toluenesulfonyl-6-(4-fluorophenyl)-3-{4-[(1H-2-methylimidazo[4.5-c]pyridyl)methyl]benzoyl}indole,
1-N,N-dimethylcarbamoyl-6-(4-fluorophenyl)-3-[(3H-2-methylimidazo[4.5-c]pyrid-3-yl)pent-5-ylcarbonyl]indole,
1-N,N-dimethylcarbamoyl-6-(4-fluorophenyl)-3-[(1H-2-methylimidazo[4.5-c] pyrid-1-yl)pent-5-ylcarbonyl]indole,
1-N,N-dimethylcarbamoyl-6-(4-fluorophenoxy)-3-{4-[(3H-2 -methylimidazo[4.5-c]pyrid-3-yl)methyl]benzoyl}indole,
1-N,N-dimethylcarbamoyl-6-(4-fluorophenoxy)-3-{4-[(1H-2 -methylimidazo[4.5-c]pyrid-1-yl)methyl]benzoyl}indole,
1-N,N-dimethylcarbamoyl-6-phenylmethyl-3-{4-[(3H-2-methylimidazo[4.5 -c]pyrid-3-yl)methyl]benzoyl}indole,
1-N,N-dimethylcarbamoyl-6-phenylmethyl-3-{4-[(1H-2-methylimidazo[4.5 -c]pyrid-1-yl)methyl]benzoyl}indole,
1-N,N-dimethylcarbamoyl-4-methoxycarbonyl-3-{4-[(3H-2 -methylimidazo[4.5-c]pyrid-3-yl)methyl]benzoyl}indole,
1-N,N-dimethylcarbamoyl-4-methoxycarbonyl-3-{4-[(1H-2 -methylimidazo[4.5-c]pyrid-1-yl)methyl]benzoyl}indole,
1-N,N-dimethylcarbamoyl-3-{4-[(1H-2-methylimidazo[4.5-c]pyrid-1 -yl)methyl]phenylsulfonyl}indole,
1-(morpholin-4-ylcarbonyl)-6-(4-fluorophenyl)-3-{4-[(1H-2 -methylimidazo[4.5-c]pyridyl)methyl]benzoyl}indole,
1-(N,N-dimethylcarbamoylmethyl)-6-(4-fluorophenyl)-3-{4-[(1H-2-methylimidazo[4.5-c]pyridyl)methyl]benzoyl}indole,
4,7-dimethoxycarbonyl-3-{4-[(1H-2-methylimidazo[4,5-c]pyrid-1 -yl)methyl]benzoyl}indole,
4,7-dimethyl-3-{4-[(1H-2-methylimidazo[4,5-c]pyrid-1 -yl)methyl]benzoyl}indole,
4,7-dimethyl-3-{4-[(3H-2-methylimidazo[4,5-c]pyrid-3 -yl)methyl]benzoyl}indole,
7-benzyloxy-3-{4-[(1H-2-methylimidazo[4,5-c]pyrid-1 -yl)methyl]benzoyl}indole,
7-(4-fluorophenyl)-3-{4-[(1H-2-methylimidazo[4,5-c]pyrid-1 -yl)methyl]benzoyl}indole,
6-(4-fluorophenyl)-3-{N-[3-(1H-2-methylimidazo[4.5-c]pyrid-1 -yl)propyl]sarcosyl}indole-1-carboxylic acid dimethyl amide,
1-N,N-dimethylcarbamoyl-4-methoxycarbonyl-3-{3-fluoro-4-[(1H-2 -methylimidazo[4,5-c]pyrid-1-yl)methyl]benzoyl}indole,
1-N,N-dimethylcarbamoyl-6-benzyloxy-3-{4-[(1H-2-methylimidazo[4.5 -c]pyrid-1-yl)methyl]benzoyl}indole,
1-N,N-dimethylcarbamoyl-4-methoxycarbonyl-3-{5-[(1H-2 -methylimidazo[4,5-c]pyrid-1-yl)methyl]thien-2-oyl}indole,
1-N,N-dimethylcarbamoyl-6-(4-fluorophenyl)-3-{4-[(1H-2 -methylimidazo[4.5-c]pyrid-1-yl)methyl]phenylaminocarbonyl}indole hydrochloride,
1-N,N-dimethylcarbamoyl-5-(4-fluorophenyl)-3-{4-[(1H-2 -methylimidazo[4.5-c]pyrid-1-yl)methyl]benzoyl}indole,
1-N,N-dimethylcarbamoyl-6-(4-fluorophenyl)3-{4-[(1H-2 -methylimidazo[4.5-c]pyrid-1-yl)methyl]phenylsulfonyl}indole,
1-N,N-dimethylcarbamoyl-4-bromo-3-{4-[(1H-2-methylimidazo[4.5-c]pyrid-1-yl)methyl]benzoyl}indole,
1-N,N-dimethylcarbamoyl-4-acetyl-3-{4-[(1H-2-methylimidazo[4.5-c]pyrid-1-yl)methyl]benzoyl}indole,
1-N,N-dimethylcarbamoyl-4-(fur-2-yl)-3-{4-[(1H-2-methylimidazo[4.5 -c]pyrid-1-yl)methyl]benzoyl}indole,
1-N,N-dimethylcarbamoyl-4-(benzo[b]fur-2-yl)-3-{4-[(1H-2 -methylimidazo[4.5-c]pyrid-1-yl)methyl]benzoyl}indole,
1-N,N-dimethylcarbamoyl-4-(trimethylsilylethynyl)-3-{4-[(1H-2 -methylimidazo[4.5-c]pyrid-1-yl)methyl]benzoyl}indole,
1-N,N-dimethylcarbamoyl-4-ethynyl-3-{4-[(1H-2-methylimidazo[4.5 -c]pyrid-1-yl)methyl]benzoyl}indole,
4-(4-fluorophenyl)-3-{4-[(1H-2-methylimidazo[4.5-c]pyrid-1 -yl)methyl]benzoyl}indole,
1-N,N-dimethylcarbamoyl-4-chloro-3-{4-[(1H-2-methylimidazo[4.5-c]pyrid- 1-yl)methyl]benzoyl}indole,
1-N,N-dimethylcarbamoyl-4-fluoro-3-{4-[(1H-2-methylimidazo[4.5-c]pyrid- 1-yl)methyl]benzoyl}indole,
1-N,N-dimethylcarbamoyl-2-methyl-3-{4-[(1H-2-methylimidazo[4.5-c]pyrid-1-yl)methyl]benzoyl}indole,
1,4-di-N,N-dimethylcarbamoyl-3-{4-[(1H-2-methylimidazo[4.5-c]pyrid-1 -yl)methyl]benzoyl}indole,
1-N,N-dimethylcarbamoyl-5-methoxycarbonyl-3-{4-[(1H-2 -methylimidazo[4.5-c]pyrid-1-yl)methyl]benzoyl}indole,
1-N,N-dimethylcarbamoyl-4-methoxycarbonyl-6-(4-fluorophenyl)-3-{4-[(1H- 2-methylimidazo[4.5-c]pyrid-1-yl)methyl]benzoyl}indole,
4-methoxycarbonyl-3-{4-[(1H-2-methylimidazo[4.5-c]pyrid-1 -yl)methyl]benzoyl}indole,
4-methoxycarbonyl-1-(pyrrolidin-1-ylcarbonyl)-3-{4-[(1H-2 -methylimidazo[4.5-c]pyrid-1-yl)methyl]benzoyl}indole,
1-N,N-dimethylcarbamoyl-4-benzyloxycarbonyl-3-{4-[(1H-2 -methylimidazo[4.5-c]pyrid-1-yl)methyl]benzoyl}indole,
1-N,N-dimethylcarbamoyl-3-{4-[(1H-2-methylimidazo[4.5-c]pyrid-1 -yl)methyl]benzoyl}indole-4-carboxylic acid,
1-N,N-dimethylcarbamoyl-4-(N-nonylcarbamoyl)-3-{4-[(1H-2 -methylimidazo[4.5-c]pyrid-1-yl)methyl]benzoyl}indole,
1-N,N-dimethylcarbamoyl-4-(dec-1-yloxycarbonyl)-3-{4-[(1H-2 -methylimidazo[4.5-c]pyrid-1-yl)methyl]benzoyl}indole,
1-N,N-dimethylcarbamoyl-4-methoxy-3-{4-[(1H-2-methylimidazo[4.5 -c]pyrid-1-yl)methyl]benzoyl}indole,
1-N,N-dimethylcarbamoyl-4-methyl-3-{4-[(1H-2-methylimidazo[4.5-c]pyrid-1-yl)methyl]benzoyl}indole,
1-N,N-dimethylcarbamoyl-4-methoxycarbonyl-3-[(1H-2-methylimidazo[4.5-c]pyrid-1-yl)hex-6-ylcarbonyl]indole,
1-N,N-dimethylcarbamoyl-4-methoxycarbonyl-3-{4-[(1H-2 -methylbenzimidazolyl)methyl]benzoyl}indole,
4-methoxycarbonyl-1-(pyrrolidin-1-ylcarbonyl)3-{4-[(1H-2 -methylbenzimidazolyl)methyl]benzoyl}indole,
1-N,N-dimethylcarbamoyl-4-methoxycarbonyl-3-[(1H-2-methylimidazo[4.5-c]pyrid-1-yl)pent-5-ylcarbonyl]indole,
1-N,N-dimethylcarbamoylmethyl-4-methoxycarbonyl-3-[(1H-2 -methylimidazo[4.5-c]pyrid-1-yl)pent-5-ylcarbonyl]indole,
1-N,N-dimethylcarbamoyl-4-methoxycarbonyl-3-[(1H-2-methylimidazo[4.5-c]pyrid-1-yl)pent-5-ylcarbonyl]indole,
1-(2-ethoxyethyl)-4-methoxycarbonyl-3-{4-[(1H-2-methylimidazo[4.5-c]pyrid-1-yl)methyl]benzoyl}indole,
1-N,N-dimethylsulfamoyl-4-methoxycarbonyl-3-{4-[(1H-2 -methylimidazo[4.5-c]pyrid-1-yl)methyl]benzoyl}indole,
1-N,N-dimethylsulfamoyl-4-methoxycarbonyl-3-{4-[(1H-2 -methylimidazo[4.5-c]pyrid-1-yl)methyl]benzoyl}indole,
1-acetoxymethyl-4-methoxycarbonyl-3-{4-[(1H-2-methylimidazo[4.5-c]pyrid-1-yl)methyl]benzoyl}indole,
1-(2-propanesulfonyl)-4-methoxycarbonyl-3-{4-[(1H-2-methylimidazo[4.5-c]pyrid-1-yl)methyl]benzoyl}indole, 1-(1-pinacolyl)-4-methoxycarbonyl-3-{4-[(1H-2-methylimidazo[4.5-c]pyrid-1yl)methyl]benzoyl}indole,
1-carbamoyl-4-methoxycarbonyl-3-{4-[(1H-2-methylimidazo[4.5-c]pyrid-1-yl)methyl]benzoyl}indole,
1-N-methylcarbamoyl-4-methoxycarbonyl-3-{4-.[(1H-2-methylimidazo[4.5-c]pyrid-1-yl)methyl]benzoyl}indole,
1-(2-ethoxyethyl)-4-chloro-3-{4-[(1H-2-methylimidazo[4.5-c]pyrid-1-yl)methyl]benzoyl}indole,
1-N,N-dimethylcarbamoyl-4-methoxycarbonyl-3-{3-methoxy-4-[(1H-2-methylimidazo[4.5-c]pyrid-1-yl)methyl]benzoyl}indole,
1-N,N-dimethylcarbamoyl-4-methoxycarbonyl-3-{3-methoxy-4-[(3H-2-methylimidazo[4.5-c]pyrid-3-yl)methyl]benzoyl}indole,
1-N,N-dimethylcarbamoyl-4-methoxycarbonyl-3-{4-[(1H-2-methylimidazo[4.5-c]pyrid-1-yl)methyl]phenylsulfonyl}indole,
1-N,N-dimethylcarbamoyl-4-methoxycarbonyl-3-{4-[(1H-2-methylimidazo[4.5-c]pyrid-1-yl)methyl]phenylsulfonyl}indole,
1-N,N-dimethylcarbamoyl-4-ethynyl-3-{4-[(1H-2-methylimidazo[4.5-c]pyrid-1-yl)methyl]benzoyl}indole,
1-N,N-dimethylcarbamoyl-4-hydroxy-3-{4-[(1H-2-methylimidazo[4.5-c]pyrid-1-yl)methyl]benzoyl}indole,
1-N,N-dimethylcarbamoyl-6-bromo-4-methoxycarbonyl-3-{4-[(1H-2-methylimidazo[4.5-c]pyrid-1-yl)methyl]benzoyl}indole,
1N,N-dimethylcarbamoyl-6-(benzo[b]fur-2-yl)-4-methoxycarbonyl-3-{4-[(1H-2-methylimidazo[4.5-c]pyrid-1-yl)methyl]benzoyl}indole,
1-N,N-dimethylcarbamoyl-6-(fur-2-yl)-4-methoxycarbonyl-3-{4-[(1H-2-methylimidazo[4.5-c]pyrid-1-yl)methyl]benzoyl}indole,
1N,N-dimethylcarbamoyl-4-(N,N-dimethylaminocarbonyloxy)-3-{4-[(1H-2-methylimidazo[4.5-c]pyrid-1-yl)methyl]benzoyl}indole,
1-N,N-dimethylcarbamoyl-4-(N,N-dimethylaminocarbonylamino)-3-{4-[(1H-2-methylimidazo[4.5-c]pyrid-1-yl)methyl]benzoyl}indole,
1-N,N-dimethylcarbamoyl-4-cyano-3-{4-[(1H-2-methylimidazo[4.5-c]pyrid-1-yl)methyl]benzoyl}indole hydrochloride,
1-N,N-dimethylcarbamoyl-4-methoxycarbonyl-3-{4-[(1H-2-methylimidazo[4.5-c]pyrid-1-yl)methyl]benzyl}indole,
1-N,N-dimethylcarbamoyl-4-chloro-3-{4-[(1H-2-methylimidazo[4.5-b]pyrid-1-yl)methyl]benzoyl}indole,
1-N,N-dimethylcarbamoyl-4-methoxycarbonyl-3-{4-[(3H-2-methylimidazo[4.5-b]pyrid-3-yl)methyl]benzoyl}indole,
1-N,N-dimethylcarbamoyl-4-methoxycarbonyl-3-{4-[(1H-2-methylimidazo[4.5-b]pyrid-1-yl)methyl]benzoyl}indole,
1-N,N-dimethylcarbamoyl-4-methoxycarbonyl-3-{4-[1-(1H-2-methylimidazo[4.5-c]pyrid-1-yl)eth-1-yl]benzoyl}indole,
1-N,N-dimethylcarbamoyl-4-methoxycarbonyl-3-{4-[1—(1H-imidazo[4.5-c]pyrid-1-yl)eth-1-yl]benzoyl}indole,
1-N,N-dimethylcarbamoyl-4-methoxycarbonyl-3-{4-[(1H-2-methyl-5-, and 6 -chlorobenzimidazolyl)methyl]benzoyl}indole,
1-N,N-dimethylcarbamoyl-4-chloro-3-{4-[(1H-2-methyl-5-, and 6 -chlorobenzimidazolyl)methyl]benzoyl}indole,
1-(2-ethoxyethyl)-4-methoxycarbonyl-3-{4-[(1H-2-methyl-5-, and 6 -chlorobenzimidazolyl)methyl]benzoyl}indole,
1-(pyrrolidin-1-ylcarbonyl)-4-methoxycarbonyl-3-{4-[(1H-2-methyl-5-, and 6-chlorobenzimidazolyl)methyl]benzoyl}indole,
1-N,N-dimethylcarbamoyl-4-methoxycarbonyl-3-{4-[(1H-2-(trifluoromethyl)benzimidazolyl)methyl]benzoyl}indole,
1-N,N-dimethylcarbamoyl-4-methoxycarbonyl-3-{4-[(1H-2-methyl-5- and 6 -methylbenzimidazolyl)methyl]benzoyl}indole,
1-N,N-dimethylcarbamoyl-4-methoxycarbonyl-3-{4-[(1H-2-methyl-4- and 7 -methylbenzimidazolyl)methyl]benzoyl}indole,
1-N,N-dimethylcarbamoyl-4-methoxycarbonyl-3-{4-[(1H-2-methyl-5- and 6 -methylbenzimidazolyl)methyl]benzoyl}indole,
1-N,N-dimethylcarbamoyl-4-methoxycarbonyl-3-{4-[(1H-2-methyl-5- and 6 -nitrobenzimidazolyl)methyl]benzoyl}indole,
1-N,N-dimethylcarbamoyl-4-methoxycarbonyl-3-{4-[(1H-2-methyl-5, 6 -dichlorobenzimidazolyl)methyl]benzoyl}indole,
1-N,N-dimethylcarbamoyl-4-methoxycarbonyl-3-{4-[(1H-2-methyl-5- and 6 -methoxycarbonylbenzimidazolyl)methyl]benzoyl}indole,
1-(pyrrolidin-1-ylcarbonyl)-4-methoxycarbonyl-3-{4-[(1H-2-methyl-5- and 6 -methoxycarbonylbenzimidazolyl)methyl]benzoyl}indole,
1-(pyrrolidin-1-ylcarbonyl)-4-methoxycarbonyl-3-{4-[(1H-2-methyl-5- and 6 -methylbenzimidazolyl)methyl]benzoyl}indole,
1-N,N-dimethylcarbamoyl-4-methoxycarbonyl-3-{4-[(3H-2,4,6 -trimethylimidazo[4.5-c]pyrid-3-yl)methyl]benzoyl}indole,
1-(pyrrolidin-1-ylcarbonyl)-4-methoxycarbonyl-3-{4-[(1H-5-trifluoromethyl-2-methylmethylbenzimidazolyl)methyl]benzoyl}indole,
1-N,N-dimethylcarbamoyl-4-methoxycarbonyl-3-{4-[(5-oxide-1H-2-methylimidazo[4.5-c]pyrid-1-yl)methyl]benzoyl}indole,
1-N,N-dimethylcarbamoyl-4-methoxycarbonyl-3-{4-[(4-chloro-1H-2-methylimidazo[4.5-c]pyrid-1-yl)methyl]benzoyl}indole,
1-N,N-dimethylcarbamoyl-4-methoxycarbonyl-3-{4-[(1-H-2-methylimidazo[4.5-c]pyrid-4-one-1-yl)methyl]benzoyl}indole,
1-N,N-dimethylcarbamoyl-4-ethoxycarbonyl-3-{4-[(1H-2-methylimidazo[4.5-c]pyrid-1-yl)methyl]benzoyl}indole,
1-N,N-dimethylcarbamoyl-4-(2-propyloxycarbonyl)-3-{4-[(1H-2-methylimidazo[4.5-c]pyrid-1-yl)methyl]benzoyl}indole, and
1-N,N-dimethylcarbamoyl-4-methoxycarbonyl-3-{4-[(1H-2-methylnaphtho[2,3-d]imidazol-1-yl)methyl]benzoyl}indole.

8. A compound or pharmaceutically acceptable salt thereof selected from the group consisting of
1-N,N-dimethylcarbamoyl-4-(N,N-dimethylaminocarbonyloxy)-3-{3-fluoro-4-[(1H-2-methylimidazo[4,5-c]pyrid-1-yl)methyl]benzoyl}indole,
1-N,N-dimethylcarbamoyl-4-ethynyl-3-{3-fluoro-4-[(1H-2-methylimidazo-[4,5-c]pyrid-1-yl)methyl]benzoyl}indole,
1-N,N-dimethylcarbamoyl-4-ethynyl-3-{4-[(1H-2-methylimidazo-[4.5-c]pyrid-1-yl)methyl]benzoyl}indole,
1-N,N-dimethylcarbamoyl-4-(N,N-dimethylaminocarbonyloxy)-3-{4-[(1H-2-methylimidazo[4.5-c]pyrid-1-yl)methyl]benzoyl}indole, and
1-N,N-Dimethylcarbamoyl-4-methoxycarbonyl-3-{4-[(1H-2-methylimidazo[4.5-c]pyrid-1-yl)methyl]benzoyl}indole.

9. A pharmaceutical composition useful for inhibiting PAF in a mammal in need of such treatment comprising a PAF-inhibitive effective amount of a compound as defined by claim 1 in combination with a pharmaceutically acceptable carrier.

10. A method of treating PAF-mediated disorders comprising administering to a mammal in need of such treatment a therapeutically effective amount of a compound as defined by claim 1.

* * * * *

UNITED STATES PATENT AND TRADEMARK OFFICE
CERTIFICATE OF CORRECTION

PATENT NO.    : 5,486,525
DATED         : January 23, 1996
INVENTOR(S)   : James B. Summers, Jr., et al.

It is certified that error appears in the above-indentified patent and that said Letters Patent is hereby corrected as shown below:

Column 109, Line 62, change "portion io" to --portion is--.

Column 112, Line 24, change "[ 4.5]" to --[4.5]--.

Column 112, Line 62, change "[(3 H-2" to --[(3H-2--.

Signed and Sealed this

Third Day of December, 1996

Attest:

BRUCE LEHMAN

*Attesting Officer*        *Commissioner of Patents and Trademarks*